(12) United States Patent
Eyre et al.

(10) Patent No.: US 12,329,477 B2
(45) Date of Patent: Jun. 17, 2025

(54) SURGICAL ROBOTICS SYSTEMS WITH IMPROVED ROBOTIC ARMS

(71) Applicant: Auris Health, Inc., Redwood City, CA (US)

(72) Inventors: Nicholas J. Eyre, Sunnyvale, CA (US); Aren Calder Hill, Mountain View, CA (US); Sven Wehrmann, Redwood City, CA (US); Colin Allen Wilson, Burlingame, CA (US); Yanan Huang, Foster City, CA (US); Jason Tomas Wilson, Redwood City, CA (US); David Stephen Mintz, Mountain View, CA (US)

(73) Assignee: Auris Health, Inc., Santa Clara, CA (US)

( * ) Notice: Subject to any disclaimer, the term of this patent is extended or adjusted under 35 U.S.C. 154(b) by 0 days.

(21) Appl. No.: 18/440,678

(22) Filed: Feb. 13, 2024

(65) Prior Publication Data

US 2024/0252262 A1 Aug. 1, 2024

Related U.S. Application Data

(63) Continuation of application No. 17/146,035, filed on Jan. 11, 2021, now abandoned, which is a
(Continued)

(51) Int. Cl.
*A61B 34/30* (2016.01)
*A61B 17/00* (2006.01)
(Continued)

(52) U.S. Cl.
CPC .............. *A61B 34/30* (2016.02); *A61G 13/04* (2013.01); *A61G 13/06* (2013.01); *A61G 13/08* (2013.01);
(Continued)

(58) Field of Classification Search
None
See application file for complete search history.

(56) References Cited

U.S. PATENT DOCUMENTS 2,556,601 A 6/1951 Schofield
2,566,183 A 8/1951 Forss
(Continued)

FOREIGN PATENT DOCUMENTS

CN 101500470 A 8/2009
CN 102015759 A 4/2011
(Continued)

OTHER PUBLICATIONS

Final Notice of Preliminary Rejection; Korean Patent Application No. 10-2020-7023590; Apr. 4, 2024; 12 pages.
(Continued)

*Primary Examiner* — Carl H Layno
*Assistant Examiner* — Manolis Pahakis
(74) *Attorney, Agent, or Firm* — Frost Brown Todd LLP

(57) ABSTRACT

A robotic surgical system can include one or more adjustable arm supports that support one or more robotic arms. The adjustable arm supports and/or robotic arms can be configured to be deployed from low mount positions, for example, from positions below the surface of the table. The robotic arms can include a plurality of joints providing a plurality of degrees of freedom. The joints may be grouped into a proximal shoulder, an elbow, and a distal wrist. The robotic arms can include one or more redundant degrees of freedom. An insertion mechanism, associated with the robotic arm and configured for providing insertion of an instrument along an assertion axis, can be provided at a distal end of the robotic arms.

20 Claims, 77 Drawing Sheets

Related U.S. Application Data continuation of application No. 16/235,062, filed on Dec. 28, 2018, now Pat. No. 10,888,386.

(60) Provisional application No. 62/618,500, filed on Jan. 17, 2018.

(51) Int. Cl.
| | | |
|---|---|---|
| *A61G 13/04* | (2006.01) | |
| *A61G 13/06* | (2006.01) | |
| *A61G 13/08* | (2006.01) | |
| *A61G 13/10* | (2006.01) | |

(52) U.S. Cl.
CPC .... *A61G 13/10* (2013.01); *A61B 2017/00477* (2013.01); *A61B 2034/301* (2016.02); *A61B 2034/306* (2016.02); *A61G 2210/50* (2013.01)

(56) References Cited

U.S. PATENT DOCUMENTS

| | | | |
|---|---|---|---|
| 2,623,175 A | 12/1952 | Finke | |
| 2,730,699 A | 1/1956 | Gratian | |
| 2,884,808 A | 5/1959 | Mueller | |
| 3,294,183 A | 12/1966 | Riley, Jr. | |
| 3,472,083 A | 10/1969 | Schnepel | |
| 3,513,724 A | 5/1970 | Box | |
| 3,595,074 A | 7/1971 | Johnson | |
| 3,734,207 A | 5/1973 | Fishbein | |
| 3,739,923 A | 6/1973 | Totsuka | |
| 3,784,031 A | 1/1974 | Niitu | |
| 3,790,002 A | 2/1974 | Guilbaud | |
| 3,921,536 A | 11/1975 | Savage | |
| 3,926,386 A | 12/1975 | Stahmann | |
| 4,141,245 A | 2/1979 | Brandstetter | |
| 4,241,884 A | 12/1980 | Lynch | |
| 4,243,034 A | 1/1981 | Brandt | |
| 4,351,493 A | 9/1982 | Sonnek | |
| 4,357,843 A | 11/1982 | Peck | |
| 4,384,493 A | 5/1983 | Grunbaum | |
| 4,507,026 A | 3/1985 | Lund | |
| 4,530,471 A | 7/1985 | Inoue | |
| 4,555,960 A | 12/1985 | King | |
| 4,688,555 A | 8/1987 | Wardle | |
| 4,745,908 A | 5/1988 | Wardle | |
| 4,784,150 A | 11/1988 | Voorhies | |
| 4,857,058 A | 8/1989 | Payton | |
| 4,907,168 A | 3/1990 | Boggs | |
| 4,945,790 A | 8/1990 | Golden | |
| 5,207,128 A | 5/1993 | Albright | |
| 5,234,428 A | 8/1993 | Kaufman | |
| 5,256,150 A | 10/1993 | Quiachon | |
| 5,277,085 A | 1/1994 | Tanimura | |
| 5,350,101 A | 9/1994 | Godlewski | |
| 5,426,687 A | 6/1995 | Goodall | |
| 5,507,725 A | 4/1996 | Savage | |
| 5,524,180 A | 6/1996 | Wang | |
| 5,559,294 A | 9/1996 | Hoium | |
| 5,709,661 A | 1/1998 | Van Egmond | |
| 5,767,840 A | 6/1998 | Selker | |
| 5,779,623 A | 7/1998 | Bonnell | |
| 5,792,135 A | 8/1998 | Madhani | |
| 5,797,900 A | 8/1998 | Madhani | |
| 5,855,583 A | 1/1999 | Wang | |
| 5,921,968 A | 7/1999 | Lampropoulos | |
| 5,967,934 A | 10/1999 | Ishida | |
| 6,077,219 A | 6/2000 | Viebach | |
| 6,084,371 A | 7/2000 | Kress | |
| 6,154,000 A | 11/2000 | Rastegar | |
| 6,171,234 B1 | 1/2001 | White | |
| 6,185,478 B1 | 2/2001 | Koakutsu | |
| 6,272,371 B1 | 8/2001 | Shlomo | |
| 6,289,579 B1 | 9/2001 | Viza | |
| 6,394,998 B1 | 5/2002 | Wallace | |
| 6,401,572 B1 | 6/2002 | Provost | |
| 6,436,107 B1 | 8/2002 | Wang | |
| 6,487,940 B2 | 12/2002 | Hart | |
| 6,491,701 B2 | 12/2002 | Tierney | |
| 6,695,818 B2 | 2/2004 | Wollschlager | |
| 6,726,675 B1 | 4/2004 | Beyar | |
| 6,786,896 B1 | 9/2004 | Madhani | |
| 6,827,712 B2 | 12/2004 | Tovey | |
| 7,044,936 B2 | 5/2006 | Harding | |
| 7,172,580 B2 | 2/2007 | Hruska | |
| 7,276,044 B2 | 10/2007 | Ferry | |
| 7,615,042 B2 | 11/2009 | Beyar | |
| 7,635,342 B2 | 12/2009 | Ferry | |
| 7,766,856 B2 | 8/2010 | Ferry | |
| 7,938,809 B2 | 5/2011 | Lampropoulos | |
| 7,974,674 B2 | 7/2011 | Hauck | |
| 7,998,020 B2 | 8/2011 | Kidd | |
| 8,052,636 B2 | 11/2011 | Moll | |
| 8,157,308 B2 | 4/2012 | Pedersen | |
| 8,182,415 B2 | 5/2012 | Larkin | |
| 8,277,417 B2 | 10/2012 | Fedinec | |
| 8,291,791 B2 | 10/2012 | Light | |
| 8,317,746 B2 * | 11/2012 | Sewell | A61B 90/11 604/95.04 |
| 8,414,505 B1 | 4/2013 | Weitzner | |
| 8,425,465 B2 | 4/2013 | Nagano | |
| 8,671,817 B1 | 3/2014 | Bogusky | |
| 8,720,448 B2 | 5/2014 | Reis | |
| 8,746,252 B2 | 6/2014 | McGrogan | |
| 8,870,815 B2 | 10/2014 | Bhat | |
| 8,961,533 B2 | 2/2015 | Stahler | |
| 8,968,333 B2 | 3/2015 | Yu | |
| 8,992,542 B2 | 3/2015 | Hagag | |
| 9,173,713 B2 | 11/2015 | Hart | |
| 9,204,933 B2 | 12/2015 | Reis | |
| 9,326,822 B2 | 5/2016 | Lewis | |
| 9,333,042 B2 * | 5/2016 | Diolaiti | A61B 90/361 |
| 9,408,669 B2 | 8/2016 | Kokish | |
| 9,446,177 B2 | 9/2016 | Millman | |
| 9,452,018 B2 | 9/2016 | Yu | |
| 9,457,168 B2 | 10/2016 | Moll | |
| 9,498,601 B2 | 11/2016 | Tanner | |
| 9,504,604 B2 | 11/2016 | Alvarez | |
| 9,517,106 B2 * | 12/2016 | Hourtash | A61B 34/25 |
| 9,561,083 B2 | 2/2017 | Yu | |
| 9,622,827 B2 | 4/2017 | Yu | |
| 9,636,184 B2 | 5/2017 | Lee | |
| 9,636,483 B2 | 5/2017 | Hart | |
| 9,668,814 B2 | 6/2017 | Kokish | |
| 9,713,509 B2 | 7/2017 | Schuh | |
| 9,727,963 B2 | 8/2017 | Mintz | |
| 9,737,371 B2 | 8/2017 | Romo | |
| 9,737,373 B2 | 8/2017 | Schuh | |
| 9,744,335 B2 | 8/2017 | Jiang | |
| 9,763,741 B2 | 9/2017 | Alvarez | |
| 9,788,910 B2 | 10/2017 | Schuh | |
| 9,844,412 B2 | 12/2017 | Bogusky | |
| 9,867,635 B2 | 1/2018 | Alvarez | |
| 9,918,681 B2 | 3/2018 | Wallace | |
| 9,931,025 B1 | 4/2018 | Graetzel | |
| 9,949,749 B2 | 4/2018 | Noonan | |
| 9,955,986 B2 | 5/2018 | Shah | |
| 9,962,228 B2 | 5/2018 | Schuh | |
| 9,980,785 B2 | 5/2018 | Schuh | |
| 9,993,313 B2 | 6/2018 | Schuh | |
| 10,016,900 B1 | 7/2018 | Meyer | |
| 10,022,192 B1 | 7/2018 | Ummalaneni | |
| 10,046,140 B2 | 8/2018 | Kokish | |
| 10,080,576 B2 | 9/2018 | Romo | |
| 10,136,959 B2 | 11/2018 | Mintz | |
| 10,143,360 B2 | 12/2018 | Roelle | |
| 10,145,747 B1 | 12/2018 | Lin | |
| 10,149,720 B2 | 12/2018 | Romo | |
| 10,159,532 B1 | 12/2018 | Ummalaneni | |
| 10,159,533 B2 | 12/2018 | Moll | |
| 10,169,875 B2 | 1/2019 | Mintz | |
| 10,434,660 B2 | 10/2019 | Meyer | |
| 10,464,209 B2 | 11/2019 | Ho | |
| 10,470,830 B2 | 11/2019 | Hill | |
| 10,482,599 B2 | 11/2019 | Mintz | |

(56) References Cited

U.S. PATENT DOCUMENTS

| | | | |
|---|---|---|---|
| 10,524,866 B2 | 1/2020 | Srinivasan | |
| 10,539,478 B2 | 1/2020 | Lin | |
| 10,555,778 B2 | 2/2020 | Ummalaneni | |
| 10,569,052 B2* | 2/2020 | Kokish | A61B 34/37 |
| 10,639,114 B2 | 5/2020 | Schuh | |
| 11,877,813 B2* | 1/2024 | Schmid | A61B 34/10 |
| 2001/0042643 A1 | 11/2001 | Krueger | |
| 2002/0045905 A1 | 4/2002 | Gerbi | |
| 2002/0098938 A1 | 7/2002 | Milbourne | |
| 2002/0100254 A1 | 8/2002 | Dharssi | |
| 2002/0107573 A1 | 8/2002 | Steinberg | |
| 2002/0117017 A1 | 8/2002 | Bernhardt | |
| 2002/0161355 A1 | 10/2002 | Wollschlager | |
| 2002/0161426 A1 | 10/2002 | Iancea | |
| 2002/0177789 A1 | 11/2002 | Ferry | |
| 2003/0056561 A1 | 3/2003 | Butscher | |
| 2003/0212308 A1 | 11/2003 | Bendall | |
| 2004/0015053 A1 | 1/2004 | Bieger | |
| 2004/0152972 A1 | 8/2004 | Hunter | |
| 2004/0243147 A1 | 12/2004 | Lipow | |
| 2004/0254566 A1 | 12/2004 | Plicchi | |
| 2005/0004579 A1 | 1/2005 | Schneider | |
| 2005/0177026 A1 | 8/2005 | Hoeg | |
| 2005/0183532 A1 | 8/2005 | Najafi | |
| 2005/0222554 A1* | 10/2005 | Wallace | A61B 8/12 606/1 |
| 2006/0041245 A1 | 2/2006 | Ferry | |
| 2006/0111692 A1 | 5/2006 | Hlavka | |
| 2006/0146010 A1 | 7/2006 | Schneider | |
| 2006/0201688 A1 | 9/2006 | Jenner | |
| 2006/0229587 A1 | 10/2006 | Beyar | |
| 2006/0237205 A1 | 10/2006 | Sia | |
| 2007/0000498 A1 | 1/2007 | Glynn | |
| 2007/0005002 A1 | 1/2007 | Millman | |
| 2007/0013336 A1 | 1/2007 | Nowlin | |
| 2007/0060879 A1* | 3/2007 | Weitzner | A61M 25/1011 604/95.04 |
| 2007/0100201 A1 | 5/2007 | Komiya | |
| 2007/0100254 A1 | 5/2007 | Murakami | |
| 2007/0112355 A1 | 5/2007 | Salahieh | |
| 2007/0119274 A1 | 5/2007 | Devengenzo | |
| 2007/0149946 A1 | 6/2007 | Viswanathan | |
| 2007/0191177 A1 | 8/2007 | Nagai | |
| 2007/0239028 A1 | 10/2007 | Houser | |
| 2007/0245175 A1 | 10/2007 | Zheng | |
| 2007/0299427 A1 | 12/2007 | Yeung | |
| 2008/0039255 A1 | 2/2008 | Jinno | |
| 2008/0046122 A1 | 2/2008 | Manzo | |
| 2008/0065103 A1* | 3/2008 | Cooper | A61B 17/00234 606/130 |
| 2008/0147011 A1 | 6/2008 | Urmey | |
| 2008/0177285 A1 | 7/2008 | Brock | |
| 2008/0214925 A1 | 9/2008 | Wilson | |
| 2008/0243064 A1* | 10/2008 | Stahler | A61B 34/71 604/95.01 |
| 2008/0249536 A1 | 10/2008 | Stahler | |
| 2008/0253108 A1 | 10/2008 | Ellenburg | |
| 2008/0262301 A1 | 10/2008 | Gibbons | |
| 2008/0287963 A1 | 11/2008 | Rogers | |
| 2008/0302200 A1 | 12/2008 | Tobey | |
| 2009/0082722 A1 | 3/2009 | Munger | |
| 2009/0098971 A1 | 4/2009 | Ho | |
| 2009/0105645 A1 | 4/2009 | Kidd | |
| 2009/0163948 A1 | 6/2009 | Sunaoshi | |
| 2009/0171371 A1 | 7/2009 | Nixon | |
| 2009/0247944 A1* | 10/2009 | Kirschenman | A61B 34/30 604/95.04 |
| 2009/0248039 A1 | 10/2009 | Cooper | |
| 2010/0030023 A1 | 2/2010 | Yoshie | |
| 2010/0069833 A1 | 3/2010 | Wenderow | |
| 2010/0073150 A1 | 3/2010 | Olson | |
| 2010/0130923 A1 | 5/2010 | Cleary | |
| 2010/0130987 A1 | 5/2010 | Wenderow | |
| 2010/0175701 A1* | 7/2010 | Reis | A61B 34/30 74/461 |
| 2010/0204646 A1 | 8/2010 | Plicchi | |
| 2010/0210923 A1 | 8/2010 | Li | |
| 2010/0240989 A1* | 9/2010 | Stoianovici | A61B 34/30 600/429 |
| 2010/0248177 A1 | 9/2010 | Mangelberger | |
| 2010/0249506 A1 | 9/2010 | Prisco | |
| 2010/0274078 A1 | 10/2010 | Kim | |
| 2011/0015484 A1 | 1/2011 | Alvarez | |
| 2011/0015648 A1 | 1/2011 | Alvarez | |
| 2011/0015650 A1 | 1/2011 | Choi | |
| 2011/0028991 A1 | 2/2011 | Ikeda | |
| 2011/0130718 A1 | 6/2011 | Kidd | |
| 2011/0147030 A1 | 6/2011 | Blum | |
| 2011/0152880 A1 | 6/2011 | Alvarez | |
| 2011/0238083 A1 | 9/2011 | Moll | |
| 2011/0261183 A1 | 10/2011 | Ma | |
| 2011/0277775 A1 | 11/2011 | Holop | |
| 2011/0288573 A1 | 11/2011 | Yates | |
| 2011/0306836 A1 | 12/2011 | Ohline | |
| 2012/0071821 A1 | 3/2012 | Yu | |
| 2012/0071894 A1 | 3/2012 | Tanner | |
| 2012/0071895 A1 | 3/2012 | Stahler | |
| 2012/0143226 A1 | 6/2012 | Belson | |
| 2012/0150154 A1 | 6/2012 | Brisson | |
| 2012/0186194 A1 | 7/2012 | Schlieper | |
| 2012/0191107 A1 | 7/2012 | Tanner | |
| 2012/0232476 A1 | 9/2012 | Bhat | |
| 2012/0239012 A1 | 9/2012 | Laurent | |
| 2012/0277730 A1 | 11/2012 | Salahieh | |
| 2012/0283747 A1 | 11/2012 | Popovic | |
| 2013/0018400 A1 | 1/2013 | Milton | |
| 2013/0144116 A1 | 6/2013 | Cooper | |
| 2013/0231678 A1 | 9/2013 | Wenderow | |
| 2013/0239392 A1 | 9/2013 | Solomon et al. | |
| 2013/0304084 A1 | 11/2013 | Beira | |
| 2013/0317519 A1 | 11/2013 | Romo | |
| 2013/0345519 A1 | 12/2013 | Piskun | |
| 2014/0000411 A1 | 1/2014 | Shelton, IV | |
| 2014/0066944 A1 | 3/2014 | Taylor | |
| 2014/0069437 A1 | 3/2014 | Reis | |
| 2014/0142591 A1 | 5/2014 | Alvarez | |
| 2014/0166023 A1 | 6/2014 | Kishi | |
| 2014/0171778 A1 | 6/2014 | Tsusaka | |
| 2014/0180063 A1 | 6/2014 | Zhao | |
| 2014/0222019 A1 | 8/2014 | Brudniok | |
| 2014/0243849 A1 | 8/2014 | Saglam | |
| 2014/0276233 A1 | 9/2014 | Murphy | |
| 2014/0276389 A1 | 9/2014 | Walker | |
| 2014/0276394 A1 | 9/2014 | Wong | |
| 2014/0276594 A1 | 9/2014 | Tanner | |
| 2014/0276935 A1 | 9/2014 | Yu | |
| 2014/0276936 A1 | 9/2014 | Kokish | |
| 2014/0277334 A1 | 9/2014 | Yu | |
| 2014/0309649 A1 | 10/2014 | Alvarez | |
| 2014/0357984 A1 | 12/2014 | Wallace | |
| 2014/0358161 A1* | 12/2014 | Hourtash | B25J 9/1607 901/15 |
| 2014/0364870 A1 | 12/2014 | Alvarez | |
| 2014/0375784 A1 | 12/2014 | Massetti | |
| 2015/0012134 A1 | 1/2015 | Robinson | |
| 2015/0051592 A1 | 2/2015 | Kintz | |
| 2015/0090063 A1 | 4/2015 | Lantermann | |
| 2015/0119637 A1 | 4/2015 | Alvarez | |
| 2015/0119638 A1* | 4/2015 | Yu | A61B 1/0057 600/102 |
| 2015/0133963 A1 | 5/2015 | Barbagli | |
| 2015/0142013 A1 | 5/2015 | Tanner | |
| 2015/0144514 A1 | 5/2015 | Brennan | |
| 2015/0148600 A1 | 5/2015 | Ashinuma | |
| 2015/0150635 A1 | 6/2015 | Kilroy | |
| 2015/0164594 A1 | 6/2015 | Romo | |
| 2015/0164596 A1 | 6/2015 | Romo | |
| 2015/0182250 A1 | 7/2015 | Conlon | |
| 2015/0231364 A1 | 8/2015 | Blanchard | |
| 2015/0327939 A1 | 11/2015 | Kokish | |
| 2015/0335480 A1 | 11/2015 | Alvarez | |
| 2015/0374445 A1 | 12/2015 | Gombert | |

(56) References Cited

U.S. PATENT DOCUMENTS

| | | |
|---|---|---|
| 2016/0000512 A1 | 1/2016 | Gombert |
| 2016/0001038 A1* | 1/2016 | Romo ............... A61M 25/0012 604/526 |
| 2016/0157945 A1 | 6/2016 | Madhani |
| 2016/0166234 A1 | 6/2016 | Zhang |
| 2016/0184032 A1* | 6/2016 | Romo ................... B25J 13/085 901/46 |
| 2016/0192860 A1 | 7/2016 | Allenby |
| 2016/0206389 A1 | 7/2016 | Miller |
| 2016/0213435 A1 | 7/2016 | Hourtash |
| 2016/0235946 A1 | 8/2016 | Lewis |
| 2016/0270865 A1 | 9/2016 | Landey |
| 2016/0287279 A1 | 10/2016 | Bovay |
| 2016/0331477 A1* | 11/2016 | Yu ....................... A61B 1/00149 |
| 2016/0338783 A1 | 11/2016 | Romo |
| 2016/0338785 A1 | 11/2016 | Kokish |
| 2016/0346049 A1 | 12/2016 | Allen |
| 2016/0354582 A1 | 12/2016 | Yu |
| 2016/0374541 A1 | 12/2016 | Agrawal |
| 2016/0374771 A1 | 12/2016 | Mirbagheri et al. |
| 2017/0007337 A1 | 1/2017 | Dan |
| 2017/0007343 A1 | 1/2017 | Yu |
| 2017/0065364 A1 | 3/2017 | Schuh |
| 2017/0071684 A1 | 3/2017 | Kokish |
| 2017/0100199 A1 | 4/2017 | Yu |
| 2017/0105804 A1 | 4/2017 | Yu |
| 2017/0119413 A1 | 5/2017 | Romo |
| 2017/0119481 A1 | 5/2017 | Romo |
| 2017/0119484 A1 | 5/2017 | Tanner |
| 2017/0151028 A1 | 6/2017 | Ogawa |
| 2017/0165011 A1 | 6/2017 | Bovay |
| 2017/0172673 A1 | 6/2017 | Yu |
| 2017/0202627 A1 | 7/2017 | Sramek |
| 2017/0209073 A1 | 7/2017 | Sramek |
| 2017/0209672 A1 | 7/2017 | Hart |
| 2017/0251902 A1 | 9/2017 | Jogasaki |
| 2017/0252540 A1 | 9/2017 | Weitzner |
| 2017/0258534 A1 | 9/2017 | Hourtash |
| 2017/0281049 A1 | 10/2017 | Yamamoto |
| 2017/0290631 A1 | 10/2017 | Lee |
| 2017/0296784 A1 | 10/2017 | Kokish |
| 2017/0312481 A1 | 11/2017 | Covington |
| 2017/0333679 A1 | 11/2017 | Jiang |
| 2017/0340396 A1 | 11/2017 | Romo |
| 2017/0367782 A1 | 12/2017 | Schuh |
| 2018/0025666 A1 | 1/2018 | Ho |
| 2018/0042464 A1 | 2/2018 | Arai |
| 2018/0049792 A1 | 2/2018 | Eckert |
| 2018/0056044 A1 | 3/2018 | Choi |
| 2018/0104820 A1 | 4/2018 | Troy |
| 2018/0116735 A1 | 5/2018 | Tierney |
| 2018/0177383 A1 | 6/2018 | Noonan |
| 2018/0177556 A1 | 6/2018 | Noonan |
| 2018/0206927 A1 | 7/2018 | Prisco |
| 2018/0214011 A1 | 8/2018 | Graetzel |
| 2018/0221038 A1 | 8/2018 | Noonan |
| 2018/0221039 A1 | 8/2018 | Shah |
| 2018/0243035 A1 | 8/2018 | Kopp |
| 2018/0250083 A1 | 9/2018 | Schuh |
| 2018/0271616 A1 | 9/2018 | Schuh |
| 2018/0279852 A1 | 10/2018 | Rafii-Tari |
| 2018/0280660 A1 | 10/2018 | Landey |
| 2018/0289243 A1 | 10/2018 | Landey |
| 2018/0289431 A1 | 10/2018 | Draper |
| 2018/0296299 A1 | 10/2018 | Iceman |
| 2018/0303566 A1 | 10/2018 | Soundararajan |
| 2018/0325499 A1 | 11/2018 | Landey |
| 2018/0326181 A1 | 11/2018 | Kokish |
| 2018/0333044 A1 | 11/2018 | Jenkins |
| 2018/0360435 A1 | 12/2018 | Romo |
| 2018/0360554 A1* | 12/2018 | Nakanishi ............... A61B 34/37 |
| 2019/0000559 A1 | 1/2019 | Berman |
| 2019/0000560 A1 | 1/2019 | Berman |
| 2019/0000566 A1* | 1/2019 | Graetzel ................ A61B 90/98 |
| 2019/0000568 A1* | 1/2019 | Connolly ............. A61B 90/361 |
| 2019/0000576 A1 | 1/2019 | Mintz |
| 2019/0083183 A1 | 3/2019 | Moll |
| 2019/0110839 A1 | 4/2019 | Rafii-Tari |
| 2019/0110843 A1 | 4/2019 | Ummalaneni |
| 2019/0142537 A1 | 5/2019 | Covington |
| 2019/0151148 A1 | 5/2019 | Alvarez |
| 2019/0167366 A1 | 6/2019 | Ummalaneni |
| 2019/0175009 A1 | 6/2019 | Mintz |
| 2019/0175062 A1 | 6/2019 | Rafii-Tari |
| 2019/0175287 A1 | 6/2019 | Hill |
| 2019/0175799 A1 | 6/2019 | Hsu |
| 2019/0183585 A1 | 6/2019 | Rafii-Tari |
| 2019/0183587 A1 | 6/2019 | Rafii-Tari |
| 2019/0216548 A1 | 7/2019 | Ummalaneni |
| 2019/0216550 A1* | 7/2019 | Eyre ....................... A61G 13/08 |
| 2019/0216576 A1 | 7/2019 | Eyre |
| 2019/0223974 A1 | 7/2019 | Romo |
| 2019/0228525 A1 | 7/2019 | Mintz |
| 2019/0246882 A1 | 8/2019 | Graetzel |
| 2019/0262086 A1 | 8/2019 | Connolly |
| 2019/0269468 A1 | 9/2019 | Hsu |
| 2019/0274764 A1 | 9/2019 | Romo |
| 2019/0290109 A1 | 9/2019 | Agrawal |
| 2019/0298160 A1 | 10/2019 | Ummalaneni |
| 2019/0298460 A1 | 10/2019 | Al-Jadda |
| 2019/0298465 A1 | 10/2019 | Chin |
| 2019/0328213 A1 | 10/2019 | Landey |
| 2019/0336238 A1 | 11/2019 | Yu |
| 2019/0350660 A1 | 11/2019 | Moll |
| 2019/0365209 A1 | 12/2019 | Ye |
| 2019/0365479 A1 | 12/2019 | Rafii-Tari |
| 2019/0365486 A1 | 12/2019 | Srinivasan |
| 2019/0374297 A1 | 12/2019 | Wallace |
| 2019/0375383 A1 | 12/2019 | Auer |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054408 A1 | 2/2020 | Schuh |
| 2020/0060516 A1 | 2/2020 | Baez, Jr. |
| 2020/0086087 A1 | 3/2020 | Hart |
| 2020/0091799 A1 | 3/2020 | Covington |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0129252 A1 | 4/2020 | Kokish |
| 2020/0146769 A1 | 5/2020 | Eyre |
| 2020/0155245 A1 | 5/2020 | Yu |
| 2020/0155801 A1 | 5/2020 | Kokish |

FOREIGN PATENT DOCUMENTS

| | | |
|---|---|---|
| CN | 102316817 A | 1/2012 |
| CN | 102458295 A | 5/2012 |
| CN | 102665590 A | 9/2012 |
| CN | 102973317 A | 3/2013 |
| CN | 103037799 A | 4/2013 |
| CN | 103735313 A | 4/2014 |
| CN | 105050526 A | 11/2015 |
| CN | 105559850 A | 5/2016 |
| CN | 105559886 A | 5/2016 |
| DE | 19649082 C1 | 1/1998 |
| DE | 102004020465 B3 | 9/2005 |
| EP | 1442720 A1 | 8/2004 |
| EP | 2567670 A1 | 3/2013 |
| EP | 3025630 A1 | 6/2016 |
| JP | H07136173 A | 5/1995 |
| JP | 2005204999 A | 8/2005 |
| JP | 2009139187 A | 6/2009 |
| JP | 2010046384 A | 3/2010 |
| WO | 2002074178 A2 | 9/2002 |

(56) References Cited

FOREIGN PATENT DOCUMENTS

| WO | 2007146987 A2 | 12/2007 |
|---|---|---|
| WO | 2009092059 A2 | 7/2009 |
| WO | 2011005335 A1 | 1/2011 |
| WO | 2012037506 A2 | 3/2012 |
| WO | 2013179600 A1 | 12/2013 |
| WO | 2015127231 A1 | 8/2015 |
| WO | 2016088205 A1 | 6/2016 |
| WO | 2016164824 A1 | 10/2016 |
| WO | 2016187054 A1 | 11/2016 |
| WO | 2017015599 A1 | 1/2017 |
| WO | 2017059412 A1 | 4/2017 |
| WO | 2017099234 A1 | 6/2017 |
| WO | 2017151993 A1 | 9/2017 |

OTHER PUBLICATIONS

International search report and written opinion dated Mar. 14, 2019 for PCT/US2018/067968.
Mayo Clinic, Robotic Surgery, https://www.mayoclinic.org/tests-procedures/robotic-surgery/about/pac-20394974?p=1, downloaded from the internet on Jul. 12, 2018, 2 pp.
Extended European Search Report from European Patent Application No. 18901145.5, dated Sep. 30, 2021, 8 pages.
Notice of Reasons for Refusal; Japanese Patent Application No. 2020-539226; Dec. 8, 2022; 14 pages.
Office Action; Chinese Patent Application No. 201880091422.0; Feb. 10, 2023; 16 pages.
Notice of Reasons for Refusal; Japanese Patent Application No. 2020-539226; Aug. 30, 2023; 17 pages.
European Communication dated Mar. 20, 2025, for Application No. 18901145.5, 8 pages.

\* cited by examiner

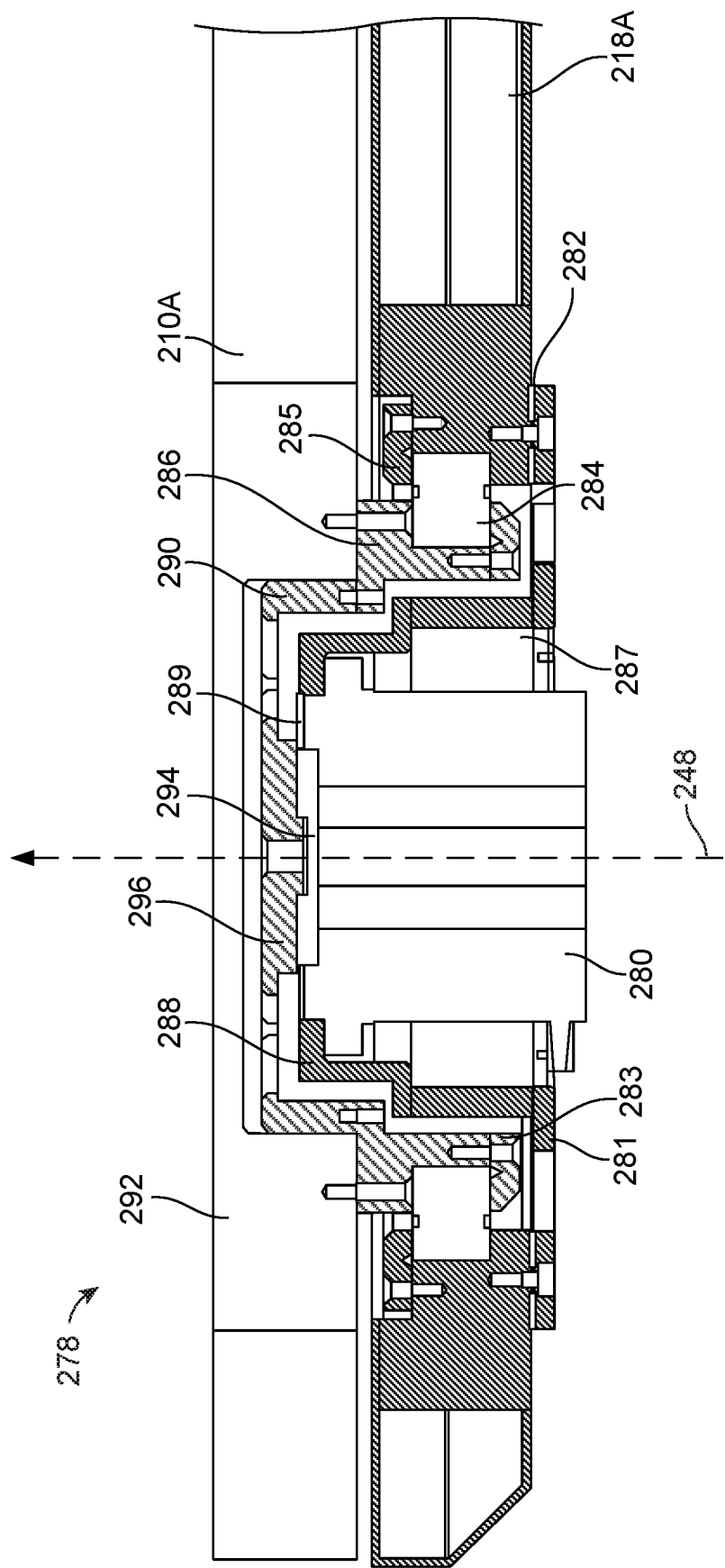

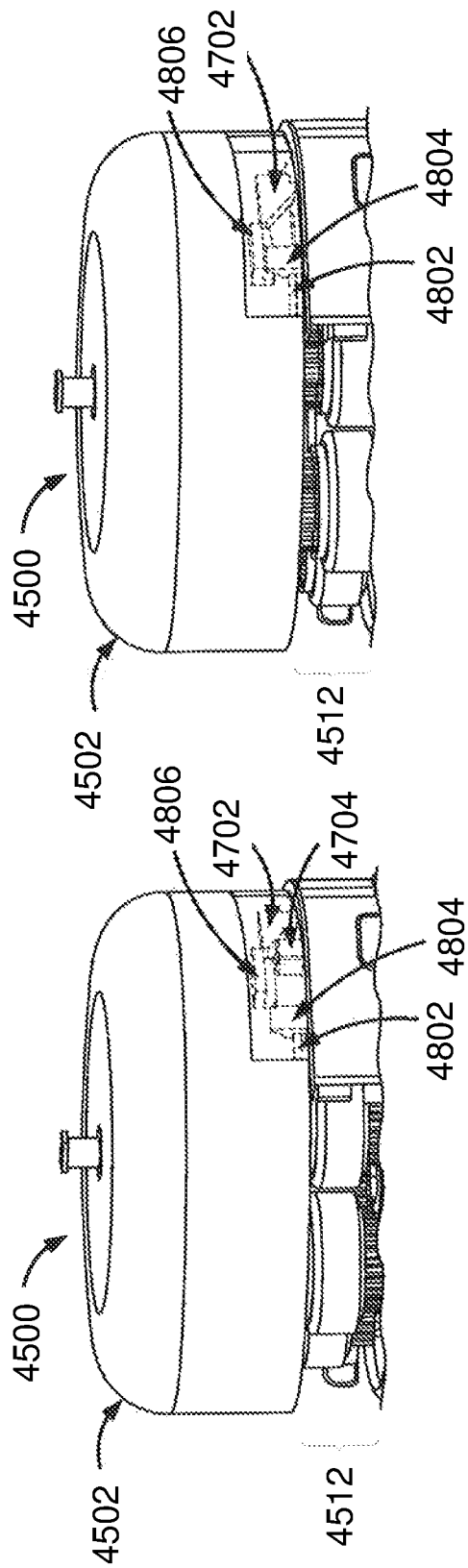

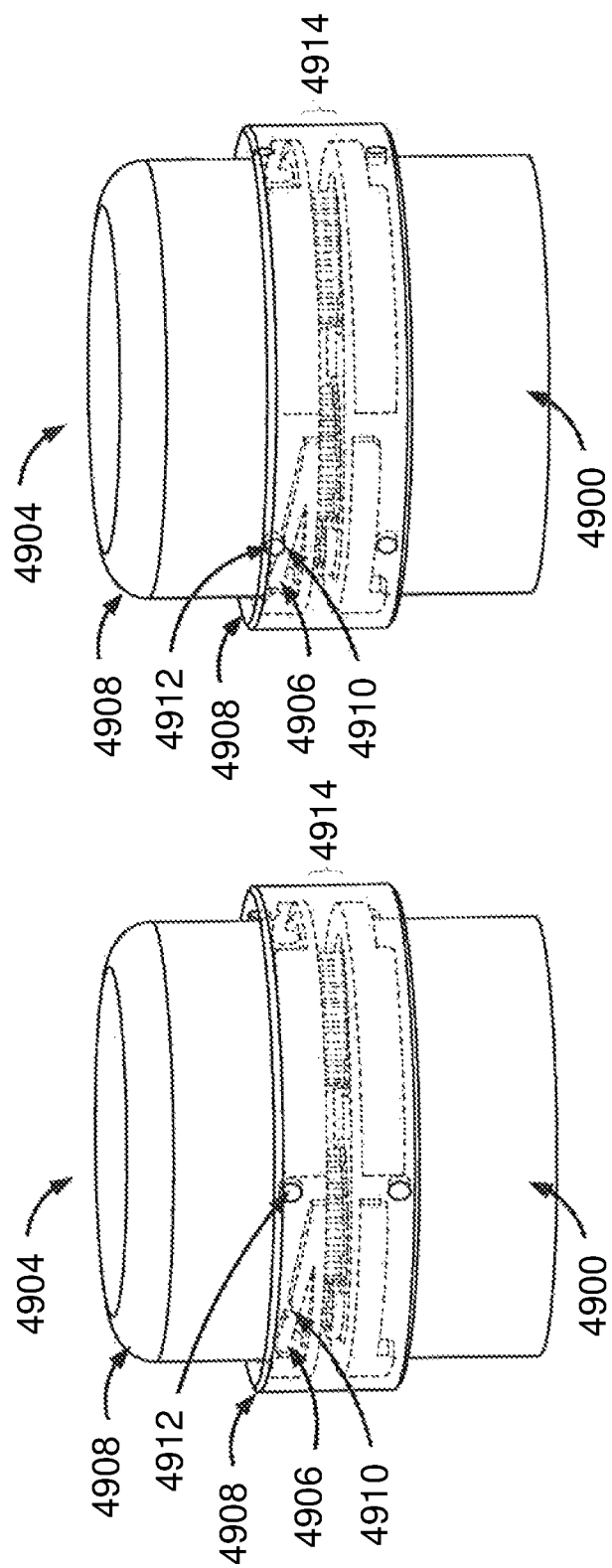

SURGICAL ROBOTICS SYSTEMS WITH IMPROVED ROBOTIC ARMS

INCORPORATION BY REFERENCE TO ANY PRIORITY APPLICATIONS

This application is a continuation of U.S. application Ser. No. 17/146,035, filed Jan. 11, 2021, published as U.S. Publication No. 2021/0205034, now abandoned, which is a continuation of U.S. application Ser. No. 16/235,062, filed Dec. 28, 2018, now U.S. Pat. No. 10,888,386, which claims priority to U.S. Provisional Application No. 62/618,500, filed Jan. 17, 2018, each of which is incorporated herein by reference. Any and all applications for which a foreign or domestic priority claim is identified in the Application Data Sheet as filed with the present application are hereby incorporated by reference under 37 CFR 1.57.

BACKGROUND

Field

This description generally relates to surgical or medical robotics, and particularly to a robotics system configurable for a variety of surgical or medical procedures.

Description

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. Recently, physicians have started using robotic arms to help perform surgical procedures. For instance, physicians use robotic arms to control surgical instruments inside a patient. However, existing medical systems including robotic arms have a high capital cost and are typically specialized to perform limited types of surgical procedures. Thus, physicians or their assistants may need to obtain multiple robotic arm systems to accommodate a range of surgical procedures. Manually reconfiguring a robotic arm system for each surgical procedure is also time-consuming and physically demanding for the physicians.

SUMMARY

A surgical (or medical) robotics system with robotic arms is configurable to perform a variety of surgical (or medical) procedures. A surgical robotics system can include one or more adjustable arm supports that support one or more robotic arms. The adjustable arm supports can be configured to attach to either a table, a column support of the table, or a base of the table to deploy the adjustable arm supports and robotic arms from a position below the table. In some examples, the adjustable arm supports include at least three or four degrees of freedom that allow for adjustment of the position of a bar or rail to which the robotic arms are mounted. One of the degrees of freedom can allow the adjustable arm support to be adjusted vertically relative to the table. A robotic surgical system can include two adjustable arm supports, each supporting one or more robotic arms. The two adjustable arm supports can be independently adjusted. For example, each arm support can be adjusted to a different height relative to the table.

A surgical robotics system can also include one or more robotic arms. The one or more robotic arms can be configured to be mounted to the adjustable arm supports. In some embodiments, the robotic arms are configured to be deployed from low mount positions, for example, from positions below the surface of the table, although in other embodiments, the robotic arms can be deployed from positions above the surface of the table. The robotic arms can include a plurality of joints providing a plurality of degrees of freedom. In some embodiments, the robotic arms can include one or more redundant degrees of freedom.

In a first aspect, a system can include a table, a table support below the table, an arm support coupled to at least one of the table or table support, and a first robotic arm coupled to the arm support. The first robotic arm can include a proximal portion and a distal portion and at least four powered joints between the proximal portion and the distal portion, wherein each of the joints is capable of being actuated independently of the other joints, wherein the first robotic arm comprises an instrument drive mechanism configured to drive a surgical instrument. The system can also include an insertion mechanism associated with the first robotic arm to provide insertion of the instrument along an insertion axis, and a second robotic arm coupled to the arm support.

The system may also include one or more of the following features in any combination: (a) wherein the first robotic arm is translatable relative to the second robotic arm; (b) wherein the insertion mechanism is built within the instrument itself independently of the first robotic arm; (c) wherein the insertion mechanism is built within the first robotic arm; (d) wherein the insertion mechanism is configured to translate the instrument drive mechanism relative to an insertion body housing to translate the instrument along the insertion axis; (e) wherein the first robotic arm is capable of at least seven degrees of freedom, wherein at least one of the degrees of freedom is redundant; and/or (f) wherein the first robotic arm and the second robotic arm are capable of being stowed beneath the table.

In another aspect, a system includes a table, a table support below the table, an arm support coupled to at least one of the table or table support, and a first robotic arm coupled to the arm support, wherein the first robotic arm comprises a proximal link and a distal link and at least three joints coupled to a distal end of the distal link, wherein each of the joints is capable of being actuated independently of the other joints, wherein the first robotic arm comprises an instrument drive mechanism configured to drive a surgical instrument. The system may also include an insertion mechanism associated with the first robotic arm to provide insertion of the instrument along an insertion axis.

The system may also include one or more of the following features in any combination: (a) wherein at least two of the joints are rotary joints; (b) wherein at least one of the joints comprises an insertion axis; (c) wherein at least one of the joints rolls the instrument about the instrument axis; (d) wherein the at least one joint that rolls the instrument about the instrument axis is part of the first robotic arm or part of the instrument itself; (e) a second robotic arm coupled to the arm support; (f) wherein the first robotic arm is translatable relative to the second robotic arm; and/or (g) wherein the first robotic arm is capable of at least seven degrees of freedom, wherein at least one of the degrees of freedom is redundant.

In another aspect, a system includes a table, a table support for supporting the table, an arm support coupled to at least one of the table or the table support, and a first robotic arm coupled to the arm support, the first robotic arm capable of being stowed below the table and elevated. The first robotic arm includes a proximal portion and a distal portion, wherein the proximal portion comprises a base coupled to the arm support and the distal portion comprises an instrument drive mechanism comprising a plurality of motors, wherein the instrument drive mechanism is configured to drive a surgical instrument attached thereto. The system also includes a plurality of powered joints between the proximal portion and the distal portion thereby accommodating movement of the instrument in multiple degrees of freedom, wherein each of the joints is capable of being actuated independently of the other joints, an insertion mechanism associated with the first robotic arm to provide insertion of the instrument along an insertion axis, and a second robotic arm coupled to the arm support, the second robotic arm capable of being stowed below the table and elevated.

The system may also include one or more of the following features in any combination: (a) wherein the insertion mechanism is built within the instrument itself independently of the first robotic arm; (b) wherein the first robotic arm is capable of at least seven degrees of freedom, wherein at least one of the degrees of freedom is redundant; (c) wherein the first robotic arm comprises proximal link and a distal link, wherein at least three joints are coupled to a distal end of the distal link, and wherein at least two of the joints coupled to the distal end of the distal link are rotary joints; and/or (d) wherein the surgical instrument comprises an endoscopic instrument.

In a another aspect, a system can include a table for supporting a patient positioned on the table, a table support below the table, and an arm support coupled to at least one of the table or table support. The system can also include a first robotic arm coupled to the arm support, wherein the first robotic arm comprises a proximal portion and a distal portion and at least four powered joints between the proximal portion and the distal portion, wherein each of the joints is capable of being actuated independently of the other joints, wherein the first robotic arm comprises an instrument drive mechanism configured to drive a surgical instrument. The system can also include an insertion mechanism associated with the first robotic arm to provide insertion of the instrument along an insertion axis. The system may include a second robotic arm coupled to the arm support.

The system may include one or more of the following features in any combination: (a) wherein the first robotic arm is translatable relative to the second robotic arm; (b) wherein the insertion mechanism is built within the instrument itself independently of the first robotic arm; (c) wherein the insertion mechanism is built within the first robotic arm; (d) wherein the insertion mechanism is configured to translate the instrument drive mechanism relative to an insertion body housing to translate the instrument along the insertion axis; (e) wherein the first robotic arm is capable of at least five degrees of freedom; (f) wherein the first robotic arm is capable of at least six degrees of freedom; (g) wherein the first robotic arm is capable of at least seven degrees of freedom; (h) wherein at least one of the seven degrees of freedom is redundant; (i) a second arm support, wherein the arm support and second arm support can have a height differential; (j) wherein the arm support is capable of adjusting its tilt angle; (k) wherein the first robotic arm and the second robotic arm are capable of being stowed beneath the table; (l) wherein the table support comprises a base, wherein the first robotic arm and the second robotic arm are capable of being stowed in the base; (m) at least one computer-readable memory having stored thereon executable instructions, and at least one processor in communication with the at least one computer-readable memory and configured to execute the instructions to cause the system to move the first and second robotic arms from a stowed position in the base to a vertically elevated position adjacent the table; (n) an instrument having a handle attached to the instrument drive mechanism of the first robotic arm; (o) wherein roll is provided in the handle of the instrument or the instrument drive mechanism; (p) wherein the first robotic arm further comprises a second instrument drive mechanism; and/or (q) wherein the arm support is capable of vertical adjustment relative to the table.

In another aspect, a system can include a table, a table support for supporting the table, an arm support coupled to at least one of the table or the table support, and a first robotic arm coupled to the arm support, the first robotic arm capable of being stowed below the table and elevated. The first robotic arm can include a proximal portion and a distal portion, wherein the proximal portion comprises a base coupled to the arm support and the distal portion comprises an instrument drive mechanism comprising a plurality of motors, wherein the instrument drive mechanism is configured to drive a surgical instrument attached thereto; and a plurality of powered joints between the proximal portion and the distal portion thereby accommodating movement in multiple degrees of freedom, wherein each of the joints is capable of being actuated independently of the other joints. The system can include an insertion mechanism associated with the first robotic arm to provide insertion of the instrument along an insertion axis. The system may include a second robotic arm coupled to the arm support, the second robotic arm capable of being stowed below the table and elevated.

The system may include one or more of the following features in any combination: (a) at least one computer-readable memory having stored thereon executable instructions, and at least one processor in communication with the at least one computer-readable memory and configured to execute the instructions to cause the system to at least move the first and second robotic arms from a stowed position to a vertically elevated position adjacent the table; (b) wherein the first robotic arm is capable of rolling the instrument about its axis, inserting the surgical instrument along its axis, and pitching and yawing the instrument about a point along its axis; (c) wherein the insertion mechanism is built within the instrument itself independently of the first robotic arm; (d) wherein the instrument drive mechanism is part of a wrist of the first robotic arm; (e) wherein the wrist comprises the instrument drive mechanism and an insertion body housing, wherein the insertion mechanism is configured to translate the instrument drive mechanism relative to the insertion body housing to translate the instrument along the insertion axis; (f) wherein at least one of the first robotic arm and the second robotic arm is capable of translating along the arm support; (g) wherein the first robotic arm comprises a wrist with at least three powered rotational joints, and wherein the wrist is capable of pitch and yaw; and/or (h) wherein at least one of the first robotic arm and the second robotic arm holds a camera.

In another aspect, provided is a method that can include: moving a robotic arm from a stowed position, in which the robotic arm is located below a surface of a patient-support table, to an active position, in which at least a distal portion of the robotic arm is located above the surface of the table; wherein, in the active position, an axis of an instrument coupled to the distal portion of the robotic arm is aligned with a port into a body of a patient on the surface of the table. In some embodiments, the robotic arm is attached to at least one of the table or a table support positioned below the table.

In another aspect, a system is provided that can include a robotic arm comprising: a base configured to mount to an arm support; a proximal link comprising a proximal end and a distal end, the proximal end of the proximal link connected to the base by a shoulder; a distal link comprising a proximal end and a distal end, the proximal end of the distal link connected to the distal end of the proximal link by an elbow; and a wrist at the distal end of the distal link. The system can include at least one computer-readable memory having stored thereon executable instructions, and at least one processor in communication with the at least one computer-readable memory and configured to execute the instructions to cause the system to at least move the robotic arm from a stowed position, in which the robotic arm is located below a surface of a table configured to a support a patient, to an active position, in which at least a distal portion of the robotic arm is located above the surface of the table. In some embodiments, in the active position, an axis of an instrument coupled to the distal portion of the robotic arm is aligned with a port into a body of a patient on the surface of the table. In some embodiments, the robotic arm is attached to at least one of the table or a table support positioned below the table.

In another aspect provided is a method that can include: inserting, with a robotic arm, an instrument into a patient through a port, the instrument located at a distal end of the robotic arm; manipulating, with the robotic arm, at least one of pitch, yaw, or roll of the instrument relative to the port; and manipulating the robotic arm to adjust a position of a proximal end of the robotic arm relative to the port.

The method can include one or more of the following features in any combination: (a) wherein manipulating the instrument with the robotic arm and manipulating the robotic arm occur simultaneously; and/or (b) wherein further manipulating the robotic arm to adjust the position of the proximal end of the robotic arm does not affect the position or orientation of the instrument attached to the distal end of the robotic arm.

In another aspect, provided is a method that can include: inserting, with a robotic arm, an instrument into a patient through a port, the instrument located at a distal end of the robotic arm; and manipulating the robotic arm to adjust the position of a proximal end of the robotic arm relative to the port without affecting the position or orientation of the instrument. The method may also include manipulating, with the robotic arm, at least one of pitch, yaw, or roll of the instrument relative to the port.

In another aspect, provided is a system that can include a first robotic arm coupled to the arm support, the robotic arm comprising: a base configured to mount to an arm support; a proximal link comprising a proximal end and a distal end, the proximal end of the proximal link connected to the base by a powered shoulder; a distal link comprising a proximal end and a distal end, the proximal end of the distal link connected to the distal end of the proximal link by a powered elbow; a powered wrist at the distal end of the distal link; and an insertion mechanism at a distal end of the robotic arm and configured to provide insertion of an instrument along an insertion axis, the insertion mechanism attached to the wrist. The system may also include a port, wherein the instrument extends through the port to assist in a surgical procedure.

In some embodiments, the system may include one or more of the following features in any combination: (a) wherein at least one of the shoulder, elbow or wrist is motorized; (b) wherein the insertion mechanism comprises a mechanism built within the instrument itself to provide insertion of the instrument along the insertion axis; (c) wherein the insertion mechanism comprises a shaft of the instrument moving relative to a handle of the instrument along the insertion axis; (d) wherein the insertion mechanism comprises an instrument drive mechanism that is configured to translate along an insertion body housing to provide insertion of the instrument along the insertion axis; (e) wherein the wrist comprises at least two degrees of freedom; (f) wherein the wrist is capable of pitch and yaw; (g) wherein the elbow comprises at least one degree of freedom; (h) wherein the shoulder comprises at least two degrees of freedom; (i) wherein the at least two degrees of freedom of the shoulder includes at least pitch and yaw or pitch and translation; ( ) wherein the base is configured to mount to the arm support via a linear joint configured to allow the base to translate along a rail of the arm support; and/or (k) wherein the shoulder, the elbow, and the wrist are configured to provide at least six degrees of freedoms to allow the robotic arm to position the instrument at a remote center and control at least pitch, yaw, and roll of the instrument about the remote center.

In another aspect, provided is a system that can include a table, an arm support positioned relative to the table, and a robotic arm coupled to the arm support. The robotic arm can include a base configured to mount to the arm support; a proximal link comprising a proximal end and a distal end, the proximal end of the proximal link connected to the base by a powered shoulder; a distal link comprising a proximal end and a distal end, the proximal end of the distal link connected to the distal end of the proximal link by a powered elbow; and a powered wrist at the distal end of the distal link and configured to couple to an instrument. In some embodiments, the shoulder, the elbow, and the wrist are configured to provide at least six degrees of freedoms to allow the robotic arm to position the instrument at a remote center and control at least pitch, yaw, and roll of the instrument about the remote center, and wherein the base is translatable relative to the arm support. The system can include an insertion mechanism at a distal end of the robotic arm and configured to provide insertion of an instrument along an insertion axis, and a port, wherein the instrument extends through the port to assist in a surgical procedure.

The system can include one or more of the following features in any combination: (a) wherein the wrist comprises a joint configured to provide at least three degrees of freedom to permit adjustment of at least pitch, yaw, and roll of an instrument; (b) wherein the wrist comprises a partial spherical joint; (c) wherein the base is configured to mount to an arm support via a linear joint configured to allow the base to translate along a rail of the arm support, the arm support is located below a surface of a table, and the table configured to support a patient; and/or (d) wherein the rail is located below the surface of the table.

In another aspect, provided is a system that can include a robotic arm comprising a base configured to mount to an arm support; a proximal link comprising a proximal end and a distal end, the proximal end of the proximal link connected to the base by a shoulder; a distal link comprising a proximal end and a distal end, the proximal end of the distal link connected to the distal end of the proximal link by an elbow; and a wrist at the distal end of the distal link. The system can also include at least one computer-readable memory having stored thereon executable instructions, and at least one processor in communication with the at least one computer-readable memory and configured to execute the instructions to cause the system to at least: actuate at least one of the wrist, the elbow, and the shoulder to adjust a position of the robotic arm; position an instrument with the robotic arm such that an axis of the instrument extends through a remote center aligned with a port in the body of the patient; and in response to receiving a command, actuate at least one of the wrist, the elbow, and the shoulder, to manipulate the instrument according to the command.

The system can include one or more of the following features in any combination: (a) wherein the instructions, when executed cause the system to actuate at least one of the wrist, the elbow, and the shoulder to adjust a position of the robotic arm relative to at least one of a patient, a table support the patient, a medical imaging device, and an additional robotic arm; (b) wherein the additional robotic arm is mounted to the arm support; (c) an arm support mounted to a column supporting the table, the arm support including a rail, the base of the robotic arm mounted to the rail via a linear motorized joint; (d) wherein the instructions, when executed, further cause the at least one processor to cause the system to actuate at least the linear motorized joint to translate the base along the rail; (e) wherein the rail is located below a surface of the table; and/or (f) wherein the instructions, when executed, further cause the system to actuate at least the linear joint to translate the base along the rail in response to the command simultaneously with actuating at least one of the wrist, the elbow, and the shoulder, to manipulate the instrument according to the command.

BRIEF DESCRIPTION OF THE DRAWINGS

FIG. 2F is a cross sectional view of the swivel mechanism shown in FIG. 2E according to one embodiment.

FIGS. 36A and 36B illustrate a process of engaging and disengaging a surgical tool from a sterile adapter, according to one embodiment.

FIGS. 37A and 37B illustrate a process of engaging and disengaging a surgical tool from a sterile adapter, according to an additional embodiment.

Reference will now be made in detail to several embodiments, examples of which are illustrated in the accompanying figures. It is noted that wherever practicable similar or like reference numbers may be used in the figures and may indicate similar or like functionality. The figures depict embodiments of the described system (or method) for purposes of illustration only. One skilled in the art will readily recognize from the following description that alternative embodiments of the structures and methods illustrated herein may be employed without departing from the principles described herein.

DETAILED DESCRIPTION

I. System Overview

Figure 1:
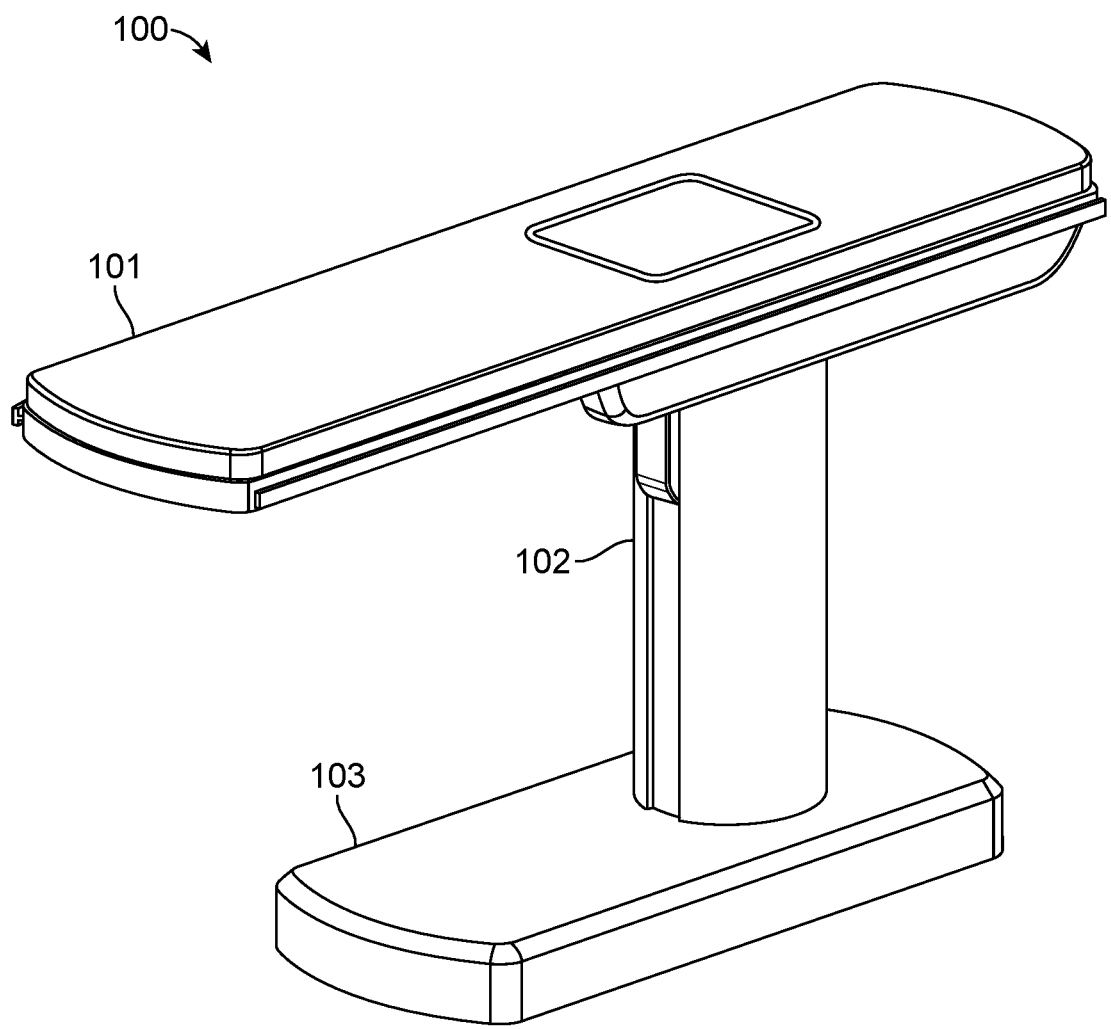
FIG. 1 is an isometric view of a surgical robotics system according to an embodiment.

FIG. 1 is an isometric view of a surgical robotics system 100 according to an embodiment. A user, e.g., a physician or assistant, uses the surgical robotics system 100 to perform robotically-assisted surgery on a patient. The surgical robotics system 100 includes a table 101, column 102, and base 103 physically coupled together. Although not shown in FIG. 1, the table 101, column 102, and/or base 103 may house, connect to, or use electronics, fluidics, pneumatics, aspiration, or other electrical and mechanical components that support the function of the surgical robotics system 100.

The table 101 provides support for a patient undergoing surgery using the surgical robotics system 100. Generally, the table 101 is parallel to the ground, though the table 101 may change its orientation and configuration to facilitate a variety of surgical procedures. The table 101 is further described with reference to FIGS. 2A-I in Section II. Table.

The column 102 is coupled to the table 101 on one end and coupled to the base 103 on the other end. Generally, the column 102 is cylindrically shaped to accommodate column rings coupled to the column 102, which are further described with reference to FIGS. 5A-E in Section V. Column Ring, however the column 102 may have other shapes such as oval or rectangular. The column 102 is further described with reference to FIGS. 3A-B in Section III. Column.

The base 103 is parallel to the ground and provides support for the column 102 and the table 101. The base 103 may include wheels, treads, or other means of positioning or transporting the surgical robotics system 100. The base 103 is further described with reference to FIGS. 8A-E in Section VIII. Base.

Alternative views and embodiments of the surgical robotics system 100 including the above mentioned components are further illustrated and described at least in U.S. Provisional Application No. 62/162,486 filed May 15, 2015 and U.S. Provisional Application No. 62/162,467 filed May 15, 2015.

II. Table

Figure 2A:
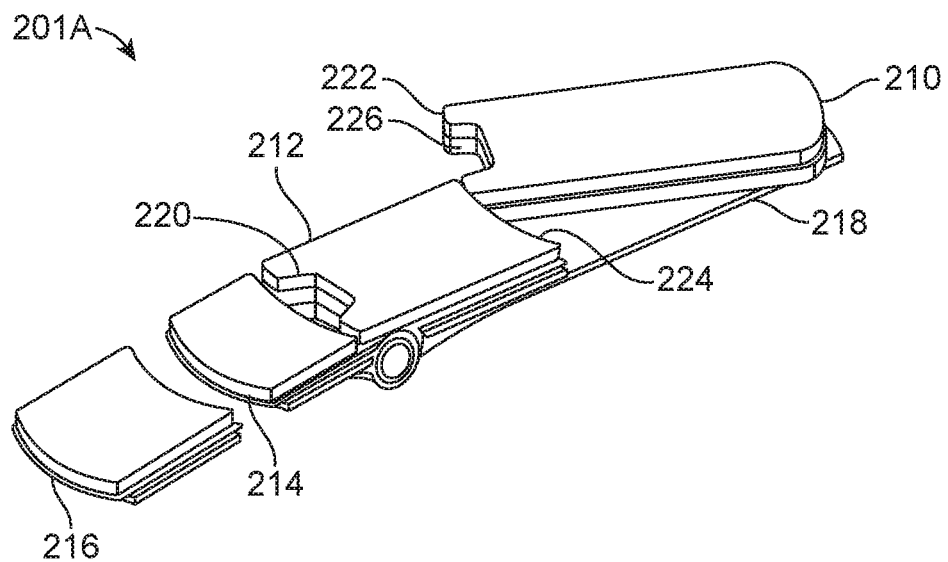
FIG. 2A is an isometric view of a table of the surgical robotics system according to one embodiment.

FIG. 2A is an isometric view of a table 201A of the surgical robotics system 100 according to one embodiment. The table 201A is an embodiment of the table 101 in FIG. 1. The table 201A includes a set of one or more segments.

Generally, a user changes the configuration of the table 201A by configuring the set of segments. The surgical robotics system 100 may also configure the segments automatically, for example, by using a motor to reposition a segment of the set of segments. An example set of segments is shown in FIG. 2A, and includes a swivel segment 210, center segment 212, foldable segment 214, detachable segment 216, and table base 218. The swivel segment 210, center segment 212, and foldable segment 214 are coupled to the table base 218. FIG. 2A shows the detachable segment 216 separated from the table base 218, though the detachable segment 216 may also be coupled to the table base 218. In various implementations, additional or fewer segments may be used.

An advantage of configuring the set of segments of the table 201A is that a configured table 201A may provide greater access to a patient on the table 201A. For instance, the surgical robotics system 100 performs a surgical procedure on the patient that requires access to the groin area of the patient. When a patient is laying face-up on a typical surgical bed, there is more access to the patient's head, arms, and legs than to the patient's groin area. Since the groin area is located toward the center of the patient's body, the legs often obstruct access to the groin area. The detachable segment 216 is detachable from the table 201A. The table 201A without the detachable segment 216 provides greater access to the groin area of a patient lying on the table 201A with the patient's head toward the side of the table 201A with the swivel segment 210. In particular, removing the detachable segment 216 opens more space, for example, to insert a surgical instrument into the groin area. If additional space is required to access the groin area, the foldable segment 214 may be folded down, away from the patient (further described in FIG. 2H). The center segment 212 includes a cutout section 220, which also provides greater access to the groin area.

The swivel segment 210 pivots laterally relative to the table 201A. The swivel segment 210 includes an arcuate edge 222 and the center segment 212 also includes in arcuate edge 224. Due to the arcuate edges, there is minimal gap between the swivel segment 210 and the center segment 212 as the swivel segment 210 pivots away from or toward the table 201A. A configuration of the table 201A with the swivel segment 210 pivoted away from the table 201A provides greater access to the groin area because the other segments of the table 201A are not obstructing the groin area. An example of this configuration is further described with respect to FIGS. 7C-D in Section VII. A. Lower Body Surgery. Additionally, the swivel segment 210 also includes a cutout section 226, which provides yet greater access to the groin area.

Figure 2B:
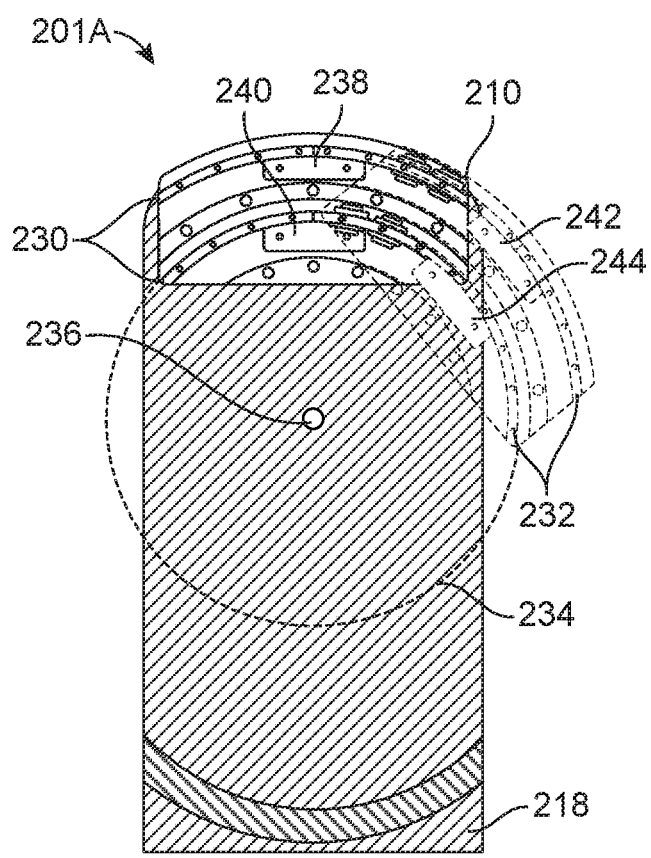
FIG. 2B is a top view of the table according to one embodiment.

FIG. 2B is a top view of the table 201A according to one embodiment. Specifically, FIG. 2B shows the table base 218 with a partial cutaway view and a portion of the swivel segment 210. Components inside the swivel segment 210 are exposed for purposes of illustration. The table base 218 includes double curved rails 230, that is, two curved linear rails (also referred to as a first bearing subassembly). The swivel segment 210 also includes double curved rails 232 (also referred to as a second bearing subassembly). The first bearing assembly coupled to the second bearing assembly may be referred to as a bearing mechanism. The double curved rails 230 of the table base 218 engage with the double curved rails 232 of the swivel segment 210. Both double curved rails are concentric to a virtual circle 234. The swivel segment 210 pivots about an axis passing through a point 236 at the center of the virtual circle 234 perpendicular to the plane of the table base 218. The double curved rails 230 of the table base 218 include a first carriage 238 and a second carriage 240. Similarly, the double curved rails 232 of the swivel segment 210 include a first carriage 242 and a second carriage 244. The carriages provide structural support and negate moment loads, which enables the double curved rails to support high cantilevered loads up to at least 500 pounds. For instance, pivoting a patient away from the table 201A generates a high cantilevered load on the double curved rails supporting the patient's weight. The table base 218 and swivel segment 210 may include additional load-sharing components such as rollers, cam followers, and bearings. In some embodiments, the swivel segment 210 and table base 218 each include a single curved rail instead of double curved rails. Further, each curved rail may include additional or fewer carriages.

Figure 2C:
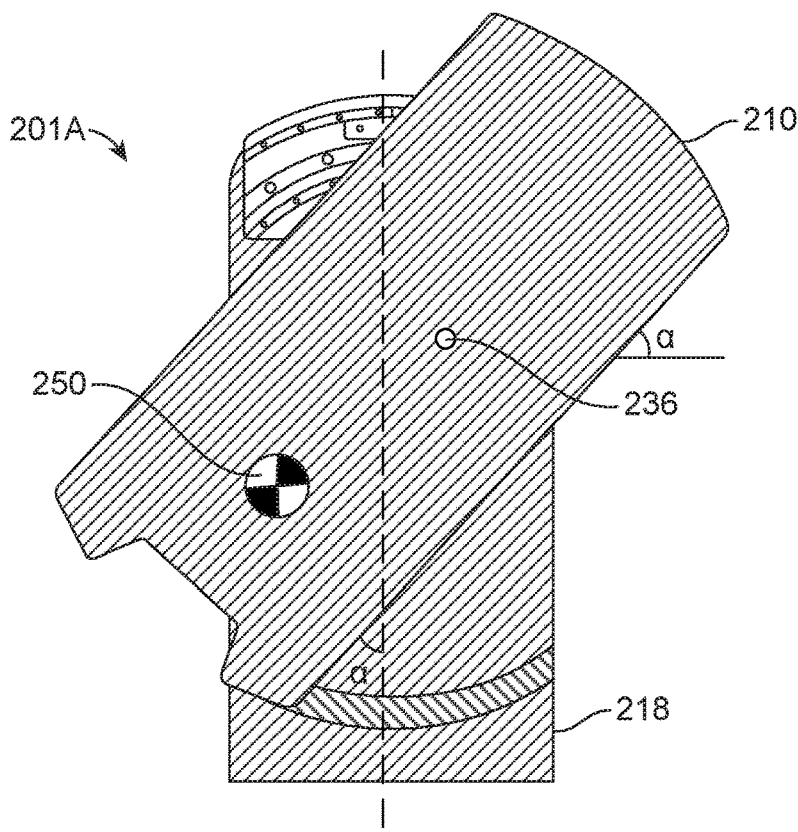
FIG. 2C is a top view of a swivel segment of a table according to one embodiment.
Figure 2D:
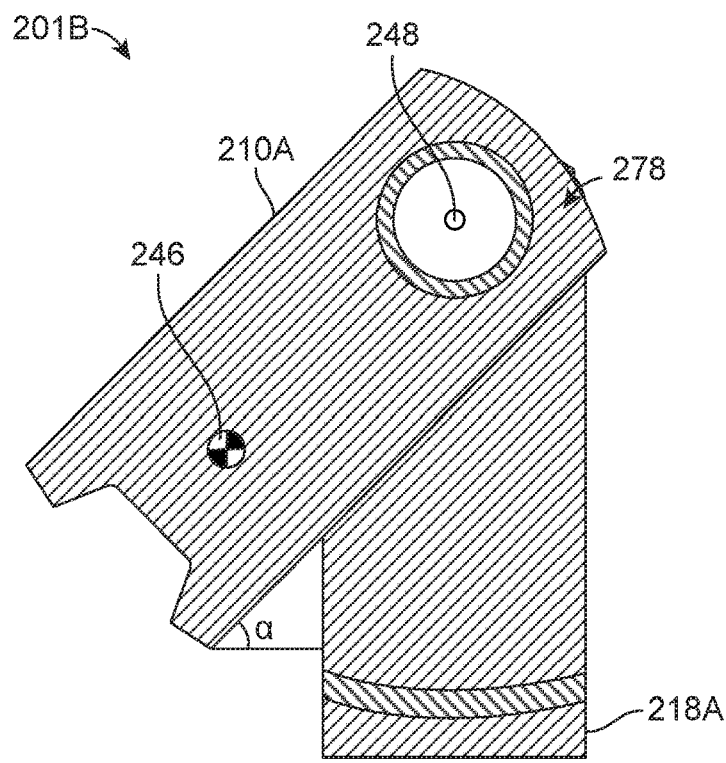
FIG. 2D is a top view of a swivel segment of the table according to one embodiment.

FIG. 2C is a top view of the swivel segment 210 of the table 201A according to one embodiment. The center of mass 250 illustrates the center of mass of the swivel segment 210 and a patient (not shown) lying on the swivel segment 210. The swivel segment 210 is pivoted at an angle α about the axis 236. Compared to the center of mass 246 shown in FIG. 2D, the center of mass 250 is closer toward the table base 218 (corresponding to table base 218B in FIG. 2D), even though the swivel segments in both FIG. 2C and FIG. 2D are each pivoted at the same angle α. Keeping the center of mass 250 close toward the table 218 helps the swivel segment 210 support greater cantilever loads-due to the patient-without tipping over the surgical robotics system. In some embodiments, the swivel segment 210 may be rotated up to an angle of 30 degrees or 45 degrees relative to table base 218, while keeping the center of mass of the swivel segment 210 above the table 201A.

FIG. 2D is a top view of a swivel segment 210A of a table 201B according to one embodiment. Specifically, the table 201B includes a table base 218A and a swivel segment 210A. The table 201B does not include double curved rails, but instead includes a swivel mechanism 278 that is further described below with reference to FIGS. 2E-G. The center of mass 246 illustrates the center of mass of the swivel segment 210A and a patient (not shown) lying on the swivel segment 210A. The swivel segment 210A is pivoted at an angle α about an axis 248. Accordingly, the center of mass 246 is positioned off of the table base 218A.

Figure 2E:
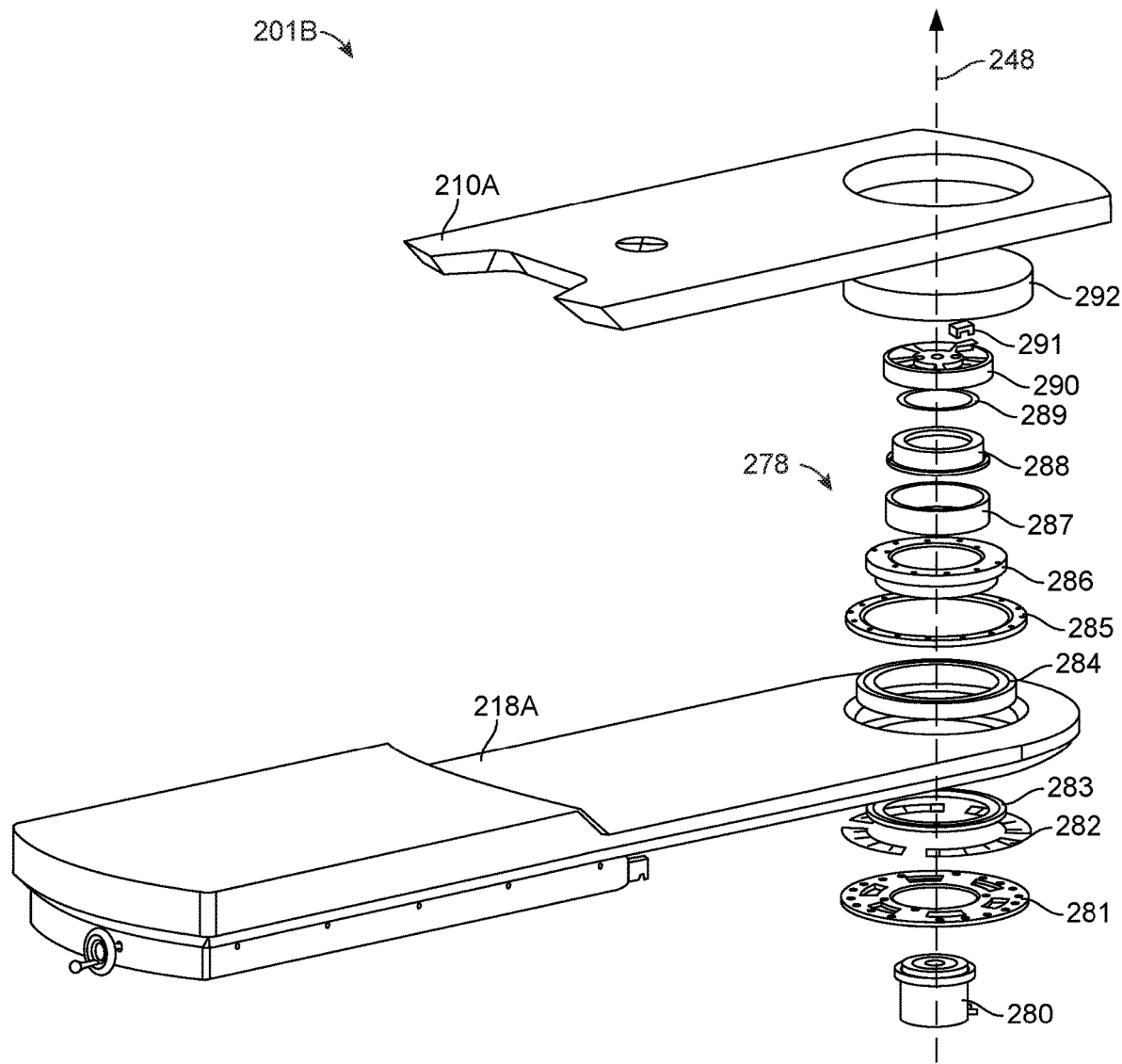
FIG. 2E is an isometric exploded view of components of a swivel mechanism according to one embodiment.

FIG. 2E is an isometric exploded view of components of a swivel mechanism 278 (which can also be referred to as a bearing mechanism) of the table 201B according to one embodiment. The swivel mechanism 278 includes a first bearing subassembly coupled to a second bearing subassembly. In particular, the swivel mechanism 278 includes a harmonic drive motor 280, static plate 281, shim 282, inner bearing race 283, bearing 284, outer bearing race cleat 285, inner bearing race support 286, static ring 287, motor housing mount 288, encoder strip 289, drive plate 290, encoder sensor 291, and swivel insert 292. The motor housing mount 288 is stationary relative to the table base 218A. The harmonic drive motor 280 rotates the swivel segment 210A about the axis 248. The first bearing subassembly includes the components described above that are coupled to the table base 218A. The second bearing subassembly includes the components described above that are coupled to the swivel segment 210A.

FIG. 2F is a cross sectional view of the swivel mechanism 278 shown in FIG. 2E according to one embodiment. The harmonic drive motor 280 is coupled to the motor housing mount 288. The motor housing mount 288 is coupled to the static ring 287 and the static plate 281. The static plate 281 is coupled to the table base 218A using the shim 282 such that the harmonic drive motor 280 is also stationary relative to the table base 218A.

The harmonic drive motor 280 includes a driving axle 294 coupled to a driving face 296 such that the driving axle 294 and driving face 296 rotate together. The driving face 296 is coupled to the drive plate 290. The drive plate 290 is coupled to the inner bearing race support 286. The inner bearing race support 286 is coupled to the swivel insert 292 and the inner bearing race cleat 283. The inner bearing race support 286 is movably coupled to the table base 218A by the bearing 284 (e.g., a cross roller bearing). The swivel insert 292 is coupled to the swivel segment 210A such that rotating the driving axle 294 and driving face 296 causes the swivel segment 210A to rotate in the same direction. Though not shown in FIG. 2F, the swivel mechanism 278 may include additional components between the static plate 281 and the inner bearing race cleat 283 to provide additional stability, e.g., in the form of a physical hard stop. Further, though not shown in FIG. 2F, the encoder sensor 291 is coupled to the motor housing mount 288 by the encoder strip 289. The encoder sensor 291 records information about the rotation of the swivel segment 210A, e.g., the position of the swivel segment 210A up to an accuracy of 0.1 degrees at 0.01 degree resolution. FIG. 2F shows several screws (or bolts) that are used to couple components of the swivel mechanism, though it should be noted that the components may be coupled using other methods, e.g., welding, press fit, gluing, etc.

The swivel mechanism 278 allows the harmonic drive motor 280 to rotate the swivel segment 210A with precise control, while supporting a load of up to 500 pounds, e.g., from a patient lying on the swivel segment 210A. In particular, the harmonic drive motor 280 may rotate the swivel segment 210A up to a rotational velocity of 10 degrees per second, and up to 45 degrees in either direction about the axis 248. Further, the swivel segment 210A is rotated such that the maximum velocity of the center of mass of the patient is 100 millimeters per second, and the time to the maximum velocity is 0.5 seconds. In some embodiments, one of the bearings of the swivel mechanism is a cross roller bearing—e.g., with ball bearings with a bearing friction coefficient of approximately 0.0025—that helps further provide stability to allow the precise rotation of the swivel segment 210A, while maintaining cantilever loads from the patient's weight. The harmonic drive motor 280 can generate up to 33 Newton meters of torque to rotate the swivel segment 210A with the weight of the patient. In some embodiments, the harmonic drive motor 280 includes an internal brake with a holding torque of at least 40 Newton meters.

Figure 2G:
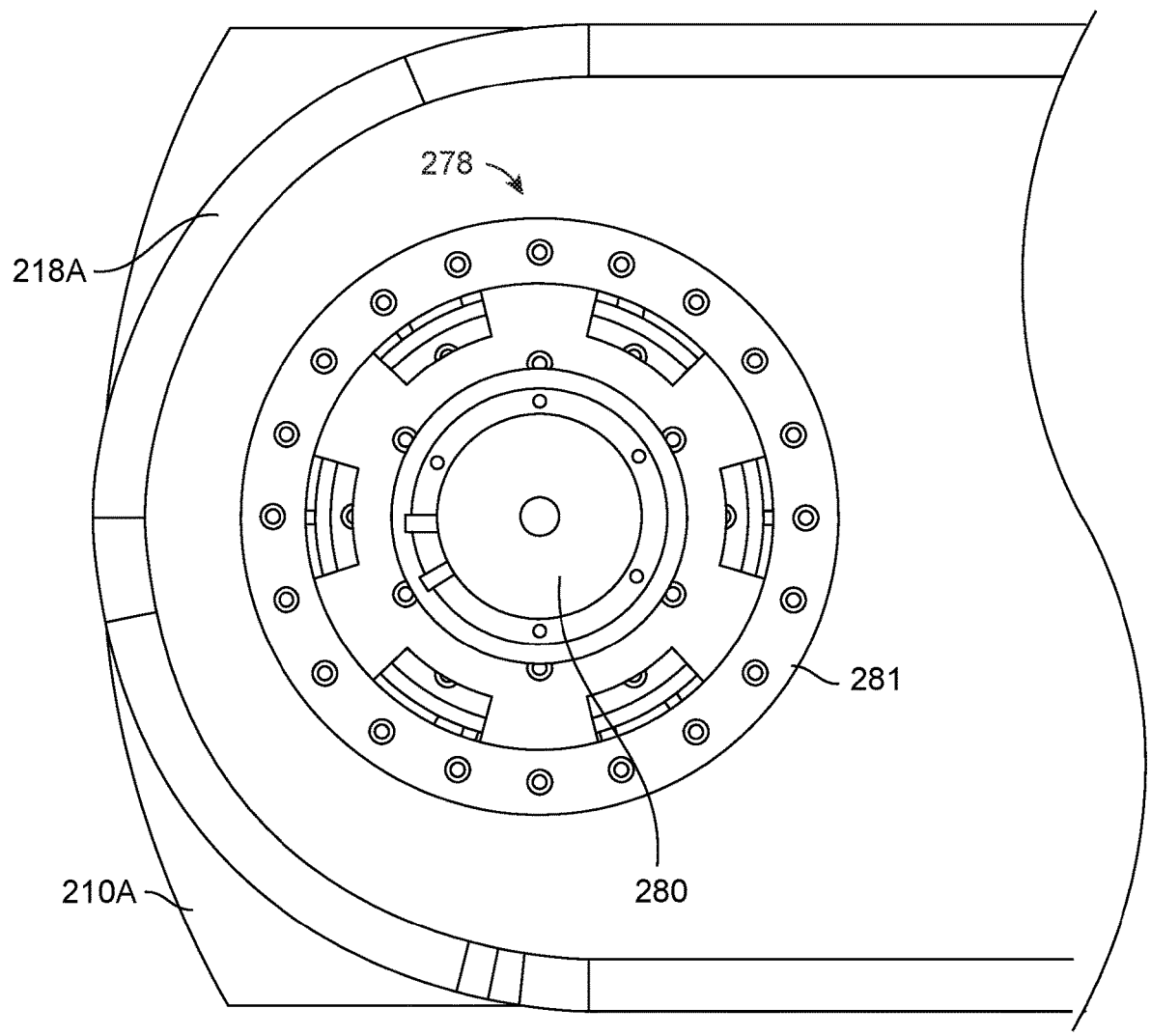
FIG. 2G is a bottom view of the swivel mechanism shown in FIG. 2E according to one embodiment.

FIG. 2G is a bottom view of the swivel mechanism shown in FIG. 2E according to one embodiment. The harmonic drive motor 280 is exposed such that electrical wires, e.g., from a column of the surgical robotics system, may be coupled to the harmonic drive motor 280 to provide control signals to the harmonic drive motor 280.

Figure 2H:
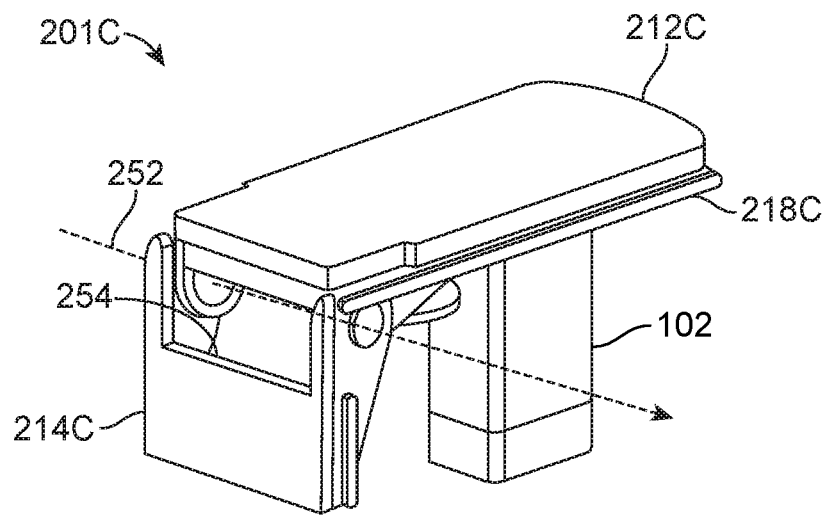
FIG. 2H is an isometric view of a folding segment of the table according to one embodiment.

FIG. 2H is an isometric view of a foldable segment 214C of a table 201C according to one embodiment. The table 201C is an embodiment of table 201A in FIG. 2A. The table 201C also includes a center segment 212C coupled to a table base 218C. The foldable segment 214C rotates using bearings about an axis 252 parallel to the table base 218C. The foldable segment 214C is rotated such that the foldable segment 214C is orthogonal to the table base 218C and the center segment 212C. In other embodiments, the foldable segment 214C may be rotated to other angles relative to the table base 218C and the center segment 212C. The foldable segment 214C includes a cutout section 254, for example, to provide greater access to a patient lying on the table 201C. In other embodiments, the foldable segment 214C does not include a cutout section.

Figure 2I:
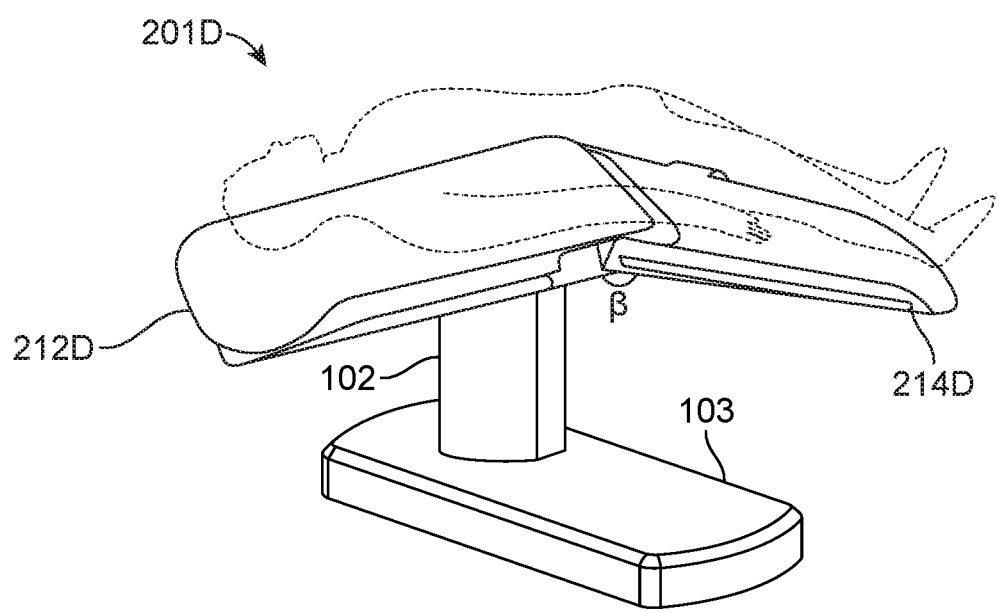
FIG. 2I is another isometric view of a folding segment of the table according to one embodiment.

FIG. 2I is another isometric view of a foldable segment 214D of a table 201D according to one embodiment. The table 201D is an embodiment of table 201A in FIG. 2A. The foldable segment 214D is rotated such that the foldable segment 214D and the table base 218D is positioned at an angle 3 relative to each other. The table 201D includes a mechanism for the foldable segment 214D and the center segment 212D to maintain the rotated position while supporting the weight of a patient on the table 201D. For example, the mechanism is a friction brake at the joint of the foldable segment 214D and the center segment 212D that holds the two segments at the angle 3. Alternatively, the foldable segment 214D rotates about the center segment 212D using a shaft and the mechanism is a clutch that locks the shaft, and thus keeps the two segments at a fixed position. Though not shown in FIG. 2I, the table 201D may include motors or other actuators to automatically rotate and lock the foldable segment 214D to a certain angle relative to the center segment 212D. Rotating the foldable segment 214D is advantageous, for example, because the corresponding configuration of the table 201D provides greater access to the area around the abdomen of a patient lying on the table 201D.

Figure 2J:
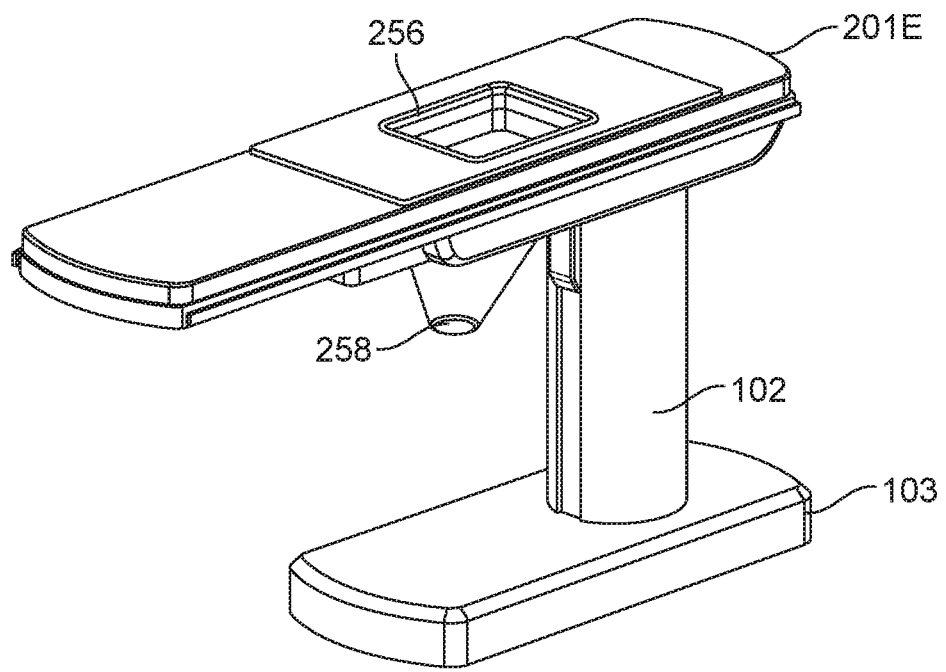
FIG. 2J is an isometric view of a trapdoor of the table according to one embodiment.

FIG. 2J is an isometric view of a trapdoor 256 of a table 201E according to one embodiment. The table 201E is an embodiment of table 201A in FIG. 2A. Specifically, the table 201E includes the trapdoor 256 and a drainage component 258 positioned below the trapdoor 256. The trapdoor 256 and drainage component 258 collect waste materials such as fluid (e.g., urine), debris (e.g., feces) that are secreted or released by a patient lying on the table during a surgical procedure. A container (not shown) may be positioned below the drainage component 258 to collect and store the waste materials. The trapdoor 256 and drainage component 258 are advantageous because they prevent waste materials from soiling or de-sterilizing equipment such as other components of the surgical robotic system 100 or other surgical tools in an operating room with the surgical robotic system 100.

Figure 2K:
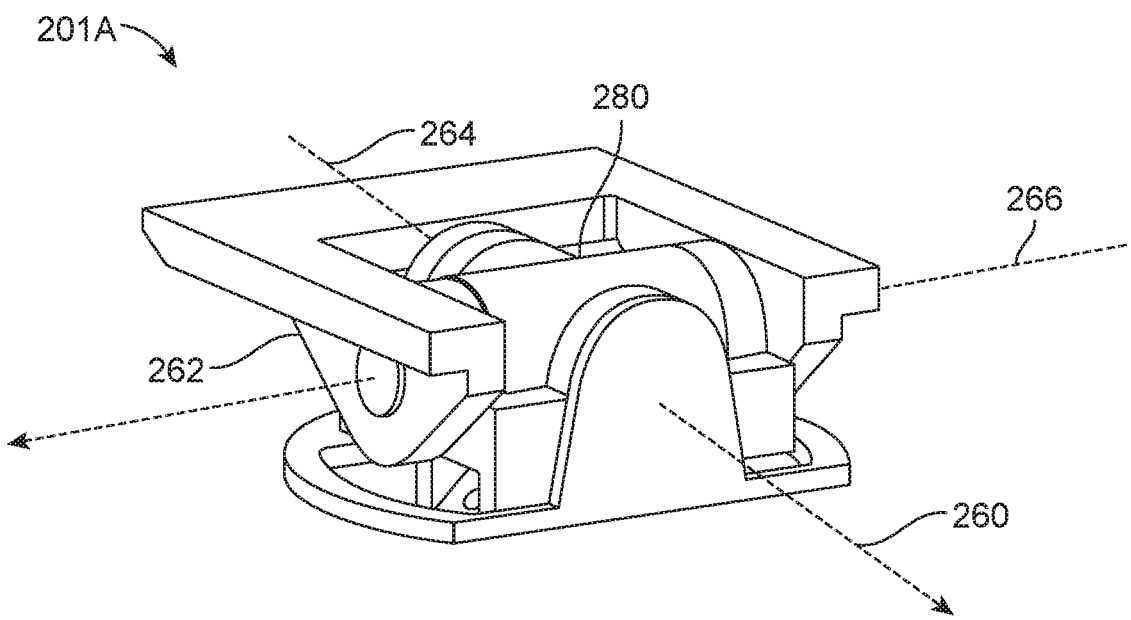
FIG. 2K is an isometric view of pivots of the table according to one embodiment.

FIG. 2K is an isometric view of pivots of the table 201A according to one embodiment. Specifically, the table 201A includes a first pivot 260 and a second pivot 262. The table 201A rotates about a first axis 264. A user, e.g., a physician, may rotate the table 201A about the first axis 264 or the second axis 266 manually or assisted by the surgical robotics system 100. The surgical robotics system 100 may also rotate the table 201A automatically, for example, by using control signals to operate a motor coupled to the first pivot 260 or the second pivot 262. The motor 280 is coupled to the first pivot 260. Rotation of the table 201A may provide greater access to certain areas of a patient lying on the table 201A during a surgical procedure. Specifically, the table 201A is configured to orient a patient lying on the table 201A in a Trendelenburg position by rotating about the first axis 264. Rotation of the table 201A is further described in FIGS. 2L-M.

Figure 2L:
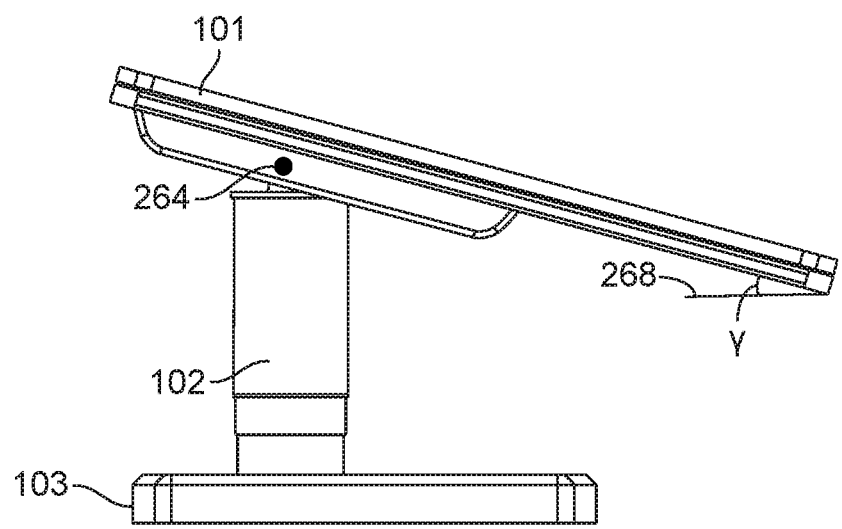
FIG. 2L is a side view of the table rotated about an axis of pitch according to one embodiment.

FIG. 2L is a side view of the table 201A rotated about the axis of pitch 264 according to one embodiment. Specifically, the table 201A is rotated to an angle γ relative to a plane 268 parallel to the ground.

Figure 2M:
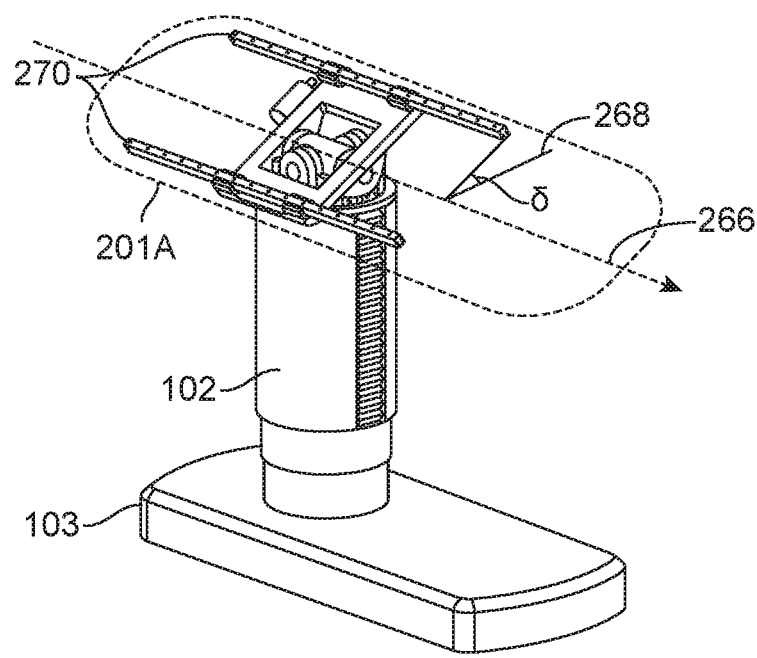
FIG. 2M is an isometric view of the table rotated about an axis of row according to one embodiment.

FIG. 2M is an isometric view of the table 201A rotated about the axis of row 266 according to one embodiment.

Specifically, the table 201A is rotated to an angle δ relative to the plane 268 parallel to the ground. The table 201A is illustrated as transparent to expose components underneath the table 201A. The table includes a set of rails 270. The table 201A may translate laterally along an axis 266 parallel to the set of rails 270. The surgical robotics system 100 translates the table 201A laterally using, for example, a motor or other means of actuation (not shown). A user of the surgical robotics system 100 may also manually translate the table 201A, or with assistance from the surgical robotics system 100.

Alternative views and embodiments of the table 201A including the above mentioned components are further illustrated and described at least in U.S. Provisional Application No. 62/235,394 filed Sep. 30, 2015.

III. Column

Figure 3A:
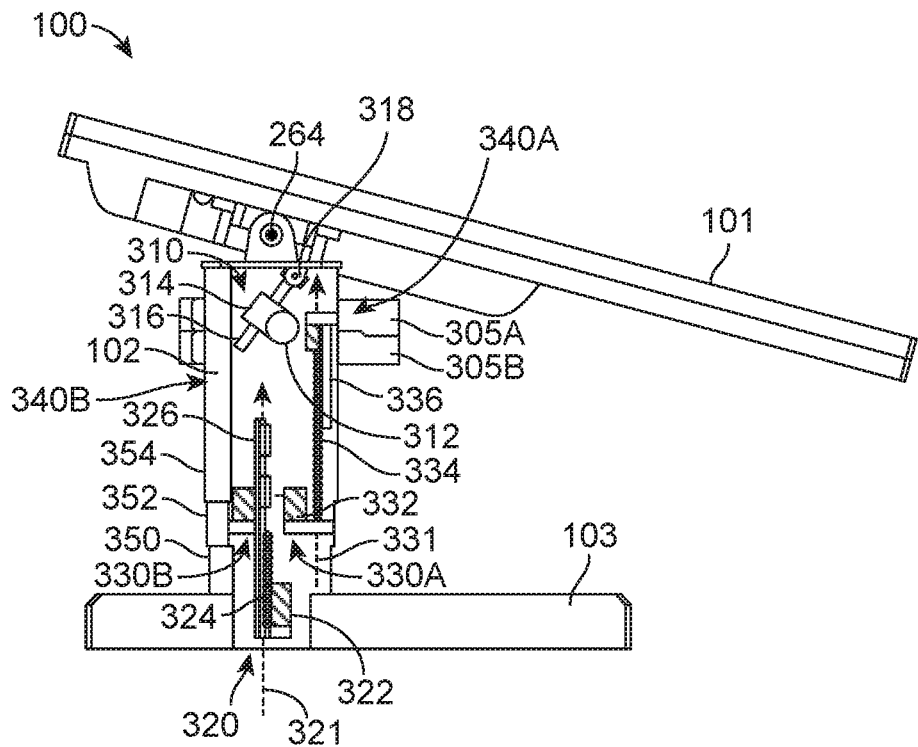
FIG. 3A is a side cutaway view of a column of the surgical robotics system according to one embodiment.

FIG. 3A is a side cutaway view of the column 102 of the surgical robotics system 100 according to one embodiment. The column 102 includes electrical and mechanical and other types of components to perform functions of the surgical robotics system 100. The column 102 includes a pitch rotation mechanism 310, column telescoping mechanism 320, ring telescoping mechanisms 330A and 330B, and ring rotation mechanisms 340A and 340B. The ring rotation mechanisms 340A and 340B are further described in FIG. 3B.

The surgical robotics system 100 rotates the table 101 about the axis of pitch 264 (also illustrated previously in FIGS. 2K-L) using the pitch rotation mechanism 310. The pitch rotation mechanism 310 includes a pitch rotation motor 312, right angle gearbox 314, pitch rotation lead screw 316, and pitch rotation bracket 318. The pitch rotation motor 312 is coupled to the right angle gearbox 314. The pitch rotation motor 312 is orthogonal to the pitch rotation lead screw 316. The pitch rotation lead screw 316 is movably coupled to the pitch rotation bracket 318. The right angle gearbox 314 is coupled to the pitch rotation lead screw 316. Output rotation of the pitch rotation motor 312 causes translational motion of the pitch rotation lead screw along an axis 311. Accordingly, translational motion of the pitch rotation lead screw 318 causes the table 101 to rotate about the axis of pitch 264.

The surgical robotics system 100 translates the table vertically using the column telescoping mechanism 320. The column telescoping mechanism 320 includes a column telescoping motor 322, column telescoping lead screw 324, and column telescoping rail 326. The column telescoping motor 322 is coupled to the column telescoping lead screw 324. The column telescoping motor 322 and the column telescoping lead screw 324 are stationary relative to the base 103. The column telescoping lead screw 324 is engaged with the column telescoping rail 326. Output rotation of the column telescoping motor 322 causes the column telescoping rail 326 to translate along a vertical axis 321 along the column telescoping lead screw 324. As the column telescoping rail 326 translates in the positive direction along the vertical axis 321, the height of the column 102 and the table 101 increases.

The column 102 also includes a lower column segment 350, middle column segment 352, and upper column segment 354. The lower column segment 350 is coupled to the base 103 and stationary relative to the base 103. The middle column segment 352 is movably coupled to the lower column segment 350. The upper column segment 354 is movably coupled to the middle column segment 352. In other embodiments, a column 102 may include additional or fewer column segments.

The upper column segment 354 and/or the middle column segment 352 also translate along the vertical axis 321 to extend the height of the column 102. Similarly, as the column telescoping rail 326 translates in the negative direction along the vertical axis 321, the height of the column 102 and the table 101 decreases. Further, the upper column segment 354 and/or the middle column segment 352 also translate along the vertical axis 321, collapsing over the lower column segment 350. A table 101 with adjustable height is advantageous because the table 101 facilitates a variety of surgical procedures. Specifically, one surgical procedure requires a patient lying on the table 101 to be positioned at a height lower than the height of a patient lying on the table 101 for a different surgical procedure. In some embodiments, the column telescoping mechanism 320 uses other means of actuation such as hydraulics or pneumatics instead of—or in addition to—motors.

The surgical robotics system 100 translates column rings 305A and 305B vertically using the ring telescoping mechanisms 330A and 330B. The ring telescoping mechanism 330A includes a ring telescoping motor 332, ring telescoping lead screw 334, and ring telescoping rail 336. Column rings are further described with reference to FIGS. 5A-E in Section V. Column Ring. Column rings 305A and 305B are movably coupled to the column 102 and translate along a vertical axis 331. Generally, a column 102 includes a ring telescoping mechanism for each column ring of the column 102. Specifically, the column 102 includes ring telescoping mechanism 330A and second ring telescoping mechanism 330B. The ring telescoping motor 332 is coupled to the ring telescoping lead screw 334. The ring telescoping motor 332 and the ring telescoping lead screw 334 are stationary relative to the base 103. The ring telescoping lead screw 334 is engaged with the ring telescoping rail 336. The ring telescoping rail 336 is coupled to the column ring 305A. Output rotation of the ring telescoping motor 332 causes the ring telescoping rail 336 to translate along the vertical axis 331 and along the ring telescoping lead screw 334. As the ring telescoping rail 336 translates in the positive direction or negative direction along the vertical axis 331, the height of a corresponding column ring increases or decreases, respectively.

Figure 3B:
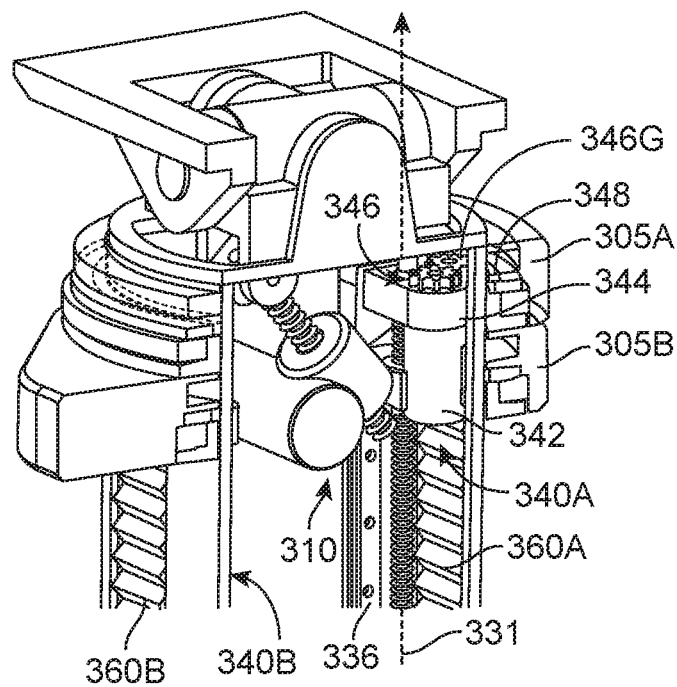
FIG. 3B is an isometric cutaway view of the column according to one embodiment.

FIG. 3B is an isometric cutaway view of the column 102 according to one embodiment. The column 102 includes a first accordion panel 360A and a second accordion panel 360B. The accordion panels 360A and 360B extend or fold as the surgical robotics system 100 translates column rings 305A and 305B in the positive direction or negative direction along the vertical axis 331, respectively. The accordion panels 360A and 360B are advantageous because they protect electrical and mechanical and other types of components inside the column 102 (e.g., the pitch rotation mechanism 310, column telescoping mechanism 320, ring telescoping mechanisms 330A and 330B, and ring rotation mechanisms 340A and 340B) from becoming soiled or de-sterilized by fluid waste and other hazards. FIG. 3B shows an isometric view of the ring rotation mechanism 340A, while the ring rotation mechanism 340B is obscured by the column 102.

The surgical robotics system 100 rotates column rings 305A and 305B using the ring rotation mechanisms 340A and 340B, respectively. The ring telescoping rail 336 is coupled to the ring rotation motor 342 by a ring rotation bracket 344. The ring rotation motor 342 is coupled to a set of gears 346. The set of gears 346 includes a driving gear 346G. The driving gear 346G is engaged with a column ring rail 348 of the column ring 305A. Output rotation of the ring rotation motor 342 causes the set of gears 346 and the driving gear 346G to rotate. Accordingly, the rotation of the driving gear 346G causes the column ring 305A to rotate about a vertical axis 341 concentric to the column 102. The column 102 includes another ring rotation mechanism 340B corresponding to the column ring 305B. Generally, both ring rotation mechanisms 340A and 340B and column rings 305A and 305B will be substantially the same, however in other implementations they may be constructed using different mechanisms.

Figure 3C:
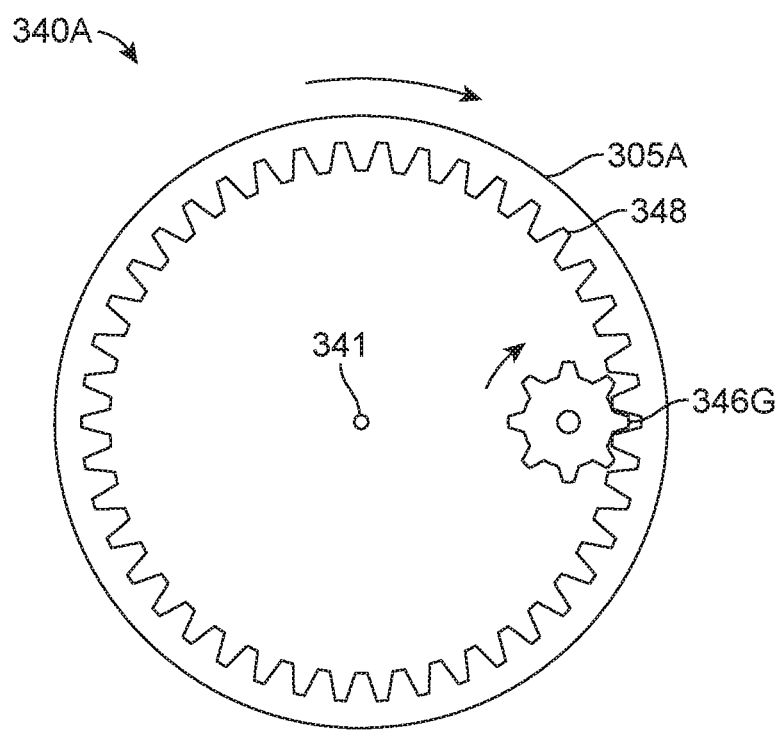
FIG. 3C is a top view of the column according to one embodiment.

FIG. 3C is a top view of the ring rotation mechanism 340A according to one embodiment. For purposes of clarity, FIG. 3C only shows the driving gear 346G, the column ring 305A, and the column ring rail 348 of the ring rotation mechanism 340A. In an example use case, the surgical robotics system 100 rotates the driving gear 346G clockwise to rotate the column ring rail 348 and thus, the column ring 305A-clockwise about the vertical axis 341.

Alternative views and embodiments of the column 103 including the above mentioned components are further illustrated and described at least in U.S. Provisional Application No. 62/162,486 filed May 15, 2015 and U.S. Provisional Application No. 62/162,467 filed May 15, 2015.

IV. Column-Mounted Robotic Arms

Figure 4A:
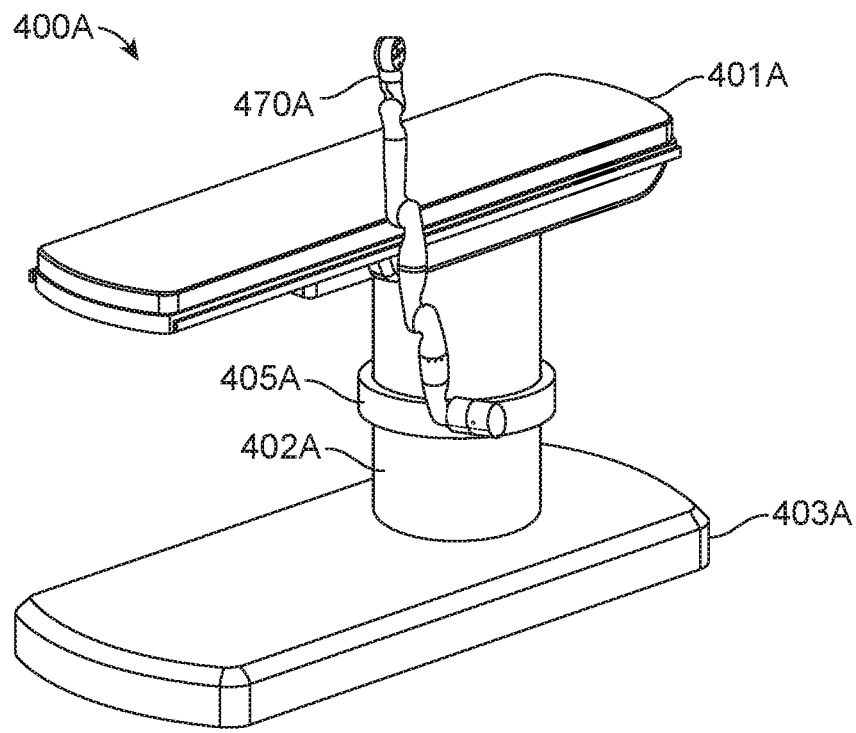
FIG. 4A is an isometric view of a surgical robotics system with a column-mounted robotic arm according to one embodiment.

FIG. 4A is an isometric view of a surgical robotics system 400A with a column-mounted robotic arm 470A according to one embodiment. The surgical robotics system 400A includes a set of robotic arms, a set of column rings, table 401A, column 402A, and base 403A. The surgical robotics system 400A is an embodiment of the surgical robotics system 100 shown in FIG. 1. Generally, the set of robotics arms includes one or more robotic arms, such as robotic arm 470A, where the robotic arms are coupled to one or more column rings, such as column ring 405A. Column rings are described in more detail with respect to FIGS. 5A-E in Section V. Column Ring below. Robotic arms are described in more detail with respect to FIGS. 6A-C in Section VI. Robotic Arm below. Column rings 405A are movably coupled to the column 402A. Thus, a robotic arm 470A attached to a column 405A may be referred to as a column-mounted robotic arm 470A. As introduced above, the surgical robotics system 400A uses robotic arms 470A to perform surgical procedures on a patient lying on the table 401A.

Figure 4B:
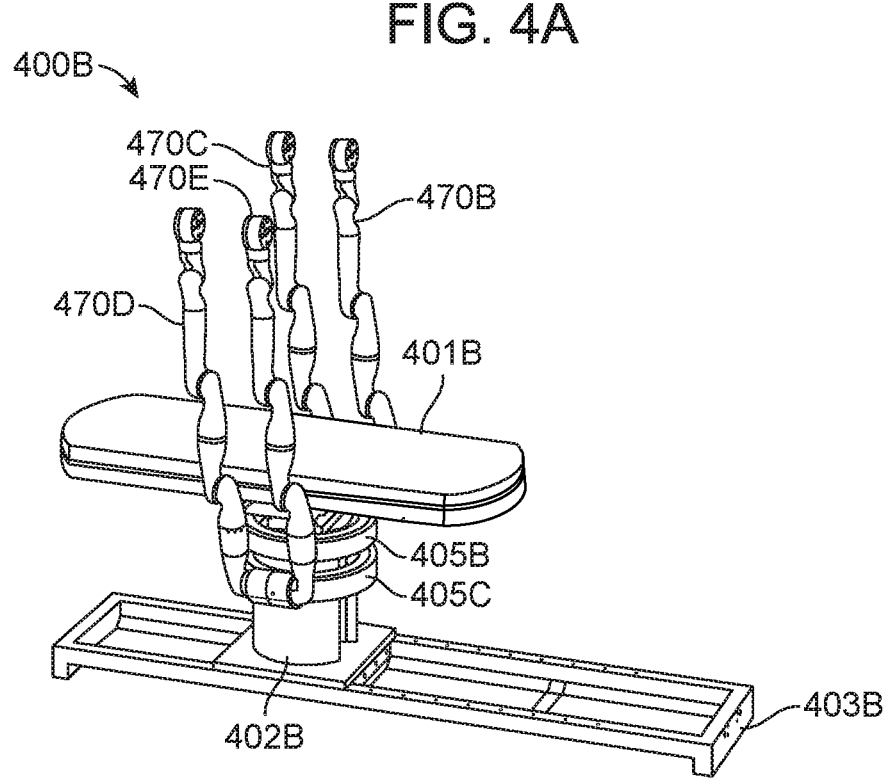
FIG. 4B is an isometric view of a surgical robotics system with column-mounted robotic arms according to one embodiment.

FIG. 4B is an isometric view of a surgical robotics system 400B with column-mounted robotic arms according to one embodiment. The surgical robotics system 400B is an embodiment of the surgical robotics system 400A shown in FIG. 4A. The surgical robotics system 400B includes multiple robotic arms, i.e., a first robotic arm 470B, second robotic arm 470C, third robotic arm 470D, and fourth robotic arm 470E, as well as multiple column rings, i.e., a first column ring 405B and second column ring 405C. In other embodiments, the surgical robotics system 400B may include additional or fewer robotic arms and/or column rings. Further, the robotic arms may be coupled to column rings in various configurations. For example, three robotic arms may be coupled to a column ring. Additionally, the surgical robotics system 400B may include three column rings each coupled to two robotic arms.

Alternative views and embodiments of the surgical robotics system 400B including the above mentioned components with column-mounted robotic arms are further illustrated and described at least in U.S. Provisional Application No. 62/162,486 filed May 15, 2015 and U.S. Provisional Application No. 62/162,467 filed May 15, 2015.

V. Column Ring

Figure 5A:
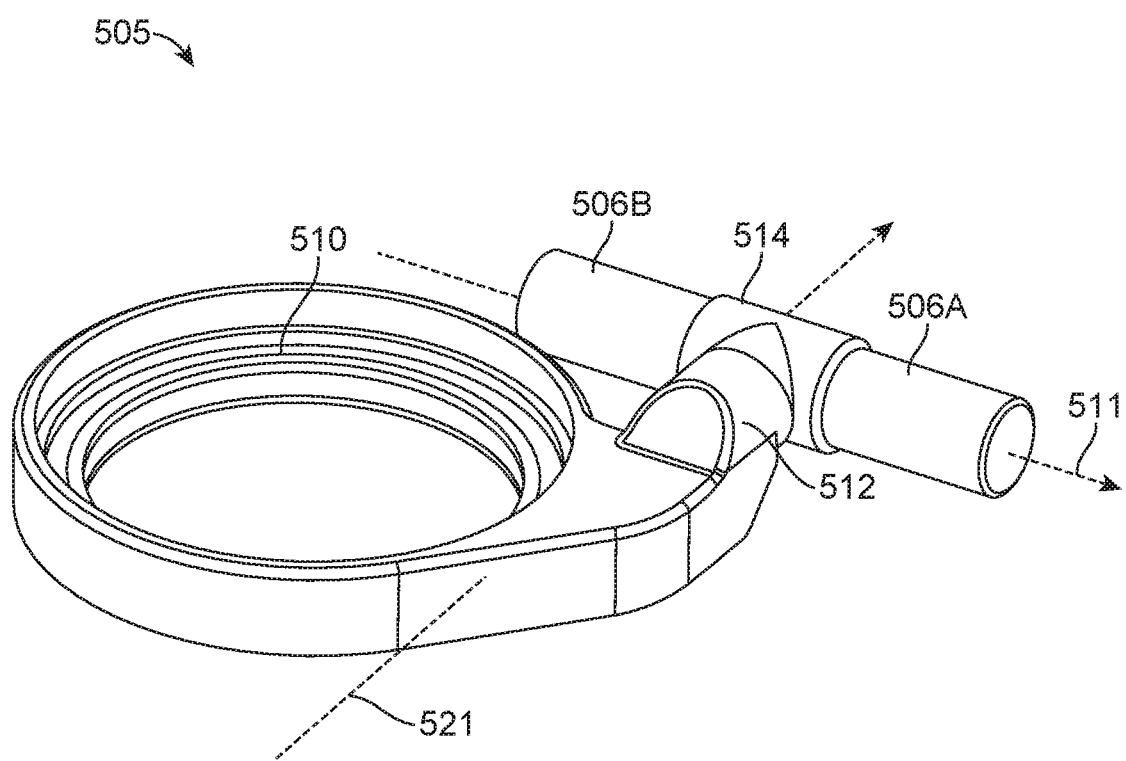
FIG. 5A is an isometric view of a column ring of the surgical robotics system according to one embodiment.

FIG. 5A is an isometric view of a column ring 505 of a surgical robotics system—for example, surgical robotics system 100, 400A, or 400B-according to one embodiment.

The column ring 505 includes a column ring rail 510, arm mount pivot 512, arm mount base 514, and a set of arm mounts. The set of arm mounts includes one or more arm mounts. Specifically, the set of arm mounts in FIG. 5A includes a first arm mount 506A and a second arm mount 506B. Generally, each arm mount of the set of arm mounts and the arm mount base 514 are cylindrically shaped.

The first arm mount 506A and the second arm mount 506B are movably coupled the arm mount base 514. The first arm mount 506A and the second arm 506B mount may rotate-together or independently—about the axis 511 concentric to the arm mount base 514. For example, the surgical robotics system 400B rotates the first arm mount 506A and the second arm mount 506B using a motor or other means of actuation (not shown) inside the arm mount base 514 or arm mounts. In some embodiments, the first arm mount 506A and the second arm mount 506B rotate at predetermined increments, e.g., increments of 15 degrees.

The arm mount base 514 is coupled to the arm mount pivot 512. The arm mount pivot 512 uses a motor or other means of actuation (not shown) inside the arm mount pivot 512 to rotate the arm mount base 514 about the axis 521 orthogonal to the axis 511. The arm mount pivot 512 is coupled to, and stationary relative to, the column ring rail 510. Rotating the arm mount base 514 is advantageous because robotic arms (and arm mounts) coupled to the arm mount base 514 may be reoriented in response to rotation of the table 401B. Accordingly, robotic arms coupled to the arm mounts of the arm mount base 514 have greater access to a patient lying on the table 401B.

Figure 5B:
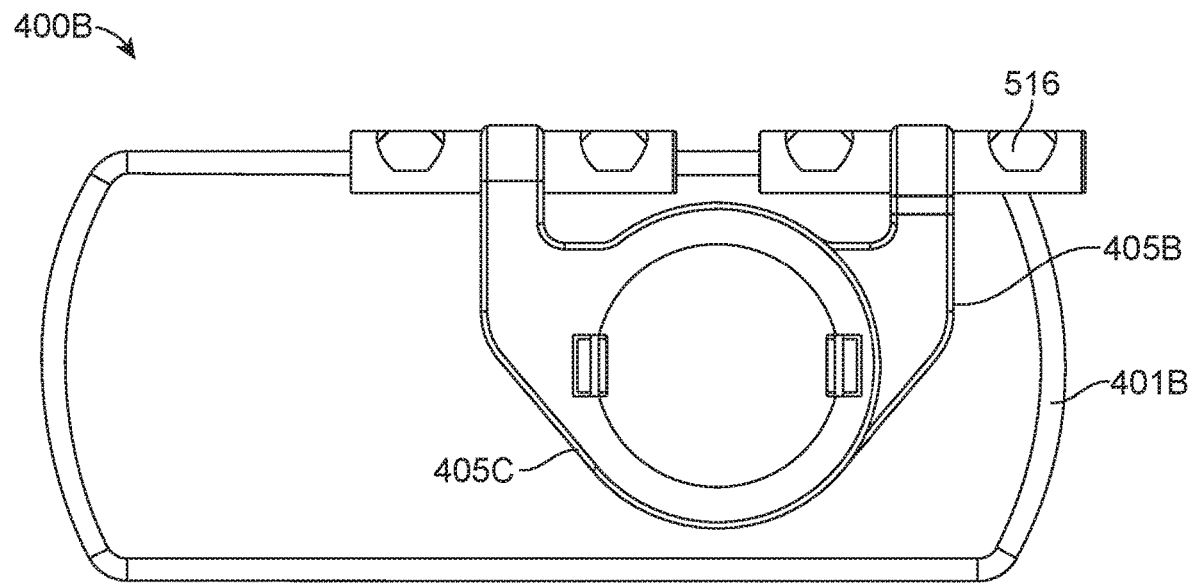
FIG. 5B is a bottom view of a set of column rings underneath a table according to one embodiment.

FIG. 5B is a bottom view of the set of column rings underneath the table 401B of FIG. 4B according to one embodiment. The set of column rings includes the first column ring 405B and the second column ring 405C. Note that FIG. 5B shows the first column ring 405B and the second column ring 405C aligned such that the arm mounts are on the same side of the table 401B, while FIG. 4B shows the first column ring 405B and the second column ring 405C positioned such that the arm mounts are on opposite sides of the table 401B. The surgical robotics system 400B may rotate the column rings 405B and 405C to position the arm mounts in other configurations. For example, two arm mounts are positioned on one side of the table 401B and two arm mounts are positioned on an opposite side of the table 401B. By rotating column rings independently from each other around the column, the surgical robotics system 400B may configure the arm mounts and thus, robotic arms mounted to the arm mounts—in a greater number of possible positions. Due to this configurability, the surgical robotics system 400B accommodates a variety of surgical procedures because the robotic arms can access any area (e.g., upper body, core body, or lower body) of the body of a patient lying on the table 401B. In some embodiments, each arm mount of the column rings include a notch 516 which facilitates the attachment of a robotic arm to the arm mount.

Figure 5C:
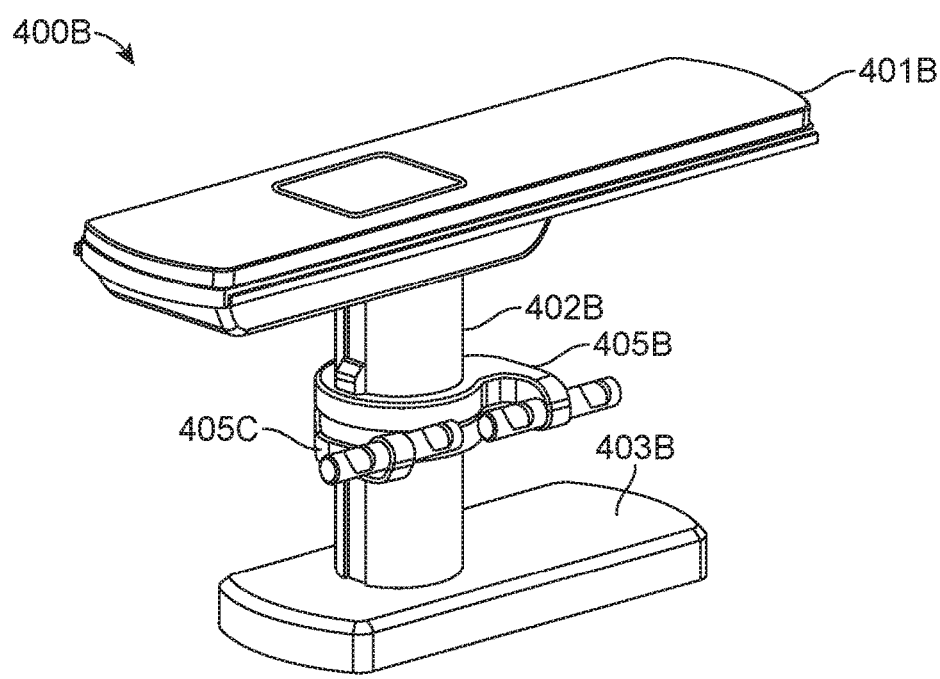
FIG. 5C is an isometric view of the set of column rings mounted to a column according to one embodiment.

FIG. 5C is an isometric view of the set of column rings mounted to the column 402B of FIG. 4B according to one embodiment. Similarly to FIG. 5B, FIG. 5C shows all the arm mounts aligned on the same side of the surgical robotics system 400B.

Figure 5D:
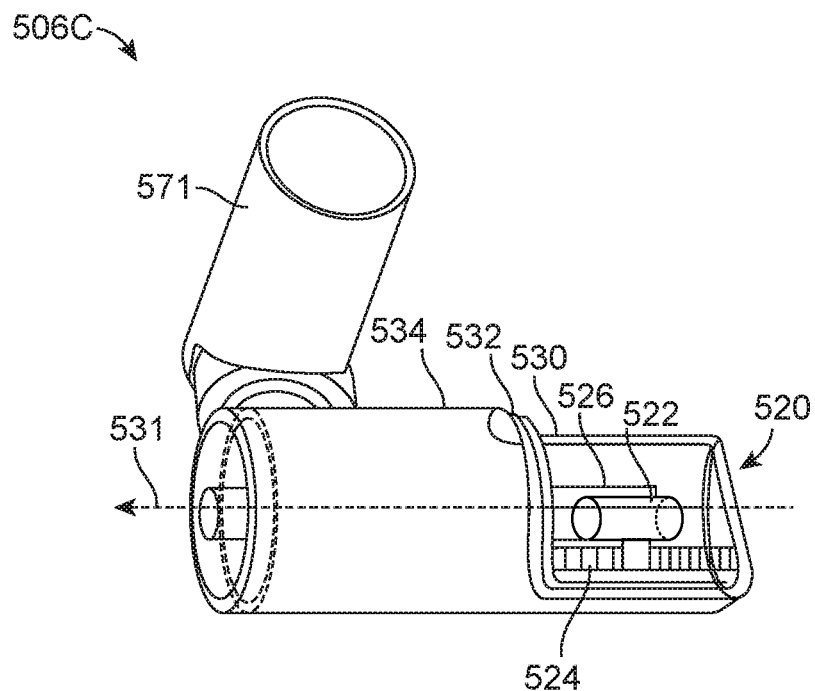
FIG. 5D is an isometric cutaway view of an arm mount of a column ring according to one embodiment.

FIG. 5D is an isometric cutaway view of an arm mount 506C of a column ring according to one embodiment. The arm mount 506C includes an arm mount telescoping mechanism 520 and a set of arm mount segments. The arm mount telescoping mechanism 520 includes an arm mount telescoping motor 522, arm mount telescoping lead screw 524, and arm mount telescoping rail 526. Generally, the set of arm mount segments includes one or more arm mount segments. Specifically, the set of arm mount segments in FIG. 5D includes a lower arm mount segment 530, middle arm mount segment 532, and upper arm mount segment 534. A robotic arm segment 571 (e.g., of the robotic arm 470B in FIG. 4B) is coupled to the upper arm mount segment 534. The middle arm mount segment 532 and the upper arm mount segment 534 are movably coupled to the lower arm mount segment 530. The lower arm mount segment 530 is coupled to an arm mount base (e.g., arm mount base 514 in FIG. 5A).

The surgical robotics system 400B translates the arm mount 506C along an axis 531 using the arm mount telescoping mechanism 520. In FIG. 5D, the axis 531 is in a horizontal orientation, though it should be noted that, in other embodiments, the axis 531 is in a vertical or any other orientation. The arm mount telescoping motor 522 is coupled to the arm mount telescoping rail 526. The arm mount telescoping rail 526 is engaged with the arm mount telescoping lead screw 524. The arm mount telescoping lead screw 524 is stationary relative to the lower arm mount segment 530. Output rotation of the arm mount telescoping motor 522 causes the arm mount telescoping rail 526 to translate along the vertical axis 531. Translation of the arm mount 506C is advantageous because, if the arm mount 506C is extended, a robotic arm mounted to the arm mount 506C may have greater access to a patient lying on the table 401B during a surgical procedure.

Figure 5E:
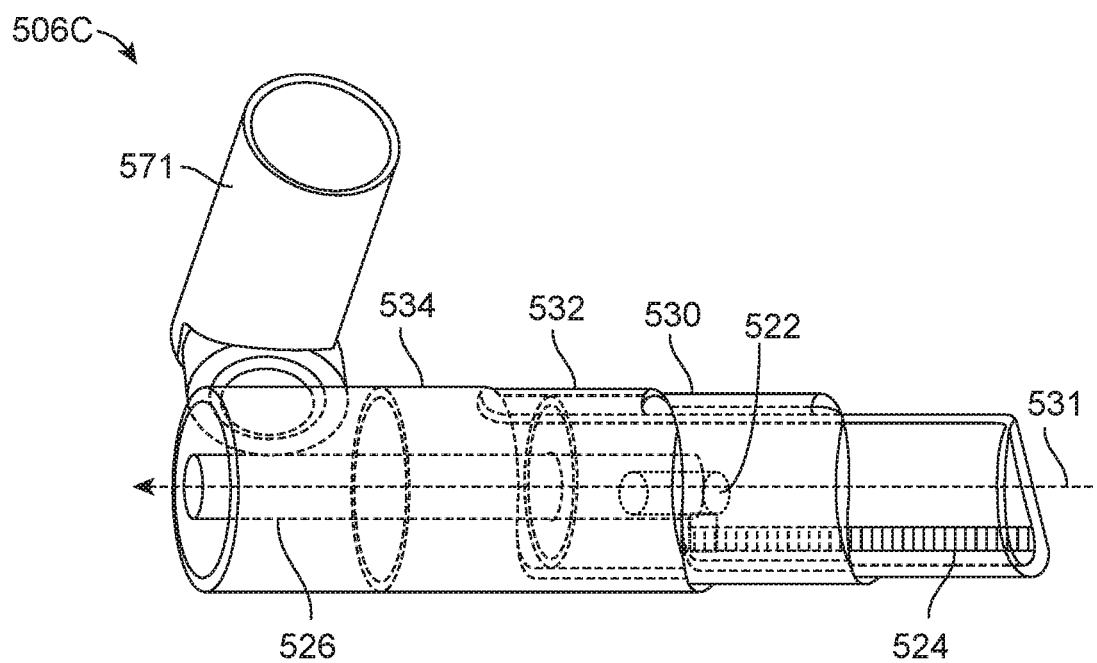
FIG. 5E is an isometric cutaway view of the arm mount in a telescoped configuration according to one embodiment.

FIG. 5E is an isometric cutaway view of the arm mount 506C in a telescoped configuration according to one embodiment. In the telescoped configuration, the upper arm mount segment 534 and the middle arm mount segment 532 extend in the positive axis 531 direction to facilitate extension of the arm mount 506C.

Alternative views and embodiments of the column ring 505 including the above mentioned components are further illustrated and described at least in U.S. Provisional Application No. 62/162,486 filed May 15, 2015 and U.S. Provisional Application No. 62/162,467 filed May 15, 2015.

VI. Robotic Arm

Figure 6A:
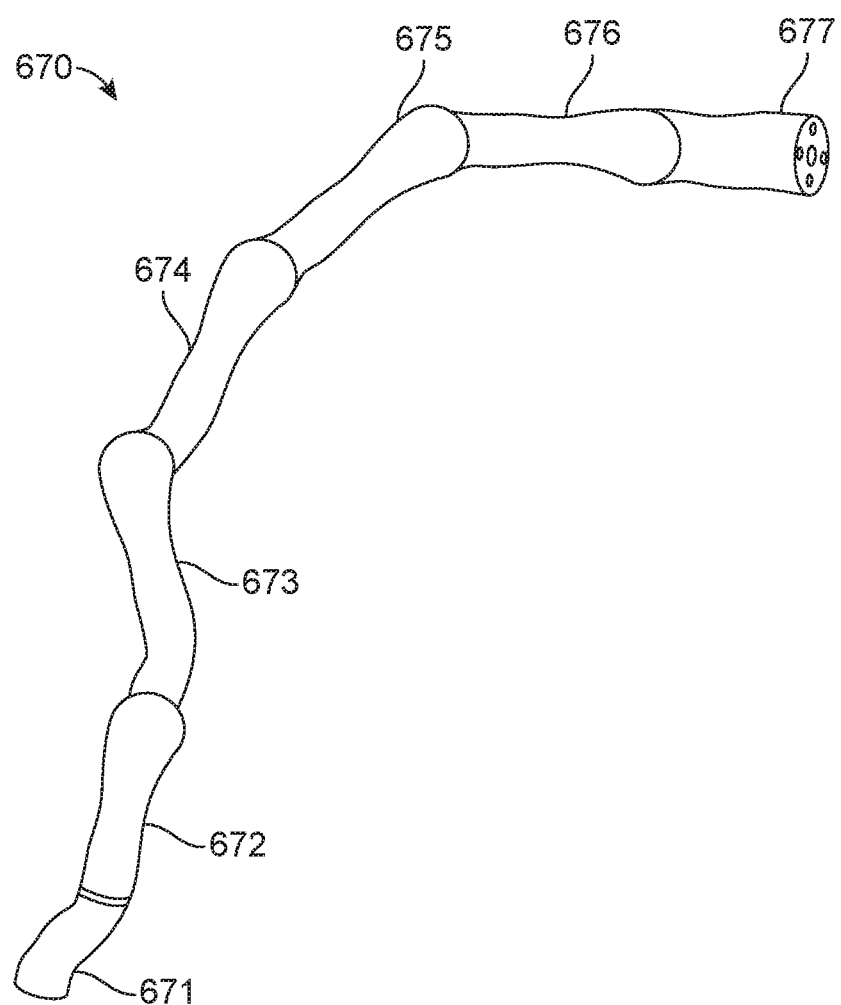
FIG. 6A is an isometric view of a robotic arm of the surgical robotics system according to one embodiment.

FIG. 6A is an isometric view of a robotic arm 670 of a surgical robotics system—for example, surgical robotics system 100, 400A, or 400B-according to one embodiment. Generally, the robotic arm 670 includes a set of robotic arm segments such as robotic arm segments 671, 672, 673, 674, 675, 676, and 677. Each arm segment is movably coupled to at least one other arm segment at an arm segment joint. In particular, the first arm segment 671 is movably coupled to the second arm segment 672, the second arm segment 672 is movably coupled to the third arm segment 673, and so forth. The first arm segment 671 is movably coupled to an arm mount (e.g., arm mount 506A in FIG. 5A). The seventh arm segment 677 (or the last arm segment of a set of arm segments including a number of arm segments different than seven), is coupled to a surgical instrument. The seventh arm segment 677 may also include mechanisms to hold a surgical instrument such as a clamp or robotic fingers. The robotic arm 670 uses electrical and mechanical components, such as motors, gears, and sensors, inside the robotic arm segments to rotate the arm segments at the arm segment joints.

The robotic arm 670 receives control signals from a robotic arm control system, for example, housed in the column 402B in FIG. 4B. In some embodiments, the robotic arm 670 receives control signals from a robotic arm control system located outside of the column 402B or separate from the surgical robotics system 400B. Generally, the robotic arm 670 may include sensors that provide sensor data to the robotic arm control system. Specifically, pressure sensors provide force feedback signals and encoders or potentiometers provide measurements of rotation of arm segments. The robotic arm control system uses the sensor data to generate the control signals provided to the robotic arm 670. Since each arm segment may rotate with respect to another adjacent segment, each arm segment provides an additional degree of freedom to the mechanical system of the robotic arm 670. By rotating the robotic arm segments, the surgical robotics system 400B positions a surgical instrument coupled to the robotic arm 670 such that the surgical instrument has access to a patient undergoing a surgical procedure. Configurations of robotic arms of the surgical robotics system 400B are further described with reference to FIGS. 7A-F in Section VII. System Orientations for Performing Surgical Procedures.

Figure 6B:
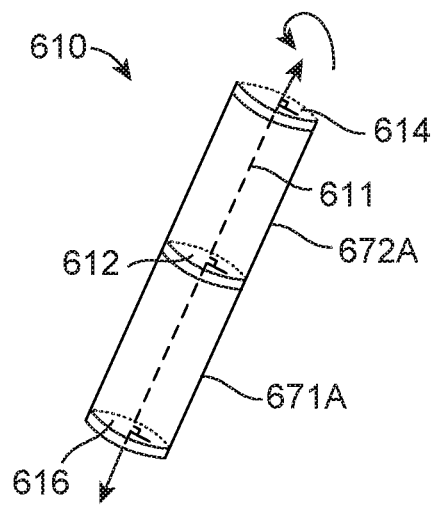
FIG. 6B is an isometric view of an arm segment joint of the robotic arm according to one embodiment.

FIG. 6B is an isometric view of an arm segment joint 610 of the robotic arm 670 according to one embodiment. The first arm segment 671A and the second arm segment 672A are embodiments of any of the arm segments in FIG. 6A. The arm segments 671A and 672A are cylindrically shaped and joined at the plane 612. The first arm segment 671A rotates relative to the second arm segment 672A about an axis 611 perpendicular to the plane 612. Further, the axis 611 is perpendicular to the plane 614 of the second arm segment 672A and perpendicular to the plane 616 of the first arm segment 671A. That is, the axis 611 is longitudinal relative to the arm segments 671A and 672A.

Figure 6C:
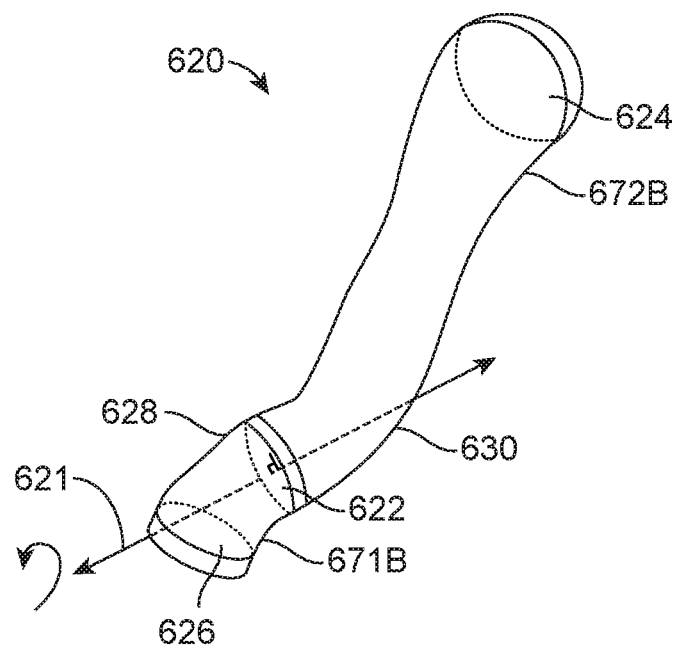
FIG. 6C is an isometric view of another arm segment joint of the robotic arm according to one embodiment.

FIG. 6C is an isometric view of another arm segment joint 620 of the robotic arm 670 according to one embodiment. The arm segments 671B and 672B are joined at the plane 622. Unlike the cylindrically shaped arm segments shown in FIG. 6B, the arm segments 671B and 672B each include a curved section 628 and 630, respectively. The first arm segment 671B rotates relative to the second arm segment 672B about an axis 621 perpendicular to the plane 622. The axis 621 is not perpendicular to the plane 624 of the arm segment 672B and not perpendicular to the plane 626 of the arm segment 671B. In some embodiments, the axis of rotation is perpendicular to a plane of one arm segment, but not perpendicular to a plane of the other arm segment of an arm segment joint.

Alternative views and embodiments of the robotic arm 670 including the above mentioned components are further illustrated and described at least in U.S. Provisional Application No. 62/162,486 filed May 15, 2015 and U.S. Provisional Application No. 62/162,467 filed May 15, 2015.

VII. System Orientations for Performing Surgical Procedures

The surgical robotics system 400B in FIG. 4B performs a variety of surgical procedures using column-mounted robotic arms of the set of robotic arms. The surgical robotics system 400B configures the column-mounted robotic arms to access portions of a patient lying on the table 401B before, during, and/or after a surgical procedure. The column-mounted robotic arms access portions near the groin of the patient for surgical procedures such as ureteroscopy, percutaneous nephrolithotomy (PCNL), colonoscopy, and fluoroscopy. The column-mounted robotic arms to access portions near the core (e.g., abdomen) area the patient for surgical procedures such as prostatectomy, colectomy, cholecystectomy, and inguinal hernia. The column-mounted robotic arms to access portions near the head of the patient for surgical procedures such as bronchoscopy, endoscopic retrograde cholangiopancreatography (ERCP).

The surgical robotics system 400B automatically reconfigures the column-mounted robotic arms, column rings, column, and table to perform different surgical procedures. The features of each subsystem and component of the surgical robotics system 400B enable the same set of robotics arms to access a large working volume, and multiple working volumes (based on the configuration), to perform a variety of surgical procedures on the patient. In particular, as mentioned above, the robotic arms may be configured in a first configuration to access the patients' groin area, in a second configuration to access the patients' abdomen area, and in a third configuration to access the patients' head area, in addition to other possible configurations. The degrees of freedom provided by the arm segments of the robotic arms, column rings, column, and table contribute to the wide range of configurations. The surgical robotics system 400B includes a computer system that stores computer program instructions, for example within a non-transitory computer-readable storage medium such as a persistent magnetic storage drive, solid state drive, etc. When executed by a processor of the computer system, the instructions cause the components of the surgical robotics system 400B to automatically reconfigure without the need for intervention, or with minimal intervention, from a user, e.g., a physician. For example, based on the instructions, the computer system sends an electronic control signal to motors of the robotics arms. In response to receiving the control signal, the motors rotate arm segments of the robotics arms into a certain position. The physician or another user may design a configuration of the surgical robotics system by creating the instructions and providing the instructions to the computer system. For example, the instructions are uploaded to a database of the computer system. The automatic configurability of the surgical robotics system 400B is an advantage because the automatic configurability saves resources. Specifically, the surgical robotics system 400B reduces the amount of time taken by users to setup the surgical robotics system 400B for a surgical procedure. Further, by using the surgical robotics system 400B for a variety of surgical procedures, users reduce the amount of surgical equipment that they need to purchase, maintain, store, and learn to operate.

Alternative views and embodiments of use cases of the surgical robotics system 400B with column-mounted robotic arms including the above mentioned components are further illustrated and described at least in U.S. Provisional Application No. 62/162,486 filed May 15, 2015 and U.S. Provisional Application No. 62/162,467 filed May 15, 2015.

VII. A. Lower Body Surgery

Figure 7A:
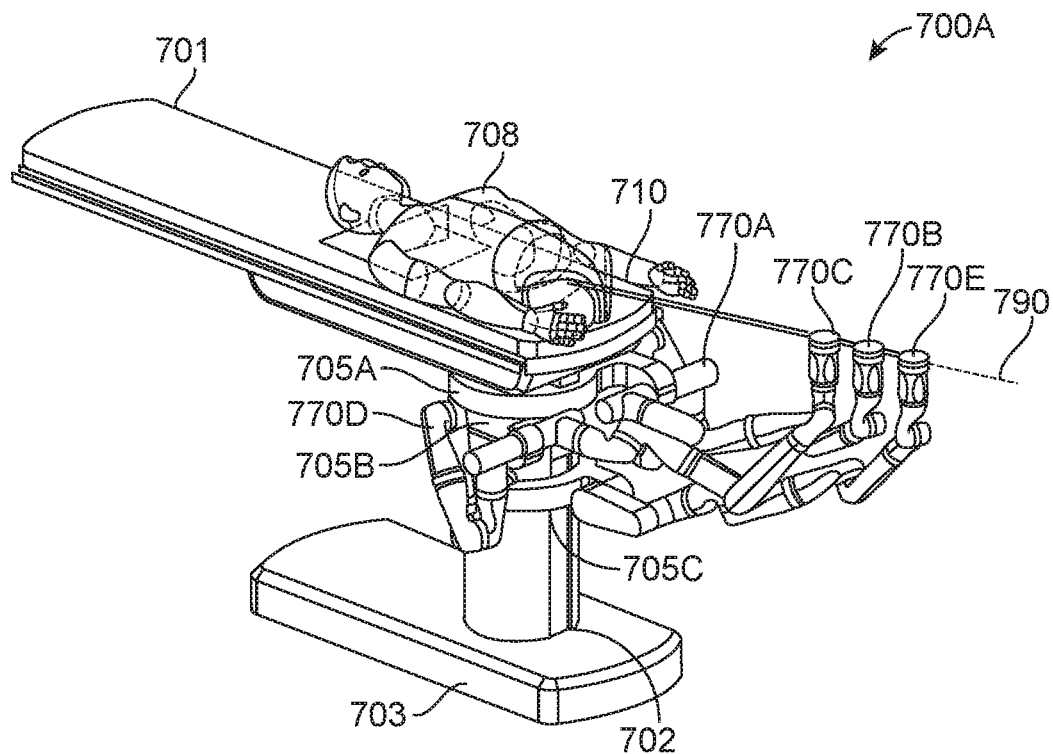
FIG. 7A is an isometric view of a surgical robotics system with column-mounted arms configured to access the lower body area of a patient according to one embodiment.

FIG. 7A is an isometric view of a surgical robotics system 700A with column-mounted arms configured to access the lower body area of a patient 708 according to one embodiment. The surgical robotics system 700A is an embodiment of—though includes more components than the surgical robotics system 400B in FIG. 4B. Specifically, the surgical robotics system 700A includes a set of robotic arms (including five robotic arms in total) and a set of three column rings. A first robotic arm 770A and a second robotic arm 770B are coupled to a first column ring 705A. A third robotic arm 770C and a fourth robotic arm 770D are coupled to a second column ring 705B. A fifth robotic arm 770E is coupled to a third column ring 705C. FIG. 7A shows a wireframe of the patient 708 lying on the table 701 undergoing a surgical procedure, e.g., ureteroscopy, requiring access to the lower body area of the patient 708. Legs of the patient 708 are not shown as to not obscure portions of the surgical robotics system 700A.

The surgical robotics system 700A configures the set of robotic arms to perform a surgical procedure on the lower body area of the patient 708. Specifically, the surgical robotics system 700A configures the set of robotic arms to manipulate a surgical instrument 710. FIG. 7A shows the set of robotic arms inserting the surgical instrument 710 along a virtual rail 790 into the groin area of the patient 708. Generally, a virtual rail 790 is a co-axial trajectory along which the set of robotic arms translates a surgical instrument (typically a telescoping instrument). The second robotic arm 770B, the third robotic arm 770C, and the fifth robotic arm 770E are coupled, e.g., holding, the surgical instrument 710. The first robotic arm 770A and the fourth robotic arm 770D are stowed to the sides of the surgical robotics system because they are not necessarily required to for the surgical procedure—or at least part of the surgical procedure-shown in FIG. 7A. The robotic arms are configured such that they manipulate the surgical instrument 710 from a distance away from the patient 708. This is advantageous, for example, because there is often limited space available closer toward the patient's body or there is a sterile boundary around the patient 708. Further, there may also be a sterile drape around surgical equipment. During a surgical procedure, only sterile objects are allowed pass the sterile boundary. Thus, the surgical robotics system 700A may still use robotic arms that are positioned outside of the sterile boundary and that are covered with sterilized drapes to perform a surgical procedure.

In one embodiment, the surgical robotics system 700A configures the set of robotic arms to perform an endoscopy surgical procedure on the patient 708. The set of robotic arms hold an endoscope, e.g., the surgical instrument 710. The set of robotic arms insert the endoscope into the patient's body via an opening in the groin area of the patient 708. The endoscope is a flexible, slender, and tubular instrument with optical components such as a camera and optical cable. The optical components collect data representing images of portions inside the patient's body. A user of the surgical robotics system 700A uses the data to assist with performing the endoscopy.

Figure 7B:
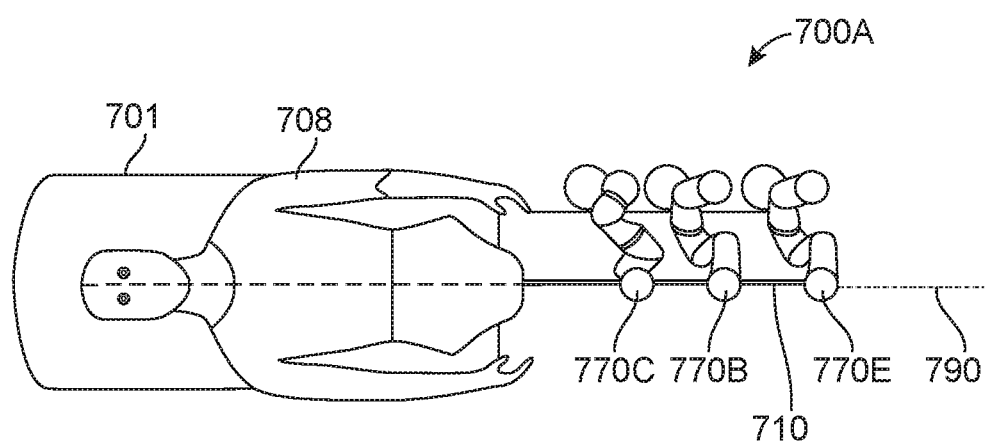
FIG. 7B is a top view of the surgical robotics system with column-mounted arms configured to access the lower body area of the patient according to one embodiment.

FIG. 7B is a top view of the surgical robotics system 700A with column-mounted arms configured to access the lower body area of the patient 708 according to one embodiment.

Figure 7C:
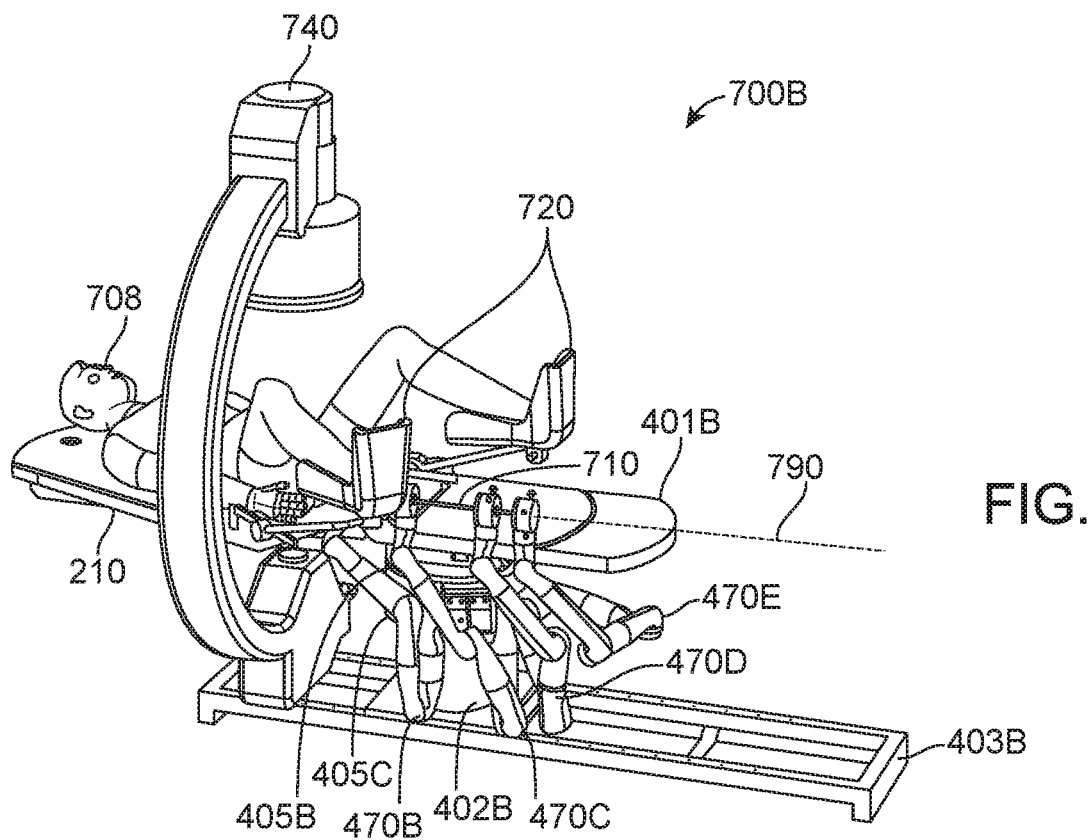
FIG. 7C is an isometric view of an imaging device and a surgical robotics system with column-mounted arms configured to access the lower body area of a patient according to one embodiment.

FIG. 7C is an isometric view of an imaging device 740 and a surgical robotics system 700B with column-mounted arms configured to access the lower body area of a patient 708 according to one embodiment. The surgical robotics system 700B is an embodiment of the surgical robotics system 400B in FIG. 4B. The surgical robotics system 700B includes a pair of stirrups 720 that support the legs of the patient 708, and thus exposing the groin area of the patient 708. Generally, the imaging device 740 captures images of body parts or other objects inside a patient 708. The imaging device 740 may be a C-arm, also referred to as a mobile C-arm, which is often used for fluoroscopy type surgical procedures, or another type of imaging device. A C-arm includes a generator, detector, and imaging system (not shown). The generator is coupled to the bottom end of the C-arm and faces upward toward the patient 708. The detector is coupled to the top end of the C-arm and faces downward toward the patient 708. The generator emits X-ray waves toward the patient 708. The X-ray waves penetrate the patient 708 and are received by the detector. Based on the received X-ray waves, the imaging system 740 generates the images of body parts or other objects inside the patient 708. The swivel segment 210 of the table 401B is rotated laterally such that the groin area of the patient 708 is aligned in between the generator and detector of the C-arm imaging device 740. The C-arm is a physically large device with a footprint that needs to be stationed underneath the patient. In particular, the generator of the C-arm needs to be underneath the operative area of the patient, e.g., the abdomen area. In typical surgical beds mounted to a column, the column interferes with the positioning of the C-arm generator, e.g., because the column is also underneath the operative area. In contrast, due to the configurability of the swivel segment 210, the surgical robotics system 700B may configure the table 401B such that the C-arm, the robotic arms, and a user (e.g., physician) have a sufficient range of access to perform a surgical procedure on a working area the patient's body. In one example use case, the table 401B is translated laterally along a longitudinal axis of the table 401B such that the robotic arms can access the groin or lower abdomen area of a patient on the table 401B. In another example use case, by rotating the swivel segment 210 away from the column 402B, the generator of the C-arm 740 may be positioned underneath the groin area of the patient 708. The swivel segment 210 with a patient lying on the swivel segment 210—may be rotated at least to 45 degrees relative to a longitudinal axis of the table 401B without tipping over the surgical robotics system. In particular, the surgical robotics system does not tip because the center of mass of the surgical robotics system (e.g., the center of mass of the combined, at least, table, bed, and base) is positioned above a footprint of the base. Outrigger casters, further described with reference to FIGS. 8G-J in Section VIII. Base, may provide further stability to prevent the surgical robotics system from tipping over when a swivel segment is rotated away from the table.

The surgical robotics system 700B uses a set of column-mounted robotic arms to manipulate a surgical instrument 710. Each of the robotic arms is coupled to, e.g., holding, the surgical instrument 710. The surgical robotics system 700B uses the robotic arms to insert the surgical instrument 710 into the groin area of the patient along a virtual rail 790.

Figure 7D:
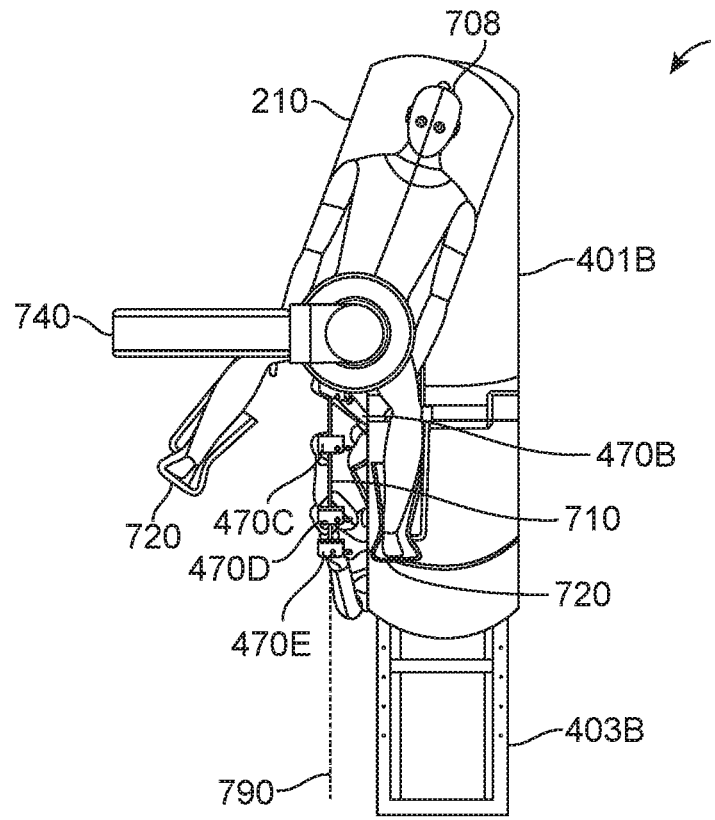
FIG. 7D is a top view of the imaging device and the surgical robotics system with column-mounted arms configured to access the lower body area of the patient according to one embodiment.

FIG. 7D is a top view of the imaging device 740 and the surgical robotics system 700B with column-mounted arms configured to access the lower body area of the patient 708 according to one embodiment.

VII. B. Core Body Surgery

Figure 7E:
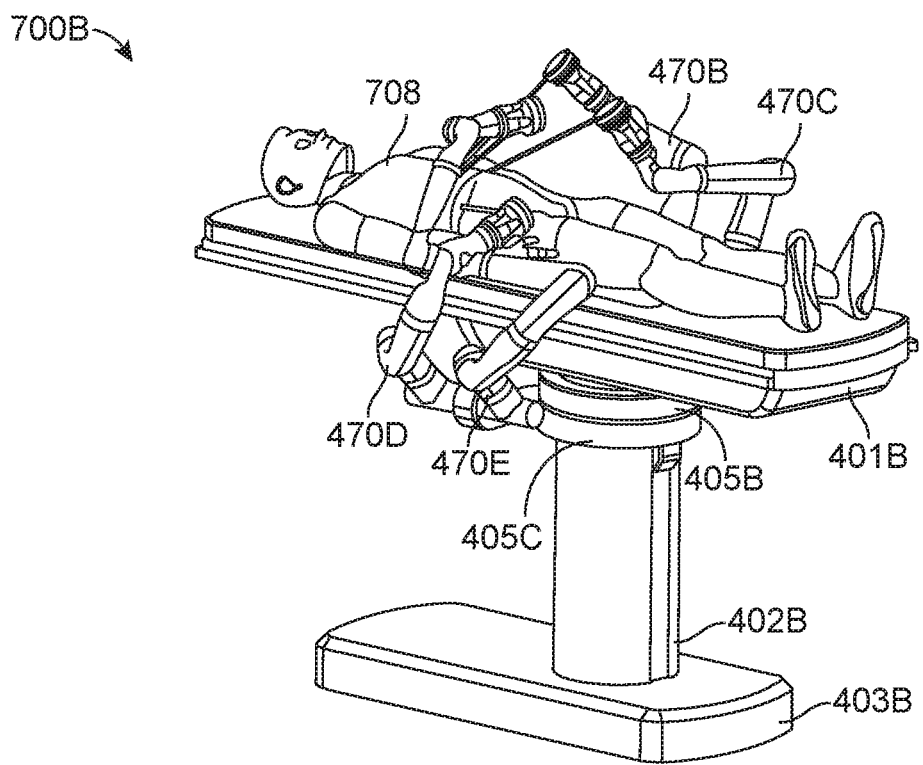
FIG. 7E is an isometric view of the surgical robotics system with column-mounted arms configured to access the core body area of a patient according to one embodiment.

FIG. 7E is an isometric view of the surgical robotics system 700B (or 400B) with column-mounted arms configured to access the core body area of a patient 708 according to one embodiment. The surgical robotics system 700B has been reconfigured from the configuration shown in FIG. 7C-D where the robotic arms access the lower body area of the patient 708. In embodiments where the table includes a swivel segment 210, the swivel segment 210 of the table is rotated in-line with the rest of the table. The patient 708 lying on the table 401B is undergoing a surgical procedure, e.g., prostatectomy or laparoscopy, requiring access to the core body area of the patient 708. Each robotic arm is manipulating a surgical instrument to perform the surgical procedure. The surgical robotics system 700B raises the column rings 405B and 405C toward the table 401B so that the robotic arms have greater access the patient 708. Further, the surgical robotics system 700B rotates the column rings such that two of the robotic arms extend from one side of the table 401B and the other two robotic arms extend from the opposite side of the 401B. Thus, the robotic arms are less likely to interfere with each other (e.g., a robotic arm blocking the motion of another robotic arm) during the surgical procedure.

VII. C. Upper Body Surgery

Figure 7F:
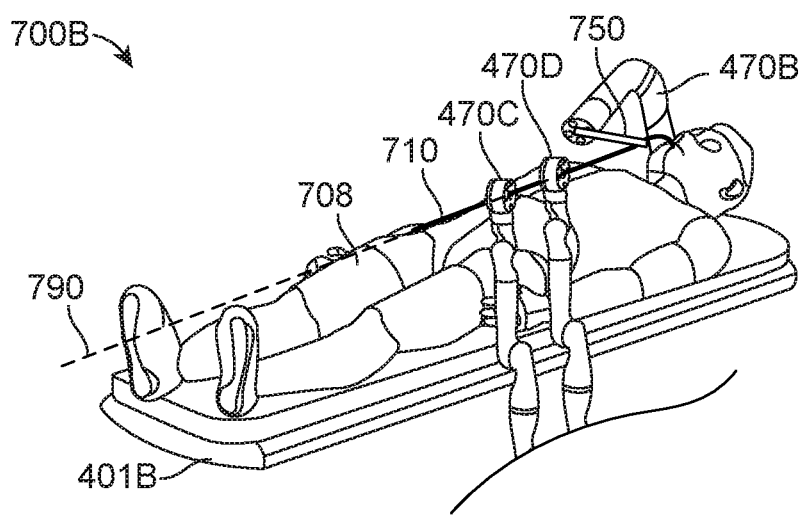
FIG. 7F is an isometric view of the surgical robotics system with column-mounted arms configured to access the upper body area of a patient according to one embodiment.

FIG. 7F is an isometric view of the surgical robotics system 700B (or 400B) with column-mounted arms configured to access the upper body area of a patient 708 according to one embodiment. The surgical robotics system 700B has been reconfigured from the configuration shown in FIG. 7E where the robotic arms access the core body area of the patient 708. In embodiments where the table includes a swivel segment 210, the swivel segment 210 of the table is rotated in-line with the rest of the table. The patient 708 lying on the table 401B is undergoing a surgical procedure, e.g., bronchoscopy, requiring access to the upper body area of the patient 708, specifically the head of the patient 708. The robotic arm 470C and the robotic arm 470D are inserting a surgical instrument 710D, e.g., a bronchoscope, into the mouth of the patient 708 along a virtual rail 790. The robotic arm 470B is coupled to, e.g., holding, an introducer 750. The introducer 750 is a surgical instrument that directs the bronchoscope into the mouth of the patient 708. Specifically, the trajectory of the bronchoscope along the virtual rail 790 begins parallel to the patient 708. The introducer 750 changes the angle of the virtual rail 790 just before the bronchoscope enters the mouth. The robotic arm 470E (not shown in FIG. 7F) is not used for the surgical procedure, and thus is stowed away.

VIII. Base

Figure 8A:
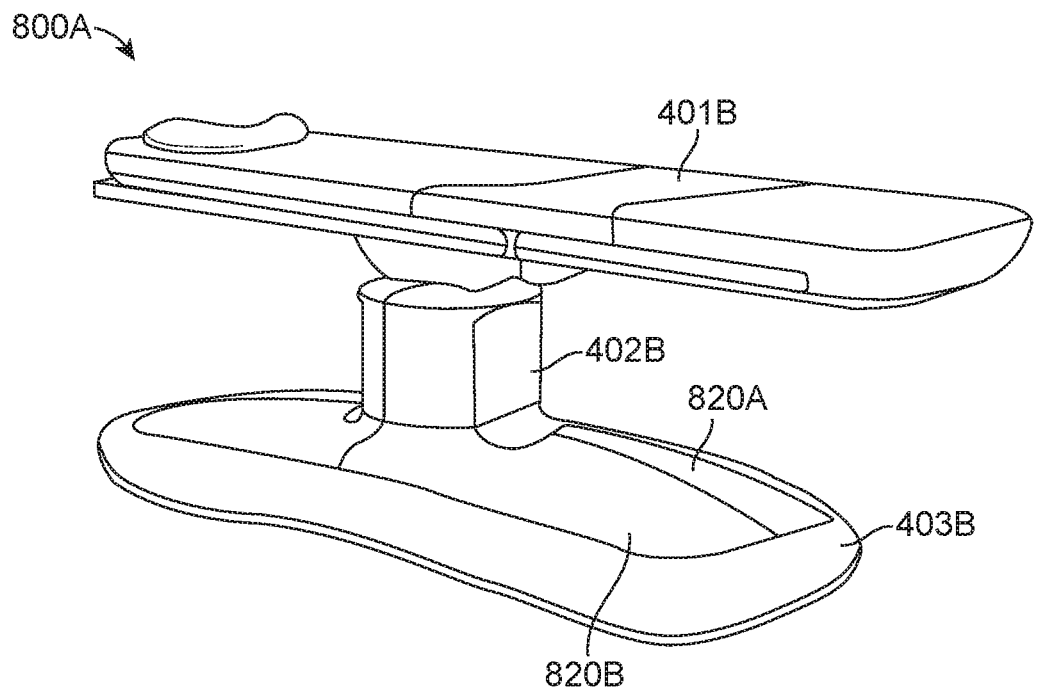
FIG. 8A is an isometric view of a base of a surgical robotics system according to one embodiment.

FIG. 8A is an isometric view of a base 403A of a surgical robotics system 800A according to one embodiment. The surgical robotics system 800A is an embodiment of the surgical robotics system 400B in FIG. 4B. The surgical robotics system 800A stores column-mounted robotic arms and/or column rings (not shown) inside the base 403B when the robotic arms are not in use. The base 403B includes a first panel 820A and a second panel 820B that cover stored robotic arms. The first panel 820A and the second panel 820B are advantageous because they prevent waste materials from de-sterilizing or otherwise contaminating stored robotic arms.

Figure 8B:
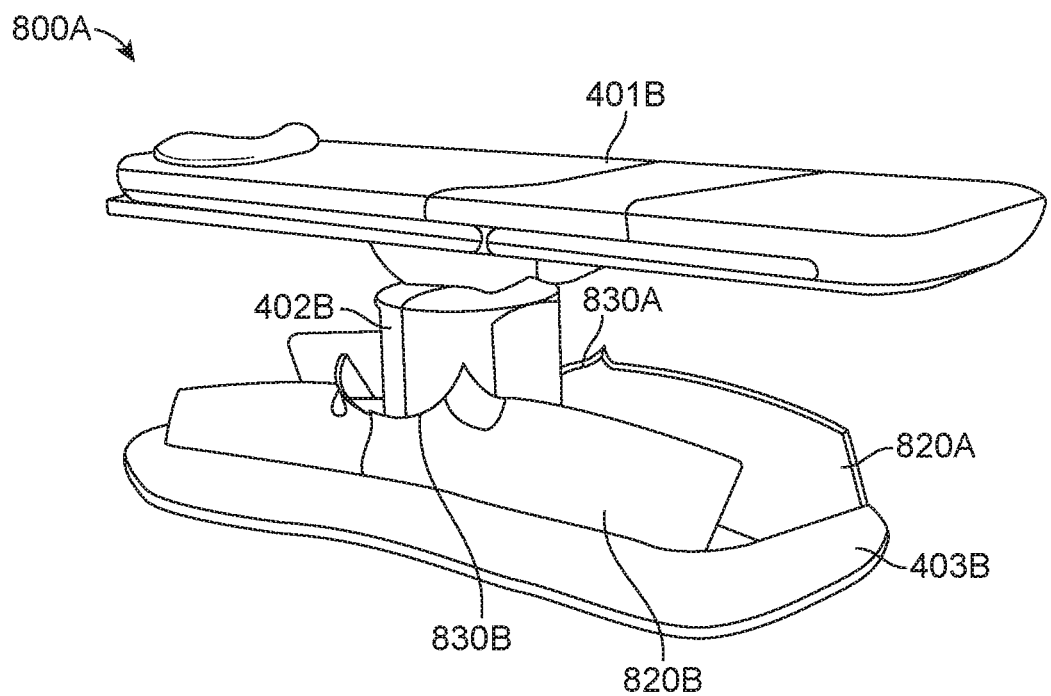
FIG. 8B is an isometric view of open panels of the base according to one embodiment.

FIG. 8B is an isometric view of open panels of the base 403B according to one embodiment. The first panel 820A and the second panel 820B pivot away from the column 802A such that column-mounted robotic arms have access to inside the base 403B. The first panel 820A includes a cutout 830A and the second panel 820B includes a cutout 830B. The cutouts 830A and 830B conform to the shape of the column 402B such that the panels 820A and 820B form a seal around the column 402B when closed. The surgical robotics system 800A may automatically open and close the first panel 820A and the second panel 820B using motors or other means of actuation. A user of the surgical robotics system 800A may also manually open and close the first panel 820A and the second panel 820B.

Figure 8C:
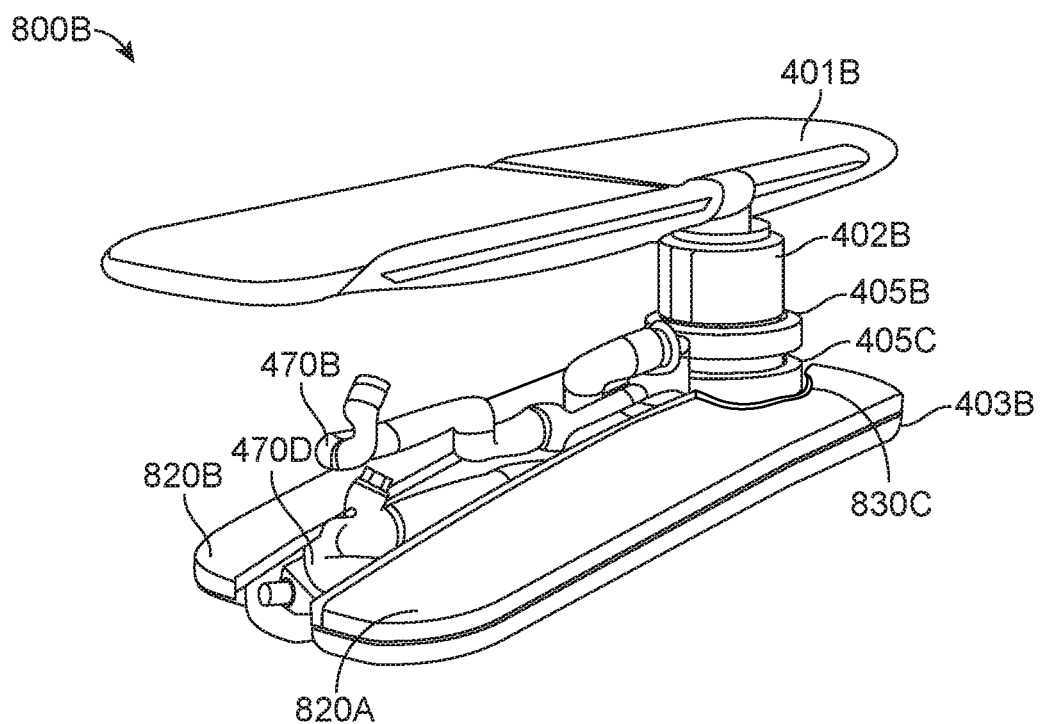
FIG. 8C is an isometric view of robotic arms stowed inside a base of a surgical robotics system according to one embodiment.

FIG. 8C is an isometric view of a robotic arm stowed inside a base 403B of a surgical robotics system 800B according to one embodiment. The surgical robotics system 800B is an embodiment of the surgical robotics system 400B in FIG. 4B. The surgical robotics system 800B stores column-mounted robotic arms 470B and 470D and column rings 405B and 405C inside the base 403B when the robotic arms are not in use. The base 403B includes a first panel 820A and a second panel 820B that cover stored robotic arms and column rings. The first panel 820A includes a cutout 830C. The second panel 820B also includes a cutout (not shown due to being obscured by other components).

The cutouts conform to the shape of the column 402B such that the panels 820A and 820B form a seal around the column 402B when closed.

The first panel 820A and a second panel 820B translate laterally to provide access for the robotic arms and column rings into the base 403B. FIG. 8C shows the first panel 820A and a second panel 820B translated to form an opening. The opening may be large enough to provide access for a robotic arm, but not too large as to still provide protection to the robotic arms even when the panels are open. The robotic arm 470D and column ring 405C are stowed inside the base 403B. The robotic arm 470B and column ring 405B are outside the base 403B, though they may also be stowed inside the base 403B. The surgical robotics system 800B may automatically open and close the first panel 820A and the second panel 820B using motors or other means of actuation. A user of the surgical robotics system 800B may also manually open and close the first panel 820A and the second panel 820B.

Figure 8D:
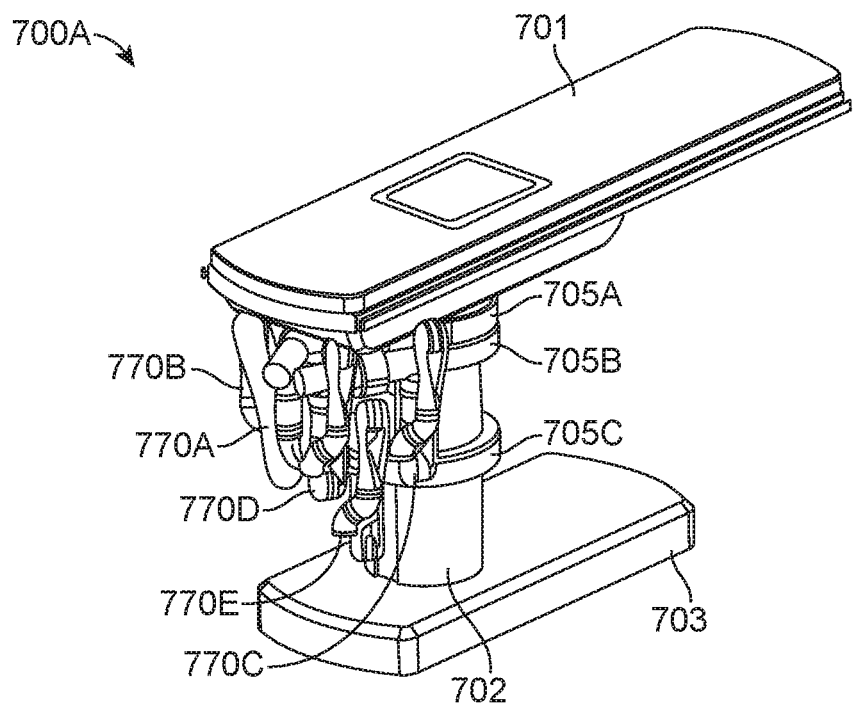
FIG. 8D is an isometric view of robotic arms stowed underneath a table of a surgical robotics system according to one embodiment. [0064] according to one embodiment.

FIG. 8D is an isometric view of robotic arms stowed underneath the table 701 of the surgical robotics system 700A according to one embodiment. Specifically, the arm segments of each robotic arm rotate such that the robotic arm is in a compact configuration for stowage. The surgical robotics system 700A raises the first column ring 705A and the second column ring 705B, and lowers the third column ring 705C toward the center of the column 702. This way, the robotic arms have enough space in the stowed configuration without interfering with each other. In one embodiment, the column 702 includes covers (e.g., similar to panels 820A and 820B) over the robotics arms to protect the robotic arms from contamination or damage.

Figure 8E:
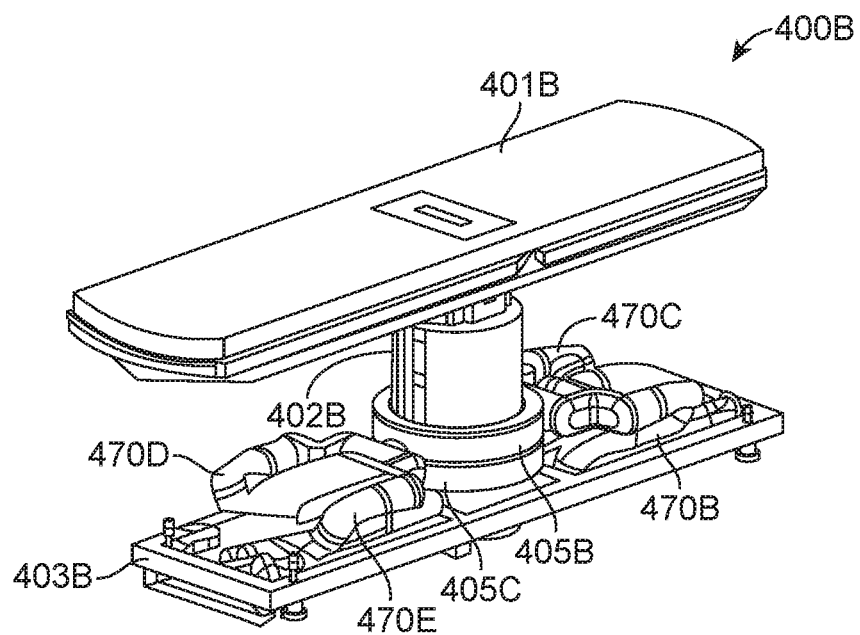
FIG. 8F is another isometric view of robotic arms stowed above a base of a surgical robotics system according to one embodiment.
FIG. 8G is an isometric view of outrigger casters on a base of a surgical robotics system according to one embodiment.
FIG. 8H is another isometric view of the outrigger casters on the base of the surgical robotics system according to one embodiment.
FIG. 8I is a side view of an outrigger caster in a mobile configuration according to one embodiment.
FIG. 8J is a side view of the outrigger caster in a stationary configuration according to one embodiment.

FIG. 8E is an isometric view of robotic arms stowed above the base 403B of the surgical robotics system 400B according to one embodiment. The robotic arms 470B, 470C, 470D, and 470E are in a stowed configuration. Specifically, the arm segments of each robotic arm rotate such that the robotic arm is in a compact configuration for stowage. The surgical robotics system 400B lowers the first column ring 405B and the second column ring 405C along the column 402B such that the stowed robotic arms rest on the base 403B and are away from the table 401B. A cover (not shown) such as a drape or panel may be used to cover the stowed robotic arms for protection from de-sterilization or other contamination.

Figure 8F:
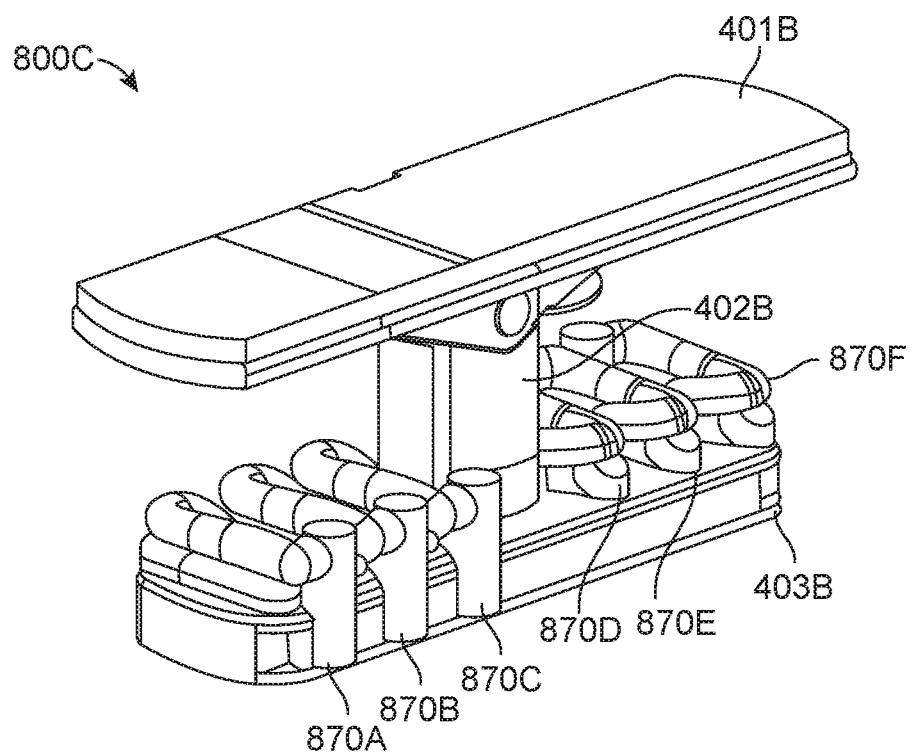

FIG. 8F is another isometric view of robotic arms stowed above the base 403B of the surgical robotics system 800C according to one embodiment. The robotic arms are rail-mounted instead of column-mounted. Rail-mounted robotic arms are further described with reference to FIGS. 9A-B and FIGS. 10A-D in Section IX. Rail-Mounted Robotic Arms and Section X. Rails, respectively. The surgical robotics system 800C is an embodiment of the surgical robotics system 900B further described with reference to FIG. 9B in Section IX. Rail-Mounted Robotic Arms. The robotic arms 870C, 870D, 870E, 870F, 870G, and 870H are in a stowed configuration.

Figure 8G:
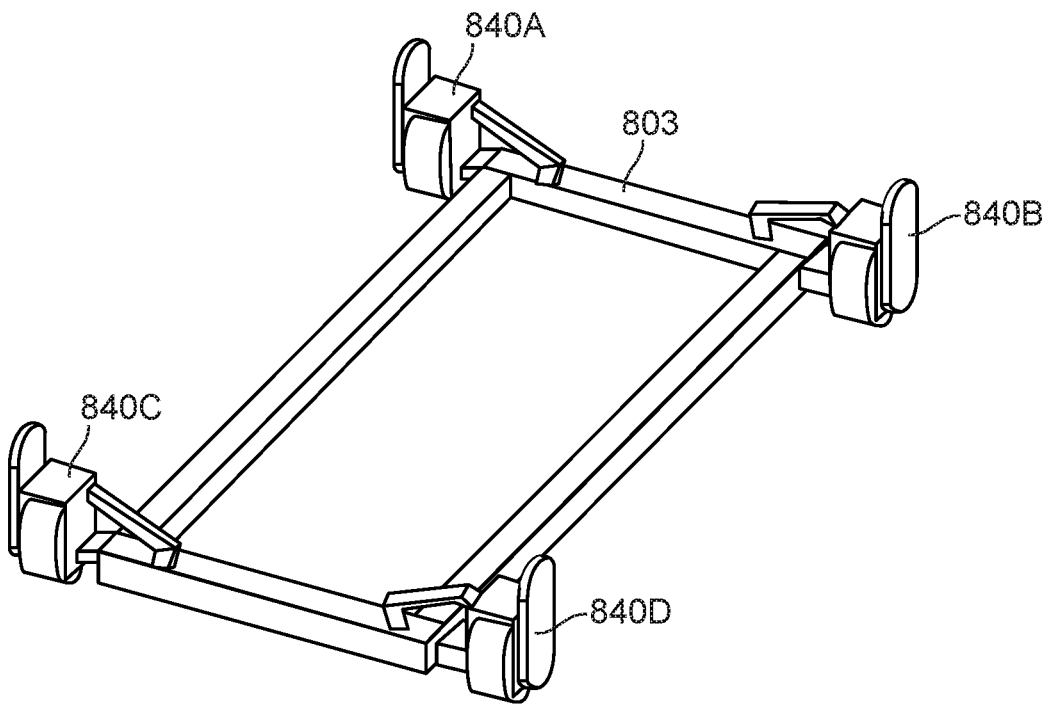

FIG. 8G is an isometric view of outrigger casters on a base 803 of a surgical robotics system according to one embodiment. The base 803 shown in FIG. 8G includes four outrigger casters 840A, 840B, 840C, and 840D, each substantially the same as each other and positioned at a different corner of the base 803, though it should be noted that, in other embodiments, a base may include any number of outrigger casters positioned in other locations on the base. The outrigger casters 840A, 840B, 840C, and 840D are each in a mobile configuration, i.e., the caster wheel physically contacts the ground. Thus, a user of the surgical robotics system may transport the surgical robotics system using the caster wheels, e.g., to a storage area when the surgical robotics system is not in use.

Figure 8H:
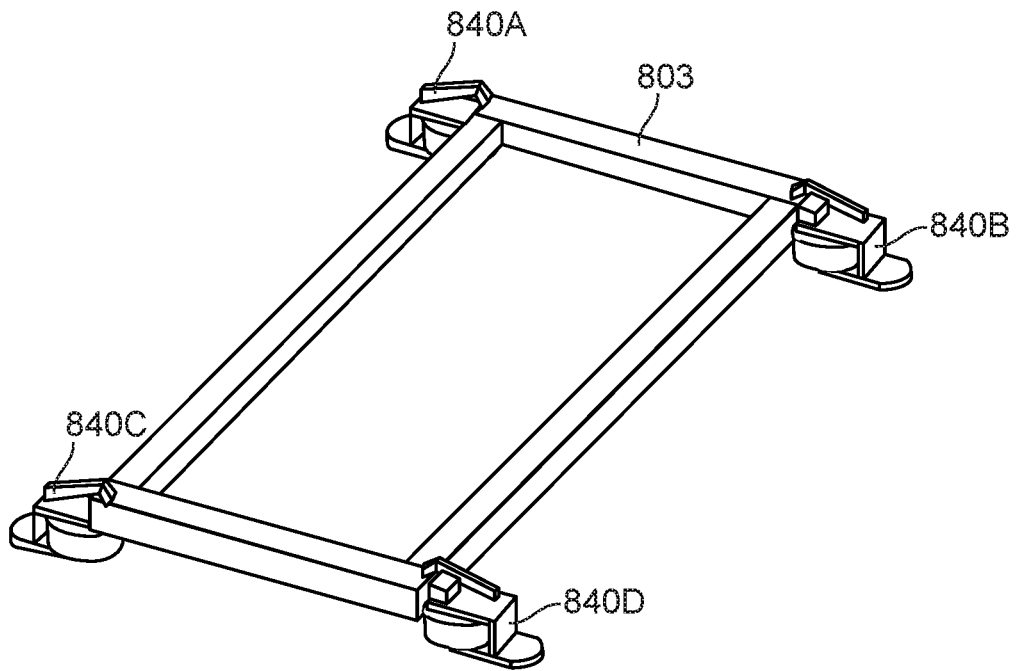

FIG. 8H is another isometric view of the outrigger casters 840A, 840B, 840C, and 840D on the base 803 of the surgical robotics system according to one embodiment. The outrigger casters 840A, 840B, 840C, and 840D are each in a stationary configuration, i.e., the outrigger caster is rotated such that the caster wheel does not physically contact the ground. Thus, the surgical robotics system may be stabilized and immobilized during a surgical procedure.

Figure 8I:
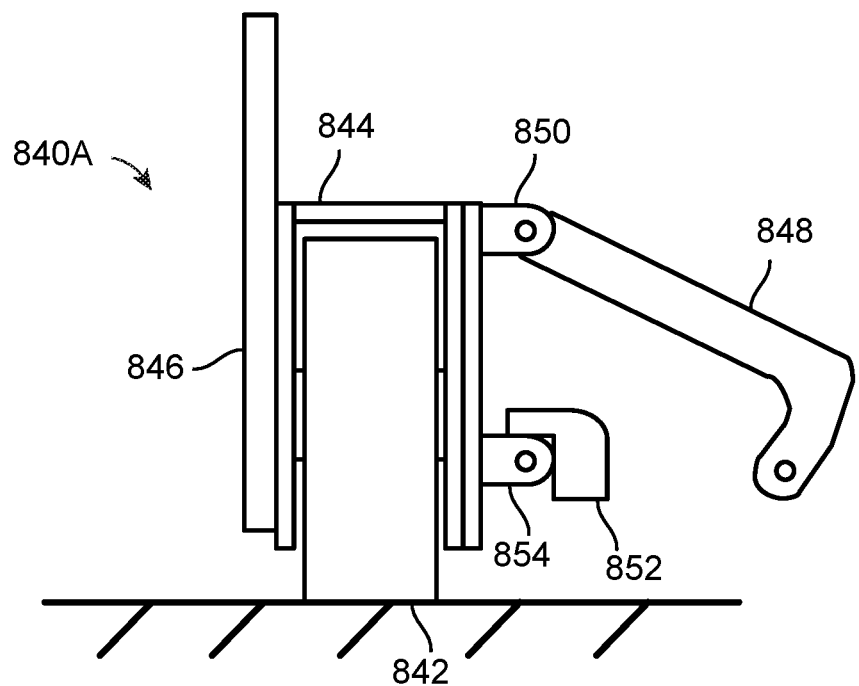

FIG. 8I is a side view of the outrigger caster 840A in a mobile configuration according to one embodiment. The outrigger caster 840A includes a caster wheel 842 movably coupled to an outrigger mount 844. The outrigger mount 844 is coupled to a foot 846. The first linkage 848 is movably coupled to the outrigger mount 844 by the first hinge 850. The second linkage 852 is movably coupled to the outrigger mount 844 by the second hinge 854. In the mobile configuration, the caster wheel 842 may rotate to move the outrigger caster 840 along the ground.

Figure 8J:
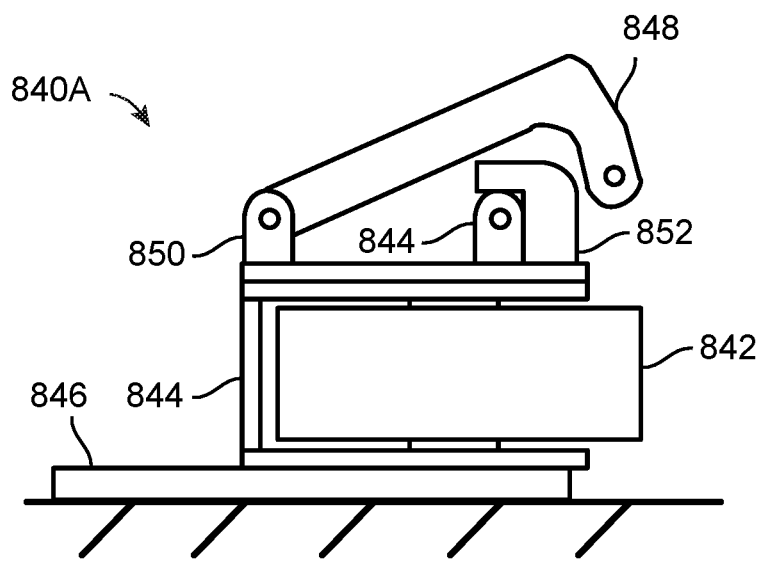

FIG. 8J is a side view of the outrigger caster 840A in a stationary configuration according to one embodiment. In the stationary configuration, the caster wheel 842 may freely rotate, but the caster wheel 842 does not move the outrigger caster 840A because the caster wheel 842 is not physically in contact with the ground. The surgical robotics system (or a user) rotates the outrigger caster 840A, e.g., 90 degrees, to change the outrigger caster 840A from the mobile configuration to the stationary configuration. Thus, the foot 846 now physically contacts the ground, and helps prevent the surgical robotics system from moving. The foot 846 may have a larger footprint relative to the caster wheel 842 to provide additional stability on the ground. The linkages 848 and 852 are positioned such that they do not interfere with the rotational path of the outrigger caster 840A. Combining the caster wheel 842 and the foot 846 in the outrigger caster 840A is advantageous, e.g., because the outrigger caster 840A allows the surgical robotics system to change between the mobile and stationary configurations using a compact mechanism, compared to having separate mechanisms for casters and stabilization. Further, in use cases of surgical robotics systems including swivel segments that rotate a patient lying on the swivel segment away from a corresponding table (e.g., as illustrated in FIGS. 7C-D), the feet of outrigger casters (in the stationary configuration) help prevent the surgical robotics system from tipping over due to the center of mass of the patient extending beyond the table base.

Alternative views and embodiments of the base 403B including the above mentioned components are further illustrated and described at least in U.S. Provisional Application No. 62/203,530 filed Aug. 11, 2015.

IX. Rail-Mounted Robotic Arms

Figure 9A:
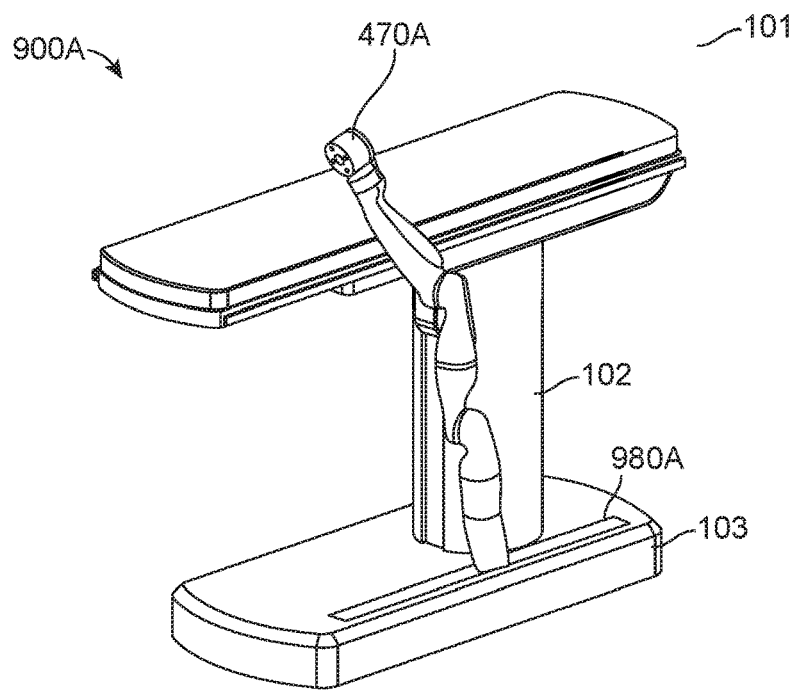
FIG. 9A is an isometric view of a surgical robotics system with a rail-mounted robotic arm according to one embodiment.

FIG. 9A is an isometric view of a surgical robotics system 900A with a rail-mounted robotic arm according to one embodiment. The surgical robotics system 900A includes a set of robotic arms (including at least arm 470A) and a set of base rails (including at least base rail 980A). The robotic arm 470A is coupled to the base rail 980A. Base rails are further described with respect to FIGS. 10A-D in Section X. Rails below. The base rail 980A is movably coupled to the base 103. Thus, the robotic arm 470A may be referred to as a rail-mounted robotic arm 470A.

Figure 9B:
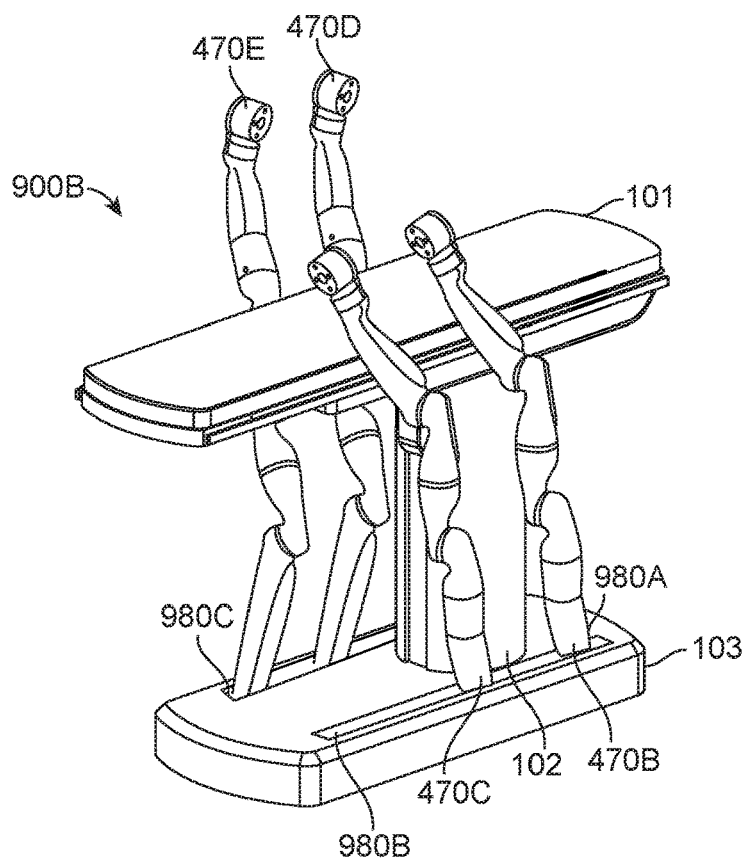
FIG. 9B is an isometric view of a surgical robotics system with rail-mounted robotic arms according to one embodiment.

FIG. 9B is an isometric view of a surgical robotics system 900B with rail-mounted robotic arms according to one embodiment. The surgical robotics system 900B includes robotic arms 470B, 470C, 470D, and 470E each coupled to a first base rail 980B or a second base rail 980C. The first base rail 980B and the second base rail 980C are movably coupled to the base 103.

In other embodiments, the surgical robotics system 900B may include additional or fewer robotic arms and/or base rails. Further, the robotic arms may be coupled to base rails in various configurations. For example, three robotic arms may be coupled to a base rail. Additionally, the surgical robotics system 900B may include three base rails each coupled to a robotic arm.

The surgical robotics system 900B may translate robotic arms mounted to a base rail by translating the base rails relative to the base 103. Base rails may translate beyond the starting footprint of the base 103, which allows the robotic arms to operate in a larger volume of space. Further, the surgical robotics system 900B may translate robotic arms mounted to a base rail independently from each other by translating the robotic arms relative to the base rail. This is advantageous, for example, because the surgical robotics system 900B may position the robotic arms in different configurations to perform a variety of surgical procedures.

Alternative views and embodiments of the surgical robotics system 900B with rail-mounted robotic arms including the above mentioned components are further illustrated and described at least in U.S. Provisional Application No. 62/193,604 filed Jul. 17, 2015 and U.S. Provisional Application No. 62/201,518 filed Aug. 5, 2015.

X. Rails

Figure 10A:
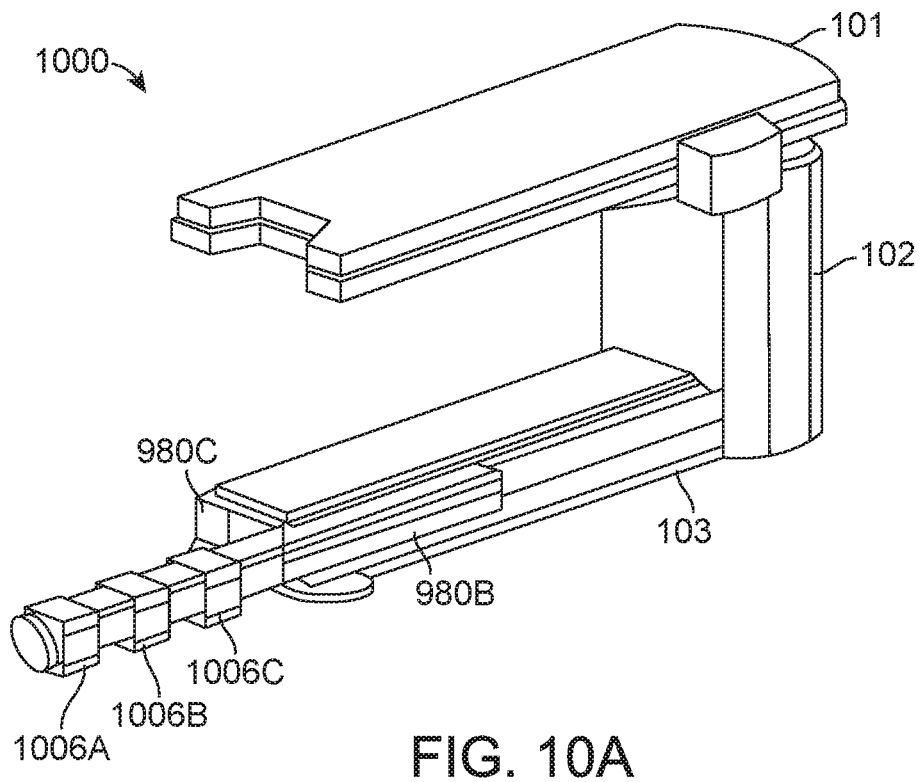
FIG. 10A is an isometric view of base rails of a surgical robotics system according to one embodiment.

FIG. 10A is an isometric view of base rails of a surgical robotics system 1000 according to one embodiment. A base rail includes a set of one or more arm mounts each movably coupled to the base rail. Further, each arm mount is an embodiment of the arm mount 506A or 506B previously described with reference to FIG. 5A in Section V. Column Ring. Specifically, the base rail 980B includes arm mounts 1006A, 1006B, and 1006C.

Figure 10B:
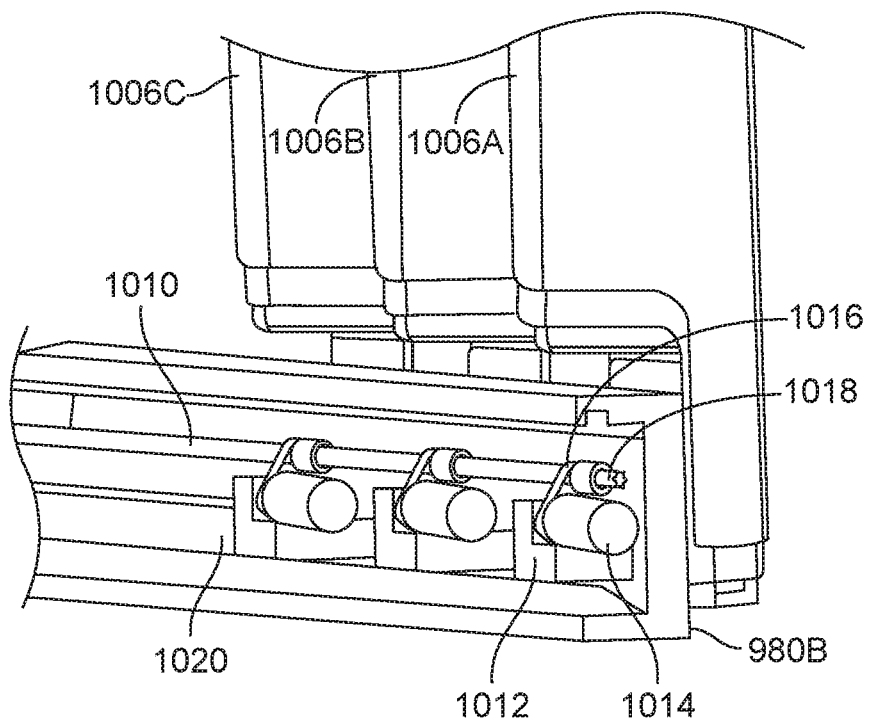
FIG. 10B is an isometric view of arm mounts on the base rail according to one embodiment.

FIG. 10B is an isometric view of arm mounts on the base rail 980B according to one embodiment. The arm mounts 1006A, 1006B, and 1006C each include a belt and pinion assembly. Specifically, the belt and pinion assembly of arm mount 1006A includes a bracket 1012, motor 1014, belt 1016, and pinion 1018. The belt and pinion assemblies of arm mount 1006B and 1006C are constructed similarly.

The surgical robotics system 1000 translates arm mounts—and thus, robotic arms mounted to the arm mounts-along base rails using the belt and pinion assemblies. Specifically, the arm mount 1006A is movably coupled to a channel 1020 of the base rail 980B by the bracket 1012. The bracket 1012 is coupled to motor 1014, belt 1016, and pinion 1018. The motor 1014 is coupled to the pinion 1018 by the belt 1016. Thus, output rotation of the motor 1014 causes the pinion 1018 to rotate. The pinion 1018 is engaged with a rail lead screw 1010 of the base rail 980B. Rotation of the pinion 1018 causes the arm mount 1006A to translate along the base rail 980B parallel to the rail lead screw 1010.

Figure 10C:
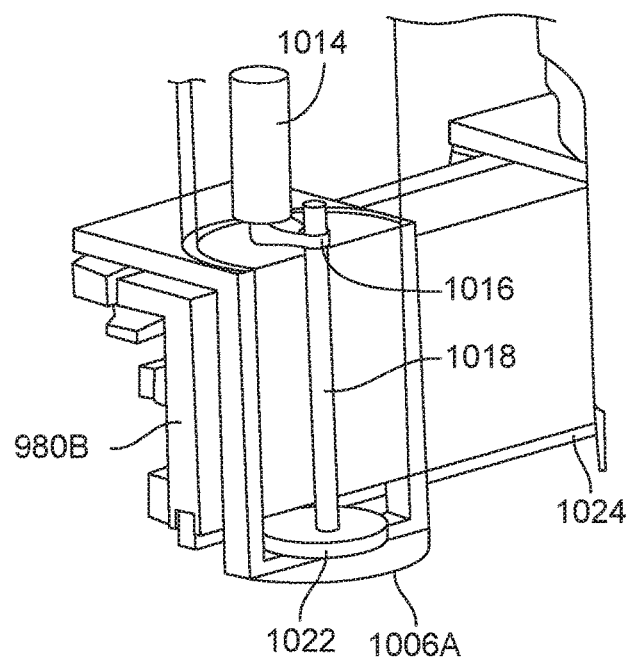
FIG. 10C is an isometric cutaway view of an arm mount on the base rail according to one embodiment.

FIG. 10C is an isometric cutaway view of an arm mount 1006A on the base rail 980B according to one embodiment. The arm mount 1006A includes a belt and pinion assembly. Specifically, the belt and pinion assembly includes a motor 1014, belt 1016, pinion 1018, and bearing 1022. The surgical robotics system 1000 translates the arm mount 1006A—and thus, a robotic arm mounted to the arm mount 1006A-along the base rail 980B using the belt and pinion assembly. The motor 1014 is coupled to the pinion 1018 by the belt 1016. Thus, output rotation of the motor 1014 causes the pinion 1018 to rotate. The pinion 1018 is coupled to the bearing 1022. In some embodiments, the bearing 1022 forms a rack and pinion assembly with the base rail 980B. Specifically, the bearing 1022 is a gear (i.e., the pinion) and is engaged with a rack 1024 of the base rail 980B. Rotation of the pinion 1018 causes the bearing 1022 to translate along the base rail 980B parallel to the rack 1024. Thus, the arm mount 1006A also translates along the base rail 980B.

Figure 10D:
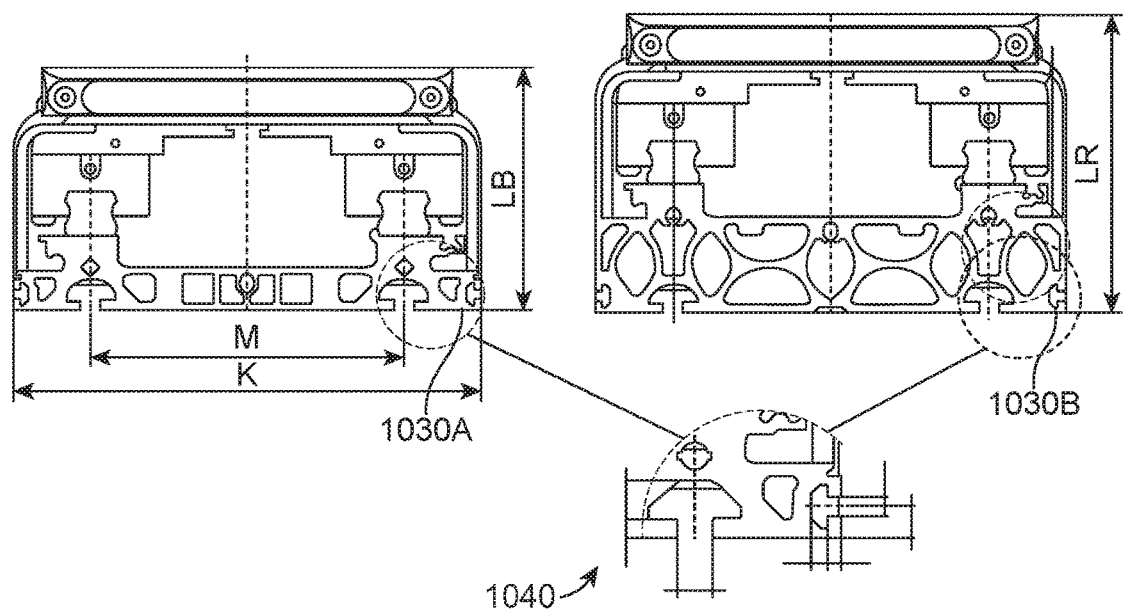
FIG. 10D is cross sectional views of the base rail according to one embodiment.

FIG. 10D is cross sectional views of the base rail 980B according to one embodiment. The cross sectional view 1000A shows a basic profile of an embodiment of the base rail 980B. The cross sectional view 1000B shows a reinforced profile of an embodiment of the base rail 980B. The lower segment 1030B of the reinforced profile is larger in size than the lower segment 1030A of the basic profile. Thus, the reinforced profile is an advantage, for example, because it enables the base rail 980B to withstand greater loads relative to the basic profile. Both the basic and the reinforced profiles have a T-slot attachment 1040, which engages with a corresponding T-slot on a base of a surgical robotics system.

Alternative views and embodiments of the base rails 980A, 980B, and 980C including the above mentioned components are further illustrated and described at least in U.S. Provisional Application No. 62/193,604 filed Jul. 17, 2015 and U.S. Provisional Application No. 62/201,518 filed Aug. 5, 2015.

XI. Alternate Configurations

XI. A. Hybrid Configuration

Figure 11:
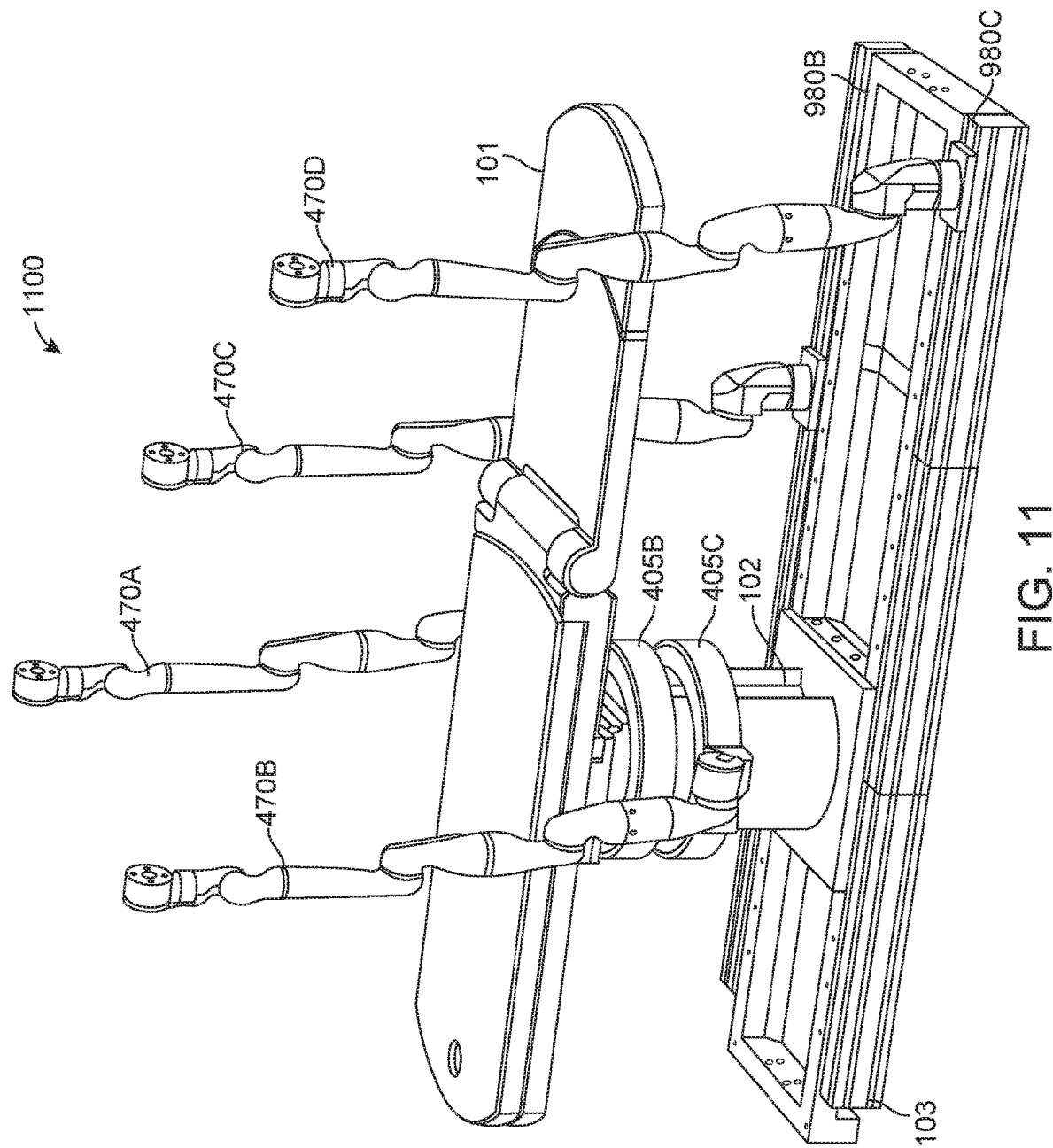
FIG. 11 is an isometric view of a surgical robotics system with column-mounted robotics arms and rail-mounted robotic arms according to one embodiment.

FIG. 11 is an isometric view of a surgical robotics system 1100 with column-mounted robotics arms and rail-mounted robotic arms according to one embodiment. Due to the hybrid configuration including both column-mounted robotics arms and rail-mounted robotic arms, the surgical robotics system 1100 may configure the robotic arms in a greater number of (or different types of) positions compared to surgical robotics systems with column-mounted robotics arms only or rail-mounted robotic arms only. Further, the surgical robotics system 1100 takes advantage of the rotational motion of robotic arms using the column rings as well as translational motion of the robotic arms using the base rails.

XI. B. Cart-Based Robotic Arm Column

Figure 12:
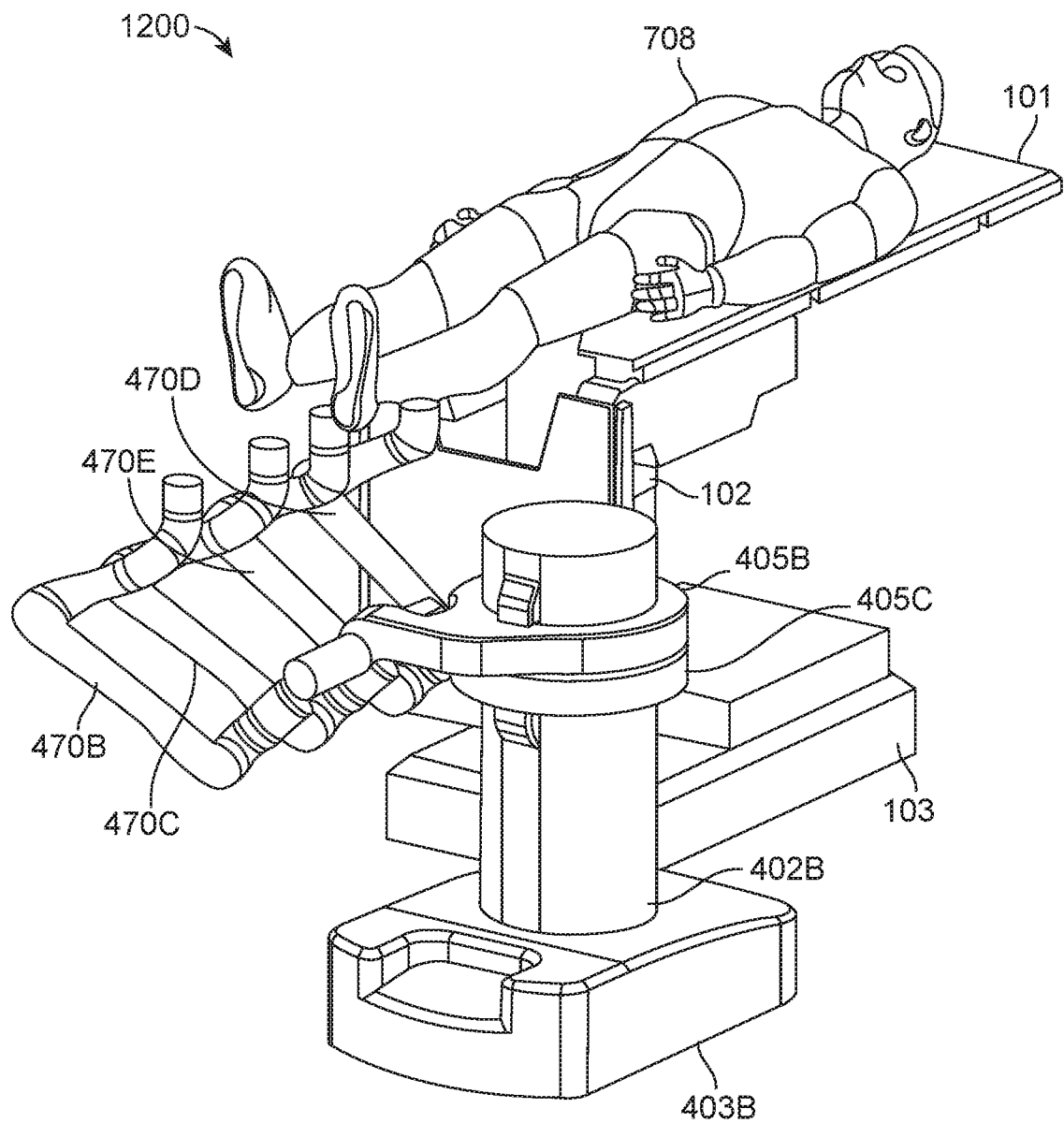
FIG. 12 is an isometric view of a surgical robotics system with column-mounted robotics arms on a platform separate from a table and a base of the surgical robotics system according to one embodiment.

FIG. 12 is an isometric view of a surgical robotics system 1200 with column-mounted robotics arms on a column 402B and base 403B separate, e.g., as a free standing cart, from a table 101, column 102, and base 103 of the surgical robotics system 1200 according to one embodiment. The surgical robotics system 1200 configures the robotic arms to access the lower body area of patient 708 lying on the table 101. In one embodiment, mounting the robotic arms on a cart including the column 402B separate from the column 102 coupled to the table 101 with the patient is advantageous. For example, because the surgical robotics system 1200 may configure the robotic arms to a greater number of (or different types of) positions compared to surgical robotics systems with robotics arms mounted to the same column as the table, which are limited at least in the angles where the table extends past the column 102. Further, the cart may include outrigger casters (e.g., previously described with reference to FIGS. 8G-J in Section VIII. Base) that allow users to more easily transport the robotic arms or keep the cart stationary. Mounting the robotic arms separately can also reduce the number of components and complexity of the column coupled to the table with the patient.

Alternative views and embodiments of the surgical robotics system 1100, the surgical robotics system 1200, and other surgical robotics systems including the above mentioned components are further illustrated and described at least in U.S. Provisional Application No. 62/162,486 filed May 15, 2015, U.S. Provisional Application No. 62/162,467 filed May 15, 2015, U.S. Provisional Application No. 62/193,604 filed Jul. 17, 2015, U.S. Provisional Application No. 62/201,518 filed Aug. 5, 2015, U.S. Provisional Application No. 62/203,530 filed Aug. 11, 2015, and U.S. Provisional Application No. 62/235,394 filed Sep. 30, 2015.

XII. Adjustable Arm Supports

Robotic surgical (or medical) systems can include adjustable arm supports as described in this section for supporting one or more robotic arms. The adjustable arm supports can be configured to attach to either a table, a column support of the table, or a base of the table to deploy the adjustable arm supports and robotic arms from a position below the table. In some embodiments, the adjustable arm supports can be attached to a bed (or table) or a cart positioned adjacent to a bed. In some examples, the adjustable arm supports includes a bar, track, or rail on which one or more robotic arms are mounted. In some embodiments, the adjustable arm supports include at least three or four degrees of freedom that allow for adjustment of the position of the bar, track, or rail. One of the degrees of freedom can allow the adjustable arm support to be adjusted vertically relative to the table. These and other features of the adjustable arm supports will be described in detail with reference to the examples of FIGS. 13A-20.

Figure 13A:
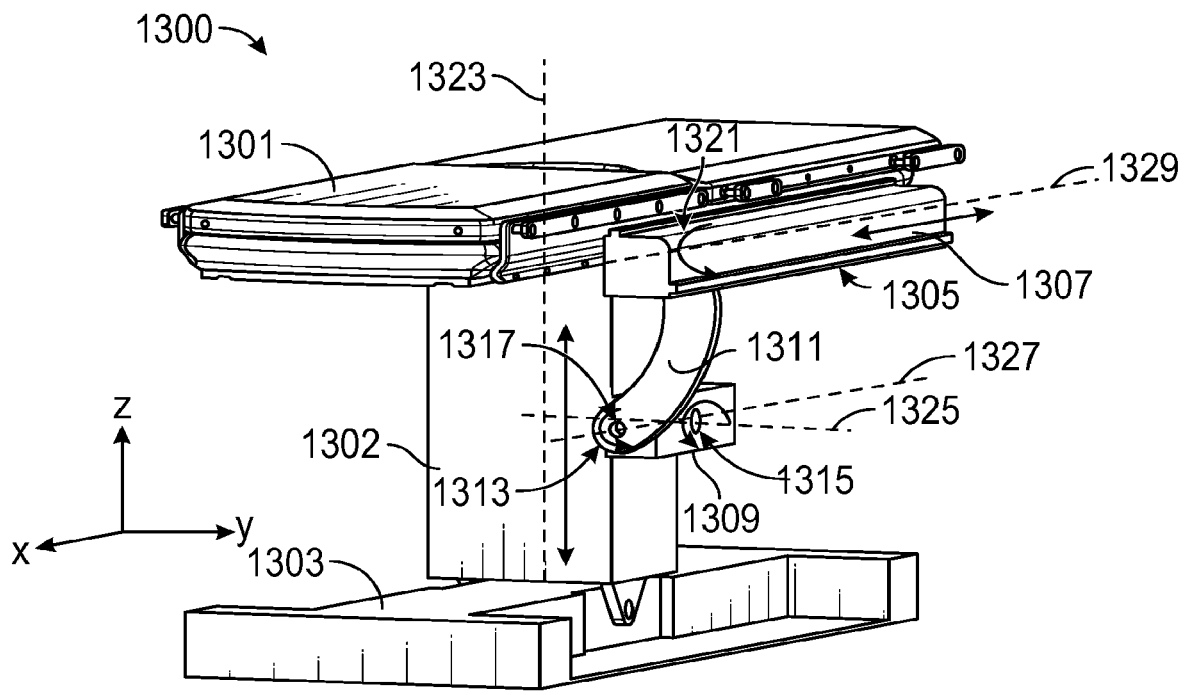
FIG. 13A is an isometric view of a surgical robotics system with an adjustable arm support according to one embodiment.
Figure 13B:
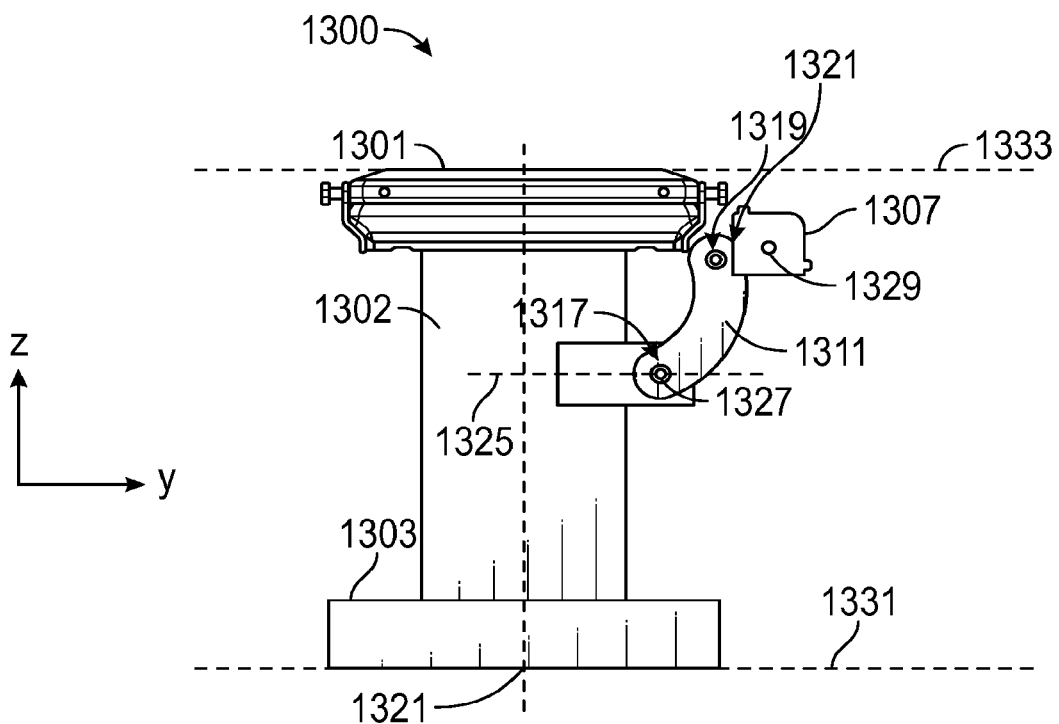
FIG. 13B is an end view of the surgical robotics system with an adjustable arm support of FIG. 13A.

FIGS. 13A and 13B are isometric and end views, respectively, of a surgical robotics system 1300 that includes an adjustable arm support 1305 according to one embodiment. The adjustable arm support 1305 can be configured to support one or more robotic arms (see, for example, FIGS. 14A-15B) relative to a table 1301. As will be described in greater detail below, the adjustable arm support 1305 can be configured so that it can move relative to the table 1301 to adjust and/or vary the position of the adjustable arm support 1305 and/or any robotic arms mounted to the adjustable arm support 1305 relative to the table 1301. For example, the adjustable arm support 1305 may include one or more degrees of freedom relative to the table 1301 to allow adjustment of the adjustable arm support 1305. Although the system 1300 illustrated in FIGS. 13A and 13B includes only a single adjustable arm support 1305, in some embodiments, systems can include multiple adjustable arm supports (see, e.g., system 1400 of FIG. 14A, which includes two adjustable arm supports 1305A, 1305B).

Surgical robotics systems including adjustable arm supports 1305 as described in this section can be designed to address one or more issues of known surgical robotics systems. For example, one issue with some surgical robotics systems is that they may be bulky, occupying large amounts of room space. This is often because large and elaborate support structures have been necessary to position robotic arms to perform robotic surgical procedures. Some surgical robotics systems include robotic arm support structures that support a plurality of robotic arms above a table that supports a patient during the robotic surgical procedure. For example, some surgical robotics systems include support structures that suspend one or more robotic arms over a table. These support structures are quite large and bulky because, for example, they must extend over and above the table.

Another issue with some surgical robotics systems is that they can be overly cumbersome. Due to, for example, the large and bulky support structures required by some surgical robotics systems as described above, these systems are not easily moved, which can be disadvantageous. Before and after surgery, it can be desirable to quickly and smoothly clear the robotic arms from a surgical area to provide easy access for loading a patient onto or removing a patient from the table. This has proven to be difficult with some surgical robotics systems because of the large and bulky support structures and the cumbersome nature of these systems. Some surgical robotics systems are not easily stored or moved.

Further, some surgical robotics systems have limited flexibility or versatility. That is, some surgical robotics systems are designed for a particular surgical procedure, and accordingly, do not work well for other types of surgical procedures. For example, a surgical robotics system that is configured for laparoscopic surgery may not work well for endoscopic surgery, or vice versa. In some instances, this is because the robotic arms used during the procedures need to be positioned in different locations relative the patient and/or table during different types of surgical procedures, and the support structures of conventional surgical robotics systems are not capable of accommodating the different positions of the robotic arms. Further, as mentioned above, some surgical robotics systems include support structures that suspend one or more robotic arms above the patient and table. It may be difficult to perform certain medical procedures with robotic arms mounted in this position.

Finally, some surgical robotics systems include robotic arms that are fixedly mounted to their corresponding support structures, and/or support structures themselves that are fixedly mounted or positioned. These systems may rely on articulation of the robotic arms alone to adjust the position of the robotic arms and/or surgical tools mounted thereto. Because the arms and/or supports are fixed in position, this can greatly limit the overall flexibility of these systems. The fixed nature of the robotic arms and/or supports of some systems may further limit the ability of these systems to avoid collisions between the arms and/or other objects (e.g., the patient, the table, other equipment, etc.) during surgery.

As shown in FIGS. 13A and 13B, for example, the system 1300, including the adjustable arm support 1305, as well as the other systems described in this application, can be configured to address (e.g., reduce or eliminate) one or more of the issues associated with some surgical robotics systems discussed above. For example, the systems described herein can be less bulky than some systems. The systems described herein can occupy less physical space than some systems. The systems described herein can be less cumbersome than some systems. For example, the systems described herein can be readily mobile and/or can be configured to store the arm supports and robotic arms quickly and easily to allow convenient access to the patient and/or table. The systems described herein can be highly flexible and configured for use in a wide variety of surgical procedures. For example, in some embodiments, the systems are configured for both laparoscopic and endoscopic procedures. The systems described herein can be configured to reduce collisions between the various robotic arms and other objects in the operating room.

In some embodiments, one or more of these advantages can be achieved by inclusion of one or more adjustable arm supports 1305 as described herein. As mentioned above, the adjustable arm supports 1305 can be configured so as to be able to move relative to the table 1301 to adjust and/or vary the position of the adjustable arm support 1305 and/or any robotic arms mounted to the adjustable arm support 1305 relative to the table 1301. For example, the adjustable arm supports 1305 can be capable of being stowed (for example, below the table 1301) and subsequently elevated for use. In some embodiments, the adjustable arm supports 1305 can be stowed in or in proximity to a base that supports the table 1301. In some embodiments, the adjustable arm supports 1305 can be stowed in one or more recesses formed along a central longitudinal axis of the base. In other embodiments, the adjustable arm supports 1305 can be stowed in one or more recesses offset from a central longitudinal axis of the base. Upon elevation, the adjustable arm supports 1305 can be positioned near the patient, but below the table 1301 (e.g., below the upper surface of the table 1301). In other embodiments, the arm supports 1305 can be raised above the table 1301 (e.g., above the upper surface of the table). Such a configuration can be useful, for example, when an adjustable arm support is positioned behind a patient lying on his side.

In some embodiments, the adjustable arm support 1305 is attached to the bed with a support structure that provides several degrees of freedom (e.g., lift, lateral translation, tilt, etc.). In the illustrated embodiment of FIGS. 13A and 13B, the arm support 1305 is configured with four degrees of freedom, which are illustrated with arrows in FIG. 13A. A first degree of freedom allows for adjustment of the adjustable arm support in the z-direction (e.g., Z-lift). For example, as will be described below, the adjustable arm support 1305 can include a carriage 1309 configured to move up or down along or relative to a column 1302 supporting the table 1301. A second degree of freedom can allow the adjustable arm support 1305 to tilt. For example, the adjustable arm support 1305 can include a rotary joint, which can, for example, permit the arm support 1305 to be aligned with a bed in a Trendelenburg position. A third degree of freedom can allow the adjustable arm support to pivot up as shown. As will be described below, this degree of freedom can be used to adjust a distance between the side of the table 1301 and the adjustable arm support 1305. A fourth degree of freedom can permit translation of the adjustable arm support 1305 along a longitudinal length of the table. Arm supports 1305 that include one or more of these degrees of freedom can address one or more of the issues associated with some systems noted above by providing a highly positionable support to which various robotic arms can be attached. The adjustable arm support 1305 can allow for adjustment of the position of the robotic arms relative to, for example, the table 1301. In some embodiments, these degrees of freedom can be controlled serially, in which one movement is performed after another. In other embodiments, different degrees of freedom can be controlled in parallel. For example, in some embodiments, one or more linear actuators can provide both Z-lift and tilt.

These degrees of freedom, as well as other features of the adjustable arm support 1305, will now be described in greater detail with continued reference to FIGS. 13A and 13B, which are isometric and end views, respectively, of the surgical robotics system 1300, which includes the adjustable arm support 1305 according to one embodiment. In the illustrated embodiment, the system 1300 includes the table 1301. In some embodiments, the table 1301 may be similar to the tables described above. In the illustrated embodiment, the table 1301 is supported by a column 1302, which is mounted to a base 1303. The base 1303 can be configured to rest on a support surface, such as a floor. Thus, the base 1303 and the column 1302 support the table 1301 relative to the support surface. FIG. 13B, a illustrates support surface plane 1331. In some embodiments, the table 1301 can be supported by one or more supports, wherein one of the supports comprises the column 1302. For example, the table 1301 can be supported by a Stewart mechanism comprising a plurality of parallel actuators.

The system 1300 can also include the adjustable arm support 1305. In the illustrated embodiment, the adjustable arm support 1305 is mounted to the column 1302. In other embodiments, the adjustable arm support 1305 can be mounted to the table 1301 or the base 1303. As mentioned above, the adjustable arm support 1305 is configured so that the position of the adjustable arm support 1305 can be adjusted relative to the table 1301. In some embodiments, the position of the adjustable arm support 1305 can also be adjusted relative to the column 1302 and/or base 1303.

The adjustable arm support 1305 can include a carriage 1309, a bar or rail connector 1311, and a rail 1307. One or more robotic arms can be mounted to the rail 1307, as shown, for example, in FIGS. 14A-15B. For example, in some embodiments, one, two, three, or more robotic arms can be mounted to the rail 1307. Further, in some embodiments, the robotic arms that are mounted to the rail can be configured to move (e.g., translate) along the rail 1307, such that the position of the robotic arms on the rail 1307 can be adjusted relative to one another, thereby reducing the risk of collision between the robotic arms. This will be described in greater detail below. In the illustrated embodiment, the rail 1307 is connected to the bar or rail connector 1311. The bar or rail connector 1311 is connected to the carriage 1309. The carriage is connected to the column 1302. Other arrangements are possible.

The column 1302 can extend along a first axis 1323. In some embodiments, the first axis 1323 is parallel to the z-axis as illustrated. In some embodiments, the first axis 1323 is a vertical axis. For example, the first axis 1323 can be perpendicular to the support surface or floor on which the system 1300 rests.

The carriage 1309 can be attached to the column 1302 by a first joint 1313. The first joint 1313 can be configured to allow the carriage 1309 (and accordingly the adjustable arm support 1305) to move relative to the column 1302. In some embodiments, the first joint 1313 is configured to allow the carriage 1309 to move along the column 1302 (for example, up and down along the column 1302). In some embodiment, the first joint 1313 is configured to allow the carriage 1309 to move along the first axis 1323 (for example, back and forth along the first axis 1323). The first joint 1313 can comprise a linear or prismatic joint. The first joint 1313 can comprise a powered joint, such as a motorized or hydraulic joint. The first joint 1313 can be configured to provide the first degree of freedom (e.g., Z-lift) for the adjustable arm support 1305.

The adjustable arm support 1305 can include a second joint 1315 as shown. The second joint 1315 can be configured to provide the second degree of freedom (tilt) for the adjustable arm support 1305. The second joint 1315 can be configured to allow the adjustable arm support 1305 to rotate around a second axis 1325 that is different than the first axis 1323. In some embodiments, the second axis 1325 is perpendicular to the first axis 1323. In some embodiments, the second axis 1325 need not be perpendicular relative to the first axis 1323. For example, in some embodiments, the second axis 1325 is at an acute angle to the first axis 1323. In some embodiments, the second axis 1325 extends in the y-direction. In some embodiments, the second axis 1325 may lie in a plane that is parallel to the support surface or floor on which the system 1300 rests. The second joint 1315 can comprise a rotational joint. The second joint 1315 can comprise a powered joint, such as a motorized or hydraulic joint.

In the illustrated embodiment, the second joint 1315 is formed between the carriage 1309 and the column 1302, such that the carriage 1309 can rotate about the second axis 1325 relative to the column 1302. In other embodiments, the second joint 1315 can be positioned in other locations. For example, the second joint 1315 can be positioned between the carriage 1309 and the rail connector 1311, or between the rail connector 1311 and the rail 1307.

As noted above, the second joint 1315 can be configured to allow the adjustable arm support 1305 to rotate about the second axis 1325 to allow for the second degree of freedom (tilt) for the adjustable arm support 1305. As will be described in greater detail with reference to FIG. 16 below, rotating the adjustable arm support 1305 about the second axis 1325 can allow adjustment of a tilt angle of the adjustable arm support 1305. That is, an angle of tilt of the bar or rail 1307 can be adjusted by rotating the adjustable arm support 1305 about the second axis 1325 (see FIG. 16).

The adjustable arm support 1305 can include a third joint 1317 as shown. The third joint 1317 can be configured to provide the third degree of freedom (pivot up) for the adjustable arm support 1305. The third joint 1317 can be configured as a rotational joint to allow the rail connector 1311 to rotate around a third axis 1327 that is different from the first axis 1323 and the second axis 1325. In some embodiments, the third axis 1327 can be perpendicular to the second axis 1325. In other embodiments, the third axis 1327 need not be parallel to the second axis 1325. For example, the third axis 1327 can be at an acute angle relative to the second axis 1325. In some embodiments, the third axis 1327 extends in the x-direction. In some embodiments, the third axis 1327 may lie in a plane that is parallel to the support surface or floor on which the system 1300 rests. The third axis 1327 may lie in the same plane or a different plane than the second axis 1325. When the adjustable arm support 1305 is positioned as shown in FIGS. 13A and 13B, the third axis 1327 can be perpendicular to the first axis 1323; however, as the adjustable arm support 1305 is rotated about the second joint 1315, the angle between the first axis 1323 and the third axis 1327 can vary. In some embodiments, the third axis 1327 can be parallel to the rail 1307.

When configured as a rotational joint, the third joint 1317 can allow the rail connector 1311 to rotate around the third axis 1327. As the rail connector 1311 rotates around the third axis 1327, a distance (for example, measured along the y-direction) between an edge of the table 1301 and the rail 1307 can be adjusted. For example, the distance between the edge of the table 1301 and the rail 1307 would increase as the rail connector 1311 is rotated downward from the position shown in FIG. 13B. Thus, the third joint 1317 can be configured to provide a degree of freedom that allows adjustment of the positioning of the rail 1307 along the y-direction. Further, when configured as a rotational joint, the third joint 1317 can also allow additional adjustment of the position of the rail 1307 along the z-direction. For example, the height of the rail 1307 (along the z-direction) would decrease as the rail connector 1311 is rotated downward from the position shown in FIG. 13B. In some embodiments, the third joint 1317 can allow the rail 1307 to pivot upwards in a "biceps curl" type fashion from a stowed position to an elevated position.

As best seen in FIG. 13B, in the illustrated embodiment, the third joint 1317 is positioned on a first end of the rail connector 1311 that connects the rail connector 1311 to the carriage. An additional joint 1319 can be included at a second end of the rail connector 1311 that connects the rail connector 1311 to the rail 1307. In some embodiments, the position of the third joint 1317 and the additional joint 1319 can be reversed. In some embodiments, the additional joint 1319 is mechanically constrained to the third joint 1317 such that the third joint 1317 and the additional joint 1319 rotate together. For example, the third joint 1317 and the additional joint 1319 can be mechanically constrained via a four-bar linkage. Other methods for mechanical constraint are also possible. Mechanical constraint between the third joint 1317 and the additional joint 1319 can be configured to maintain an orientation of the rail 1307 as the rail connector 1311 is rotated about the third axis 1327. For example, mechanical constraint between the third joint 1317 and the additional joint 1319 can be configured such that, as the rail connector 1311 rotates, an upper surface of the rail 1307 (to which one or more robotic arms can be mounted) continue to face in the same direction. In the illustrated example of FIGS. 13A and 13B, the upper face of the rail 1307 is facing upwards (in the z-direction). Mechanical constraint between the third joint 1317 and the additional joint 1319 can be configured such that the upper face of the rail 1307 remains facing upwards (in the z-direction) as the rail connector 1311 rotates. In some embodiments, mechanical constraint can be replaced with a software-defined constrained. For example, each of the third joint 1317 and the additional joint 1319 can be a powered joint, and software can be used to constrain rotation of each joint together.

In some embodiments, the third joint 1317 can comprise a linear joint or prismatic joint (in place of the rotation joint described above and illustrated in the figures) configured to allow linear displacement of the rail 1307 toward and away from the column 1302 (for example, along the y-direction).

The third joint 1317 can comprise a powered joint. In some embodiments, the third joint 1317 can comprise a motorized or hydraulic joint.

The adjustable arm support 1305 can include a fourth joint 1321 as shown. The fourth joint 1321 can be configured to provide the fourth degree of freedom (translation) for the adjustable arm support 1305. For example, the fourth joint 1321 can be configured to allow the rail 1307 to translate back and forth relative to, for example, the table 1301, the column 1302, the carriage 1309, and/or the rail connector 1311. The rail 1307 can extend along a fourth axis 1329. The fourth joint 1321 can be configured to allow the rail 1307 to translate along the fourth axis 1329. In some embodiments, the fourth axis 1329 can be parallel to third axis 1327. In other embodiments, the fourth axis 1329 can be at a non-parallel (e.g., an acute angle) to third axis 1327. In some embodiments, the fourth axis 1329 can be perpendicular to the second axis 1325. In other embodiments, the fourth axis 1329 can be at a non-perpendicular angle (e.g., an acute angle) to the second axis 1325. When the adjustable arm support 1305 is positioned as shown in FIGS. 13A and 13B, the fourth axis 1329 can be perpendicular to the first axis 1323; however, as the adjustable arm support 1305 is rotated about the second joint 1315, the angle between the first axis 1323 and the fourth axis 1329 can vary.

The fourth joint 1321 can comprise a linear or prismatic joint. The fourth joint 1321 can comprise a powered joint, such as a motorized or hydraulic joint. In the illustrated embodiment, the fourth joint 1321 is positioned between the bar or rail connector 1311 and the rail 1307.

As will be described in greater detail below with reference to FIGS. 15A and 15B, translation of the rail 1307 can be configured to provide increased longitudinal reach (for example, along the x-direction) for the system 1300. This may improve the flexibility of the system 1300, allowing the system 1300 to be used in a wider variety of surgical procedures.

In some embodiments, the adjustable arm support 1305 is configured to allow for variable positioning of the rail 1307 relative to the table 1301. In some embodiments, the position of the rail 1307 remains below a support surface plane 1333 that is parallel with an upper surface of the table 1301. This may be advantageous as it may improve the ability to maintain a sterile field above the table support surface plane 1333 during a medical procedure. In the operating environment, medical personal may desire to maintain a sterile field above the surface of the table. As such, there may be heightened requirements or stricter procedures for equipment that is positioned above the surface of the table. For example, equipment positioned above the surface of the table may need to be draped. As such, it may be desirable, and some medical personal may prefer, that the arm support is maintained below the surface of the table. In some instances, when the arm support is maintained below the surface of the table, it may not need to be draped. In other embodiments, however, the adjustable arm support 1305 can adjust the position of the rail 1307 such that it is positioned above the table support surface plane 1333.

In some embodiments, the adjustable arm support 1305 is attached to the base 1303, the column 1302, or the table 1301 at a position below the table support surface plane 1333. As will be described below with reference to FIGS. 18A and 18B, this may advantageously permit the adjustable arm support 1305 (and any attached robotic arms) to be moved to a stowed configuration in which the adjustable arm support 1305 (and any attached robotic arms) are stowed below the table 1301 (see FIG. 18B). This may advantageously make the system 1300 less bulky and/or less cumbersome when compared to previously known surgical robotics systems.

Movement of the arm support 1305 (for example, movement of one or more of the first, second, third, or fourth joints 1313, 1315, 1317, 1321) may be controlled and/or commanded in several ways. For example, the system 1300 can include a controller (e.g., a pendant) either on the bed (patient side) or a surgeon console. As another example, buttons (or other actuation mechanisms) could be included on one or more of the components of the adjustable arm support 1305 (or on one or more of the connected robotic arms). As another example, movement of the adjustable arm support 1305 can be provided automatically by system software, for example, for adjustment within the robot's null space (while maintaining the tooltip position commanded by the surgeon). Additionally, movement of the adjustable arm support 1305 can be provided automatically by system software during setup, deployment, draping, or other workflow steps when tools are not inserted into the patient. Other examples are also possible.

FIGS. 13A and 13B illustrate an embodiment that includes one adjustable arm support 1305. As noted previously, some systems can include more than one adjustable arm support 1305, each supporting one or more robotic arms. In such systems, each adjustable arm support can be configured as described above. Further, in such systems, each adjustable arm support can be controlled independently.

Figure 14A:
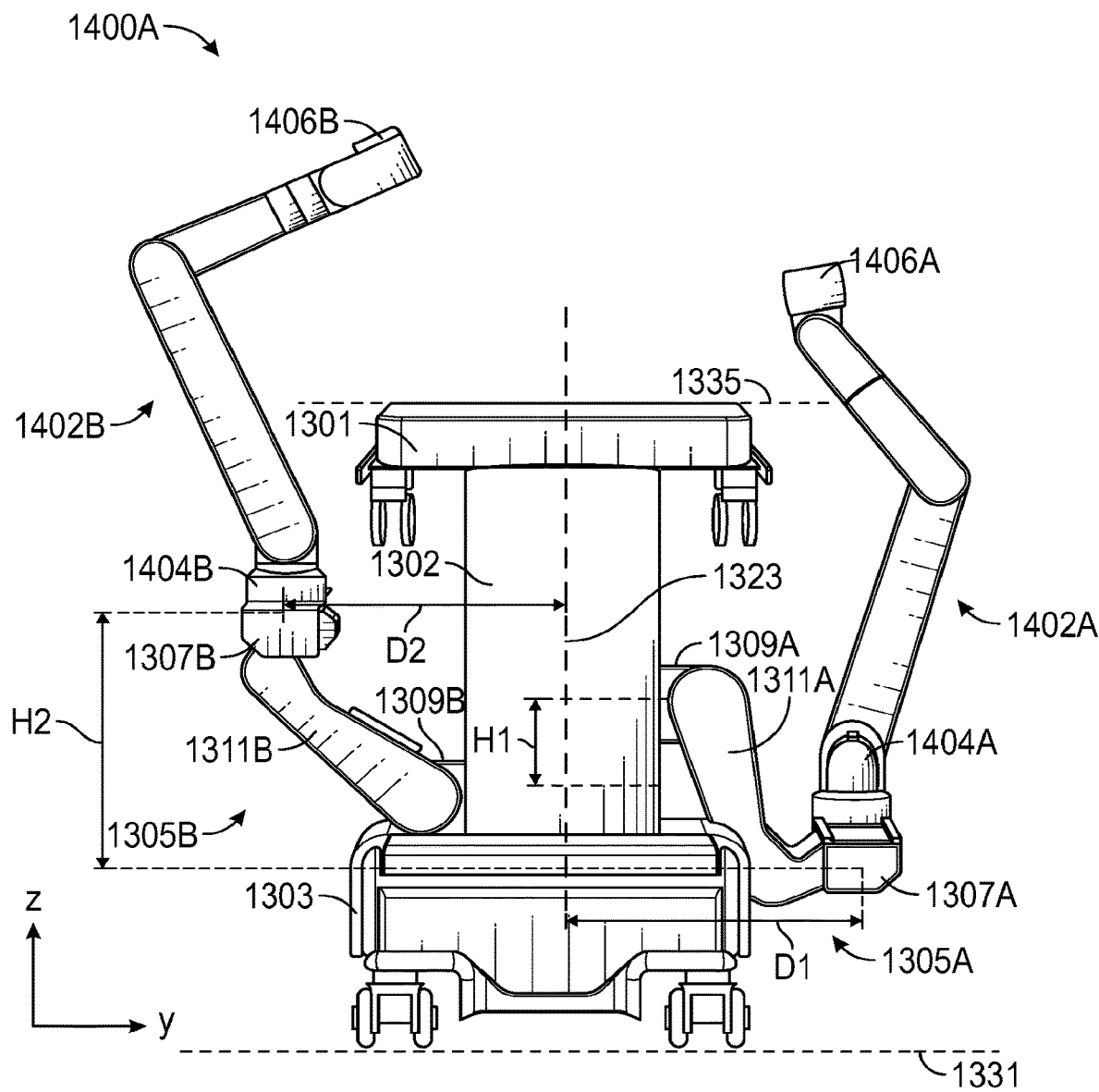
FIG. 14A is an end view of a surgical robotics system with two adjustable arm supports mounted on opposite sides of a table according to one embodiment.

FIG. 14A is an end view of a surgical robotics system 1400A with two adjustable arm supports 1305A, 1305B mounted on opposite sides of the table 1301 according to one embodiment. Each of the adjustable arm supports 1305A, 1305B can be configured as described above. In the illustrated embodiment, a first adjustable arm support 1305A is positioned on a first side of the table 1301 (e.g., the right side as shown in the figure), and a second adjustable arm support 1305B is positioned on a second side of the table 1301 (e.g., the left side as shown in the figure). The second side can be opposite the first side.

Further, a first robotic arm 1402A is illustrated attached to the bar or rail 1307A of the first adjustable arm support 1305A, and a second robotic arm 1402B is illustrated attached to the bar or rail 1307B of the second adjustable arm support 1305B. As illustrated, the first robotic arm 1402A includes a base 1404A attached to the rail 1307A. The distal end of the first robotic arm 1402A includes an instrument drive mechanism 1406A. The instrument drive mechanism 1406A can be configured to attach to one or more robotic medical instruments or tools. Similarly, the second robotic arm 1402B includes a base 1404B attached to the rail 1307B. The distal end of the second robotic arm 1402B includes an instrument drive mechanism 1406B. The instrument drive mechanism 1406B can be configured to attach to one or more robotic medical instruments or tools. Example robotic arms configured for use with the adjustable arm supports 1305 are described below in greater detail in Section XIII (see FIGS. 21-30).

FIG. 14A illustrates that the adjustable arm supports 1305A, 1305B can be independently controlled and positioned. As illustrated, the first adjustable arm support 1305A is positioned at a first height along the first axis 1323, and the second adjustable arm support 1305B is positioned at a second height along the first axis 1323. In some embodiments, the second height can be different and independent from the first height. In other embodiments, the second height can be substantially equivalent to the first height.

In the embodiment in FIG. 14A, the carriage 1309A of the first adjustable arm support 1305A is positioned at a first height along the first axis 1323, and the carriage 1309B of the second adjustable arm support 1305B is positioned at a second height along the first axis 1323 different than the first height. Thus, a height difference H1 can exist between the carriages 1309A, 1309B of the first and second adjustable arm supports 1305A, 1305B. In other embodiments, the carriages 1309A, 1309B of the first and second adjustable arm supports 1305A, 1305B can be positioned at the same height.

Further, FIG. 14A illustrates the position of the bar or rail connectors 1311A, 1311B of the first and second adjustable arm supports 1305A, 1305B, which can also be independently adjusted to have different orientations. For example, as illustrated, the rail connector 1311A of the first adjustable arm support 1305A is rotated downwardly, and the rail connector 1311B of the second adjustable arm support 1305B is rotated upwardly. A height difference H2 can exist between the rails 1307A, 1307B of the first and second adjustable arm supports 1305A, 1305B, as illustrated. Further, in this position, each of the rail connectors 1311A, 1311B, of the first and second adjustable arm supports 1305A, 1305B is positioned at a different distance from the first axis 1323. For example, the rail connector 1311A of the first adjustable arm support 1305A is positioned at a first distance D1 from the first axis 1323, and the rail connector 1311B of the second adjustable arm support 1305B is positioned at a second distance D2 from the first axis 1323. This distance D1 can be different than the distance D2. In some embodiments, the rail connectors 1311A, 1311B, of the first and second adjustable arm supports 1305A, 1305B can be rotated to the same degree and/or the distance D1 can be equal to the distance D2.

Figure 14B:
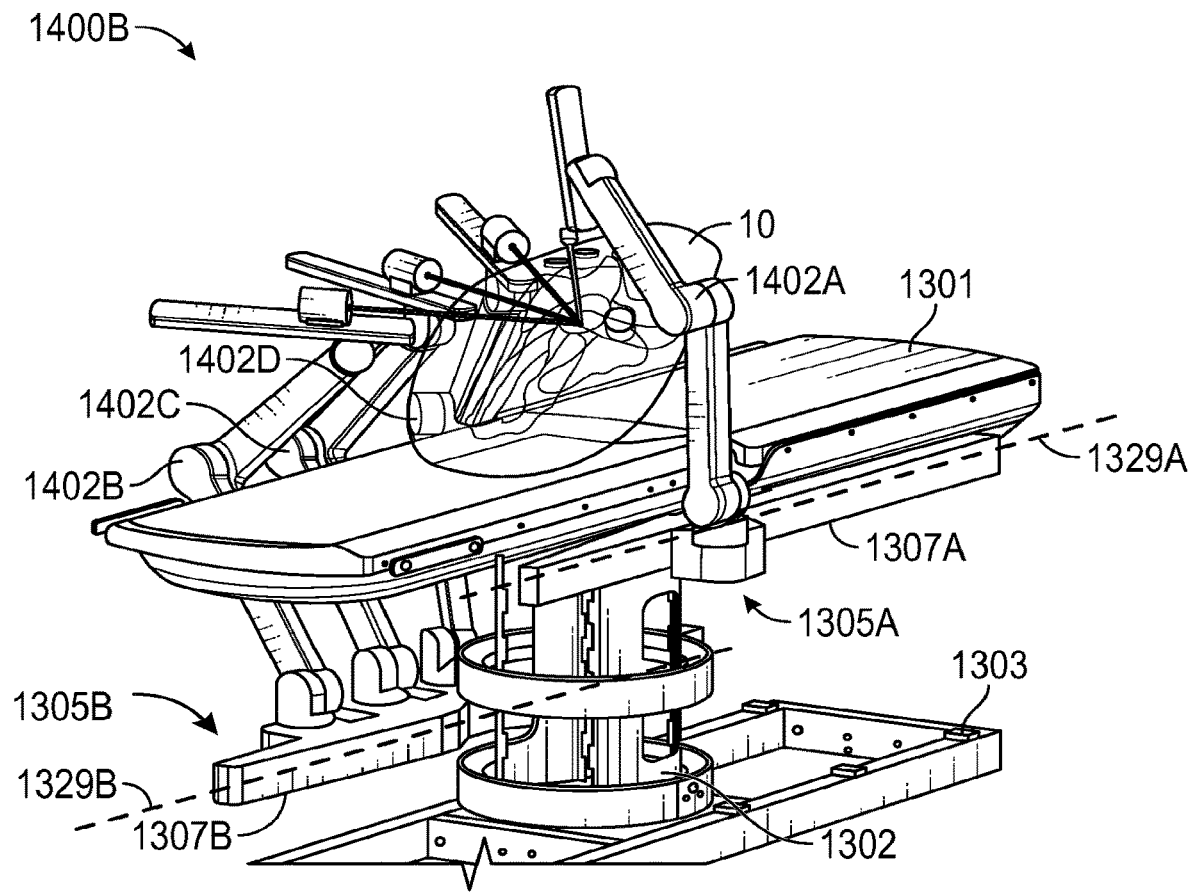
FIG. 14B is an isometric view of a surgical robotics system with two adjustable arm supports and a plurality of robotic arms configured for a laparoscopic procedure according to one embodiment.
Figure 14C:
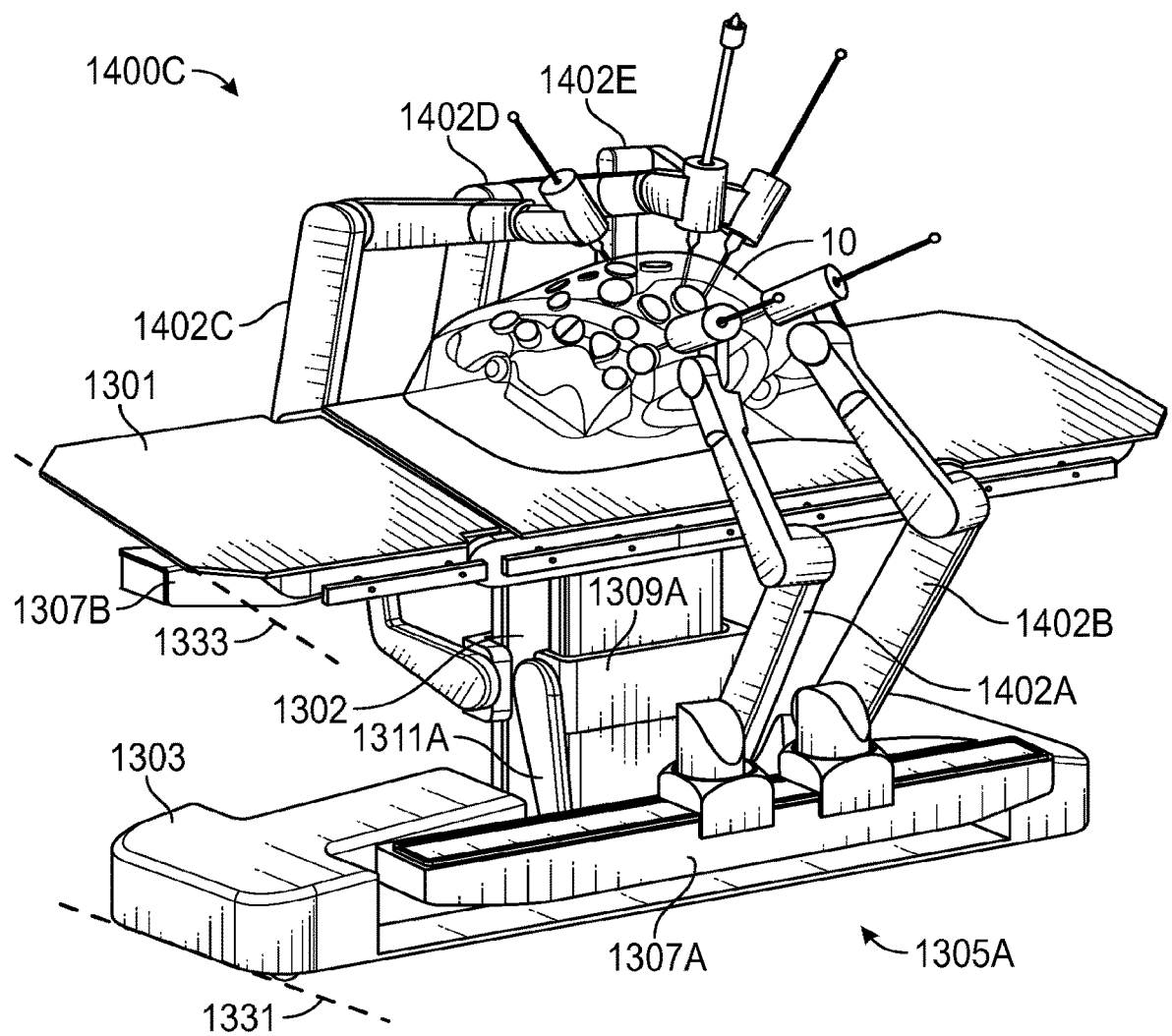
FIG. 14C is an isometric view of a surgical robotics system with two adjustable arm supports and a plurality of robotic arms configured for a laparoscopic procedure according to one embodiment.

FIG. 14A illustrates that the adjustable arm supports 1305A, 1305B can each be positioned or adjusted independently to provide different positions at which the robotic arms attached thereto are supported. FIG. 14A illustrates only one example among many. The adjustable arm supports 1305 can have continuous movement (e.g., vertical or longitudinal) and can be stopped at any point as desired by a surgeon or clinician. This can be beneficial, for example, in creating a height differential between the arm supports, which can be advantageous for certain types of surgeries, such as when one set of robotic arms needs to reach low and the other needs to reach over a patient. For example, as shown in FIG. 14A, the second adjustable arm support 1305B with attached robotic arm 1402B is raised higher than the first adjustable arm support 1305A with attached robotic arm 1402A. This position may be especially helpful when the patient is on its side (e.g., lateral decubitus), such as in a nephrectomy procedure, although one skilled in the art will appreciate that a differential can be beneficial in other procedures as well. FIGS. 14B and 14C provide additional examples.

FIG. 14B is an isometric view of a surgical robotics system 1400B with two adjustable arm supports 1305A, 1305B and a plurality of robotic arms 1402A, 1402B, 1402C, 1402D configured for a laparoscopic procedure according to one embodiment. In the illustrated embodiment, a first adjustable arm support 1305A supports a first robotic arm 1402A, and a second adjustable arm support 1305B supports a second robotic arm 1402B, a third robotic arm 1402C, and a fourth robotic arm 1402D.

The first robotic arm 1402A can be configured to translate back and forth along the rail 1307A of the first adjustable arm support 1305A. That is, the first robotic arm 1402A can be configured to translate along the fourth axis 1329A. This can allow for adjustment of the first robotic arm 1402A relative to the rail 1307A. Similarly, the second robotic arm 1402B, the third robotic arm 1402C, and the fourth robotic arm 1402D can each be configured to translate back and forth along the rail 1307B of the second adjustable arm support 1305B. That is, the second robotic arm 1402B, the third robotic arm 1402C, and the fourth robotic arm 1402D can be configured to translate along the fourth axis 1329B of the second adjustable arm support 1305B. This can allow for adjustment of the second robotic arm 1402B, the third robotic arm 1402C, and the fourth robotic arm 1402D relative to the rail 1307B. Further, each of the second robotic arm 1402B, the third robotic arm 1402C, and the fourth robotic arm 1402D can be independently moved along the rail 1307B such that the spacing between each of the second robotic arm 1402B, the third robotic arm 1402C, and the fourth robotic arm 1402D can be adjusted. Among other things, FIG. 14B illustrates that in some embodiments, the position of each robotic arm 1402 along the corresponding rail 1307 of the corresponding arm support 1305 can be independently controlled and adjusted.

Further, FIG. 14B illustrates another example of a height differential between the first and second arm supports 1305A, 1305B. In the illustrated embodiment, a patient 10 is positioned on his or her side during a laparoscopic procedure. The first adjustable arm support 1305A is positioned in a high position (but below the surface of the table 1301) such that the first robotic arm 1402A can reach over the patient 10. As illustrated, the second adjustable arm support 1305B is positioned at a lower position such that the second robotic arm 1402B, the third robotic arm 1402C, and the fourth robotic arm 1402D can access an anterior side of the patient.

In some embodiments, one or more of the robotic arms 1402A, 1402B, 1402C, 1402D can operate laparoscopic surgical instruments or tools, and one or more of the other of the 1402A, 1402B, 1402C, 1402D can operate a camera laparoscopically inserted into the patient. In some embodiments, the one or more laparoscopic surgical instruments and the camera can be sized and configured to extend through one or more laparoscopic ports in a patient.

FIG. 14C is an isometric view of a surgical robotics system 1400C with two adjustable arm supports 1305A, 1305B and a plurality of robotic arms 1402A, 1402B, 1402C, 1402D, 1402E configured for a laparoscopic procedure according to one embodiment. In the illustrated embodiment, a first adjustable arm support 1305A supports a first robotic arm 1402A and a second robotic arm 1402B, and a second adjustable arm support 1305B supports a third robotic arm 1402C, a fourth robotic arm 1402D, and a fifth robotic arm 1402E.

In the illustrated embodiment, the table 1301 supporting the patient 10 is positioned at an angle relative to the floor. That is, rather than being parallel, as illustrated for example, in FIG. 14B, a table surface plane 1333 is angled with respect to a support surface plane 1331. The first adjustable arm support 1305A, positioned on the lower side of the table 1301, can be positioned in a low position such that the first robotic arm 1402A and the second robotic arm 1402B can access the patient 10. As illustrated, the second adjustable arm support 1305B is positioned at a higher position (which may be lower than the table support surface 1333) such that the third robotic arm 1402C, the fourth robotic arm 1402D, and the fifth robotic arm 1402E can reach over and access the patient 10.

Figure 15A:
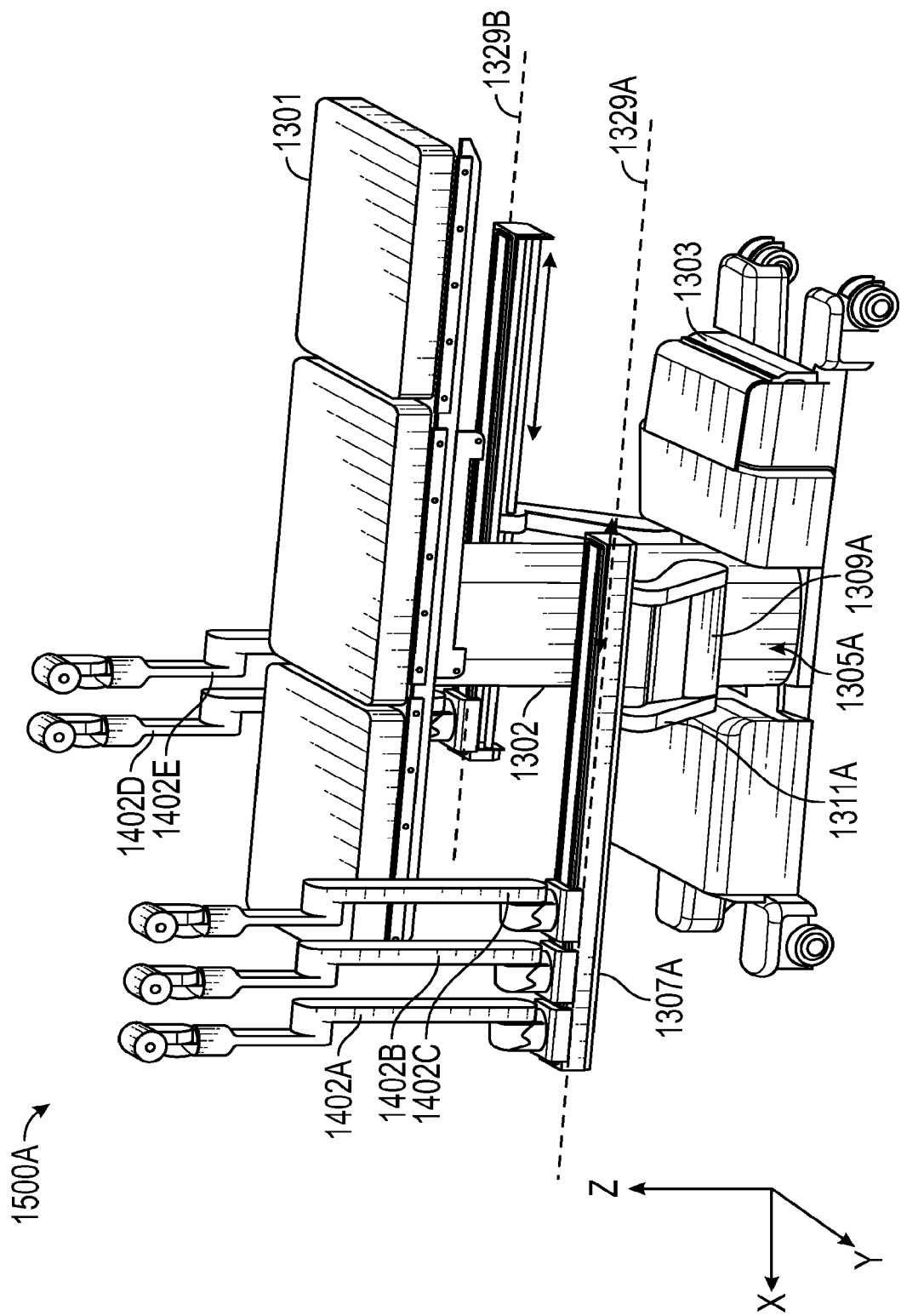
FIG. 15A is an isometric view of a surgical robotics systems with two adjustable arm supports that are configured to translate to adjust the position of the adjustable arm supports according to one embodiment.

FIG. 15A is an isometric view of a surgical robotics systems with two adjustable arm supports 1305A, 1305B that are configured to translate to adjust the position of the adjustable arm supports 1305A, 1305B according to one embodiment. As described previously, the adjustable arm support 1305 can include a fourth joint 1321 configured to allow the rail 1307 to translate along the fourth axis 1329 relative to the base 1303, column 1302, table 1301, carriage 1309, and/or rail connector 1311. FIG. 15A illustrates that, in embodiments that include two adjustable arm supports 1305A, 1305B, the rail 1307A, 1307B of each adjustable arm support 1305A, 1305B can be translated along its corresponding axis 1329A, 1329B, independently of the other rail. For example, in FIG. 15A, the rail 1307A can translate back and forth along the axis 1329A, independently from the rail 1307B, which can also translate back and forth along the axis 1329B.

In other embodiments, rails 1307 are not configured to translate along the axis 1329. For example, in some embodiments, longer rails 1307 can be used in lieu of translating rails. In some embodiments, translation of the rails 1307 permits shorter rails 1307 to be used while still maintaining the overall versatility and flexibility of the system. In some embodiments, shorter rails 1307 (with or without translation) can improved the ability of system to be stowed below the table 1301 (see FIG. 18B).

Figure 15B:
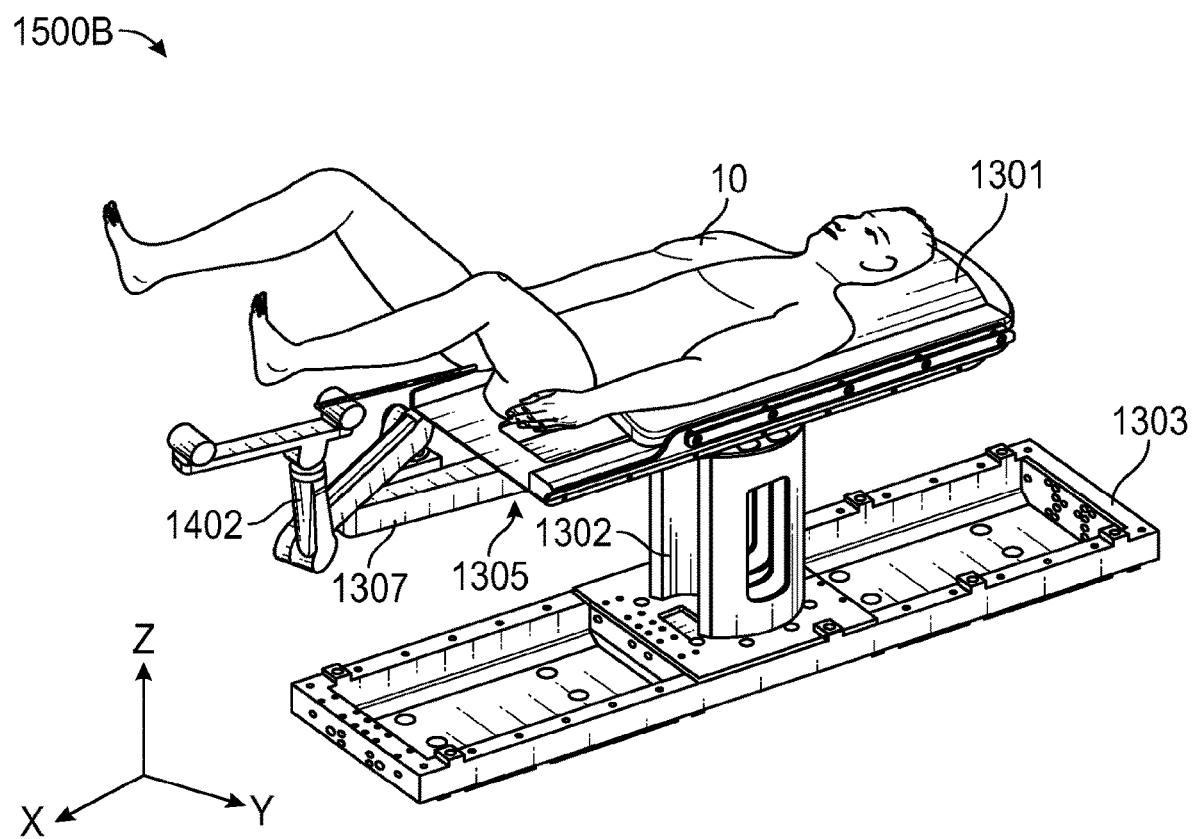
FIG. 15B is an isometric view of a surgical robotics system with an adjustable arm support and robotic arm configured for an endoscopic procedure according to one embodiment.

FIG. 15B is an isometric view of a surgical robotics system 1500B with an adjustable arm support 1305 and robotic arm 1402 configured for an endoscopic procedure according to one embodiment. FIG. 15B illustrates that, in some embodiments, a system including an adjustable arm support 1305 can be configured to provide a long longitudinal range of motion that can be useful, for example, in an endoscopic procedure, such as a ureteroscopy, wherein an endoscope is inserted into the patient through the groin area. For example, as shown in FIG. 15B, the rail 1307 can be translated all the way toward the foot of the table 1301. From there, the arm 1402 can further extend longitudinally to position an instrument between the legs of the patient 10 for access to the groin area. Although only one robotic arm 1402 is illustrated in FIG. 15B, in other embodiments, multiple robotic arms, either mounted on the same adjustable arm support 1305 or an additional arm support 1305 can be configured for use in an endoscopic procedure. FIG. 15B provides only one example of an endoscopic procedure. Systems including adjustable arm supports 1305 can be used in other types of endoscopic procedures, such as bronchoscopy, for example.

Figure 16:
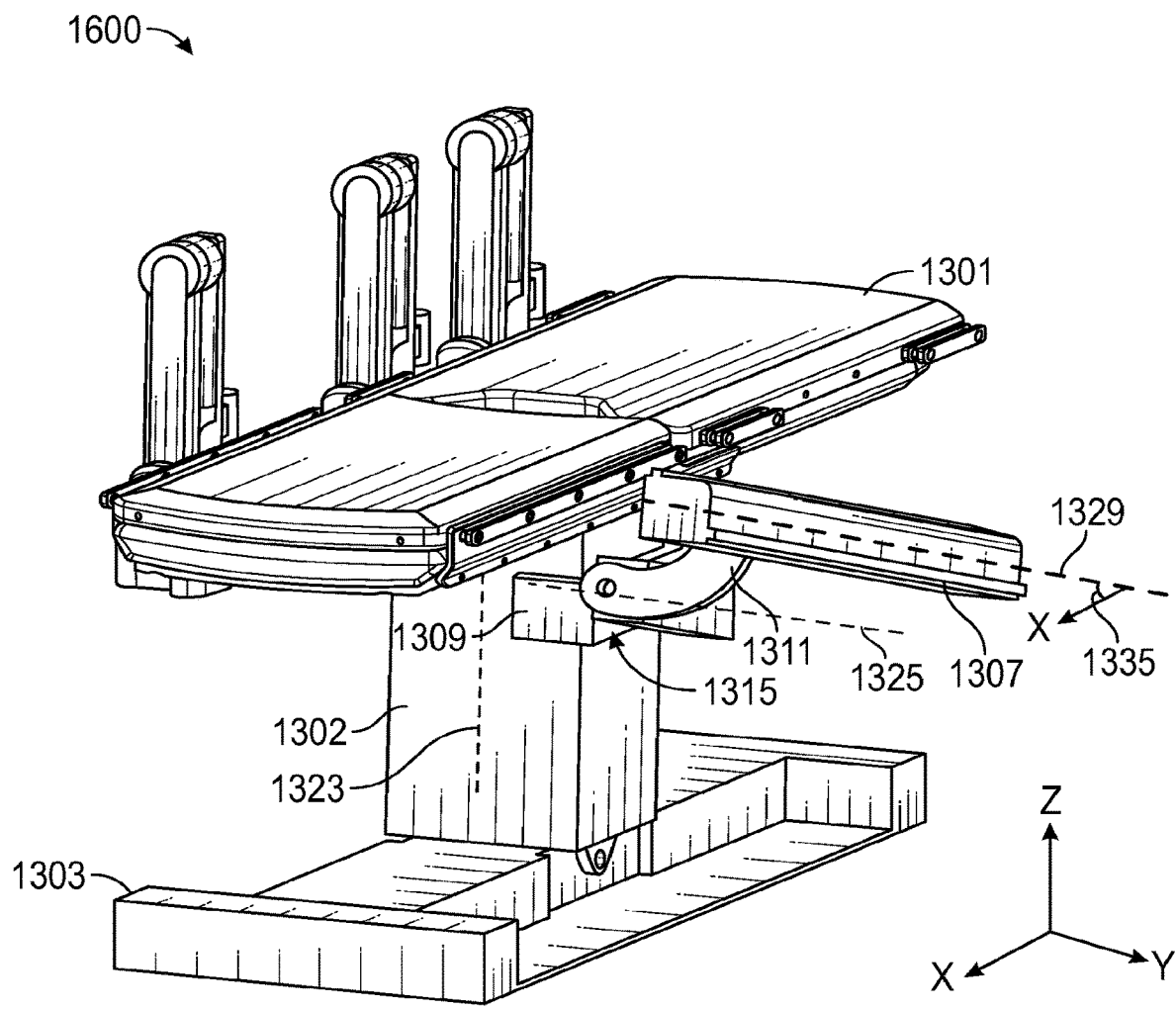
FIG. 16 is an isometric view of a surgical robotics system with an adjustable arm support configured with a rail capable of tilting according to one embodiment.

FIG. 16 is an isometric view of a surgical robotics system 1600 with an adjustable arm support 1305 configured with a rail 1307 capable of tilting according to one embodiment. As discussed previously, an arm support can include a second joint 1315 configured to allow the arm support 1305 to tilt. In the illustrated embodiment of FIG. 16, the second joint 1315 is positioned between the carriage 1309 and the rail connector 1311, although, as discussed previously, other positions for the second joint 1315 are possible. The second joint 1315 can be rotational joint configured to rotate or provide adjustment of the arm support 1305 about the second axis 1325. As shown in FIG. 16, by rotating or providing adjustment of the arm support 1305 about the second axis 1325, a tilt angle 1335 of the axis 1329 can be adjusted. The tilt angle 1335 can be measured between, for example, the axis 1329 (of the rail 1307) and the x-axis, the support surface plane 1331, or the table surface plane 1333.

In some embodiments, the second joint 1315 permits tilting of the rail relative to the table 1301. In some embodiments, the table 1301 can also pivot or tilt (for example to a Trendelenburg position), and the second joint 1315 can allow the adjustable support arm 1315 to follow the pivoting or tilting of the table 1301. This can allow surgical arms 1402 to remain in position a relative to the patient 10 and/or table 1301 as the table 1301 pivots or tilts. This may be advantageous as a surgeon or clinician may desire to pivot or tilt the table 1301 intraoperatively. In some embodiments, the second joint 1315 pivots or tilts to allow the rail 1307 to remain parallel with the table 1301 as the table tilts. In some embodiments, the rail 1307 need not remain parallel with the table 1301.

Figure 17A:
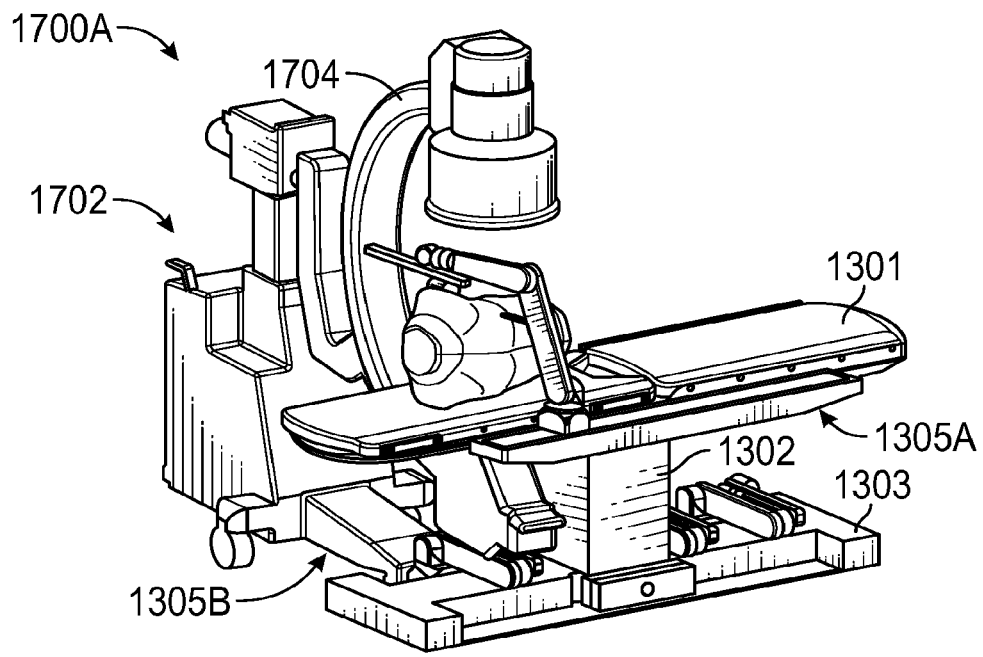
FIG. 17A is an isometric view of a surgical robotics system with adjustable arm supports positioned to allow access for a C-arm of a medical imaging device according to one embodiment.
Figure 17B:
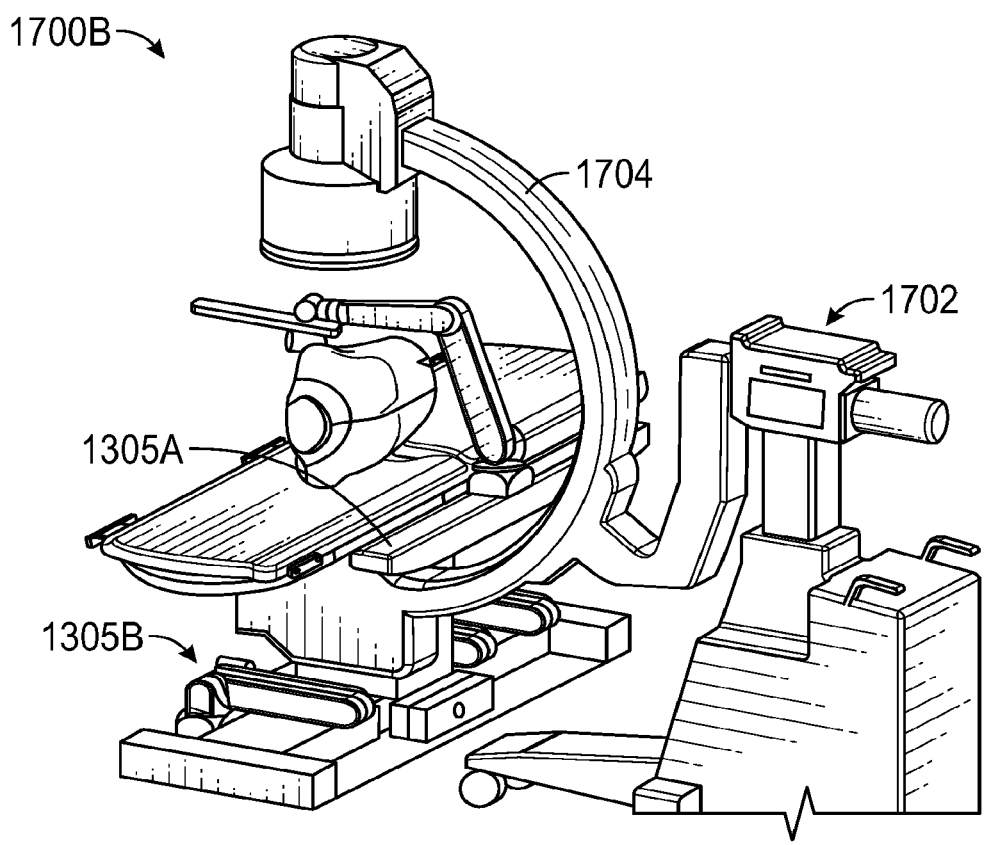
FIG. 17B is an isometric view of the surgical robotics system of FIG. 17A with the adjustable arm supports positioned to allow access for the C-arm of the medical imaging device according to another embodiment.

FIGS. 17A and 17B illustrate that systems including adjustable arm supports 1305 may provide improved access for medical imaging devices. As described above, the position of the adjustable arm support 1305 can be adjusted so as to allow access to or accommodate a medical imaging device, such as a C-arm. In addition to providing improved access for medical imaging devices, the adjustable arm supports also provide improved access for clinicians.

FIG. 17A is an isometric view of a surgical robotics system 1700A with adjustable arm supports 1305A, 1305B positioned to allow access for a C-arm 1704 of a medical imaging device 1702 according to one embodiment. As shown, the second adjustable arm support 1305B is positioned near the floor, so as to be positioned below the C-arm 1704 of the medical imaging device. The first adjustable arm support 1305A is positioned near the table 1301 such that the robotic arm can access the patient.

FIG. 17B is an isometric view of the surgical robotics system 1700B with the adjustable arm supports 1305A, 1305B positioned to allow access for the C-arm 1704 of the medical imaging device 1702 according to another embodiment. In the illustrated embodiment, the first adjustable arm support 1305A is positioned near the table 1301, such that the C-arm 1704 partially surrounds the first adjustable arm support 1305A.

The adjustability of the adjustable arm supports 1305 can advantageously allow the systems to work with will other types of medical imaging devices as well.

Figure 18A:
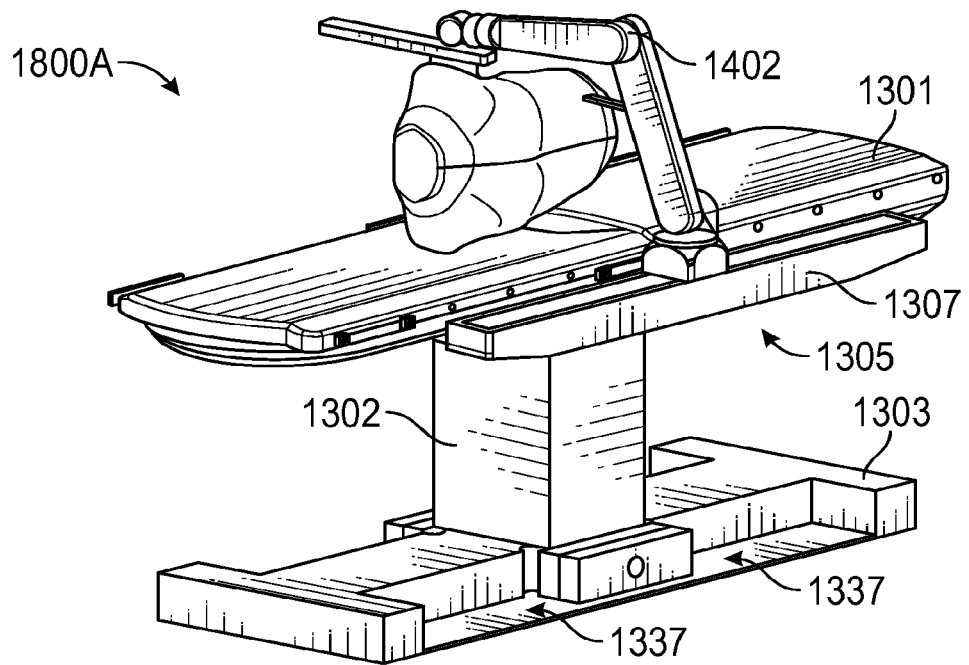
FIG. 18A is an isometric view of a surgical robotics system with adjustable arm supports positioned in a deployed configuration according to one embodiment.
Figure 18B:
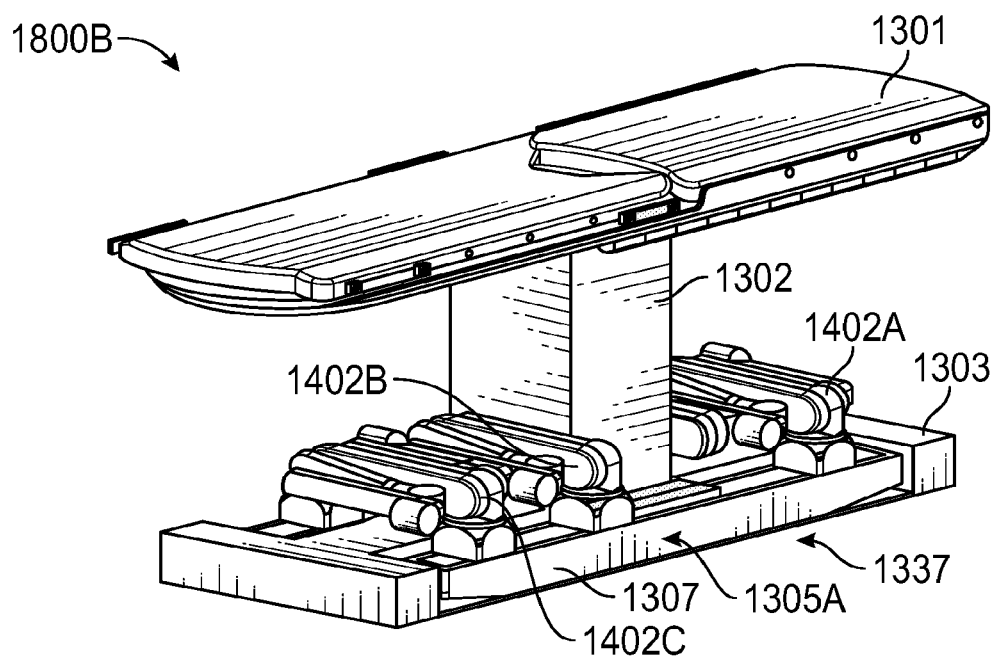
FIG. 18B is an isometric view of a surgical robotics system with adjustable arm supports positioned in a stowed configuration according to one embodiment.

FIGS. 18A and 18B illustrate that systems including adjustable arm supports 1305 can be configured to allow the adjustable arm supports 1305 and corresponding robotic arms 1402 to stow conveniently below the table 1301. This may advantageously provide that the systems are less bulky and cumbersome than some surgical robotics systems. The adjustable arm supports 1305 can transition between a stowed configuration (FIG. 18B) and a deployed configuration (FIG. 18A).

FIG. 18A is an isometric view of a surgical robotics system 1800A with an adjustable arm support 1305 positioned in a deployed configuration according to one embodiment. As shown, the adjustable arm support 1305 has been adjusted such that the rail 1307 is positioned adjacent to a side of the table 1301, and a robotic arm 1402 has been deployed so as to access the patient 10. FIG. 18A also illustrates that the base 1303 can include a recess 1337. The recess 1337 can be configured to receive the arm support 1305 in the stowed configuration, as shown for example, in FIG. 18B.

FIG. 18B is an isometric view of a surgical robotics system 1800B with adjustable arm supports 1305A, 1305B positioned in a stowed configuration according to one embodiment. As shown, bar or rails 1307A, 1307B of each arm support are received into recesses 1337 in the base 1303. In some embodiments, the robotic arms 1402A, 1402B, 1402C can fold over the arm supports 1305A, 1305B as shown. A stowed configuration, for example, with the arm supports 1305A, 1305B stored in recesses 1337 below the table 1301, as shown in FIG. 18B, can advantageously make the system less bulky and cumbersome. In other embodiments, both the arm supports and robotic arms can be stored into recesses in the base 1303. While embodiments described herein illustrate an arm support in a low position relative to the table, in other embodiments, adjustable arm supports can be provided from an elevated or suspended position above the table. These adjustable arm supports in a suspended position can have attributes similar to those that are positioned lower, including independent adjustability, height differential relative to one another, tilt, and longitudinal translation.

In some embodiments, systems including adjustable arm supports 1305 can be configured to be mobile. For example, in some embodiments, the base 1303 can include wheels to allow the system to be easily repositioned (see, e.g., FIG. 14A). For example, the system could have a separate transport cart that lifts it off the floor and moves it. In some embodiments, the system is not permanently affixed in the operating room.

Figure 19:
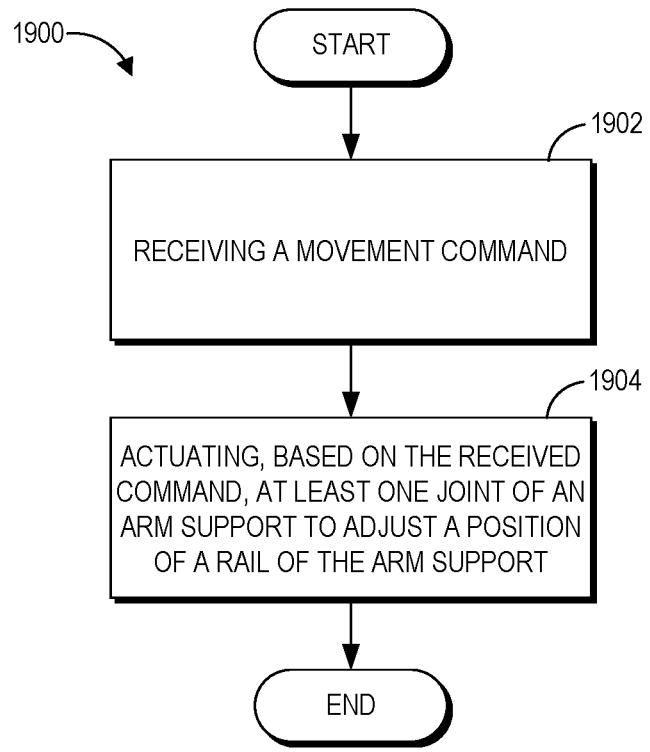
FIG. 19 is a flow chart illustrating a method for operating a surgical robotics system with adjustable arm supports according to one embodiment.

FIG. 19 is a flow chart illustrating a method 1900 for operating a surgical robotics system with adjustable arm supports according to one embodiment. For example, the method 1900 can be used to operate any of the systems described above with reference to FIGS. 13A-18B. In some embodiments, the method 1900 can be stored as computer readable instructions stored in a memory. A processor can access the memory and execute the computer readable instructions to perform the method 1900.

The method 1900 begins at block 1902 which involves receiving a command. In some embodiments, the command is received from a physician, nurse, physician assistant, surgeon staff, etc. The command may relate to the positioning of at least one of a first robotic arm, a medical instrument coupled to an end effector of the robotic first arm, and/or an arm support coupled to a base of the first robotic arm. In some embodiments, the command may be a command to stow or deploy the system.

In some embodiments, a first command actuates the at least one joint to adjust the position of the arm support along a vertical axis of the column, a second command actuates a second joint for pivoting up the arm support, a third command actuates a third joint for tilting the arm support and a fourth command causes longitudinal translation of the arm support.

At block 1904, the method 1900 involves actuating at least one joint of an adjustable arm support to adjust a position of a bar or rail of the arm support based on the received command. For example, the method 1900 may actuate one or more of the first joint, the second joint, the third joint, and/or the fourth joint. This may cause the arm support to move in one or more of its degrees of freedom.

The method 1900 may further include raising the arm support, the first robotic arm, and the second robotic arm from a stowed position below the table; positioning the arm support, the first robotic arm and the second robotic arm adjacent the table; adjusting a position of the arm support relative to the table via at least one of the first command, second command, third command, or fourth command, and adjusting a position of the first robotic arm relative to the second robotic arm along the rail of the support joint in preparation for a surgical procedure. In some embodiments, the arm support is positioned below an upper surface of the table.

In some embodiments, the method 1900 is executed by a controller for executing one or more commands based on a kinematics model, wherein the one or more commands control the positioning of one or more of the first robotic arm, the medical instrument coupled to an end effector of the robotic first arm; and an arm support coupled to a base of the first robotic arm and to a column supporting a patient-support table, wherein the arm support comprises at least one joint and a rail configured to support the first robotic arm.

Figure 20:
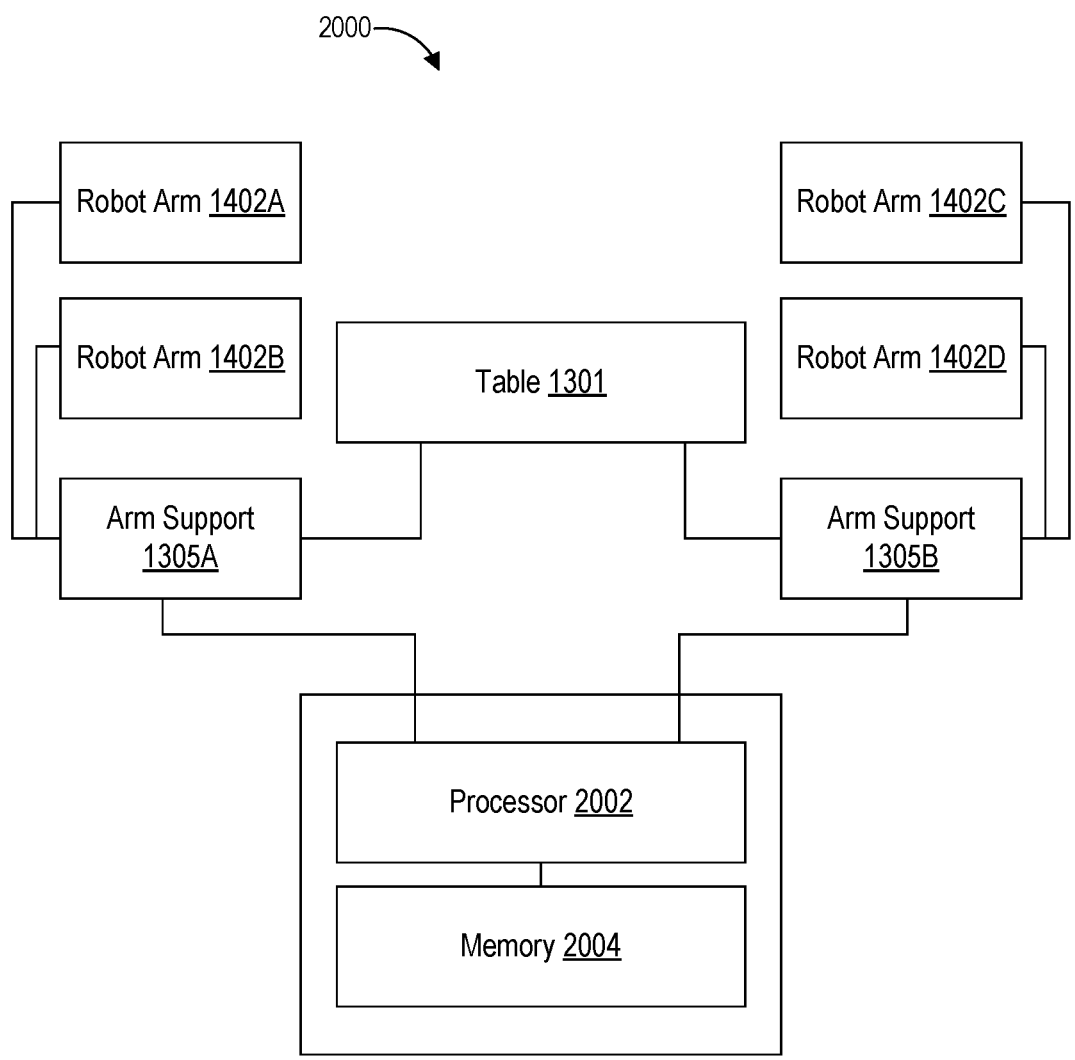
FIG. 20 is a block diagram of a surgical robotics system with adjustable arm supports according to one embodiment.

FIG. 20 is a block diagram of a surgical robotics system 2000 with adjustable arm supports 1305A, 1305B according to one embodiment. As shown, the system 2000 includes a processor 2002 in communication with a memory 2004. The processor 2002 and memory 2004 can be configured to execute, for example, the method 1900 described above.

The system also includes the table 1301. In the illustrated embodiments, two adjustable arm supports 1305A, 1305B are coupled to the table 1301. The adjustable arm supports 1305A, 1305B can be coupled to the table 1301, a column 1302 supporting a table, or a base 1303 supporting the column. Each of the adjustable arm supports 1305A, 1305B is in communication with the processor 2002 such that the process can adjust the position of the adjustable arm supports 1305A, 1305B.

In the illustrated embodiment, a set of robotic arms is attached to each of the adjustable arm supports 1305A, 1305B. For example, robotic arms 1402A, 1402B are coupled to adjustable arm support 1305A, and robotic arms 1402C, 1402D are coupled to adjustable arm support 1305B. In other embodiments, other numbers of robotic arms (e.g., one, three, four, etc.) can be coupled to each arm support 1305A, 1305B. Example robotic arms are described in section XIII below. In some embodiments, as the arm supports support multiple robotic arms, the stiffness of the arm supports can be increased. This increased stiffness provides an added benefit of stability when used with multiple arms, as this can reduce the shaking of the robotic arms during a surgical process.

In some embodiments, the processor 2002 is configured to execute instructions stored in the memory 2004 to adjust a position of the bar or rail along the first axis in response to receiving a command. The command can comprise a command to adjust a position of a robotic medical tool coupled to a robotic arm coupled to the arm support. In some embodiments, the processor 2002 is further configured to execute the instructions to cause the system to at least adjust a position of a rail or the arm supports 1305A, 1305B in response to a physician selected procedure. In some embodiments, the processor 2002 is further configured to execute the instructions to cause the system 2000 to at least adjust a position of the rail to avoid a collision between the robotic arm and at least one of: the table, a patient, an additional robotic arm, and a medical imaging device. The system 2000 may further be configured to avoid collision with other items in the environment of the system, such as, pendants, stirrups, things that clip onto the bed rail, a nurse, etc.). In addition to collision avoidance, the processor 2002 can further be configured to adjust the position of the arm supports 1305A, 1305B to optimize pose or improve manipulability of the robotic arms 1402A, 1402B, 1402C, 1402D.

XIII. Robot Arms Associated with Adjustable Arm Supports

The adjustable arm supports described above can be configured to mount to the table, the column, or the base, and can be adjustable (moveable in various degrees of freedom) to support robotic arms positioned on the adjustable arm supports. As the adjustable arm supports can be configured to mount below the surface of the table, in accordance with some embodiments, it can be advantageous to employ certain types of robotic arms with the adjustable arm supports. In some embodiments, the arms support(s) and/or the robotic arms coupled thereto can be mounted at least partially or wholly above the surface of the table. This section outlines certain features of robotic arms configured for use with the adjustable arm supports described above.

The robotic arms described in this section can be optimized for low mount positions relative to a table top (e.g., below a table top), which can face challenges such as collisions with the table top and other robotic arms. One skilled in the art will appreciate, however, that the robotic arms described in this section are not limited to low mount positions, and include features that are beneficial when attached to arm supports that are positioned above a surface of a table or suspended above a patient. In some embodiments, the robotic arms include several degrees of freedom (e.g., seven degrees of freedom) with at least one redundant degree freedom to provide greater flexibility to the robotic arm. As used herein, a robotic arm with redundant degrees of freedom can be one that contains more degrees of freedom than are necessary to perform a given task, and can accomplish the task in a wide variety of ways. For example, a robotic arm with redundant degrees of freedom can contain more degrees of freedom than are necessary to position an end effector (e.g., the end of a tool) in a desired location in a patient, and can achieve the desired position of the end effector in a wide variety of ways.

The robotic arms described in this section can further be optimized for rotating a tool with an end effector about a given point in space (e.g., the "remote center;" as used herein, a remote center can be considered as a fixed point around which a medical instrument rotates, with no physical revolute joint of the robotic system physically located at the remote center) while being supported, in some embodiments, by a mount point below the remote center (e.g., below a table top). The robotic arms can be optimized to operate in close proximity to (e.g., within a defined distance of) other robotic arm(s).

In some embodiments, the robotic arms described in this section may address (e.g., mitigate, resolve or eliminate) one or more issues that can occur in an operating room. For example, issues that the robotic arms and systems described in this application are designed to address can include operating in a limited space. In particular, space may be limited for a system with robotic arms coming from below a table. The issues that the robotic arms and systems described in this application are designed to address can include collisions with other robotic arms and/or other objects in the environment (e.g., the table, patient, doctors, medical imaging equipment, etc.). Additionally, the issues that the robotic arms and systems described in this application are designed to address can include challenges associated with a system coming from below a table. Such a system may need added flexibility to perform particular surgical procedures in which the robotic arms must position tools so as to access patient locations that are positioned above the laparoscopic ports (e.g., a ventral hernia procedure), e.g., to avoid collisions (e.g., with the table). The features and advantages of the robotic arms described herein will become apparent from the following discussion of FIGS. 21-30.

Figure 21:
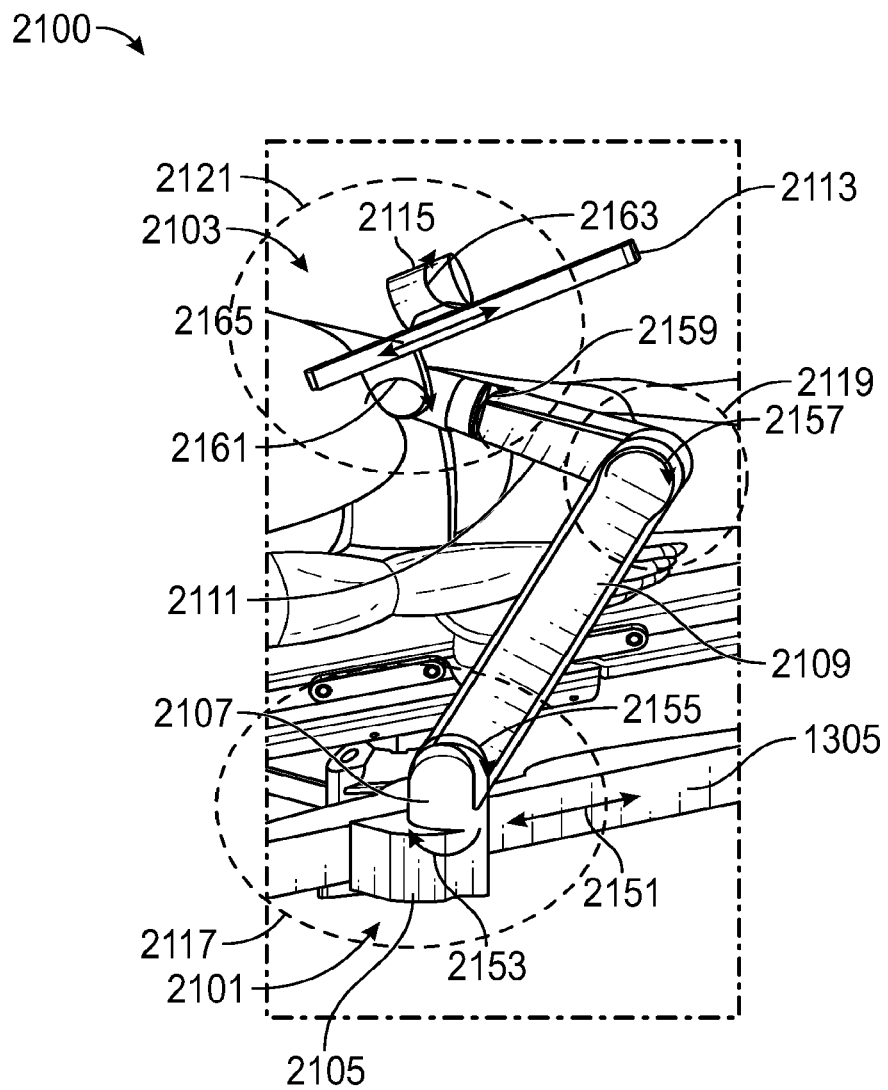
FIG. 21 is an isometric view of a robotic arm according to one embodiment.

FIG. 21 is an isometric view of a robotic arm 2100 according to one embodiment. The robotic arm 2100 can be configured for use with the adjustable arm support(s) 1305 described above. The robotic arm 2100 extends between a proximal portion 2101 and a distal portion 2103. The proximal portion 2101 can be configured to mount or attach to an adjustable arm support 1305. For example, the proximal portion 2101 of the robotic arm 2100 can be configured to mount or attach to a bar, track, or rail 1307 of an adjustable arm support 1305. As described above, the adjustable arm support 1305 can be configured with one or more degrees of freedom so as to position the robotic arm 2100 relative to a table. In some embodiments, the adjustable arm support 1305 and/or the robotic arm 2100 are configured to transition between a stowed state and a deployed state. In the stowed state, the adjustable arm support 1305 and the robotic arm 2100 may be positioned below the table (see, e.g., FIG. 18B). In the deployed state, at least a portion of the robotic arm 2100 may extend above the surface of the table (see, e.g., FIG. 18A). The adjustable arm support 1305 may be positioned below the surface of the table in the deployed state. In some embodiments, the adjustable arm support 1305 (or a bar or rail 1307 thereof) may be positioned above the surface of the table in the deployed state.

An instrument driver 2115, also referred to as an instrument drive mechanism (IDM), can be positioned at the distal portion 2103 of the robotic arm 2100. The instrument driver 2115 can be configured to attach or connect to a medical instrument. The instrument can be, for example, a laparoscopic instrument, an endoscopic instrument, a camera, etc. The instrument driver 2115 may be configured to actuate the instrument. For example, the instrument driver 2115 may include one or more motors, pulleys, capstans, or cables configured to actuate the instrument. As will be described below (see Section XIV), an insertion mechanism associated with the robotic arm 2100 may be included at the distal portion 2103 of the robotic arm 2100 and configured to insert (or retract) at least a portion of the instrument along an axis. As explained below, the insertion mechanism can be configured as part of the robotic arm 2100 itself (e.g., FIG. 21) or as part of the instrument attached to the instrument driver 2115 (e.g., FIG. 24).

The robotic arm 2100 may comprise a plurality of components arranged serially. The components can be connected by one or more joints (e.g., motorized or hydraulic joints) configured to allow movement or articulation of the robotic arm 2100. As illustrated, for some embodiments, the joints can be grouped into the shoulder 2117, the elbow 2119, and the wrist 2121 as shown in FIG. 21. That is, in some embodiments, the robotic arm 2100 includes the shoulder 2117, the elbow 2119, and the wrist 2121, and that one or more of the shoulder 2117, the elbow 2119, and the wrist 2121 can include a plurality of joints. For example, in the illustrated example, the shoulder 2117 includes three joints, the elbow 2119 includes one joint, and the wrist 2121 includes two joints. Stated another way, in some embodiments, one or more of the shoulder 2117, the elbow 2119, or the wrist 2121 can provide more than one degree of freedom for the robotic arm 2100. For example, in the illustrated embodiment, the shoulder 2117 is configured to provide three degrees of freedom, the elbow 2119 is configured to provide one degree of freedom, and the wrist 2121 is configured to provide two degrees of freedom. In some embodiments, the wrist can include an insertion degree of freedom such that the robotic arm 2100 can include at least seven degrees of freedom in accordance with some embodiments. In other embodiments, the shoulder 2117, the elbow 2119, or the wrist 2121 can be configured with other numbers of joints and/or to provide other numbers of degrees of freedom.

The shoulder 2117 can be located generally at the proximal portion 2101 of the robotic arm 2100. The wrist 2121 can be located generally at the distal portion 2103 of the robotic arm 2100. The elbow 2119 can be located generally between the proximal portion 2101 and the distal portion 2103. In some embodiments, the elbow 2119 is located between the proximal link 2109 and the distal link 2111. In some embodiments, the robotic arm 2100 can include other joints or regions of joints than those illustrated in FIG. 21. For example, the robotic arm 211 could include a second elbow (comprising one or more joints) between the elbow 2119 and the wrist 2121 and/or between the elbow 2110 and the shoulder 2117.

The various degrees of freedom of the robotic arm 2100 of FIG. 21 are illustrated with arrows. The arrows are intended to indicate the motions provided by each degree of freedom. The illustrated embodiment includes the following degrees of freedom. Not all degrees of freedom need be included in all embodiments, and in other embodiments, additional degrees of freedom can be included. The joints providing the various degrees of freedom can be powered joints, such as motorized joints or hydraulically powered joints, for example.

As illustrated, the robotic arm 2100 includes a degree of freedom 2151 permitting shoulder translation. This degree of freedom can allow the robotic arm 2100 to move along the arm support 1305. For example, this degree of freedom can allow the robotic arm 2100 to move linearly along the arm support 1305, for example, along the rail 1307 of the arm support. When multiple robotic arms 2100 are attached to the arm support 1305, the translation advantageously reduces the risk of collision between the different arms.

The robotic arm 2100 can also include a degree of freedom 2153 permitting shoulder yaw. The degree of freedom 2153 can permit, for example, rotation of the shoulder housing 2107 (and correspondingly the remainder of the robotic arm 2100) relative to the base 2105.

The robotic arm 2100 can also include a degree of freedom 2155 permitting shoulder pitch. This degree of freedom 2155 can permit, for example, adjustment of the proximal link 2109 relative to the shoulder housing 2107. For example, this degree of freedom can be used to adjust an angle of the proximal link 2109.

The shoulder 2117 can be configured to provide the shoulder yaw degree of freedom 2153 and the shoulder pitch degree of freedom 2155. For example, the shoulder 2117 can include one or more joints near the arm support 1305 that can allow the proximal link 2109 to point from the base 2105 of the arm 2100 in any direction. In some embodiments, these shoulder degrees of freedom can be arranged such that the proximal and distal links, for example, point inward toward the remote center (see, for example, FIG. 22).

The robotic arm 2100 can also include a degree of freedom 2157 permitting elbow pitch. This degree of freedom 2157 can permit adjustment of the distal link 2111 relative to the proximal link 2109. For example, this degree of freedom 2157 can permit adjustment of an angle between the distal link 2111 and the proximal link 2109. This degree of freedom can be provided by the elbow 2119. In some embodiments, this degree of freedom is provided by a pivot joint that ensures that the distal link 2111 and the proximal link 2109 remain aligned (for example within a single plane or parallel planes). This alignment advantageously reduces the risk of collision among the arms, as the arms fan out and stay away from one another. Further, as described below, due to the enhanced motion of the wrist 2121 (e.g., providing multiple degrees of freedom), the motion at the elbow 2119 can be minimized, with the fastest motions of the robotic arm 2100 occurring at the wrist 2121.

The robotic arm 2100 can also include a degree of freedom 2159 permitting wrist yaw. This degree of freedom 2159 can allow adjustment of a component connected to the distal link 2111 relative to the distal link 2111. For example, this degree of freedom 2159 can allow adjustment between an insertion axis body 2113 or an instrument driver 2115 and the distal link 2111. In some embodiments, this degree of freedom 2159 is used to adjust an angle of rotation of the component attached to the distal link 2111 relative to the distal link 2111. Rotation can be measured, for example, around an axis of the distal link 2111.

The robotic arm 2100 can also include a degree of freedom 2161 permitting wrist pitch. This degree of freedom 2161 can allow additional adjustment of the component connected to the distal link 2111 relative to the distal link 2111. In some embodiment, this degree of freedom 2161 permits adjustment of an angle of tilt between the component connected to the distal link 2111 and the distal link 2111.

The robotic arm 2100 can also include a degree of freedom 2163 permitting instrument driver roll. This degree of freedom 2163 can be configured allow an instrument attached to the instrument driver (or the instrument driver itself) to be rolled around its axis.

In some embodiments, the wrist 2121 is configured to provide the wrist yaw, wrist pitch, and instrument driver roll degrees of freedom. In some embodiments, the wrist 2121 may comprise a partially spherical or spherical joint in some embodiments. The wrist 2121 can allow the robotic arm 2100 to pitch and yaw an instrument connected thereto about a remote center while minimizing movement of the robotic arm's other links. In other words, the wrist 2121 can allow motion to be minimized on other parts of the robotic arm 2100, such as the elbow 2119. The wrist 2121 can allow the instrument or tool to be delivered close to a patient, without having to move the whole robotic arm 2100, thereby reducing the risk of collisions between the robotic arm 2100 and other objects in the environment.

An insertion degree of freedom 2165 can also be associated with the robotic arm 2100. The insertion degree of freedom can be configured to permit insertion (or retraction) of the instrument (or tool) attached to the instrument driver mechanism 2115 along an axis of the instrument or an axis of the instrument driver 2115. This axis, which can be referred to as an insertion axis, can be coaxial with the axis of rotation for the instrument driver roll degree of freedom 2163 discussed above. In some embodiments, the instrument can be inserted a certain depth into a patient via the insertion axis. The instrument can be held in the instrument driver 2115, and the instrument driver 2115 can translate relative to the insertion axis body 2113. In some embodiments, the insertion axis (or the insertion degree of freedom) allows the insertion depth in the patient to be decoupled from the pitch and yaw motion of the tool shaft (e.g., caused by the wrist 2121). That is, in some embodiments, insertion of the instrument can be accomplished without requiring movement or articulation of the arm 2100.

As noted above, in some embodiments, the insertion degree of freedom can be provided by (e.g., built into) the robotic arm 2100. The robotic arm 2100 of FIG. 21 illustrates an embodiment in which the insertion degree of freedom can be provided by (e.g., built into) the robotic arm 2100. As shown, the robotic arm 2100 includes an insertion axis body (or housing) 2113 attached (via one or more joints of the wrist 2121) to the distal link 2111. The insertion axis body 2113 can extend along an axis. The axis of the insertion axis body 2113 can be parallel to the insertion axis. The instrument driver 2115 can be attached to the insertion axis body 2113. A joint between the instrument driver 2115 and the insertion axis body 2113 can be configured to allow the instrument driver 2115 to translate along the insertion axis body 2113 (e.g., back and forth along the insertion axis body 2113). As the instrument driver 2115 translates along the insertion axis body 2113, an instrument attached to the instrument driver 2115 can be inserted (or retracted) along the insertion axis.

In some embodiments, the wrist 2121 (positioned on a distal portion 2103 of the robotic arm 2100) combined with the insertion degree of freedom (also provided at the distal portion 2103 of the robotic arm 2100) may provide unique advantages, especially when deployed in connection with the adjustable arm supports 1305 discussed above. For example, this arrangement can provide one or more robotic arms 2100 that can be stowed and subsequently deployed in a compact fashion. This can, for example, aid in collision avoidance and make the robotic arms 2100 more successful or useful in setups where the end effector is above the incision.

In some embodiments, the insertion degree of freedom can be provided by (e.g., built into) the instrument that is attached to the robotic arm 2100. For example, the instrument can include an instrument based insertion architecture that allows the at least a portion of the instrument to be inserted along the insertion axis. In this embodiment, the robot arm loses a degree of freedom, as the insertion degree of freedom is built in the instrument itself. In such embodiments, the instrument driver 2115 can be attached to (via one or more joints of the wrist 2121), for example, to the distal link 2111. The instrument can comprise a handle and a shaft. The instrument handle can be attached to the instrument driver 2115, and the instrument can provide insertion of at least a portion of the instrument along the instrument axis (for example, relative to the handle). Examples of embodiments in which the insertion degree of freedom can be provided by (e.g., built into) the instrument that is attached to the robotic arm 2100 are described in greater detail below with reference to FIG. 24.

In some embodiments, six or more degrees of freedom (e.g., seven or eight) may be desirable to provide sufficient manipulability to perform a robotic medical procedure. For example, it may be desirable to have a robot arm with three degrees of freedom to position the instrument in three-dimensional space, for example, at a remote center, and three additional degrees of freedom to control the pitch, yaw, and roll of the instrument about the remote center. In some embodiments, it may be advantageous to include additional degrees of freedom beyond the six degrees of freedom required. These degrees of freedom can be referred to as redundant degrees of freedom. Redundant degrees of freedom can be advantageous, for example, in multi-arm setups, for optimizing arm pose and avoiding collisions. In some embodiments, redundant degrees of freedom can allow the robotic arm to be repositioned while maintaining the instrument position and the base position stationary. In some embodiments, the robotic arm 2100 includes three, four, five, six, seven, eight, nine, ten, or more degrees of freedom. In some embodiments, the robotic arm 2100 includes one, two, three, four, five, or more redundant degrees of freedom.

In addition to the robotic arm 2100 having the mechanisms described above for accommodating the multiple degrees of freedom described, the arm support 1305 on which robotic arm 2100 is mounted (and to which other robotic arms can also be mounted) can also provide additional degrees of freedom as discussed in the preceding section. Further, in some embodiments, multiple adjustable arm supports 1305 can be provided (for example, on opposite sides of the table), each supporting one or more robotic arms 2100. In some of these embodiments, all of the robotic arms 2100 on one side of the table are mounted on a shared translation bar, track, or rail 1307. These two rails 1307, one on each side of the bed, can be positioned independently of each other, and could foreseeably have three degrees of freedom (e.g., lift, lateral translation, and tilt) as described above. Placing multiple robotic arms 2100 on a shared rail 1307 can reduce the set-up degrees of freedom necessary for a system and can provide a good stiffness path to ground.

Figure 22:
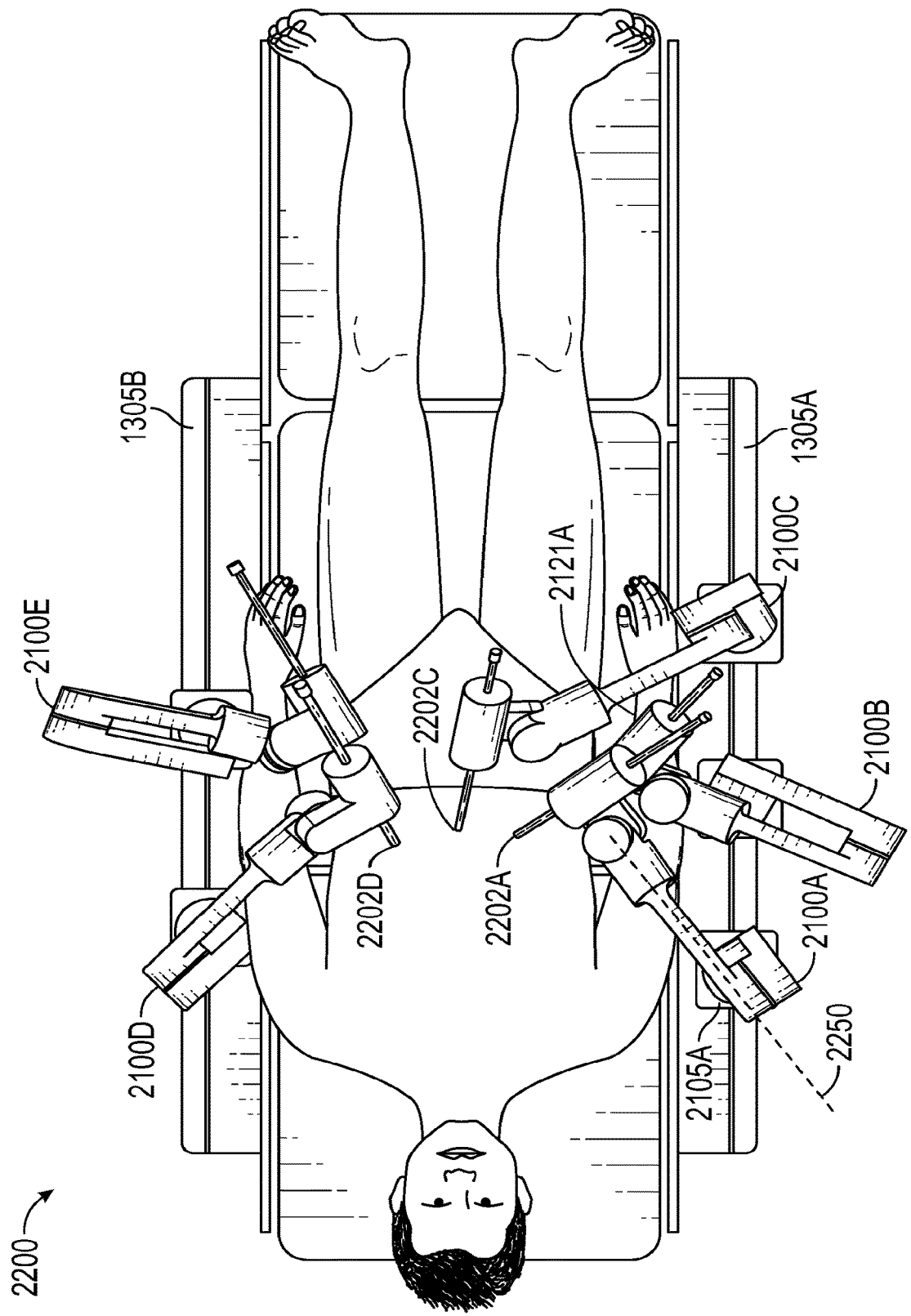
FIG. 22 is an overhead view of a robotic surgical system including a plurality of robotic arms performing a laparoscopic procedure according to one embodiment.

FIG. 22 is an overhead view of a robotic surgical system 2200 including a plurality of robotic arms 2100A, 2100B, 2100C, 2100D, 2100E performing a laparoscopic according to one embodiment. The robotic arms 2100A, 2100B, 2100C are mounted on a first adjustable arm support 1305A, and the robotic arms 2100D, 2100E are mounted on a second adjustable arm support 1305B, located opposite the first adjustable arm support 1305A. As shown, the robotic arms 2100A, 2100B, 2100C, 2100D, 2100E are holding laparoscopic tools or instruments. The robotic arms 2100A, 2100B, 2100C, 2100D, 2100E can insert the laparoscopic tools through laparoscopic ports (e.g., laparoscopic ports 2202A, 2202C, 2202D) to gain access to a treatment site within the patient. In some embodiments, for each robotic arm 2100, the corresponding laparoscopic port 2202 can be positioned at a remote center of the robotic arm 2100. That is, an insertion axis of the robotic arm can be aligned with and extend through the remote center. The robotic arm 2100 can be configured to manipulate the pitch, roll, and yaw of the instrument about the remote center. In the present embodiment, the adjustable arm supports 1305A, 1305B are sized and configured to support multiple arms. As the adjustable arm supports 1305A, 1305B can have a thickness to support these arms, the adjustable arm supports have added stability to reduce the risk of shakiness.

FIG. 22 also illustrates that, in some embodiments, the robotic arm 2100 can be configured such that the wrist 2121 and the shoulder base 2105 of the robotic arm can lie along a substantially straight line 2250 when viewed from above. This is illustrated, for example, with respect to the wrist 2121A and shoulder base 2105A of the robotic arm 2100. In some embodiments, the wrist 2121, elbow 2119 and shoulder 2117 can lie along a substantially straight line 2250 (from a top down view). In some embodiments, the wrist 2121, elbow 2119 and shoulder 2117 can substantially align in a plane that is perpendicular to a table. Advantageously, by being substantially aligned in the same plane, the plane of the robotic arm remains substantially perpendicular to the table during a surgical procedure. This configuration is desirable as it allows one robot arms to avoid one another, and is in partly enabled by the wrist configuration. In some embodiments, the robotic arm can be positioned such that the wrist 2121, elbow 2119 and shoulder 2117 lie in a plane and the plane need not be parallel to the table. For example, the plane may be at an acute angle relative to the table.

Figure 23:
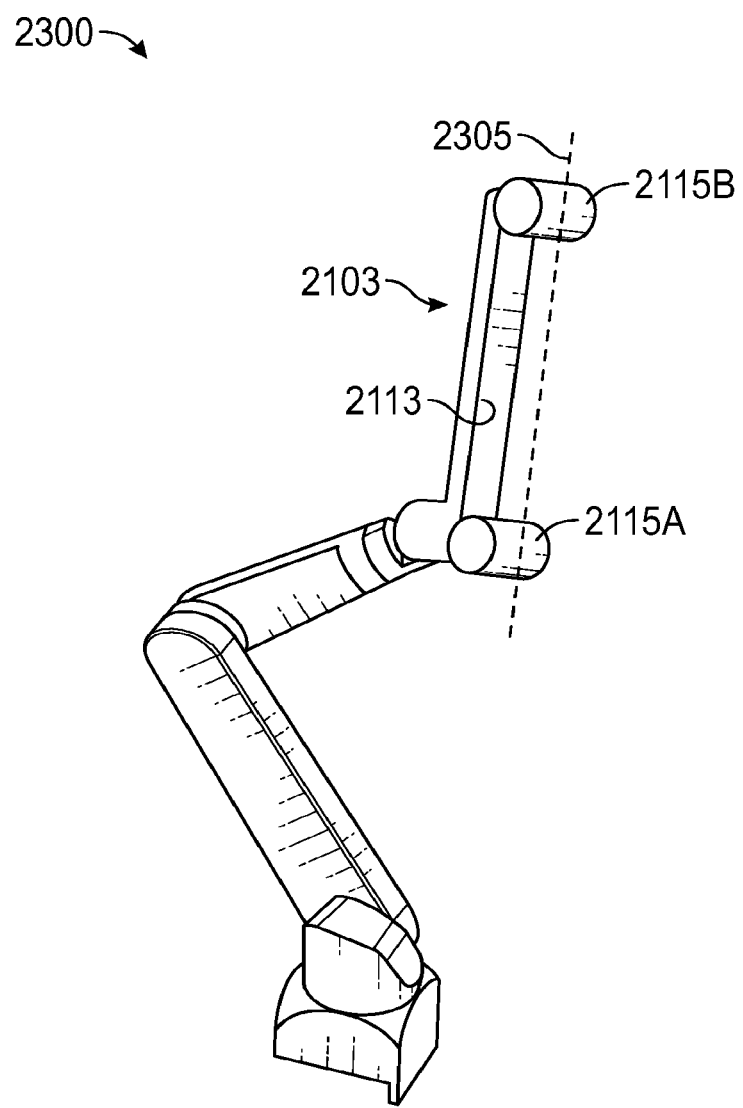
FIG. 23 is an isometric view of a robotic arm that includes two instrument drive mechanisms according to one embodiment.

FIG. 23 is an isometric view of an alternative robotic arm 2300 that includes two instrument drivers 2115A, 2115B according to one embodiment. In the illustrated embodiment, the two instrument drivers 2115A, 2115B are positioned at the distal portion 2103 of the robotic arm 2300. Each of the instrument drivers 2115A, 2115B can be configured to receive a corresponding instrument. In some embodiments, the instruments are telescoping instruments, wherein one instrument is positioned within a working channel of the other instrument. For example, one instrument can be an endoscope and the other instrument can be an outer sheath that surrounds the endoscope. The instrument drivers 2115A, 2115B can be configured to drive their corresponding instrument independently. In some embodiments, each instrument can be inserted along an insertion axis. In some embodiments, the two axes are coaxial, such as the insertion axis 2305 illustrated. In the illustrated embodiment, one or both of the instrument drivers 2115A, 2115B can be configured translate along the insertion axis body 2113 to provide insertion or retraction of the instruments. In other embodiments, the insertion of the tools is provided by the instruments themselves, as described below. In some embodiments, one or both of the instrument drivers can be removable.

Figure 24:
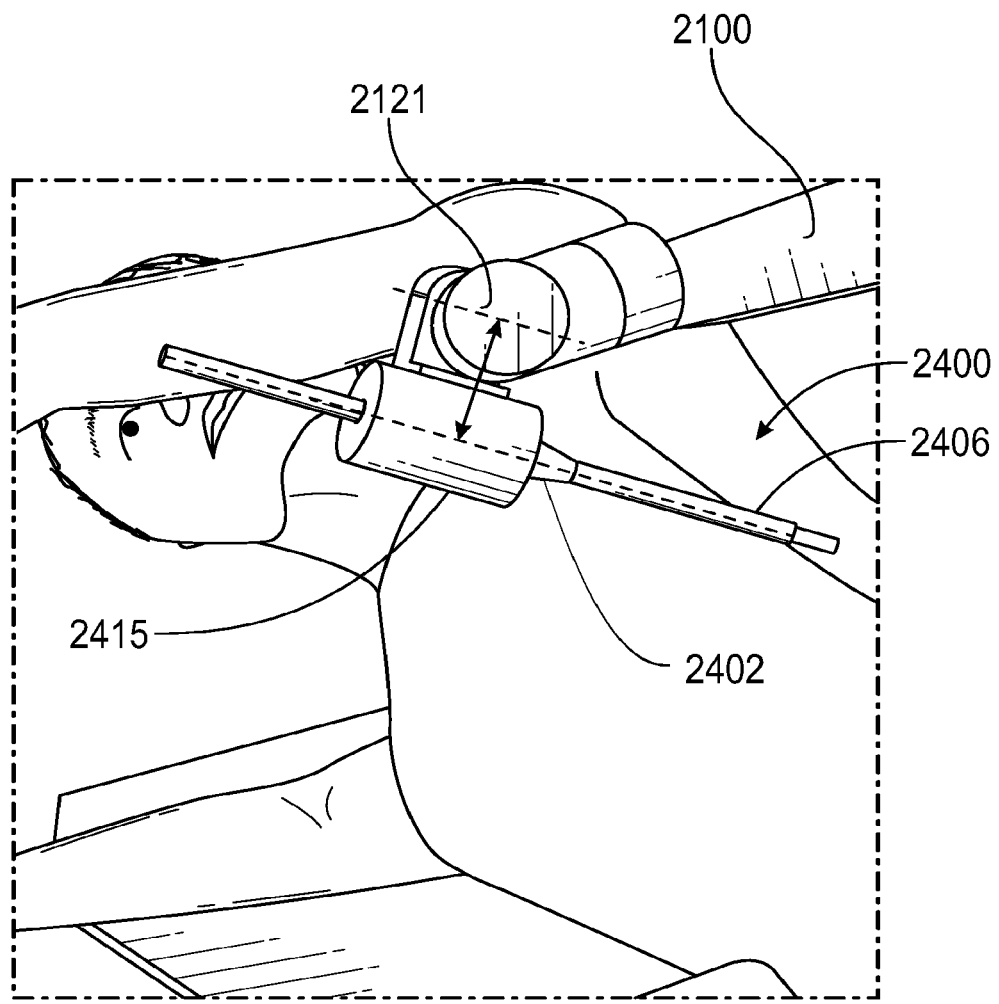
FIG. 24 is an isometric view of an instrument with an instrument based insertion architecture attached to a distal end of a robotic arm according to one embodiment.

FIG. 24 is an isometric view of an instrument 2400 with an instrument based insertion architecture attached to a distal end of an alternative robotic arm 2100 according to one embodiment. As mentioned above, in some embodiments, the instrument 2400 itself has an architecture that allows it to translate at least a portion of the instrument 2400 along an insertion axis. This can minimize the movement of the robot arm 2100 during insertion. For example, in the embodiment of FIG. 21, the insertion drive mechanism 2115 moves along the insertion axis body 2113 to provide insertion along the insertion axis. In contrast, in the embodiment of FIG. 24, the insertion drive mechanism 2415 can remain in the same position, while the architecture of the instrument 2400 itself causes at least a portion of the instrument 2400 to be inserted.

As illustrated, the instrument can comprise an instrument shaft 2406 and a cannula 2402 attached to an instrument handle (not shown). The instrument handle can be configured to attach and couple to the instrument driver 2415. The instrument shaft 2406 can, in some embodiments, extend through the instrument handle and/or the instrument driver 2415. The instrument driver 2415 can be attached to the wrist 2121 at the distal end of the robotic arm 2100. The instrument 2400 can have a built-in architecture whereby the instrument shaft 2406 translates relative to the handle.

In some other robotic systems, a portion of the robotic arm often translates in order to achieve insertion (thereby increasing swing mass caused by the robot arm). In the present embodiment of FIG. 24, the instrument 2400 itself has an architecture that accommodates insertion. Thus, in this and similar embodiments, the insertion axis is eliminated from the robotic arm 2100 and the overall size and motion of the robotic arm 2100 can be reduced. This can remove one degree of freedom from the robotic arm 2100, but does not reduce the capability of the robotic 2100, as the degree of freedom is moved to the instrument 2400 itself rather than the robotic arm 2100. Section XIV, below, provides several examples of such instrument-based insertion architectures.

An additional advantage that may be present in some embodiments, like that shown in FIG. 24, is that an offset angle or distance between the wrist 2121 and the instrument roll axis or insertion axis can be reduced. In some embodiments, this allows for more reach with shorter links and less elbow motion for the robotic arm 2100. Another advantage of the present embodiment in FIG. 24 is that the instrument driver can be below the wrist. This can be beneficial for particular procedures, such as ventral hernia type procedures.

Figure 25B:
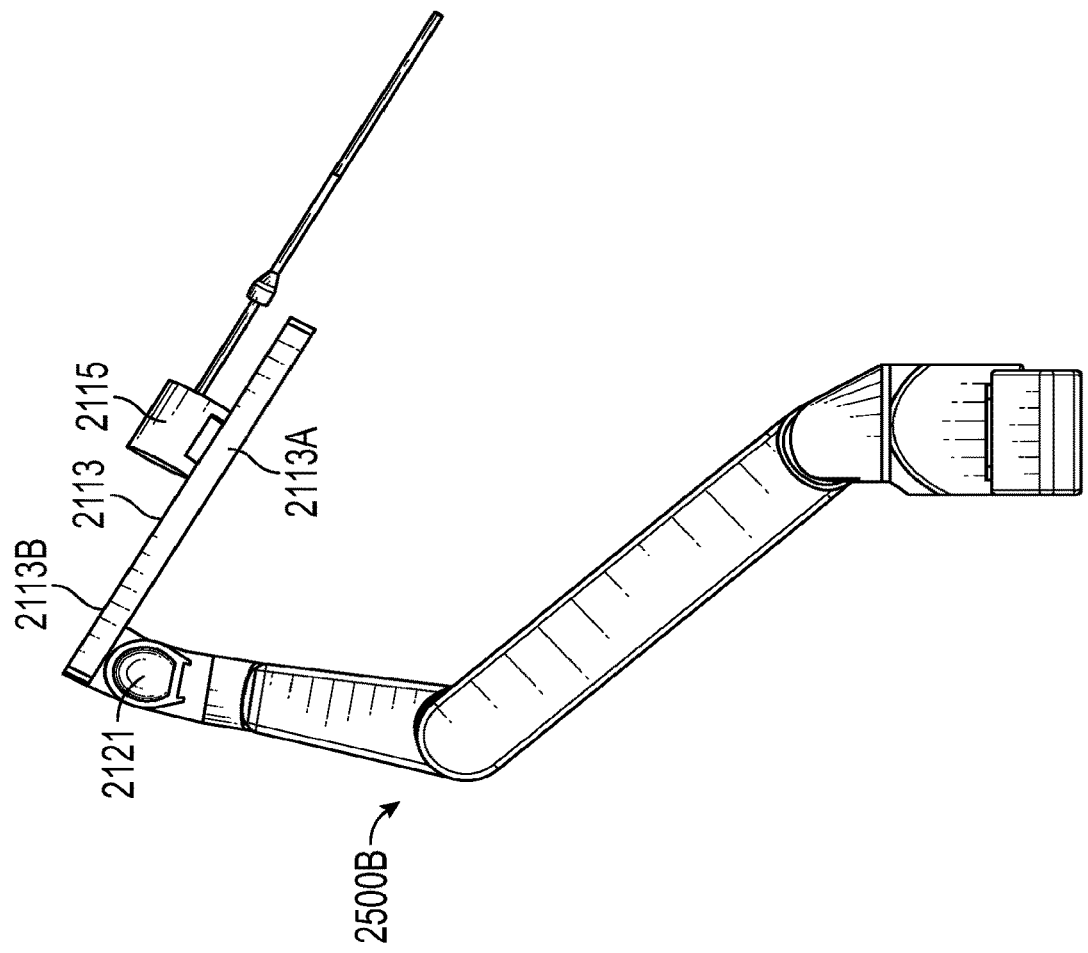
FIG. 25B is a side view of the robotic arm of FIG. 25A with the insertion axis body positioned in a second orientation according to one embodiment.
Figure 25A:
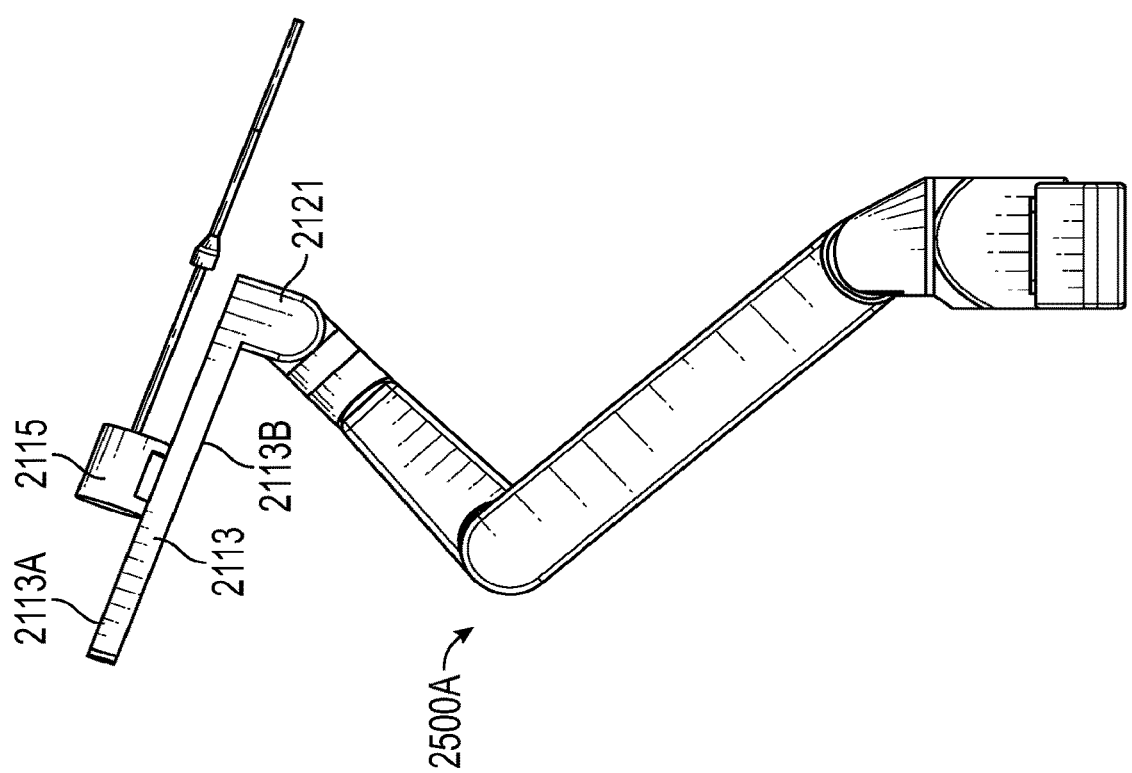
FIG. 25A is a side view of a robotic arm with an insertion axis body positioned in a first orientation according to one embodiment.

FIGS. 25A and 25B illustrate that, in some embodiments, the robotic arm 2100 can be configured such that the insertion axis body 2113 can be configured to be generally reversible. In some embodiments, having an ability to operate a robotic arm 2100 with an instrument driver 2115 far from the remote center can mitigate arm collisions. To facilitate this, the robotic arm 2100 can be configured such that a cannula can be mounted on either side 2113A, 2113B of the insertion axis housing 2113. This can be used to changes the distance of separation between the remote center and the wrist 2121. This can provide an additional option to control to vary the position of the robotic arm 2100.

FIG. 25A is a side view of a robotic arm 2500A with the insertion axis body 2113 positioned in a first orientation according to one embodiment. As shown, the instrument driver 2115 is positioned on a first side 2113A of the insertion axis body 2113. Further, the insertion axis body 2113 is oriented so as to be positioned away from a remote center. As shown, this generally brings the wrist 2121 closer to the remote center.

In contrast, FIG. 25B is a side view of a robotic arm 2500B with the insertion axis body positioned in a second orientation according to one embodiment. As shown, the instrument driver 2115 is positioned on a second side 2113B of the insertion axis body 2113. Further, the insertion axis body 2113 is oriented so as to be positioned toward from a remote center. As shown, this generally moves the wrist 2121 away from the remote center.

In some embodiments, the instrument driver 2115 is detachable such that it can be removed and attached to either side 2113A, 2113B of the insertion axis body 2113. In some embodiments, to move from the first position shown in FIG. 25A to the second position shown in FIG. 25B, the wrist 2121 is pivoted over the top of the robotic arm. In other embodiments, to move between the first and second positions, the wrist 2121 can be rotated about robotic arm. In these embodiments, the instrument driver 2115 can be removed and/or flipped so as to be oriented in the opposite direction, or the instrument driver 2115 can be reversible such that the instrument can be attached to either side of the instrument driver, 2115.

Figure 26A:
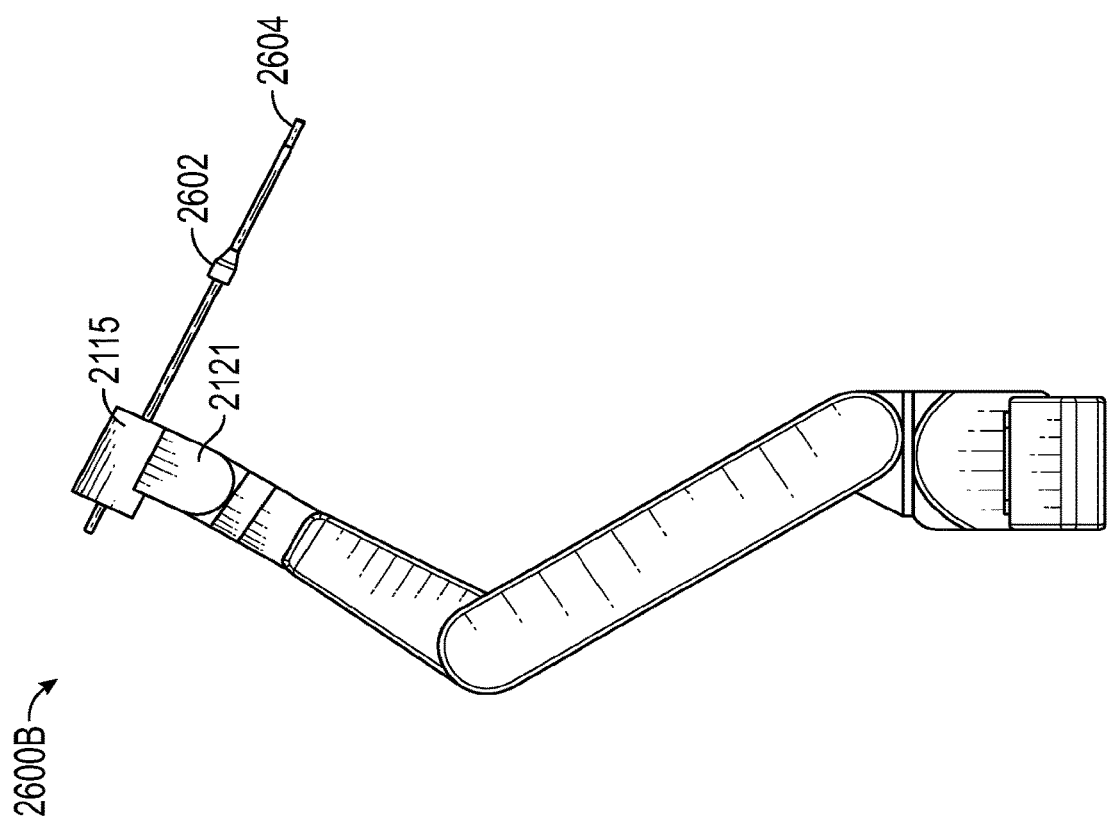
FIG. 26A is a side view of a robotic arm configured with an attached cannula according to one embodiment.
Figure 26B:
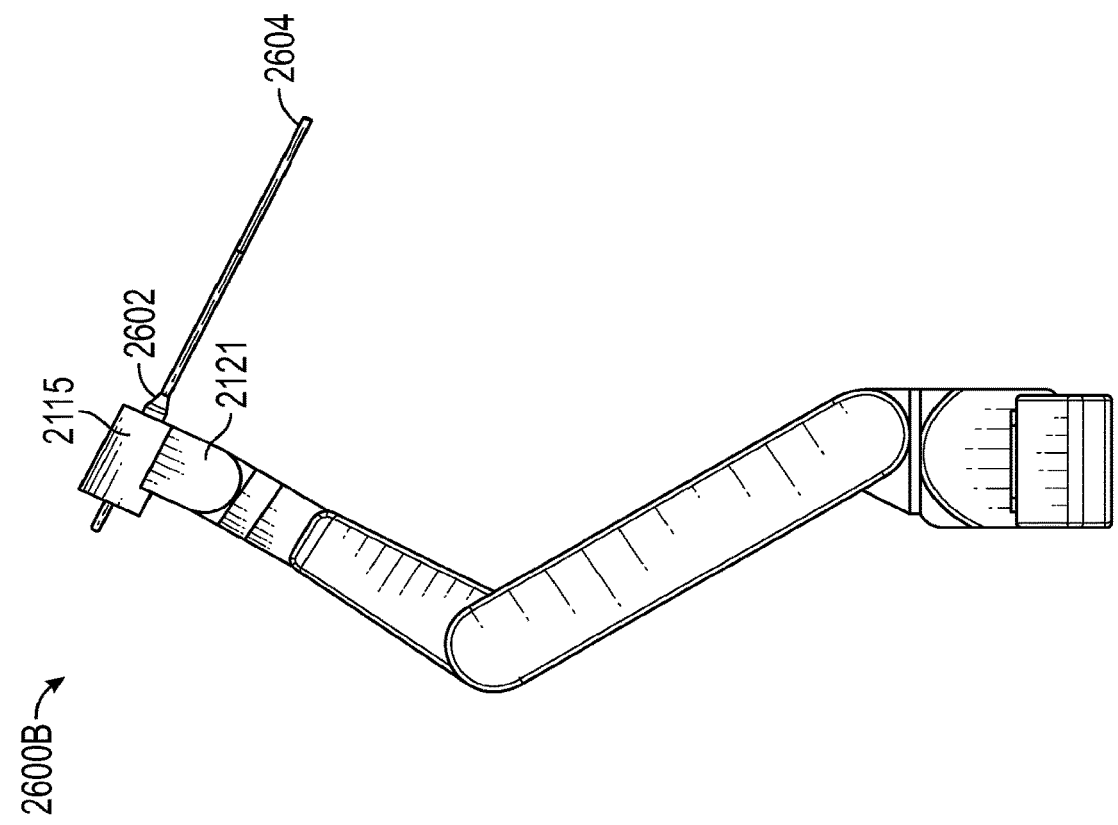
FIG. 26B is a side view of a robotic arm configured with a detached cannula according to one embodiment.

FIGS. 26A and 26B illustrate that, in some embodiments, the robotic arm 2100 can be operated with a detached cannula. This can provide similar functionality as the reversible insertion axis body 2113 described above (i.e., allowing varying position of the wrist 2121 relative to the remote center), in embodiments, that do not include an insertion axis body, such as the embodiments that include instruments that provide insertion as discussed above with reference to FIG. 24. This can effectively give the robotic arm 211 one additional null space degree of freedom, as it allows the distance between the wrist 2121 and the cannula to dynamically change while holding the tool tip stationary.

FIG. 26A is a side view of a robotic arm 2600A configured with an attached cannula 2602 according to one embodiment. As shown, the cannula 2602 is attached to the instrument driver 2115. FIG. 26B is a side view of a robotic arm 2600B configured with a detached cannula 2602 according to one embodiment. As shown, the cannula 2602 is detached from the instrument driver 2115. In this configuration, the cannula 2602 is free to move along the insertion axis as the instrument is inserted or retracted. Comparing FIGS. 26A and 26B, it can be seen that by detaching the cannula 2602, the instrument driver 2115 and/or wrist 2121 can be moved back relative to the cannula 2602 and or tool tip 2604.

Figure 27A:
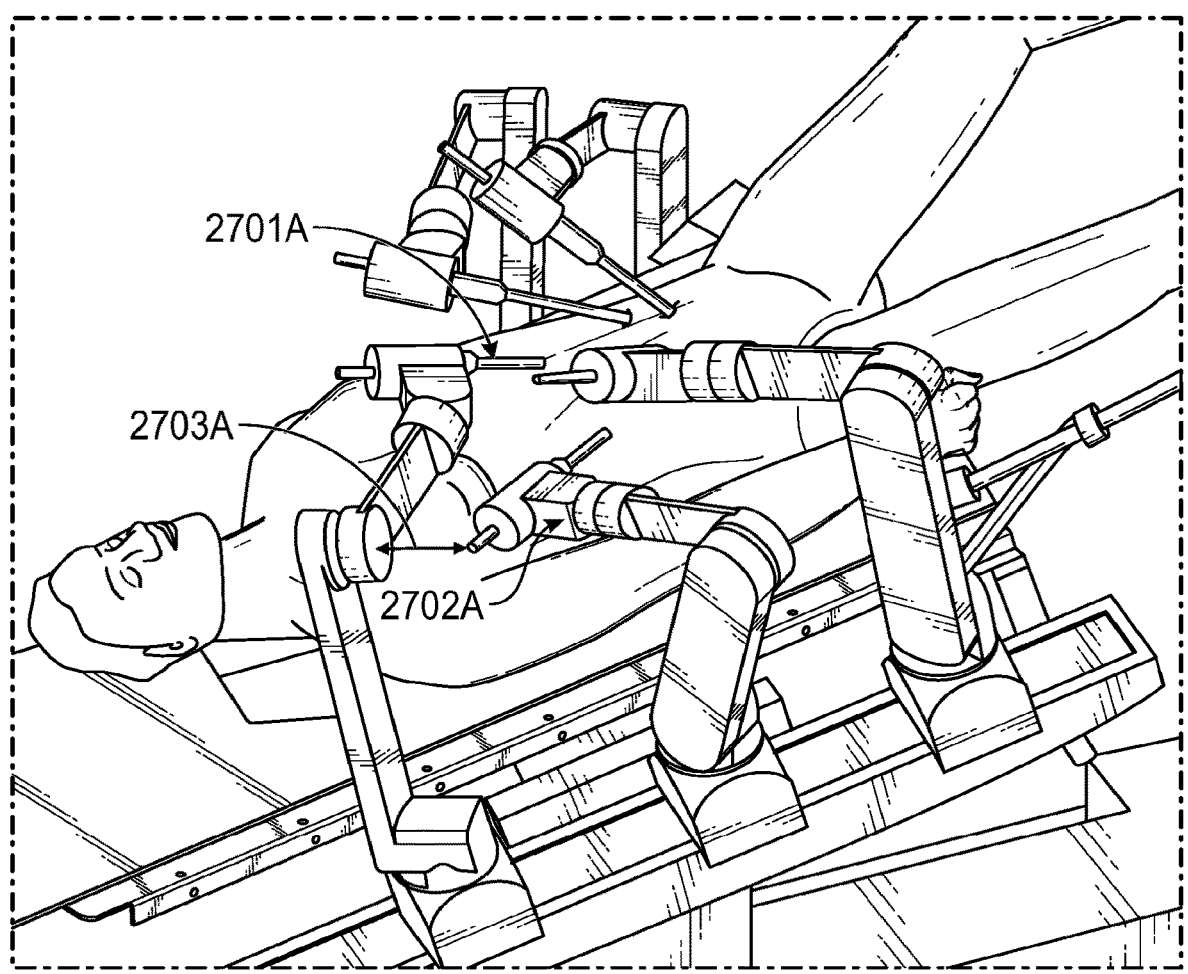
FIG. 27A is an isometric view of a system including a plurality of robotic arms performing a laparoscopic procedure, wherein one of the arms is configured with an attached cannula, according to one embodiment.
Figure 27B:
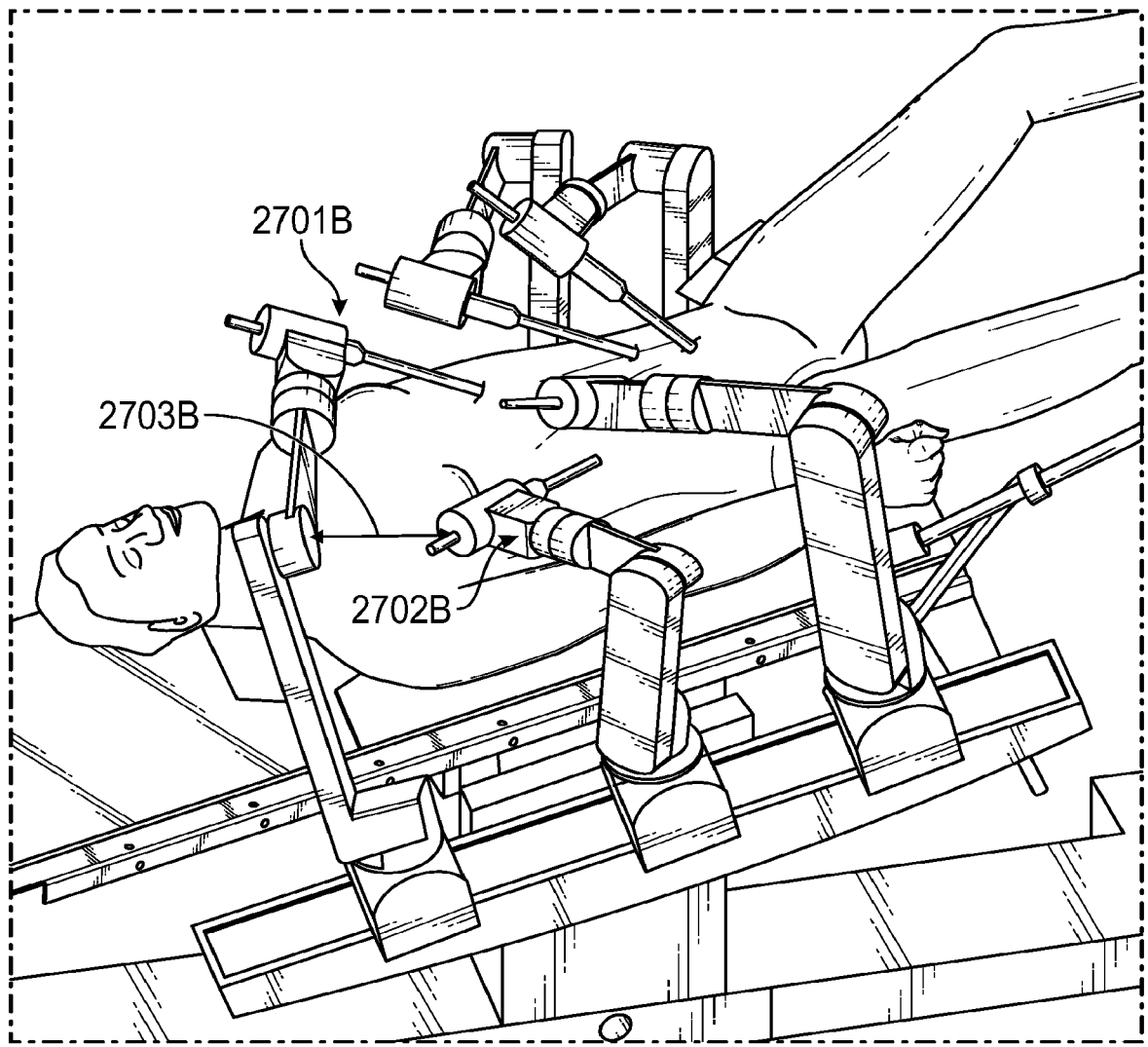
FIG. 27B is an isometric view of a system including a plurality of robotic arms performing a laparoscopic procedure, wherein one of the arms is configured with a detached cannula, according to one embodiment.

This is further illustrated in FIG. 27A (attached cannula) and 27B (detached cannula). FIG. 27A is an isometric view of a system including a plurality of robotic arms (e.g., 2701A, 2702A) performing a laparoscopic procedure, wherein one of the arms 2701A is configured with an attached cannula, according to one embodiment. As shown in FIG. 27A, in some embodiments, without detached cannula operation (i.e., with the cannula attached), the middle arm 2701A may have limited room (illustrated by the distance 2703A) to yaw before hitting the camera arm 2702A. FIG. 27B is an isometric view of a system including a plurality of robotic arms (e.g., 2701B, 2702B) performing a laparoscopic procedure, wherein one of the arms 2701B is configured with a detached cannula, according to one embodiment. As shown in FIG. 27B, in some embodiments, with detached cannula operation, the middle arm 2701B can have more room (illustrated by the distance 2703B) to yah before hitting the camera arm 2702B. Comparing FIGS. 27A and 27B, it can be seen that distance 2703B is larger than distance 2703A. As illustrated in these figures, the wrist of the robotic arm can be moved away from the remote center when the cannula is detached. This can provide additional remove for maneuvering the robotic arms. In other embodiments, a cannula can stay attached and the remote center can move slightly along the length of the cannula. In other embodiments, cannulas can be made longer to allow for a remote center to be even farther from the wrist.

In some instances, the performance of the robotic arm 2100 can be improved by inclusion of one or more of the features discussed below. For example, the present inventors have determined that the robotic arm 2100 (for example, as shown in FIG. 21) may experience several singularities during use. The singularities may represent areas of degraded performance. For example, a singularity can occur when different axes of the robotic arm align, thereby losing a degree of freedom. Other example, singularities that have been identified can include: (i) base yaw intersects spherical wrist; (ii) an overly extended arm (e.g., with elbow pitch close to 180 degrees); and (iii) an under extended arm (e.g., with wrist close to plus or minus 90 degrees or elbow close to 0 degrees. The features illustrated in FIGS. 28-29B may address one or more of these singularities.

Figure 28:
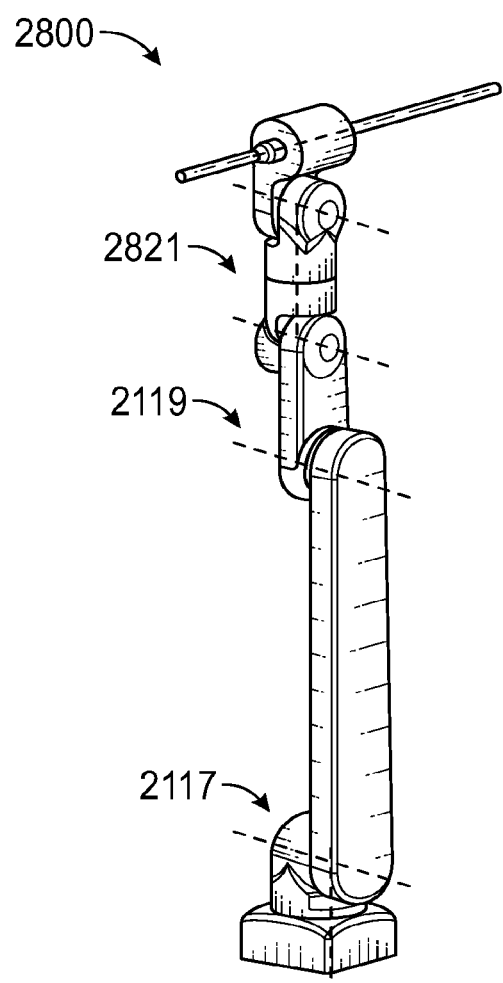
FIG. 28 is an isometric view of a robotic arm that includes a wrist having an additional rotational joint according to one embodiment.

FIG. 28 is an isometric view of a robotic arm 2800 that includes a wrist 2821 having an additional rotational joint according to one embodiment. By comparison with the robotic arm 2100 of FIG. 21, the robotic arm 2800 may include a similar shoulder 2117 and elbow 2119. However, the robotic arm 2800 includes an additional axis at the wrist 2821. For example, the robotic arm 2100 described above includes a wrist 2121 that provides two degrees of freedom, while the robotic arm 2800 includes a wrist 2821 that provides four degrees of freedom. In some embodiments, it may be desirable to add an additional rotary axis to the wrist. In some embodiments, this rotary axis does not need a high range of motion, but can be employed by control algorithms to help keep other joints away from singularity. Adding an additional redundant degree of freedom to the wrist 2821 can allow for additional possibilities of collision avoidance (especially around tightly arranged ports on the midline) in addition to allowing for singularity avoidance. The additional degree of freedom provided by the wrist 2821 can, in some embodiments, help make arm performance more uniform through the arm's workspace and can reduce peak joint requirements necessary to achieve desired tool speeds. In some embodiments, the wrist can include additional degrees of freedom, for example, three, four, five, or more degrees of freedom. These can include, for example, an instrument insertion degree of freedom, an instrument roll degrees of freedom, and one or more rotational/pivoting degrees of freedom.

Figure 29B:
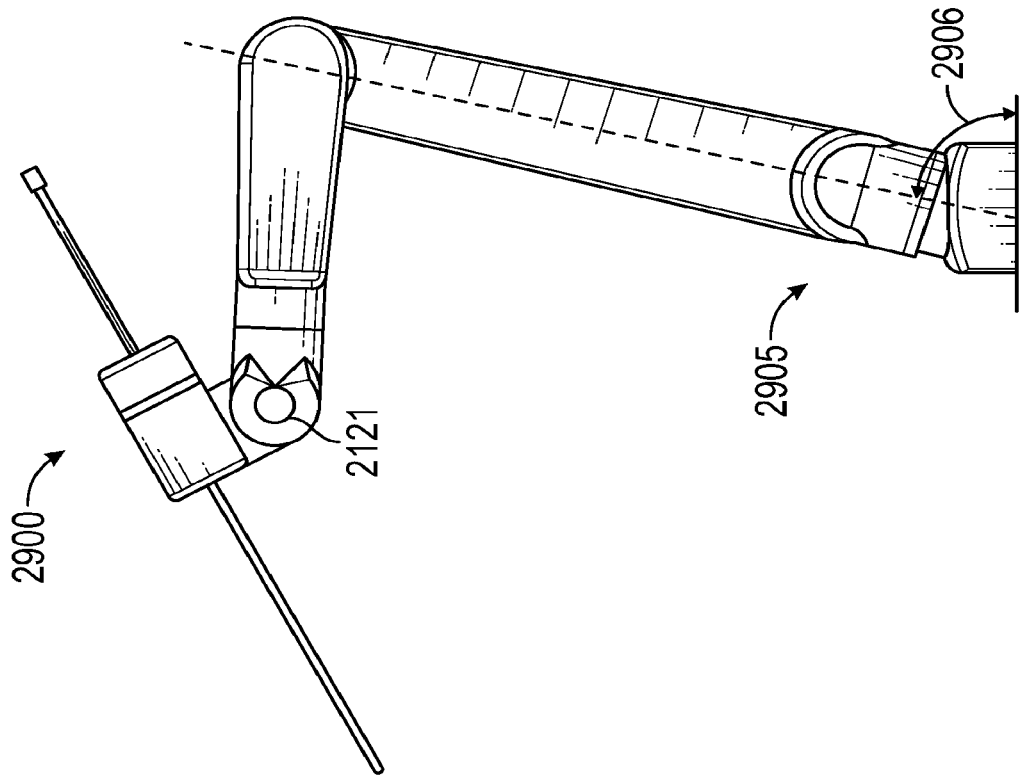
FIG. 29B is a side view of the robotic arm of FIG. 29A according to one embodiment.
Figure 29A:
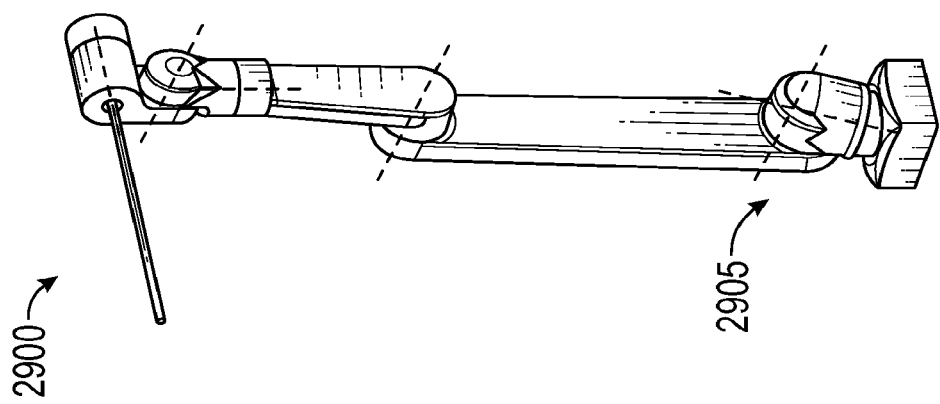
FIG. 29A is an isometric view of a robotic arm that includes a tilted base according to one embodiment.

FIGS. 29A and 29B are isometric and side views, respectively of a robotic arm 2900 that includes a tilted base 2905 according to one embodiment. As best seen in FIG. 29B, the base 2905 can be tilted by an angle 2906. The base 2905 can be tilted to adjust the yaw angle of the base. In some embodiments, this can help address the singularity that occurs when the base yaw intersects the wrist 2121 by increasing the effective distance between the axis of the base yaw joint and the wrist 2121 (as shown in FIG. 29B). In some embodiments, the tilt angle 2906 can be about 5 degrees, about 10 degrees, about 15 degrees, about 20 degrees, about 25 degrees, or about 30 degrees, 35 degrees, about 40 degrees, about 45 degrees, about 50 degrees, about 55 degrees, about 60 degrees, about 65 degrees, about 70 degrees, about 75 degrees, about 80 degrees, or about 85 degrees.

Figure 30:
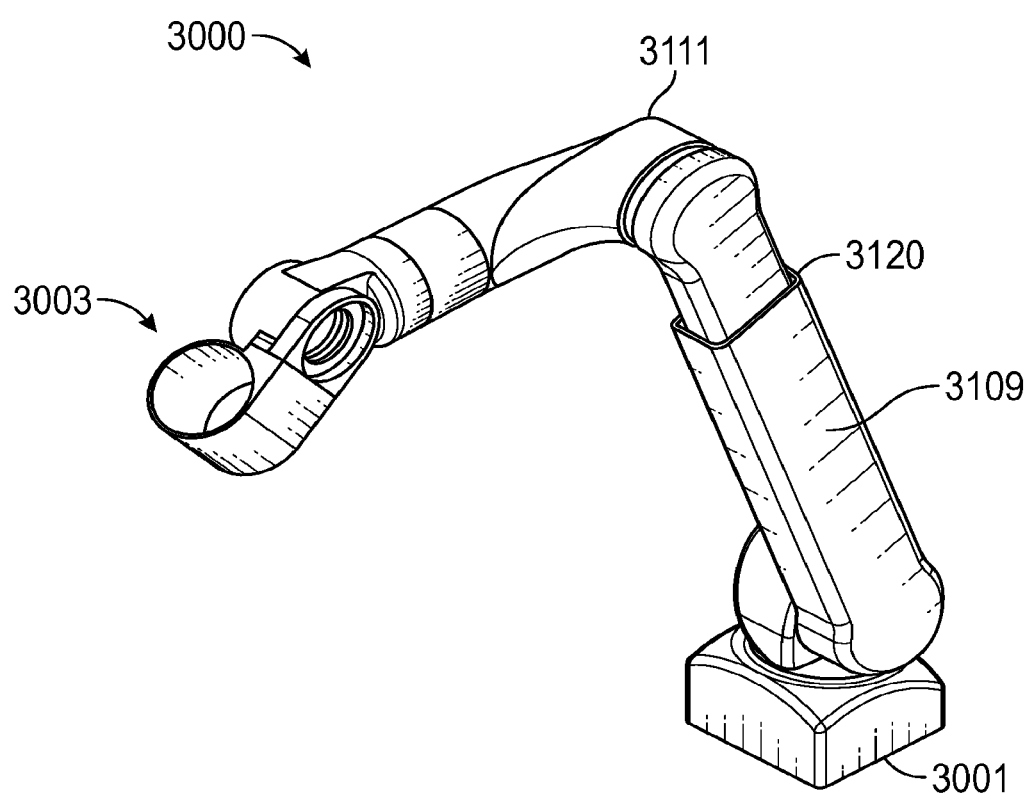
FIG. 30 is an isometric view of a robotic arm with a telescoping link according to one embodiment.

FIG. 30 is an isometric view of an alternative robotic arm 3000 that includes a telescoping link 3109. The robotic arm 3000 shares many features as previous embodiments, including a proximal portion 3001 and a distal portion 3003. The robotic arm 3000 comprises a plurality of joints arranged serially, including a shoulder, elbow and wrist, between the proximal portion 3001 and the distal portion 3003. In addition, the robotic arm 3000 includes at least a proximal link 3109 and a distal link 3111.

In some embodiments, at least one of the proximal link 3109 and the distal link 3111 comprises a prismatic telescoping joint. In the illustrated embodiment, proximal link 3109 comprises a prismatic telescoping joint 3120, whereby an inner member telescopes within an outer member. By providing the telescoping joint 3120, the robotic arm 3000 is advantageously capable of having a greater reach, thereby making it easier to use in different surgical approaches. Furthermore, such a telescoping joint 3120 can make the robotic arm 3000 suitable for use with larger-sized patients.

The robotic arms described in this section can be configured for use with the adjustable arm supports described in the preceding section. These robotic arms may be particularly advantageous when deployed from a mounting position that is below a surface of a table.

In general, to avoid collisions with a parallelogram remote center robot (commonly used in laparoscopic procedures), robotic arms are desirably set-up such that when looking from above, a straight line passes from the arm base through the remote center and into the workspace. These three points would reside in a plane that is substantially perpendicular to a table or floor. If the workspace is not aligned as such, the arms must be heavily yawed to one side, causing collisions. Conventional robotic surgical systems employ overhead support structures as described above to provide enough flexibility to allow the robotic arms to access most workspaces. However, arms coming from below and mounted alongside the table, as are arms mounted to the adjustable arm supports, may require a different structure to function as desired.

For example, in some embodiments, robotic arms configured for use with the adjustable arm supports differ from traditional parallelogram remote center robot. In one example, a robotic arm configured for use with the adjustable arm supports can comprise a shoulder with at least two degrees of freedom, an elbow with at least one degree of freedom, and wrist with at least two degrees of freedom. The kinematics associated with such an arm allow the arm base to be positioned arbitrarily relative to the workspace, allowing for setups that would be challenging for a parallelogram remote center robot mounted alongside a bed.

Further, in some embodiments, a robotic arm configured for use with the adjustable arm supports may include a wrist configured with at least three degrees of freedom. In some embodiments, the wrist can be semi-spherical or spherical. Such a wrist can allow the robotic arm to roll its wrist joint such that an instrument driver positioned at the distal end of the robotic arm can be below the arm wrist. This can enable procedures where target workspaces are far above ports.

Other surgical robotic arms include a mechanically constrained remote center with no redundant degrees of freedom. That is, for any remote center position, the distance to the base is mechanically constrained. Robotic Arms coming from below the bed, as is the case with robotic arm mounted on the adjustable arm supports described above, can be limited by their mount structures and cannot reach the optimal configurations to make parallelogram robot arms excel. To address this issue, robotic arms configured for use with the adjustable arm supports described above can include one or more redundant degrees of freedom. The redundant degrees of freedom can allow the arms to be jogged within their null space without moving the tool tip, allowing for intraoperative collision avoidance that is not possible in previously known surgical robotic arms. In addition, when the arms are jogged within their null space, they advantageously can avoid collisions among one another, as well as with a bed, patient, c-arm, etc.

XIV. Instrument-Based Insertion Architectures

As mentioned briefly above, some instruments that can be used with the robotic arms and instrument drive mechanisms described above can include an instrument-based insertion architecture. An instrument-based insertion architecture can reduce reliance on the robotic arm when linearly inserting an instrument. In particular, the systems, devices and methods described in this section provide examples of instruments having instrument-based linear insertion architectures. The instrument-based insertion architectures described in this section can be implemented with the robotic arms and adjustable arm supports described in the preceding sections.

Figure 31:
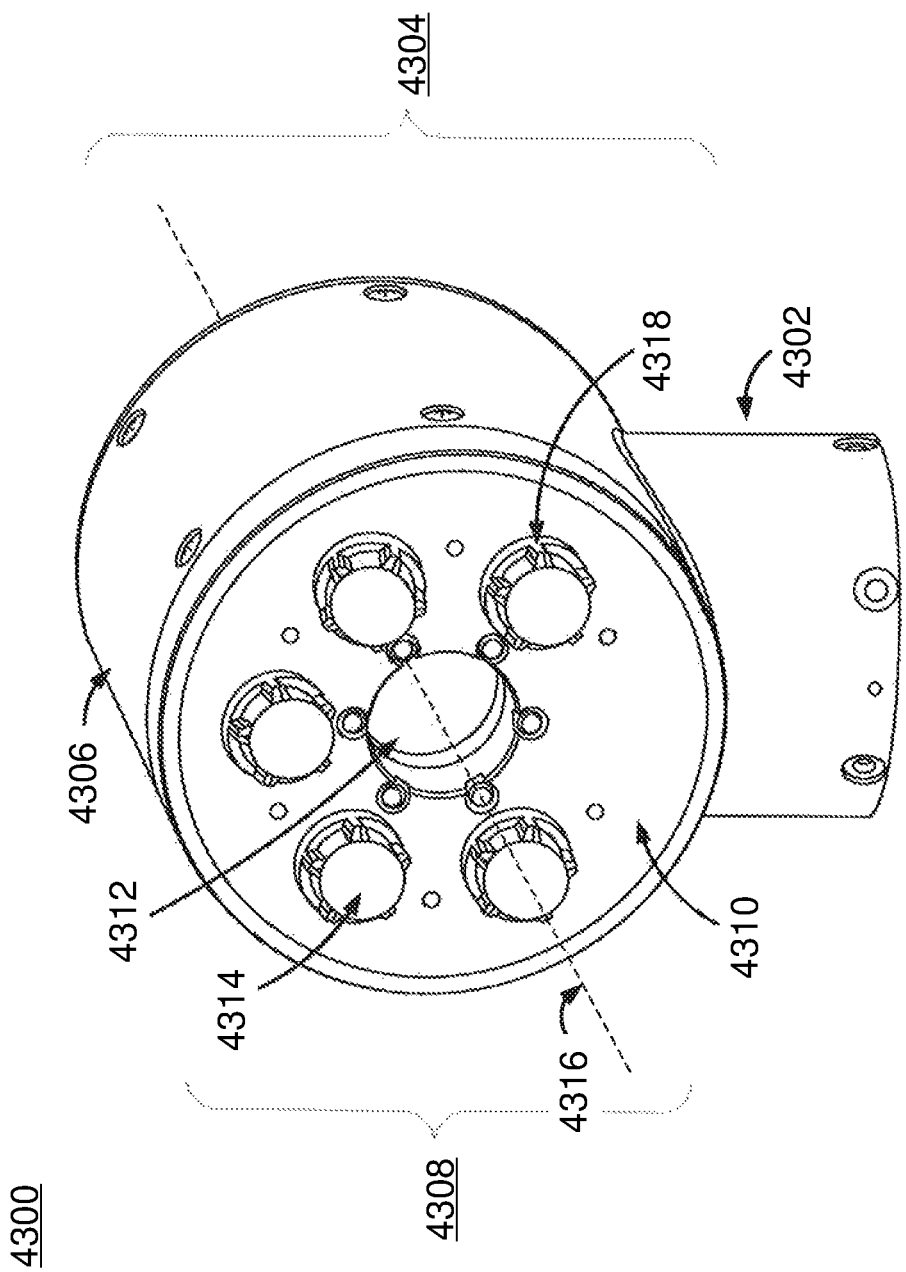
FIG. 31 illustrates a perspective view of an instrument device manipulator for a surgical robotic system, according to one embodiment.
Figure 32:
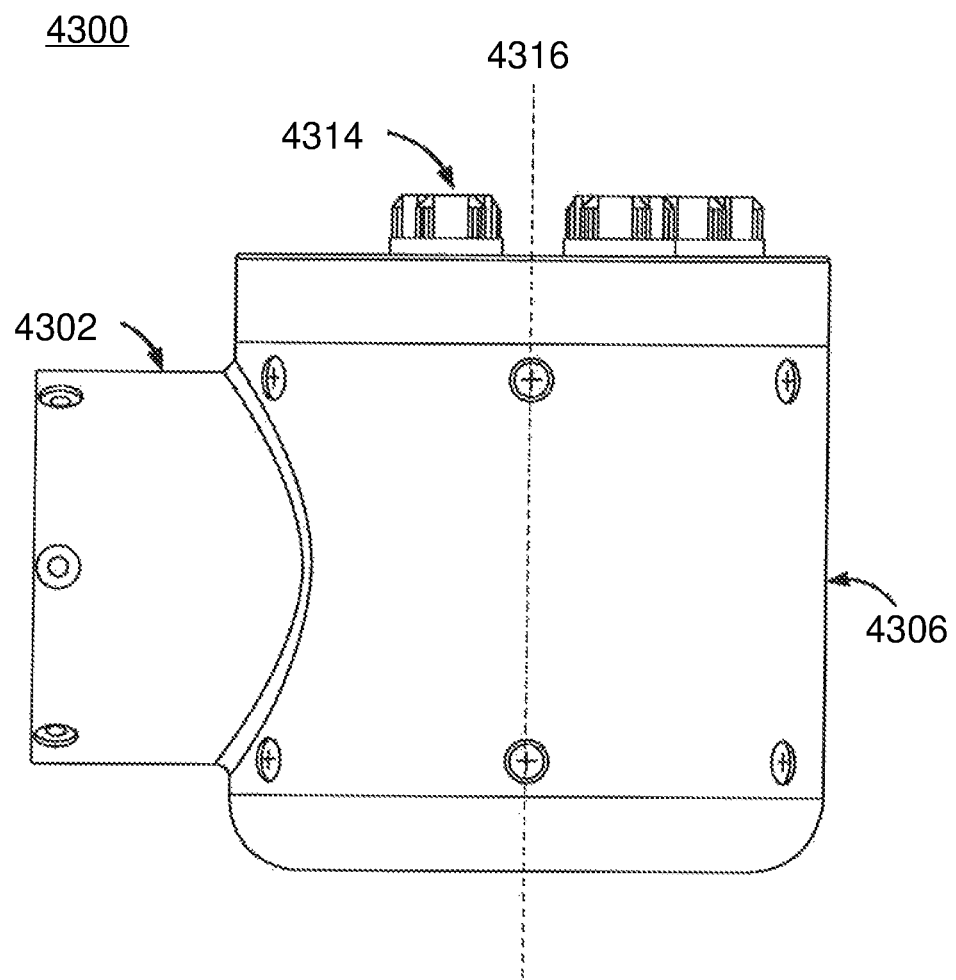
FIG. 32 illustrates a side view of the instrument device manipulator of FIG. 31, according to one embodiment.

FIG. 31 illustrates a perspective view of an instrument device manipulator (IDM) 4300 for a surgical robotic system, and FIG. 32 is a side view of the IDM 4300, according to one embodiment. The IDM 4300 is configured to attach a surgical tool or instrument to a robotic surgical arm in a manner that allows the surgical tool to be continuously rotated or "rolled" about an axis of the surgical tool. The IDM 4300 includes a base 4302 and a surgical tool holder assembly 4304 coupled to the base. The surgical tool holder assembly 4304 serves as a tool holder for holding an instrument 118. The surgical tool holder assembly 4304 further includes an outer housing 4306, a surgical tool holder 4308, an attachment interface 4310, a passage 4312, and a plurality of torque couplers 4314. In some embodiments, the passage 4312 comprises a through bore that extends from one face of the IDM 4300 to an opposing face of the IDM 4300. The IDM 4300 may be used with a variety of surgical tools (not shown in FIG. 31), which may include a handle and an elongated body (e.g., a shaft), and which may be for a laparoscope, an endoscope, or other types of end-effectors of surgical tools or instruments.

The base 4302 removably or fixedly mounts the IDM 4300 to a surgical robotic arm of a surgical robotic system. In the embodiment of FIG. 31, the base 4302 is fixedly attached to the outer housing 4306 of the surgical tool holder assembly 4304. In alternative embodiments, the base 4302 may be structured to include a platform which is adapted to rotatably receive the surgical tool holder 4308 on the face opposite from the attachment interface 4310. The platform may include a passage aligned with the passage 4312 to receive the elongated body of the surgical tool and, in some embodiments, an additional elongated body of a second surgical tool mounted coaxially with the first surgical tool or instrument.

The surgical tool holder assembly 4304 is configured to secure a surgical tool to the IDM 4300 and rotate the surgical tool relative to the base 4302. Mechanical and electrical connections are provided from the surgical arm to the base 4302 and then to the surgical tool holder assembly 4304 to rotate the surgical tool holder 4308 relative to the outer housing 4306 and to manipulate and/or deliver power and/or signals from the surgical arm to the surgical tool holder 4308 and ultimately to the surgical tool. Signals may include signals for pneumatic pressure, electrical power, electrical signals, and/or optical signals.

The outer housing 4306 provides support for the surgical tool holder assembly 4304 with respect to the base 4302. The outer housing 4306 is fixedly attached to the base 4302 such that it remains stationary relative to the base 4302, while allowing the surgical tool holder 4308 to rotate freely relative to the outer housing 4306. In the embodiment of FIG. 31, the outer housing 4306 is cylindrical in shape and fully circumscribes the surgical tool holder 4308. The outer housing 4306 may be composed of rigid materials (e.g., metals or hard plastics). In alternative embodiments, the shape of the housing may vary.

The surgical tool holder 4308 secures a surgical tool to the IDM 4300 via the attachment interface 4310. The surgical tool holder 4308 is capable of rotating independent of the outer housing 4306. The surgical tool holder 4308 rotates about a rotational axis 4316, which co-axially aligns with the elongated body of a surgical tool such that the surgical tool rotates with the surgical tool holder 4308.

The attachment interface 4310 is a face of the surgical tool holder 4308 that attaches to the surgical tool. The attachment interface 4310 includes a first portion of an attachment mechanism that reciprocally mates with a second portion of the attachment mechanism located on the surgical tool, which will be discussed in greater detail with regards to FIGS. 36A and 36B. In some embodiments, the attachment interface 4310 comprises a plurality of torque couplers 4314 that protrude outwards from the attachment interface 4310 and engage with respective instrument inputs on the surgical tool. In some embodiments, a surgical drape, coupled to a sterile adapter, may be used to create a sterile boundary between the IDM 4300 and the surgical tool. In these embodiments, the sterile adapter may be positioned between the attachment interface 4310 and the surgical tool when the surgical tool is secured to the IDM 4300 such that the surgical drape separates the surgical tool and the patient from the IDM 4300 and the surgical robotics system.

The passage 4312 is configured to receive the elongated body of a surgical tool when the surgical tool is secured to the attachment interface 4310. In the embodiment of FIG. 31, the passage 4312 is co-axially aligned with the longitudinal axis of the elongated body of the surgical tool and the rotational axis 4316 of the surgical tool holder 4308. The passage 4312 allows the elongated body of the surgical tool to freely rotate within the passage 4312. This configuration allows the surgical tool to be continuously rotated or rolled about the rotational axis 4316 in either direction with minimal or no restrictions.

The plurality of torque couplers 4314 are configured to engage and drive the components of the surgical tool when the surgical tool is secured to the surgical tool holder 4308. Each torque coupler 4314 is inserted into a respective instrument input located on the surgical tool. The plurality of torque couplers 4314 may also serve to maintain rotational alignment between the surgical tool and the surgical tool holder 4308. As illustrated in FIG. 31, each torque coupler 4314 is shaped as a cylindrical protrusion that protrudes outwards from the attachment interface 4310. Notches 4318 may be arranged along the outer surface area of the cylindrical protrusion. In some embodiments, the arrangement of the notches 4318 creates a spline interface. The instrument inputs on the surgical tool are configured to have a complementary geometry to the torque couplers 4314. For example, while not shown in FIG. 31, the instrument inputs of the surgical tool may be cylindrical in shape and have a plurality of ridges that reciprocally mate with the plurality of notches 4318 on each torque coupler 4314 and thus impart a torque on the notches 4318. In alternate embodiments, the top face of the cylindrical protrusion may include the plurality of notches 4318 configured to mate with a plurality of ridges in respective instrument inputs. In this configuration, each torque coupler 4314 fully engages with its respective instrument input.

Additionally, each torque coupler 4314 may be coupled to a spring that allows the torque coupler to translate. In the embodiment of FIG. 31, the spring causes each torque coupler 4314 to be biased to spring outwards away from the attachment interface 4310. The spring is configured to create translation in an axial direction, i.e., protract away from the attachment interface 4310 and retract towards the surgical tool holder 4308. In some embodiments, each torque coupler 4314 is capable of partially retracting into the surgical tool holder 4308. In other embodiments, each torque coupler 4314 is capable of fully retracting into the surgical tool holder 4308 such that the effective height of each torque coupler is zero relative to the attachment interface 4310. In the embodiment of FIG. 31, the translation of each torque coupler 4314 is actuated by an actuation mechanism, which will be described in further detail with regards to FIGS. 35-36. In various embodiments, each torque coupler 4314 may be coupled to a single spring, a plurality of springs, or a respective spring for each torque coupler.

In addition, each torque coupler 4314 is driven by a respective actuator that causes the torque coupler to rotate in either direction. Thus, once engaged with an instrument input, each torque coupler 4314 is capable of transmitting power to tighten or loosen pull-wires within a surgical tool, thereby manipulating a surgical tool's end-effectors. In the embodiment of FIG. 31, the IDM 4300 includes five torque couplers 4314, but the number may vary in other embodiments depending on the desired number of degrees of freedom for a surgical tool's end-effectors. In some embodiments, a surgical drape, coupled to a sterile adapter, may be used to create a sterile boundary between the IDM 4300 and the surgical tool. In these embodiments, the sterile adapter may be positioned between the attachment interface 4310 and the surgical tool when the surgical tool is secured to the IDM 4300, and the sterile adapter may be configured to transmit power from each torque coupler 4314 to the respective instrument input.

The embodiment of the IDM 4300 illustrated in FIG. 31 may be used in various configurations with a surgical robotic system. The desired configuration may depend on the type of surgical procedure being performed on a patient or the type of surgical tool being used during the surgical procedure. For example, the desired configuration of the IDM 4300 may be different for an endoscopic procedure than for a laparoscopic procedure.

In a first configuration, the IDM 4300 may be removably or fixedly attached to a surgical arm such that the attachment interface 4310 is proximal to a patient during the surgical procedure. In this configuration, hereinafter referred to as "front-mount configuration," the surgical tool is secured to the IDM 4300 on a side proximal to the patient. A surgical tool for use with the front-mount configuration is structured such that the elongated body of the surgical tool extends from a side that is opposite of the attachment interface of the surgical tool. As a surgical tool is removed from the IDM 4300 in a front-mount configuration, the surgical tool will be removed in a proximal direction to the patient.

In a second configuration, the IDM 4300 may be removably or fixedly attached to a surgical arm such that the attachment interface 4310 is distal to a patient during the surgical procedure. In this configuration, hereinafter referred to as "back-mount configuration," the surgical tool is secured to the IDM 4300 on a side distal to the patient. A surgical tool for use with the back-mount configuration is structured such that the elongated body of the surgical tool extends from the attachment interface of the surgical tool. This configuration increases patient safety during tool removal from the IDM 4300. As a surgical tool is removed from the IDM 4300 in a back-mount configuration, the surgical tool will be removed in a distal direction from the patient.

In a third configuration, the IDM 4300 may be removably or fixedly attached to a surgical arm such that at least a portion of the surgical tool is positioned above the IDM 4300. In this configuration, hereinafter referred to as a "top" or "through" configuration, a shaft of the surgical tool extends downwardly through the IDM 4300.

Certain configurations of a surgical tool may be structured such that the surgical tool can be used with an IDM in either a front-mount configuration or a back-mount configuration. In these configurations, the surgical tool includes an attachment interface on both ends of the surgical tool. For some surgical procedures, the physician may decide the configuration of the IDM depending on the type of surgical procedure being performed. For instance, the back-mount configuration may be beneficial for laparoscopic procedures wherein laparoscopic tools may be especially long relative to other surgical tools. As a surgical arm moves about during a surgical procedure, such as when a physician directs a distal end of the surgical tool to a remote location of a patient (e.g., a lung or blood vessel), the increased length of laparoscopic tools causes the surgical arm to swing about a larger arc. Beneficially, the back-mount configuration decreases the effective tool length of the surgical tool by receiving a portion of the elongated body through the passage 4312 and thereby decreases the arc of motion required by the surgical arm to position the surgical tool.

Figure 33:
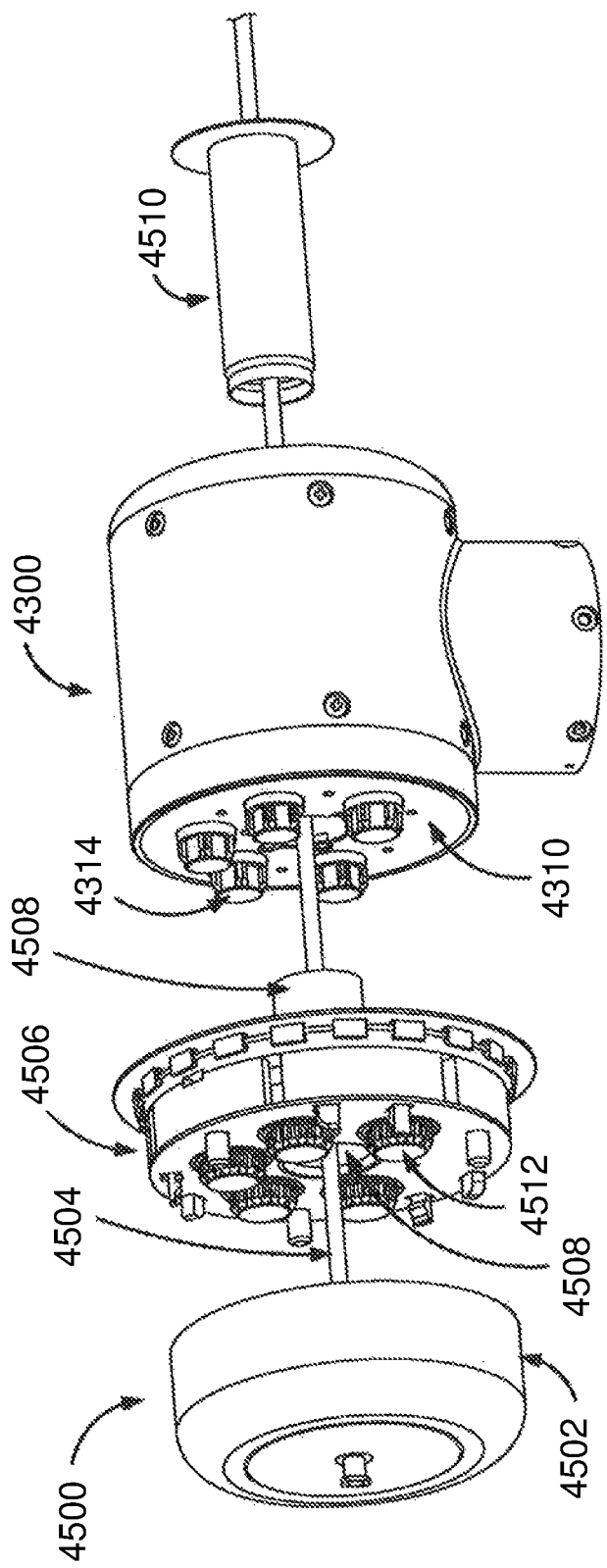
FIG. 33 illustrates a front-perspective exploded view of an example surgical tool secured to the instrument device manipulator of FIG. 31, according to one embodiment.
Figure 34:
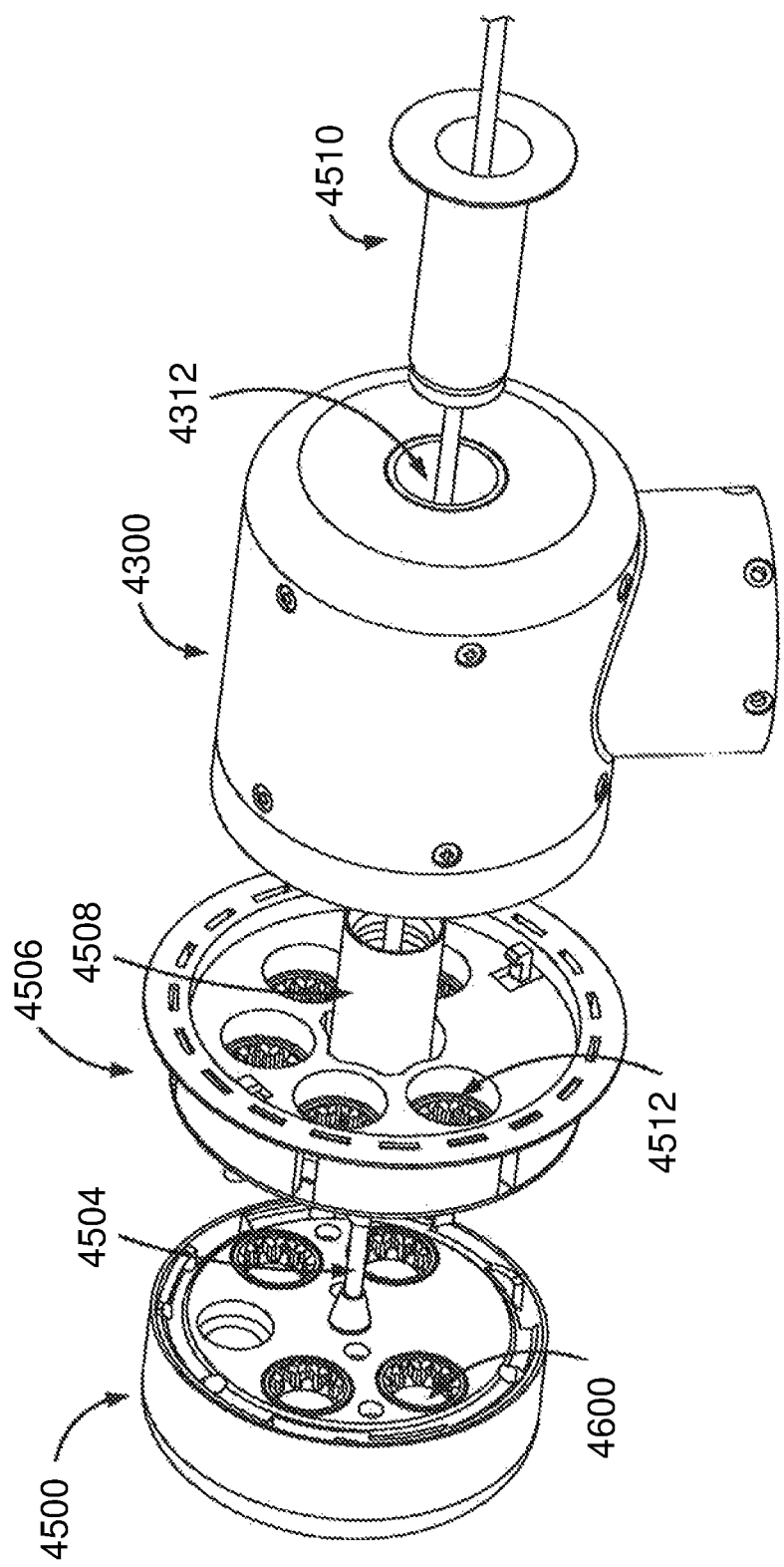
FIG. 34 illustrates a back-perspective exploded view of an example surgical tool secured to the instrument device manipulator of FIG. 31, according to one embodiment.

FIGS. 33-34 illustrate perspective exploded views of an example surgical tool 4500 secured to the instrument device manipulator 4300 of FIG. 31, according to one embodiment. The surgical tool 4500 includes a housing 4502, an elongated body 4504, and a plurality of instrument inputs 4600. As previously described, the elongated body 4504 may be a laparoscope, an endoscope, or other surgical tool having end-effectors. As illustrated, the plurality of torque couplers 4314 protrude outwards from the attachment interface 4310 to engage with the instrument inputs 4600 of the surgical tool. The structure of the instrument inputs 4600 can be seen in FIG. 34, wherein the instrument inputs 4600 have corresponding geometry to the torque couplers 4314 to ensure secure surgical tool engagement.

During a surgical procedure, a surgical drape may be used to maintain a sterile boundary between the IDM 4300 and an outside environment (i.e., an operating room). In the embodiments of FIGS. 33-34, the surgical drape comprises a sterile adapter 4506, a first protrusion 4508, and a second protrusion 4510. While not shown in FIGS. 33-34, a sterile sheet is connected to the sterile adapter and the second protrusion and drapes around the IDM 4300 to create the sterile boundary.

The sterile adapter 4506 is configured to create a sterile interface between the IDM 4300 and the surgical tool 4500 when secured to the IDM 4300. In the embodiment of FIGS. 33-34, the sterile adapter 4506 has a disk-like geometry that covers the attachment interface 4310 of the IDM 4300. The sterile adapter 4506 comprises a central hole 4508 that is configured to receive the elongated body 4504 of the surgical tool 4500. In this configuration, the sterile adapter 4506 is positioned between the attachment interface 4310 and the surgical tool 4500 when the surgical tool 4500 is secured to the IDM 4300, creating the sterile boundary between the surgical tool 4500 and the IDM 4300 and allowing the elongated body 4504 to pass through the passage 4312. In certain embodiments, the sterile adapter 4506 may be capable of rotating with the surgical tool holder 4308, transmitting the rotational torque from the plurality of torque couplers 4314 to the surgical tool 4500, passing electrical signals between the IDM 4300 and the surgical tool 4500, or some combination thereof.

In the embodiment of FIGS. 33-34, the sterile adapter 4506 further comprises a plurality of couplers 4512. A first side of a coupler 4512 is configured to engage with a respective torque coupler 4314 while a second side of a coupler 4512 is configured to engage with a respective instrument input 4600.

Similar to the structure of the plurality of torque couplers 4314, each coupler 4512 is structured as a cylindrical protrusion including a plurality of notches. Each side of the coupler 4512 has complementary geometry to fully engage with the respective torque coupler 4314 and the respective instrument input 4600. In some embodiments, the one or more instrument inputs 4600 are referred to as mechanical inputs. Each coupler 4512 is configured to rotate in a clockwise or counter-clockwise direction with the respective torque coupler 4314. This configuration allows each coupler 4512 to transfer rotational torque from the plurality of torque couplers 4314 of the IDM 4300 to the plurality of instrument inputs 4600 of the surgical tool 4500, and thus control the end-effectors of the surgical tool 4500.

The first protrusion 4508 and the second protrusion 4510 are configured to pass through the passage 4312 of the IDM 4300 and mate with each other inside the passage 4312. Each protrusion 4508, 4510 is structured to allow the elongated body 4504 to pass through the protrusion and thus the passage 4312. The connection of the first protrusion 4508 and the second protrusion 4510 creates the sterile boundary between the IDM 4300 and the outside environment (i.e., an operating room).

Figure 35:
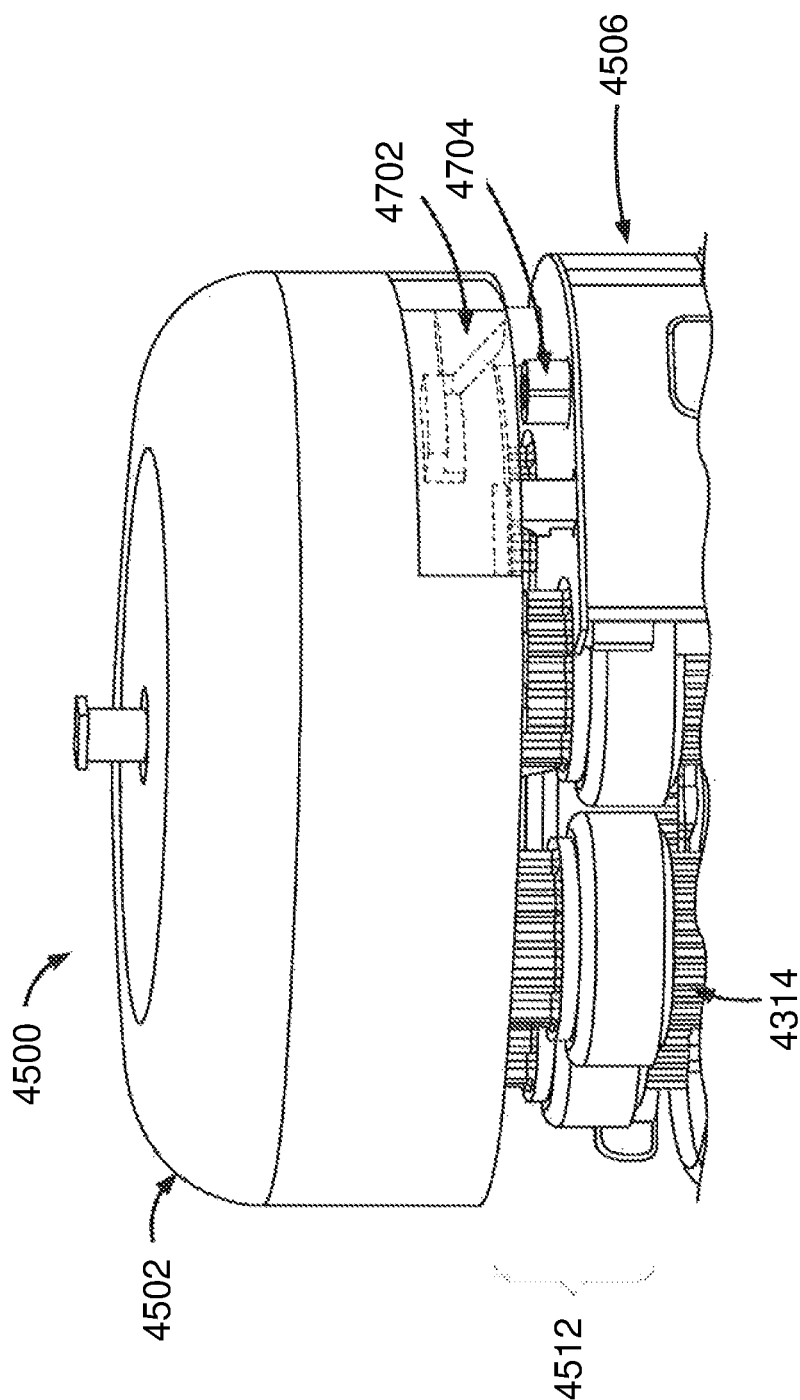
FIG. 35 illustrates a zoomed-in, perspective view of an actuation mechanism for engagement and disengagement of a surgical tool from a surgical tool holder, according to one embodiment.

FIG. 35 illustrates a zoomed-in, perspective view of an actuation mechanism for engagement and disengagement of a surgical tool 4500 from a sterile adapter 4506 of a surgical drape, according to one embodiment. Due to the configuration of the IDM 4300 as described with regards to FIG. 31, the axis of surgical tool insertion into the patient during a surgical procedure is the same as the axis of surgical tool removal. To ensure patient safety during surgical tool removal, the surgical tool 4500 can be de-articulated from the sterile adapter 4506 and the IDM 4300 before removing the surgical tool 4500. In the embodiment of FIG. 35, the plurality of couplers 4512 are configured to translate in an axial direction, i.e., protract away from and retract towards the sterile adapter 4506. The translation of the plurality of couplers 4512 is actuated by the actuation mechanism which ensures de-articulation of the surgical tool 4500 by disengaging the plurality of couplers 4512 from the respective instrument inputs 4600. The actuation mechanism includes a wedge 4702 and a pusher plate 4704.

The wedge 4702 is a structural component that activates the pusher plate 4704 during the process of surgical tool disengagement. In the embodiment of FIG. 35, the wedge 4702 is located within the housing 4502 of the surgical tool 4500 along the outer perimeter of the housing 4502. As illustrated, the wedge 4702 is oriented such that contact with the pusher plate 4704 causes the pusher plate 4704 to depress into the sterile adapter 4506 if the housing 4502 of the surgical tool 4500 is rotated clockwise relative to the sterile adapter 4506. In alternate embodiments, the wedge 4702 may be configured such that the housing 4502 of the surgical tool 4500 is rotated counter-clockwise rather than clockwise. Geometries other than a wedge may be employed, such as an arch-shaped ramp, given that the structure is able to depress the pusher plate when rotating.

The pusher plate 4704 is an actuator that disengages the plurality of couplers 4512 from the surgical tool 4500. Similar to the plurality of torque couplers 4314, each of the couplers 4512 may be coupled to one or more springs that bias each coupler 4512 to spring outwards away from the sterile adapter 4506. The plurality of couplers 4512 are further configured to translate in an axial direction, i.e., protract away from and retract into the sterile adapter 4506. The pusher plate 4704 actuates the translational movement of the couplers 4512. As the pusher plate 4704 is depressed by the wedge 4702, the pusher plate 4704 causes the spring or plurality of springs coupled to each coupler 4512 to compress, resulting in the couplers 4512 retracting into the sterile adapter 4506. In the embodiment of FIG. 35, the pusher plate 4704 is configured to cause simultaneous retraction of the plurality of couplers 4512. Alternate embodiments may retract the couplers 4512 in a specific sequence or a random order. In the embodiment of FIG. 35, the pusher plate 4704 causes the plurality of couplers 4512 to partially retract into the sterile adapter 4506. This configuration allows a surgical tool 4500 to be de-articulated from the sterile adapter 4506 before the surgical tool 4500 is removed. This configuration also allows a user to de-articulate the surgical tool 4500 from the sterile adapter 4506 at any desired time without removing the surgical tool 4500. Alternate embodiments may fully retract the plurality of couplers 4512 into the sterile adapter 4506 such that the effective height of each coupler 4512 measured is zero. In some embodiments, the pusher plate 4704 may cause the plurality of torque couplers 4314 to retract synchronously with the plurality of respective couplers 4512.

FIGS. 36A and 36B illustrate a process of engaging and disengaging a surgical tool from a sterile adapter, according to one embodiment. FIG. 36A illustrates a sterile adapter 4506 and a surgical tool 4500 in a secured position, such that the two components are secured together and the plurality of couplers 4512 are fully engaged with respective instrument inputs 4600 of the surgical tool 4500. To achieve the secured position as illustrated in FIG. 36A, the elongated body 4504 (not shown) of the surgical tool 4500 is passed through the central hole 4508 (not shown) of the sterile adapter 4506 until mating surfaces of the surgical tool 4500 and the sterile adapter 4506 are in contact, and the surgical tool 4500 and the sterile adapter 4506 are secured to each other by a latching mechanism. In the embodiments of FIGS. 36A and 36B, the latching mechanism comprises a ledge 4802 and a latch 4804.

The ledge 4802 is a structural component that secures the latch 4804 in the secured position. In the embodiment of FIG. 36A, the ledge 4802 is located within the housing 4502 of the surgical tool 4500 along the outer perimeter of the housing 4502. As illustrated in FIG. 36A, the ledge 4802 is oriented such that it rests below a protrusion on the latch 4804, preventing the latch 4804 and thereby the sterile adapter 4506 from pulling away from the surgical tool 4500 due to the sprung-up nature of the plurality of couplers 4512, as described with regards to FIG. 35.

The latch 4804 is a structural component that mates with the ledge 4802 in the secured position. In the embodiment of FIG. 36A, the latch 4804 protrudes from the mating surface of the sterile adapter 4506. The latch 4804 comprises a protrusion that is configured to rest against the ledge 4802 when the surgical tool 4500 is secured to sterile adapter 4506. In the embodiment of FIG. 36A, the housing 4502 of the surgical tool 4500 is capable of rotating independent of the rest of the surgical tool 4500. This configuration allows the housing 4502 to rotate relative to the sterile adapter 4506 such that the ledge 4802 is secured against the latch 4804, thereby securing the surgical tool 4500 to the sterile adapter 4502. In the embodiment of FIG. 36A, the housing 4502 is rotated counter-clockwise to achieve the secured position, but other embodiments may be configured for clockwise rotation. In alternate embodiments, the ledge 4802 and the latch 4804 may have various geometries that lock the sterile adapter 4506 and the surgical tool 4500 in the secured position.

FIG. 36B illustrates the sterile adapter 4506 and the surgical tool 4500 in an unsecured position, in which the surgical tool 4500 may be removed from the sterile adapter 4506. As previously described, the housing 4502 of the surgical tool 4500 is capable of rotating independent of the rest of the surgical tool 4500. This configuration allows the housing 4502 to rotate even while the plurality of couplers 4512 are engaged with the instrument inputs 4600 of the surgical tool 4500. To transition from the secured position to the unsecured position, a user rotates the housing 4502 of the surgical tool 4500 clockwise relative to the sterile adapter 4506. During this rotation, the wedge 4702 contacts the pusher plate 4704 and progressively depresses the pusher plate 4704 as it slides against the angled plane of the wedge 4702, thereby causing the plurality of couplers 4512 to retract into the sterile adapter 4506 and disengage from the plurality of instrument inputs 4600. Further rotation causes the latch 4804 to contact an axial cam 4806, which is structured similar to wedge 4702. As the latch 4804 contacts the axial cam 4806 during rotation, the axial cam 4806 causes the latch 4804 to flex outwards away from the surgical tool 4500 such that the latch 4804 is displaced from the ledge 4802. In this unsecured position, the plurality of couplers 4512 are retracted, and the surgical tool 4500 can be removed from the sterile adapter 4506, in the embodiment of FIG. 36B. In other embodiments, the axial cam 4806 may have various geometries such that rotation causes the latch 4804 to flex outwards.

In alternate embodiments, the direction of rotation of the housing 4502 of the surgical tool 4500 may be configured as counter-clockwise rotation to unsecure the latch 4804 from the ledge 4802. Additionally, alternate embodiments may include similar components but the location of the components may be switched between the sterile adapter 4506 and the surgical tool 4500. For example, the ledge 4802 may be located on the sterile adapter 4506 while the latch 4804 may be located on the surgical tool 4500. In other embodiments, an outer portion of the sterile adapter 4506 may be rotatable relative to the plurality of couplers 4512 rather than the housing 4502 of the surgical tool 4500. Alternate embodiments may also include a feature to lock the rotation of the housing 4502 of the surgical tool 4502 when the housing 4502 is fully rotated relative to the instrument inputs 4600. This configuration prevents rotation of the surgical tool if the instrument inputs 4600 have been de-articulated from the couplers 4512. In some embodiments, the retraction and protraction of the couplers 4512 may be coupled with a respective retraction and protraction of the torque couplers 4314, such that a coupler 4512 engaged with a torque coupler 4314 will translate together.

FIGS. 37A and 37B illustrate a process of surgical tool engagement and disengagement of a surgical tool from a sterile adapter, according to another embodiment. In the embodiment of FIGS. 37A and 37B, a sterile adapter 4900 may include an outer band 4902 that secures the surgical tool 4904 to the sterile adapter 4900. As illustrated in FIGS. 37A and 37B, the surgical tool 4902 comprises a ramp 4906 on the outer surface of the housing 4908. The ramp 4906 includes a notch 4910 that is configured to receive a circular protrusion 4912, which is positioned on an inner surface of the outer band 4902 of the sterile adapter 4900. The outer band 4902 is capable of rotating independent of and relative to the sterile adapter 4900 and the surgical tool 4904. As the outer band 4902 rotates in a first direction, the circular protrusion 4912 glides up the surface of the ramp 4906 until the circular protrusion 4912 is nested within the notch 4910, thereby securing the sterile adapter 4900 and the surgical tool 4904 together. Rotation of the outer band 4902 in a second direction causes the sterile adapter 4900 and the surgical tool 4904 to unsecure from each other. In certain embodiments, this mechanism may be coupled with a de-articulation of the plurality of couplers 4914 on the sterile adapter 4900, as described with regards to FIGS. 35-36.

Alternative embodiments of surgical tool disengagement may include additional features, such as an impedance mode. With an impedance mode, the surgical robotics system may control whether the surgical tool can be removed from the sterile adapter by a user. The user may initiate the disengagement mechanism by rotating the outer housing of the surgical tool and unsecuring the surgical tool from the sterile adapter, but the surgical robotics system may not release the couplers from the instrument inputs. Only once the surgical robotics system has transitioned into the impedance mode are the couplers released and the user can remove the surgical tool. An advantage of keeping the surgical tool engaged is that the surgical robotics system can control the end-effectors of the surgical tool and position them for tool removal before the surgical tool is removed to minimize damage to the surgical tool. To activate an impedance mode, the pusher plate 4704 may have a hard-stop such that the pusher plate can be depressed up to a certain distance. In some embodiments, the hard-stop of the pusher plate may be adjustable such that the hard-stop coincides with the maximum amount of rotation of the housing of the surgical tool. Thus, once the full rotation is reached, the hard-stop is also met by the pusher plate. A plurality of sensors may detect these events and trigger the impedance mode.

Certain situations may require emergency tool removal during a surgical procedure in which the impedance mode may not be desirable. In some embodiments, the hard-stop of the pusher plate may have compliance, such that the hard-stop may yield in an emergency. The hard-stop of the pusher plate may be coupled to a spring, allowing the hard-stop to yield in response to additional force. In other embodiments, the hard-stop of the pusher plate may be rigid such that emergency tool removal occurs by removing the latch that secures the surgical tool to the sterile adapter.

Figure 38A:
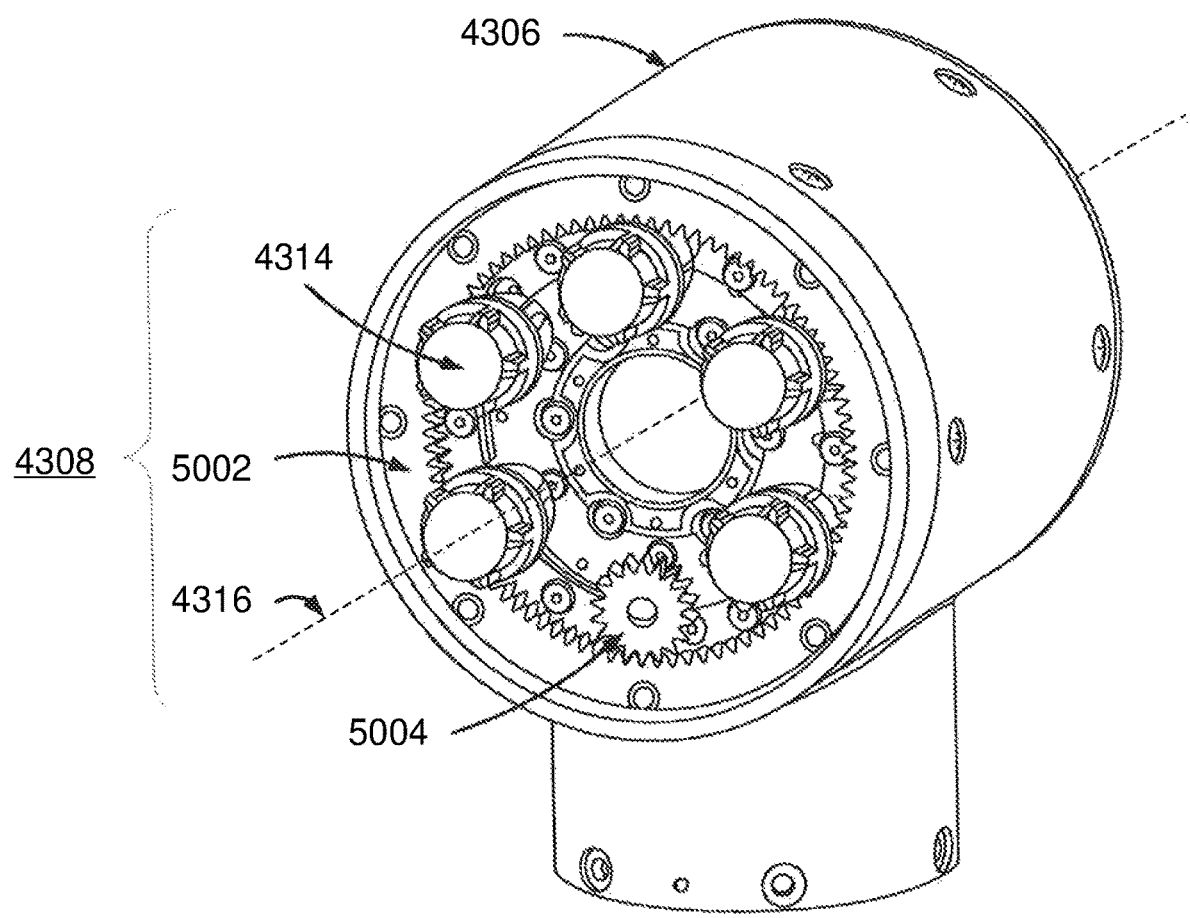
FIG. 38A illustrates a perspective view of a mechanism for rolling a surgical tool holder within an instrument device manipulator, according to one embodiment.

FIG. 38A illustrates a perspective view of a mechanism for rolling a surgical tool holder 4308 within an instrument device manipulator 4300, according to one embodiment. As illustrated in FIG. 38A, the attachment interface 4310 is removed to expose the roll mechanism. This mechanism allows the surgical tool holder 4308 to continuously rotate or "roll" about the rotational axis 4316 in either direction. The roll mechanism comprises a stator gear 5002 and a rotor gear 5004.

The stator gear 5002 is a stationary gear configured to mate with the rotor gear 5004. In the embodiment of FIG. 38A, the stator gear 5002 is a ring-shaped gear comprising gear teeth along the inner circumference of the ring. The stator gear 5002 is fixedly attached to the outer housing 4306 behind the attachment interface 4310. The stator gear 5002 has the same pitch as the rotor gear 5004, such that the gear teeth of the stator gear 5002 are configured to mate with the gear teeth of the rotor gear 5004. The stator gear 5002 may be composed of rigid materials (e.g., metals or hard plastics).

The rotor gear 5004 is a rotating gear configured to induce rotation of the surgical tool holder 4308. As illustrated in FIG. 38A, the rotor gear 5004 is a circular gear comprising gear teeth along its outer circumference. The rotor gear 5004 is positioned behind the attachment interface 4310 and within the inner circumference of the stator gear 5002 such that the gear teeth of the rotor gear 5004 mate with the gear teeth of the stator gear. As previously described, the rotor gear 5004 and the stator gear 5002 have the same pitch. In the embodiment of FIG. 38A, the rotor gear 5004 is coupled to a drive mechanism (e.g., a motor) that causes the rotor gear 5004 to rotate in a clockwise or counter-clockwise direction. The drive mechanism may receive signals from an integrated controller within the surgical tool holder assembly 4304. As the drive mechanism causes the rotor gear 5004 to rotate, the rotor gear 5004 travels along the gear teeth of the stator gear 5002, thereby causing the surgical tool holder 4308 to rotate. In this configuration, the rotor gear 5004 is capable of continuously rotating in either direction and thus allows the surgical tool holder 4308 to achieve infinite roll about the rotational axis 4316. Alternate embodiments may use similar mechanisms to allow for infinite roll, such as a configuration of a ring gear and a pinion gear.

Figure 38B:
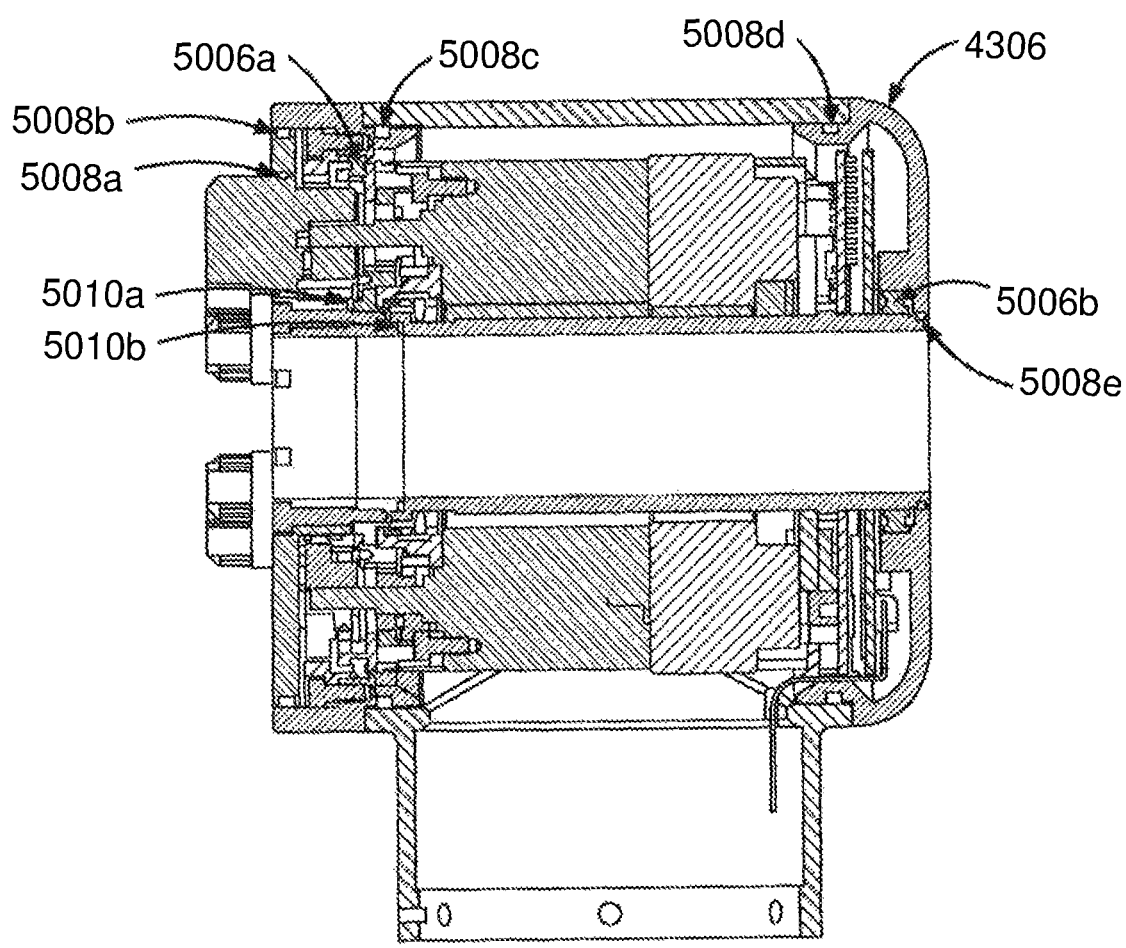
FIG. 38B illustrates a cross-sectional view of an instrument device manipulator, according to one embodiment.

FIG. 38B illustrates a cross-sectional view of an instrument device manipulator 4300, according to one embodiment. As illustrated in FIB. 38B, the roll mechanism is coupled with a plurality of bearing 5006. A bearing is a mechanical component that reduces friction between moving parts and facilitates rotation around a fixed axis. One bearing alone can support the radial or torsional loading as the surgical tool holder 4308 rotates within the outer housing 4306. In the embodiment of FIG. 38B, the IDM 4300 includes two bearings 5006a, 5006b fixedly attached to the surgical tool holder 4308 such that a plurality of components (such as balls or cylinders) within the bearings 5006 contacts the outer housing 4306. A first bearing 5006a is secured at a first end behind the attachment interface 4310 and a second bearing 5006b is secured at a second end. This configuration improves rigidity and support between the first end and the second end of the surgical tool holder 4308 as the surgical tool holder 4308 rotates within the outer housing 4306. Alternate embodiments may include additional bearings that provide additional support along the length of the surgical tool holder.

FIG. 38B also illustrates sealing components within the IDM 4300, according to one embodiment. The IDM 4300 comprises a plurality of O-rings 5008 and a plurality of gaskets 5010 which are configured to seal a junction between two surfaces to prevent fluids from entering the junction. In the embodiment of FIG. 38B, the IDM includes O-rings 5008a, 5008b, 5008c, 5008d, 5008e between junctions of the outer housing and gaskets 5010a, 5010b between junctions within the surgical tool holder 4308. This configuration helps to maintain sterility of the components within the IDM 4300 during a surgical procedure. Gaskets and O-rings are typically composed of strong elastomeric materials (e.g., rubber).

Figure 38C:
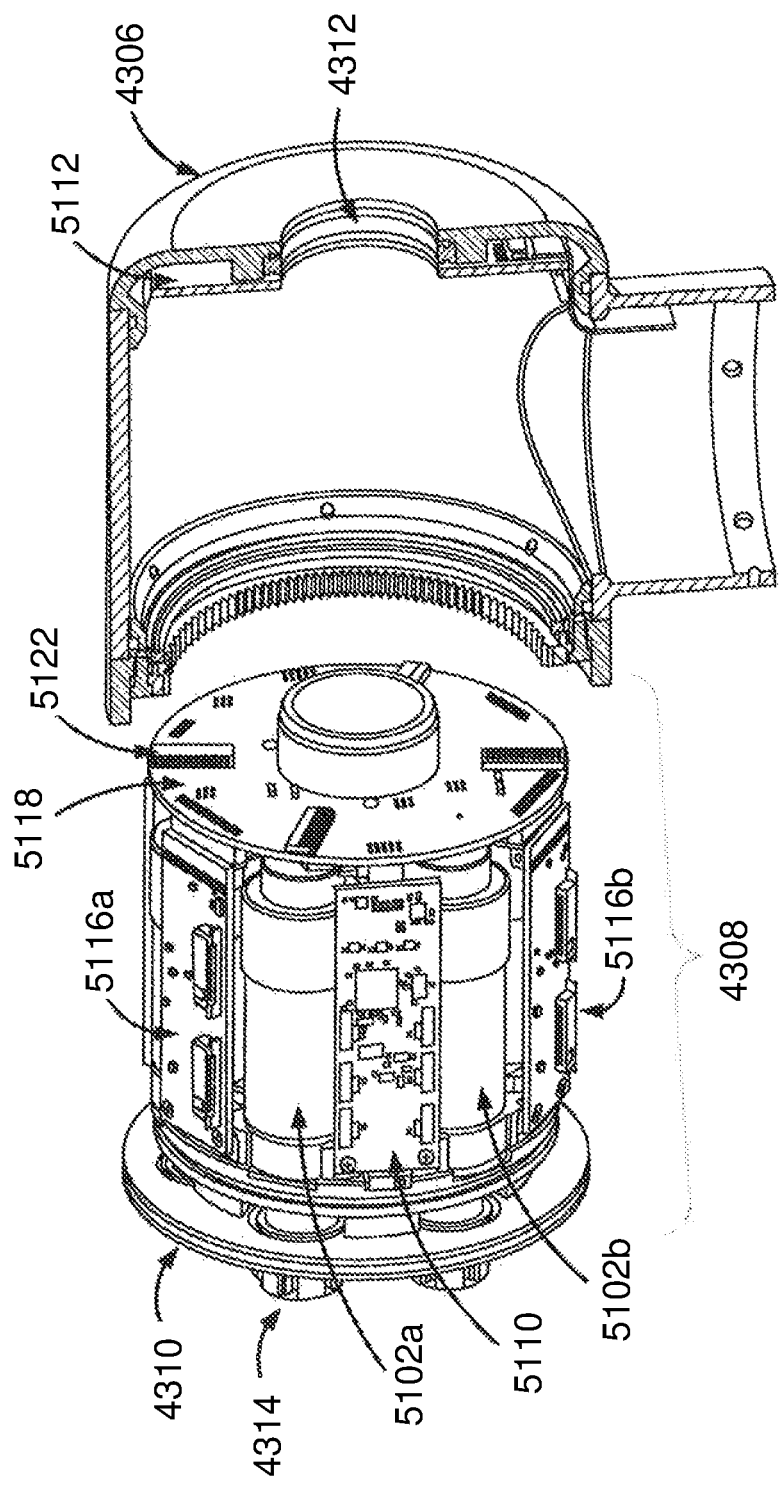
FIGS. 38C and 38D illustrates partially exploded, perspective views of the internal components of an instrument device manipulator and certain electrical components thereof, according to one embodiment.

FIG. 38C illustrates a partially exploded, perspective view of the internal components of an instrument device manipulator and certain electrical components thereof, according to one embodiment. The internal components of the surgical tool holder 4308 include a plurality of actuators 5102, a motor, a gearhead (not shown), a torque sensor (not shown), a torque sensor amplifier 5110, a slip ring 5112, a plurality of encoder boards 5114, a plurality of motor power boards 5116, and an integrated controller 5118.

The plurality of actuators 5102 drive the rotation of each of the plurality of torque couplers 4314. In the embodiment of FIG. 38C, an actuator, such as 5102a or 5102b, is coupled to a torque coupler 4314 via a motor shaft. The motor shaft may be a keyed shaft such that it includes a plurality of grooves to allow the motor shaft to securely mate to a torque coupler 4314. The actuator 5102 causes the motor shaft to rotate in a clockwise or counter-clockwise direction, thereby causing the respective torque coupler 4314 to rotate in that direction. In some embodiments, the motor shaft may be torsionally rigid but spring compliant, allowing the motor shaft and thus the torque coupler 4314 to rotate and to translate in an axial direction. This configuration may allow the plurality of torque couplers 4314 to retract and protract within the surgical tool holder 4308. Each actuator 5102 may receive electrical signals from the integrated controller 5118 indicating the direction and amount to rotate the motor shaft. In the embodiment of FIG. 38C, the surgical tool holder 4308 includes five torque couplers 4314 and thus five actuators 5102.

The motor drives the rotation of the surgical tool holder 4308 within the outer housing 4306. The motor may be structurally equivalent to one of the actuators, except that it is coupled to the rotor gear 5004 and stator gear 5002 (see FIG. 38A) for rotating the surgical tool holder 4308 relative to the outer housing 4306. The motor causes the rotor gear 5004 to rotate in a clockwise or counter-clockwise direction, thereby causing the rotor gear 5004 to travel about the gear teeth of the stator gear 5002. This configuration allows the surgical tool holder 4308 to continuously roll or rotate without being hindered by potential wind-up of cables or pull-wires. The motor may receive electrical signals from the integrated controller 5118 indicating the direction and amount to rotate the motor shaft.

The gearhead controls the amount of torque delivered to the surgical tool 4500. For example, the gearhead may increase the amount of torque delivered to the instrument inputs 4600 of the surgical tool 4500. Alternate embodiments may be configured such that the gearhead decreases the amount of torque delivered to the instrument inputs 4600.

The torque sensor measures the amount of torque produced on the rotating surgical tool holder 4308. In the embodiment shown in FIG. 38C, the torque sensor is capable of measuring torque in the clockwise and the counter-clockwise direction. The torque measurements may be used to maintain a specific amount of tension in a plurality of pull-wires of a surgical tool. For instance, some embodiments of the surgical robotics system may have an auto-tensioning feature, wherein, upon powering on the surgical robotics system or engaging a surgical tool with an IDM, the tension on the pull-wires of the surgical tool will be pre-loaded. The amount of tension on each pull-wire may reach a threshold amount such that the pull-wires are tensioned just enough to be taut. The torque sensor amplifier 5110 comprises circuitry for amplifying the signal that measures the amount of torque produced on the rotating surgical tool holder 4308. In some embodiments, the torque sensor is mounted to the motor.

The slip ring 5112 enables the transfer of electrical power and signals from a stationary structure to a rotating structure. In the embodiment of FIG. 38C, the slip ring 5112 is structured as a ring including a central hole that is configured to align with the passage 4312 of the surgical tool holder 4308, as is also shown in an additional perspective view of the slip ring 5112 in FIG. 38D. A first side of the slip ring 5112 includes a plurality of concentric grooves 5120 while a second side of the slip ring 5112 includes a plurality of electrical components for the electrical connections provided from the surgical arm and the base 4302, as described with regards to FIG. 31. The slip ring 5112 is secured to the outer housing 4306 of the surgical tool holder 4308 at a specific distance from the outer housing 4306 to allocate space for these electrical connections. The plurality of concentric grooves 5120 are configured to mate with a plurality of brushes 5122 attached to the integrated controller. The contact between the grooves 5120 and the brushes 5122 enables the transfer of electrical power and signals from the surgical arm and base to the surgical tool holder.

The plurality of encoder boards 5114 read and process the signals received through the slip ring from the surgical robotic system. Signals received from the surgical robotic system may include signals indicating the amount and direction of rotation of the surgical tool, signals indicating the amount and direction of rotation of the surgical tool's end-effectors and/or wrist, signals operating a light source on the surgical tool, signals operating a video or imaging device on the surgical tool, and other signals operating various functionalities of the surgical tool. The configuration of the encoder boards 5114 allows the entire signal processing to be performed completely in the surgical tool holder 4308. The plurality of motor power boards 5116 each comprises circuitry for providing power to the motors.

The integrated controller 5118 is the computing device within the surgical tool holder 4308. In the embodiment of FIG. 38C, the integrated controller 5118 is structured as a ring including a central hole that is configured to align with the passage 4312 of the surgical tool holder 4308. The integrated controller 5118 includes a plurality of brushes 5122 on a first side of the integrated controller 5118. The brushes 5122 contact the slip ring 5112 and receive signals that are delivered from the surgical robotics system through the surgical arm, the base 4302, and finally through the slip ring 5112 to the integrated controller 5118. As a result of the received signals, the integrated controller 5118 is configured to send various signals to respective components within the surgical tool holder 4308. In some embodiments, the functions of the encoder boards 5114 and the integrated controller 5118 may be distributed in a different manner than is described here, such that the encoder boards 5114 and the integrated controller 5118 may perform the same functions or some combination thereof.

Figure 38D:
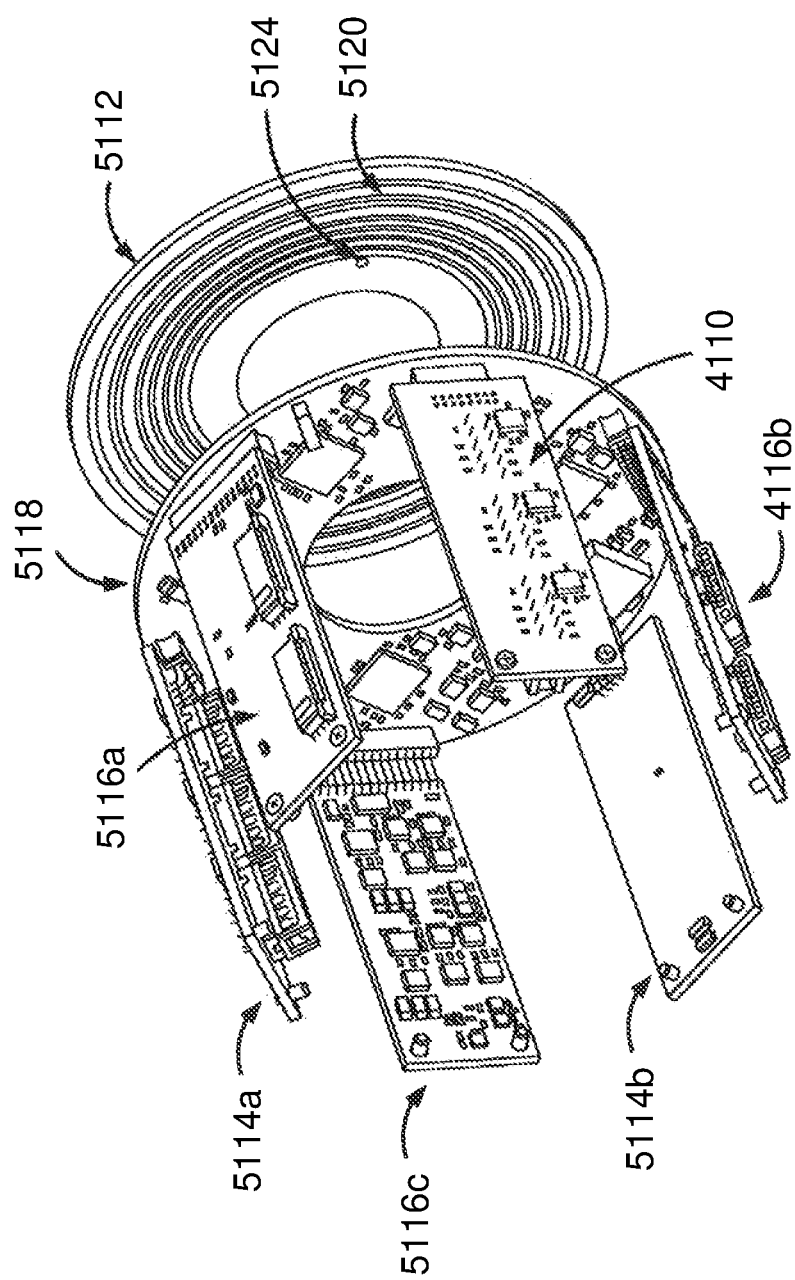

FIG. 38D illustrates a partially exploded, perspective view of the internal components of an instrument device manipulator and certain electrical components thereof, according to one embodiment. The embodiment of FIG. 38D includes two encoder boards 5114*a* and 5114*b*, a torque sensor amplifier 5110, and three motor power boards 5116*a*, 5116*b*, and 5116*c*. These components are secured to the integrated controller 5118 and protrude outwards, extending perpendicularly from the integrated controller 5118. This configuration provides room for the plurality of actuators 5102 and motor to be positioned within the electrical boards.

As discussed with regards to FIG. 38C, the slip ring 5112 is secured at a specific distance from the outer housing 4306. To ensure correct space allocation between the slip ring 5112 and the outer housing 4306 for the electrical connections from the surgical arm and base 4302 to the slip ring 5112, in the embodiment of FIG. 38D, the slip ring 5112 is supported by a plurality of alignment pins, a plurality of coil springs, and a shim. The slip ring 5112 includes a hole 5124 on each side of the center hole of the slip ring 5112 that is configured to accept a first side of an alignment pin while a second side of the alignment pin is inserted into a respective hole in the outer housing 4306. The alignment pins may be composed of rigid materials (e.g., metal or hard plastics). The plurality of coil springs is secured around the center of the slip ring 5112 and configured to bridge the space and maintain contact between the slip ring 5112 and the outer housing 4306. The coil springs may beneficially absorb any impact to the IDM 4300. The shim is ring-shaped spacer that is positioned around the center hole of the slip ring 5112 to add further support between the slip ring 5112 and the outer housing 4306. In addition, these components provide stability to the slip ring 5112 as the plurality of brushes 5122 on the integrated controller 5118 contact and rotate against the plurality of concentric grooves 5120. In alternate embodiments, the number of alignment pins, coil springs, and shims may vary until the desired support between the slip ring 5112 and the outer housing 4306 is achieved.

Figure 38E:
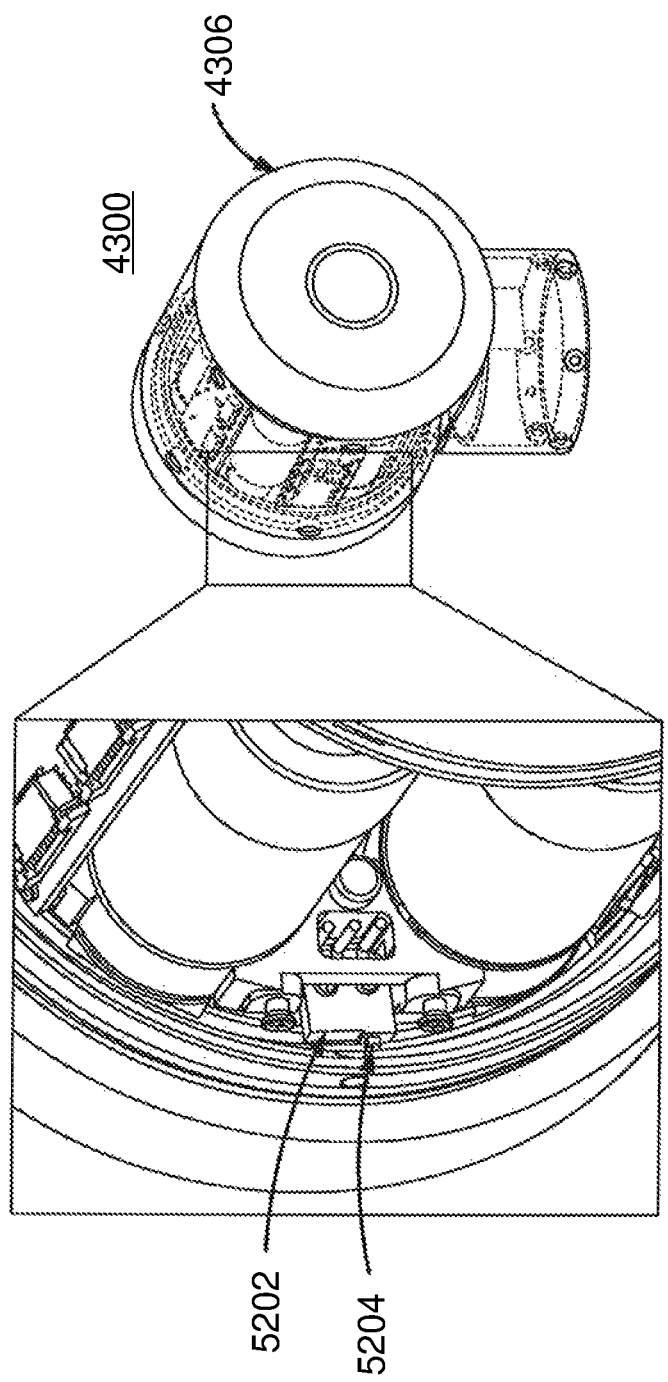
FIG. 38E illustrates a zoomed-in, perspective view of electrical components of an instrument device manipulator for roll indexing the surgical tool holder, according to one embodiment.

FIG. 38E illustrates a zoomed-in, perspective view of electrical components of an instrument device manipulator 4300 for roll indexing the surgical tool holder 4308, according to one embodiment. Roll indexing monitors the position of the surgical tool holder 4308 relative to the outer housing 4306 such that the position and orientation of the surgical tool 4500 is continuously known by the surgical robotics system. The embodiment of FIG. 38E includes a micro switch 5202 and a boss 5204. The micro switch 5202 and the boss 5204 are secured within the surgical tool holder 4308. The boss 5204 is a structure on the outer housing 4306 that is configured to contact the micro switch 5202 as the surgical tool holder 4308 rotates, thus activating the micro switch each time there is contact with the boss 5204. In the embodiment of FIG. 38E, there is one boss 5204 that serves as a single reference point for the micro switch 5202.

Various tools or instruments can attach to the IDM 4300, including instruments used for laparoscopic, endoscopic and endoluminal surgery. The instruments described herein are particularly novel, as they include instrument based insertion architectures that reduce the reliance on robotic arms for insertion. In other words, insertion of an instrument (e.g., towards a surgical site) can be facilitated by the design and architecture of the instrument. For example, in some embodiments, wherein an instrument comprises an elongated shaft and a handle, the architecture of the instrument enables the elongated shaft to translate relative to the handle along an axis of insertion.

The instruments described herein incorporate instrument based insertion architectures that alleviate many issues. Instruments that do not incorporate an instrument based insertion architecture rely on a robotic arm and its IDM for insertion. In this arrangement, to achieve instrument insertion, the IDM may need to be moved in and out, therefore requiring additional motor power and arm link size for moving the additional mass in a controlled manner. In addition, the larger volume creates a much larger swept volume that can result in collisions during operation. By incorporating instrument based insertion architectures, the instruments described herein typically have a reduced swung mass, as the instrument itself (e.g., its shaft) moves along an insertion axis with less reliance on the robotic arm.

Some embodiments of the instruments described herein may have novel instrument based insertion architectures that not only allow for insertion of the instrument, but also allow an end effector of the instrument to actuate without interference. For example, in some embodiments, an instrument comprises a first actuation mechanism for actuating an end effector and a second actuation mechanism for causing translation of a portion of the instrument (e.g., a shaft) along an axis of insertion. The first actuation mechanism is advantageously decoupled from the second actuation mechanism such that the actuation of the end effector is not affected by the insertion of the instrument, and vice versa.

Figure 39:
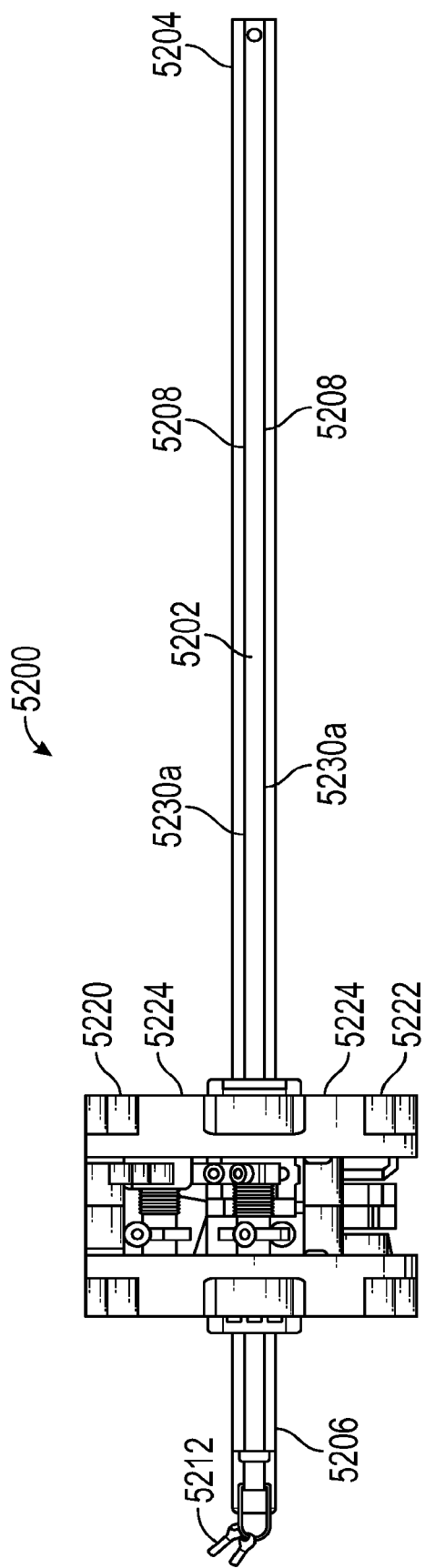
FIG. 39 illustrates a side view of an instrument having an instrument based insertion architecture, according to one embodiment.

FIG. 39 illustrates a side view of an instrument having an instrument based insertion architecture, according to one embodiment. The design and architecture of the instrument 5200 enables the instrument (e.g., its shaft) to translate along an insertion axis with less reliance on movement of a robotic arm for insertion.

The instrument 5200 comprises an elongated shaft 5202, an end effector 5212 connected to the shaft 5202, and a handle 5220 coupled to the shaft 5202. The elongated shaft 5202 comprises a tubular member having a proximal portion 5204 and a distal portion 5206. The elongated shaft 5202 comprises one or more channels or grooves 5208 along its outer surface. The grooves 5208, which are most visible in the cross-sectional view of the shaft 5202, are configured to receive one or more wires or cables 5230 therethrough. One or more cables 5230 thus run along an outer surface of the elongated shaft 5202. In other embodiments, cables 5230 can also run through the shaft 5202, as shown in the schematic drawing in FIG. 49. In some embodiments, cables 5230 that run through the shaft 5202 are not exposed. In some embodiments, manipulation of the one or more of these cables 5230 (e.g., via the IDM 4300) results in actuation of the end effector 5212.

The end effector 5212 comprises one or more laparoscopic, endoscopic or endoluminal components designed to provide an effect to a surgical site. For example, the end effector 5212 can comprise a wrist, grasper, tines, forceps, scissors, or clamp. In the present embodiment shown in FIG. 39, one or more of the cables 5230 that extend along the grooves 5208 on the outer surface of the shaft 5202 actuate the end effector 5212. The one or more cables 5230 extend from a proximal portion 5204 of the shaft 5202, through the handle 5220 and toward a distal portion 5206 of the shaft 5202, where they actuate the end effector 5212.

The instrument handle 5220, which may also be referred to as an instrument base, may generally comprise an attachment interface 5222 having one or more mechanical inputs 5224, e.g., receptacles, pulleys or spools, that are designed to be reciprocally mated with one or more torque couplers 4314 on an attachment interface 4310 of the IDM 4300 (shown in FIG. 31). The attachment interface 5222 is capable of attaching to an IDM 4300 via front-mount, back-mount and/or top mount. When physically connected, latched, and/or coupled, the mated mechanical inputs 5224 of the instrument handle 5220 may share axes of rotation with the torque couplers 4314 of the IDM 4300, thereby allowing the transfer of torque from the IDM 4300 to the instrument handle 5220. In some embodiments, the torque couplers 4314 may comprise splines that are designed to mate with receptacles on the mechanical inputs. Cables 5230 that actuate the end effector 5212 engage the receptacles, pulleys or spools of the handle 5220, such that the transfer of torque from the IDM 4300 to the instrument handle 5220 results in actuation of the end effector.

Figure 40:
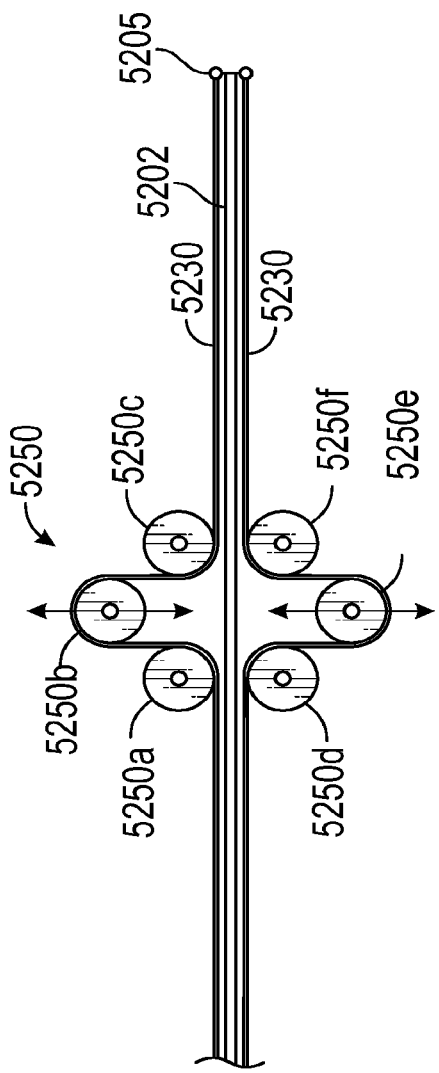
FIG. 40 illustrates a schematic diagram showing a first actuation mechanism for actuating an end effector, according to one embodiment.
Figure 44:
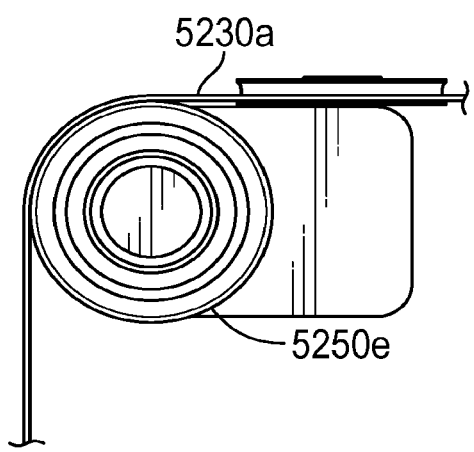
FIG. 44 illustrates a view of a pulley and cable of the instrument of FIG. 39, following actuation of the pulley, according to one embodiment.
Figure 45:
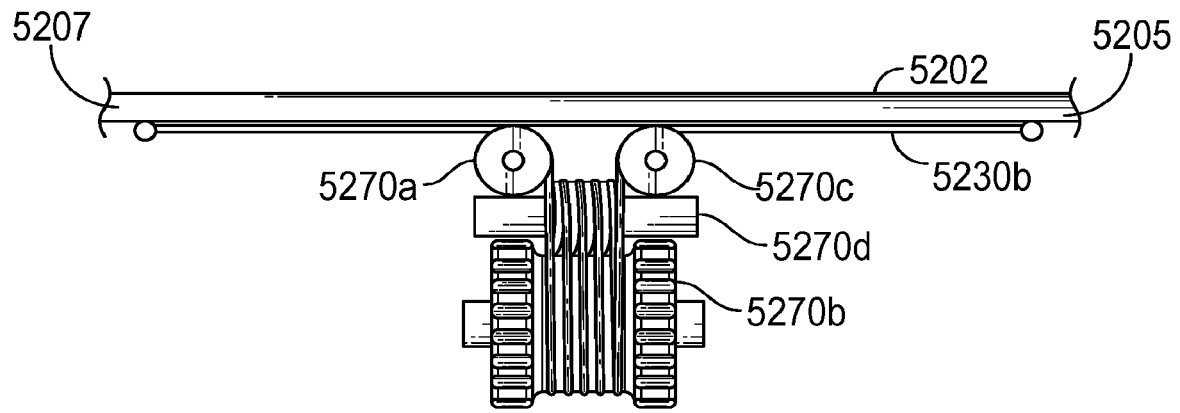
FIG. 45 illustrates a side view of a second actuation mechanism including a spool for shaft translation, according to one embodiment.

Some embodiments of the instrument 5200 comprise a first actuation mechanism that controls actuation of the end effector 5212. An embodiment of such a first actuation mechanism is schematically illustrated in FIG. 40. In addition, the instrument 5200 includes a second actuation mechanism that enables the shaft 5202 to translate relative to the handle 5220 along an axis of insertion. An embodiment of such a second actuation mechanism is shown in FIG. 45. Advantageously, the first actuation mechanism is decoupled from the second actuation mechanism, such that actuation of the end effector 5212 is not affected by the translation of the shaft 5202, and vice versa. Embodiments of the first and second actuation mechanisms that can be incorporated into a tool or instrument 5200 are described in more detail below with respect to FIGS. 40-48.

FIG. 40 illustrates a schematic diagram showing a first actuation mechanism for actuating an end effector, according to one embodiment. In some embodiments, the first actuation mechanism provides N+1 wrist motion, wherein N is the number of degrees of freedom provided by N+1 cables. The first actuation mechanism for actuating the end effector 5212 comprises at least one cable or cable segment 5230*a* that extends through at least one set of pulleys 5250. In the present embodiment, a first cable or cable segment 5230*a* extends through pulley members 5250*a*, 5250*b*, 5250*c*, while a second cable or cable segment 5230*a* extends through pulley members 5250*d*, 5250*e*, 5250*f*. The at least one cable 5230*a* is grounded at or near the proximal end 5205 of the shaft 5202, then extends through the at least one set of pulleys 5250 (which are located within the handle 5220), before terminating at the end effector 5212. Cable total path length is kept constant by grounding each cable 5230*a* at or near the proximal end 5205 of the shaft 5202, and relative length changes are made by moving pulleys (e.g., pulley members 5250*b* and 5250*e*) relative to each other (see arrows), thereby enabling actuation of the end effector 5212. In some embodiments, the pulleys can be moved via linear or rotary motion of corresponding mechanical inputs 5224. This first actuation mechanism advantageously permits free movement of the instrument shaft 5202 relative to the actuation pulleys 5250 (which will be accomplished by a second actuation mechanism described below), thereby allowing an additional cable to be included to permit insertion and retraction of the instrument shaft 5202 at the same time as end effector 5212 actuation.

Figure 41:
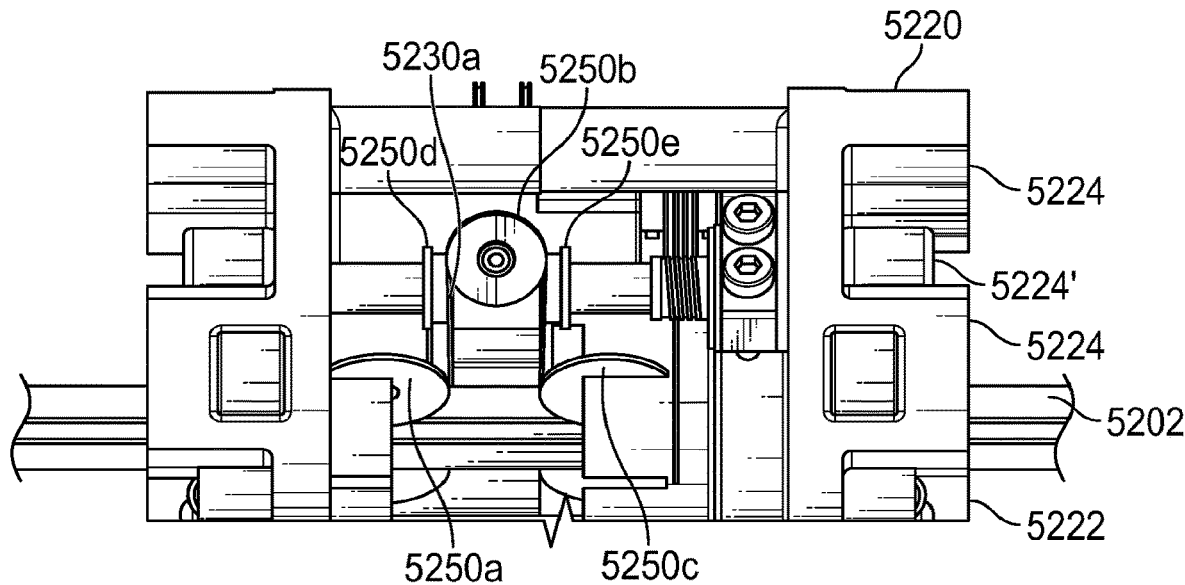
FIG. 41 illustrates a zoomed-in side view of a first actuation mechanism of the instrument of FIG. 39, according to one embodiment.
Figure 43:
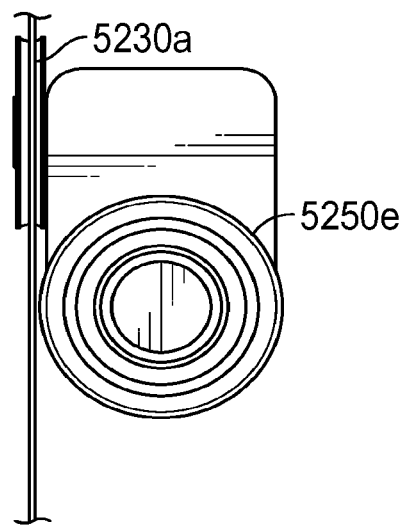
FIG. 43 illustrates a view of a pulley and cable of the instrument of FIG. 39, prior to actuation of the pulley, according to one embodiment.

FIG. 41 illustrates a zoomed-in side view of a first actuation mechanism of the instrument of FIG. 39, according to one embodiment. The first actuation mechanism corresponds with the schematic diagram shown in FIG. 40 and is designed to cause actuation of the end effector 5212, while permitting a separate second actuation mechanism to translate the shaft 5202 relative to the handle 5220. As shown in FIG. 41, the handle 5220 includes a set of bearings, spools, pulleys or pulley members 5250*a*, 5250*b*, 5250*c*, 5250*d*, 5250*e* (wherein pulleys 5250*a*, 5250*b*, 5250*c* correspond to the same set of pulleys in FIG. 40). A cable 5230*a* extends through the pulleys 5250*a*, 5250*d*, 5250*b*, 5250*e*, 5250*c*. Manipulation of a mechanical input (identified as 5224' in FIG. 41) causes rotary motion of the pulleys 5250*d*, 5250*b*, 5250*e*. The rotary motion of the pulleys 5250*d*, 5250*b*, 5250*e* changes the amount of cable 5230 that is received in the handle 5220, thereby actuating the end effector. The effect of the rotary motion of the pulleys on the cable 5230*a* is shown in FIGS. 43 and 44. Depending on the direction of the rotary motion, the pulleys 5250*d*, 5250*e* can either wound or "take up" cable 5230 in the handle 5220, or can unwound and "give out" cable 5230*a* in the handle 5220. Either way, the length of the cable 5230*a* changes within the handle 5220, thereby causing actuation of the end effector 5212. While the embodiment in FIG. 41 depicts a pulley system that is modified by rotary motion, in other embodiments, the pulley system can be modified by linear and/or rotary motion. In addition, one skilled in the art will appreciate that a change in length in the amount of cable 5230*a* in the handle 5220 can also change cable tension.

Figure 42:
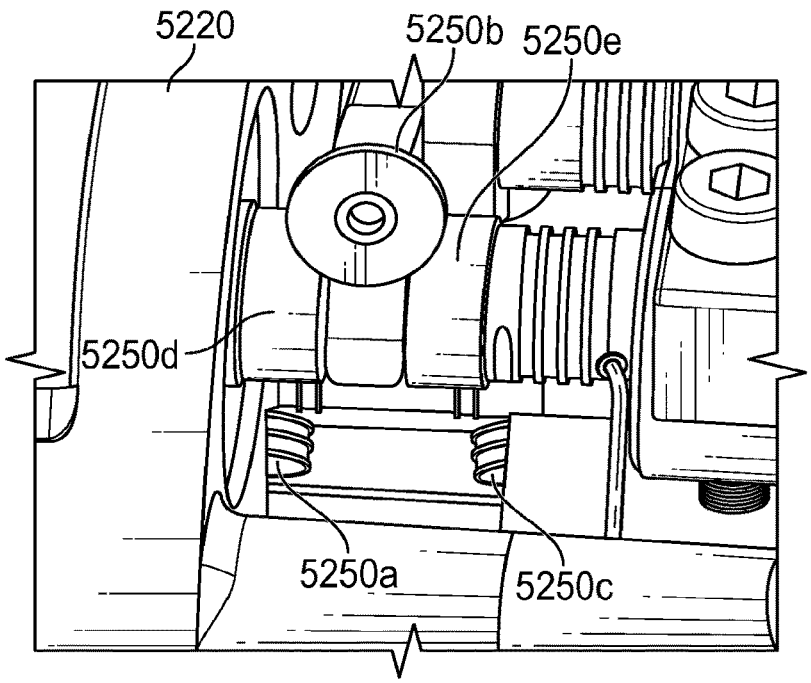
FIG. 42 illustrates a zoomed-in perspective view of a first actuation mechanism of the instrument of FIG. 39, according to one embodiment.

FIG. 42 illustrates a zoomed-in perspective view of a first actuation mechanism of the instrument of FIG. 39, according to one embodiment. From this view, one can see different details of the pulleys 5250*a-e* including the spools of the pulleys 5250*a*, 5250*c*.

FIGS. 43 and 44 illustrate a front view of a pulley member 5250*e* and cable of the instrument of FIG. 39, before and after actuation of the pulley member, according to one embodiment. Applying torque on the mechanical input 5224' rotates pulleys 5250e, 5250b and 5250d. As shown in FIG. 43, before actuation of the pulley 5250e, cable 5230a can run along one side of the pulley 5250e. As shown in FIG. 44, after actuation of the pulley 5250e, the cable 5230a is then wound and taken up by the pulley, thereby increasing the amount of cable 5230a within the handle 5220 to cause actuation of an end effector.

While embodiments in FIGS. 39-44 disclose one or more pulleys mounted on a rotary axis to change relative cable length, in other embodiments, mounting a pulley on a lever, gear or track based system to adjust location are additional options. In addition, ball spline rotary shafts that travel down a length of a tool could also be used to transmit forces in a mechanically remote way.

FIG. 45 illustrates a side view of a second actuation mechanism including a spool for shaft translation, according to one embodiment. The second actuation mechanism is designed to translate the shaft 5202 relative to the handle 5220 along an axis of insertion. Like the first actuation mechanism that actuates the end effector 5212, the second actuation mechanism can also be incorporated within the handle 5220.

The second actuation mechanism comprises a cable or cable segment 5230b that engages a set of spools 5270a, 5270b, 5270c, 5270d. One end of the cable 5230b can be attached at or near a proximal end 5205 of the shaft 5202, while the other end of the cable 5230b can be attached at or near a distal end 5207 of the shaft 5202. The cable 5230b extends through the set of spools 5270a, 5270b, 5270c, of which spool 5270b is a capstan. Rotating a mechanical input of the handle 5220 causes rotation of the capstan, thereby driving cable 5230b in and out of the capstan. As cable 5230b is driven in and out of the capstan, this causes the shaft 5202 to translate relative to the handle 5220. Advantageously, by applying adequate pre-tension to the cable 5230b that is attached at both the proximal and distal end of the shaft 5202, frictional force can be used to drive the cable 5230b in and out, thereby moving the shaft 5202 relative to the handle 5220 without slipping.

Figure 46:
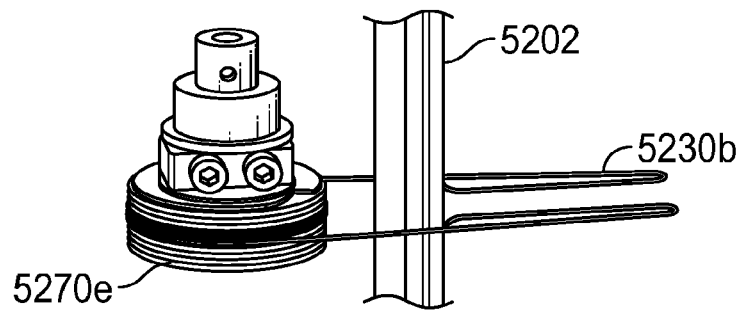
FIG. 46 illustrates a perspective view of an alternative spool using a single cable for shaft translation, according to one embodiment.
Figure 47:
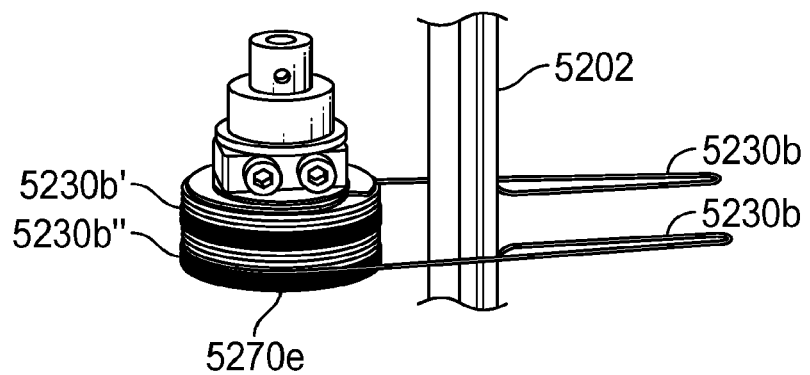
FIG. 47 illustrates a perspective view of an alternative spool using more than one cable for shaft translation, according to one embodiment.

In the present embodiment, the capstan 5270b comprises a zero-walk capstan. In other embodiments, such as shown in FIGS. 46 and 47, a capstan can be incorporated into the handle 5220 that can allow for cable walk. The zero-walk capstan architecture helps to manage multiple wraps of cable 5230b around the capstan 5270b without a helix angle on the groove to prevent the cable walk across the capstan 5270b, which could affect overall path length and change tension in the cable. By placing an additional pulley 5270d on an incline next to the capstan 5270b, a redirect to a parallel path on the capstan 5270b can be achieved, resulting in no walking action of the cable 5230b on the capstan 5270b.

FIGS. 46 and 47 present alternative embodiments to the zero-walk capstan shown in FIG. 45. In these embodiments, the capstan that drives shaft insertion is an enlarged capstan 5270e that can be incorporated into the architecture of the second actuation mechanism. With a large enough drive capstan 5270e and a small enough insertion stroke, the number of rotations of the capstan is small. For example, with a 22 mm drive capstan 5270e and a 350 mm insertion stroke, the number of rotations of the capstan 5270e for full insertion range is 5 rotations. If the distance that the cable goes to is large enough compared to the cable walk range of the capstan 5270e, the amount of fleet angle on the cable and path length change during insertion is small enough to be negligible. In some embodiments, the fleet angle can be between +/−2 degrees.

FIG. 46 illustrates a perspective view of an alternative spool using a single cable for shaft translation, according to one embodiment. The alternative spool comprises an enlarged capstan 5270e which is engaged by a single cable 5230b. In this embodiment, to actuate drive shaft insertion, the single cable 5230b has a large enough wrap angle to have enough capstan friction to drive. In some embodiments, the single cable 5230b is continuous and wraps around the capstan 5270e multiple times (e.g., 3, 4 or more times) to have a large enough wrap angle to drive the capstan and insertion.

FIG. 47 illustrates a perspective view of an alternative spool using more than one cable for shaft translation, according to one embodiment. The alternative spool comprises an enlarged capstan 5270e which is engaged by two separate segments 5230b', 5230b" of a single cable 5230b. Each of the segments 5230b', 5230b" terminates on the capstan 5270e. Unlike the embodiment in FIG. 46, the present embodiment does not rely on capstan friction to drive shaft insertion. In this embodiment, the cable 5230b is helixed to the outsides and then terminated to the spool at both the top and bottom. An advantage of the double termination approach shown in FIG. 47 is that it is resilient to loss of cable tension. As the double termination approach relies on a positive engagement rather than friction, slip cannot happen.

Figure 48:
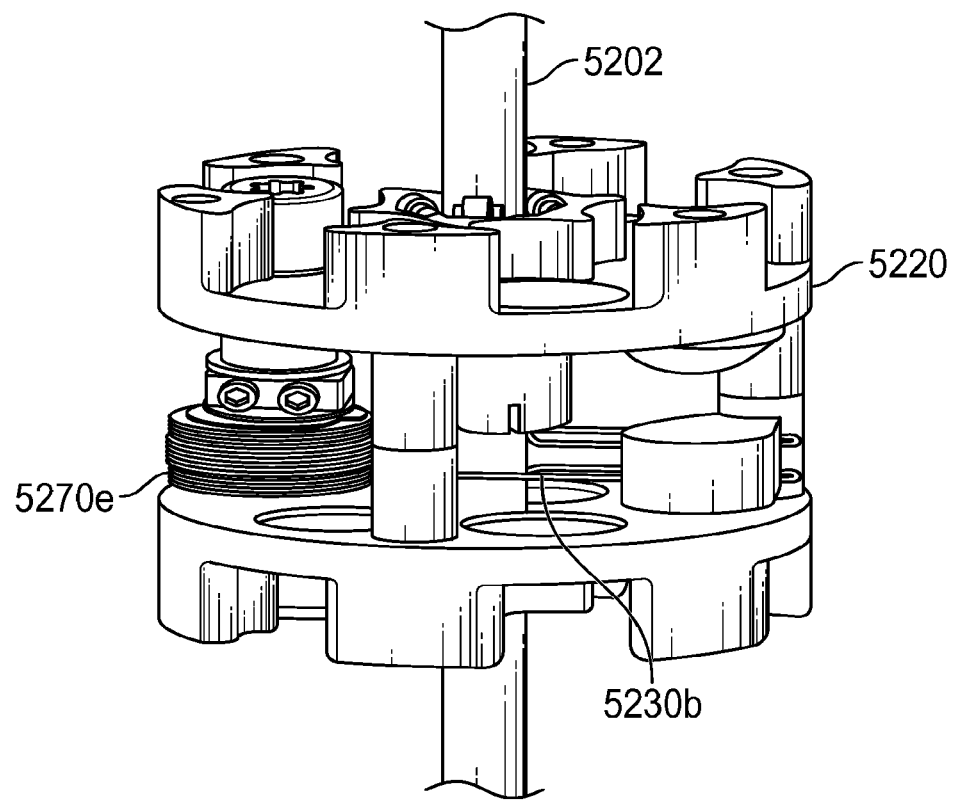
FIG. 48 illustrates a front view of a handle including the spool of FIG. 46, according to one embodiment.

FIG. 48 illustrates a front view of a handle including the spool of FIG. 46, according to one embodiment. From this view, one can see one possible position of the spool (e.g., the capstan 5270e) within the handle 5220. Advantageously, additional spools and pulleys can be provided within the handle 5220 to actuate the end effector 5212. For example, a pulley system for end effector actuation as represented in FIG. 40 can be incorporated into the handle in FIG. 48. Accordingly, the handle 5220 can incorporate multiple mechanisms for both end effector actuation and/or drive insertion. As shown in FIG. 48, the one or more pulleys guiding the cable 5230 onto the capstan 5270e are situated across the handle to increase cable distance. If the distance that the cable goes to is large enough compared to the cable walk range of the capstan 5270e, the amount of fleet angle on the cable and path length change during insertion is small enough to be negligible. In some embodiments, it is possible to have a traditional helix capstan and keep the length change and fleet angle to a minimum.

Figure 49:
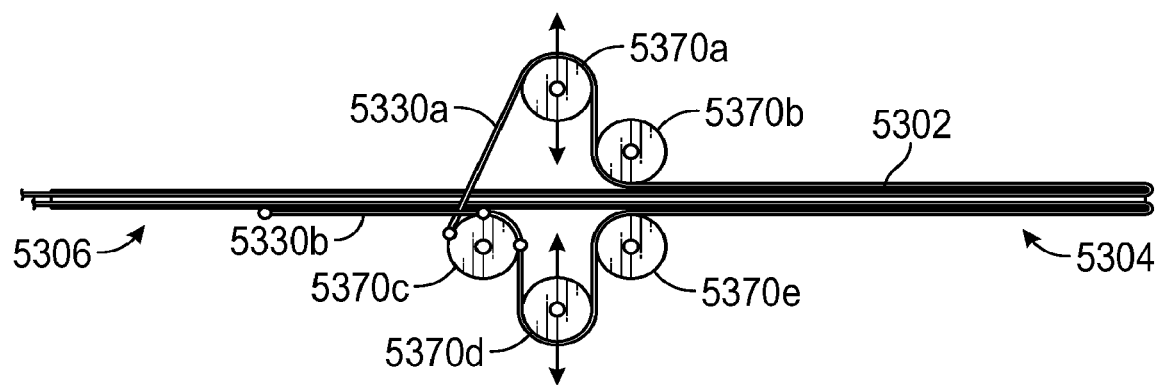
FIG. 49 illustrates a schematic diagram showing an alternative architecture for actuating an end effector and shaft translation, according to one embodiment.

FIG. 49 illustrates a schematic diagram showing an alternative architecture for actuating an end effector and shaft insertion, according to one embodiment. The architecture incorporates a first actuation mechanism for actuating an end effector and a second actuation mechanism for shaft insertion. Like prior embodiments, the first actuation mechanism and the second actuation mechanism are decoupled, such that actuation of the end effector does not impact shaft insertion, and vice versa. However, in the present embodiment, the first actuation mechanism comprises one or more cables for actuating an end effector that terminate at an insertion spool (which is also used as part of the second actuation mechanism for shaft insertion), rather than terminating on the proximal and distal portions of the shaft as in the embodiment in FIG. 40. As a result of this architecture, during shaft insertion via a second actuation mechanism, one or more cables that are wound by the insertion spool are substantially counterbalanced by a length of one or more cables (used in a first actuation mechanism to actuate an end effector) that are unwound by the insertion spool. During end effector actuation via a first actuation mechanism, one is trading off the path lengths of the cables coming off of the insertion spool.

As shown in FIG. 49, the alternative architecture for end effector actuation and shaft insertion comprises a shaft 5502 having a proximal portion 5304 and a distal portion 5306 where an end effector is located. One or more spools 5370*a*, 5370*b*, 5370*c*, 5370*d*, 5370*e* (which are part of a handle) are positioned about the shaft 5502. Spool 5370*c* comprises an insertion spool. Rotation of the insertion spool 5370*c* in a first direction causes shaft translation relative to the handle in a first direction (e.g., in a direction of insertion), while rotation of the insertion spool 5370*c* in a second direction causes shaft translation relative to the handle in a second direction (e.g., in a direction of retraction). One or more cables or cable segments 5330*a* terminate to an end effector (e.g., a wrist) on one end and an insertion spool on the other. One or more additional cables or cable segments 5330*b* also begin at the insertion spool 5370*c* before terminating at, near or towards a distal portion 5306 of the shaft 5502.

In the present embodiment, a first actuation mechanism is provided wherein manipulation of one or more spools (e.g., spools 5370*a*, 5370*d*) via linear or rotary movement causes a change of length of the one or more cables 5330*a* within the handle. In some embodiments, the change of length of the one or more cables 5330*a* within the handle can include a change of the path length of one or more cables or cable segments within the handle. In this first actuation mechanism, the one or more cables 5330*a* can be considered "end effector" cables. Any change in length of the one or more cables 5330*a* in the handle that causes actuation of the end effector is counterbalanced by a length of the one or more cables 5330*b*.

In the present embodiment, a second actuation mechanism is provided wherein manipulation of the insertion spool 5370*c* via linear or rotary movement causes a change of length of the one or more cables 5330*b* within the handle. In this second actuation mechanism, the one or more cables 5330*b* can be considered "insertion" cables. Any change in length of the one or more cables 5330*b* in the handle that causes shaft insertion or retraction is counterbalanced by a length of the one or more cables 5330*a*. Under insertion and retraction, tension is maintained because equal amounts of the one or more end effector cables 5330*a* are being paid out as the one or more insertion cables 5330*b* are being taken up. The relative path length of the one or more end effector cables 5330*a* remains unchanged, so the end effector does not move under insertion.

Figure 50A:
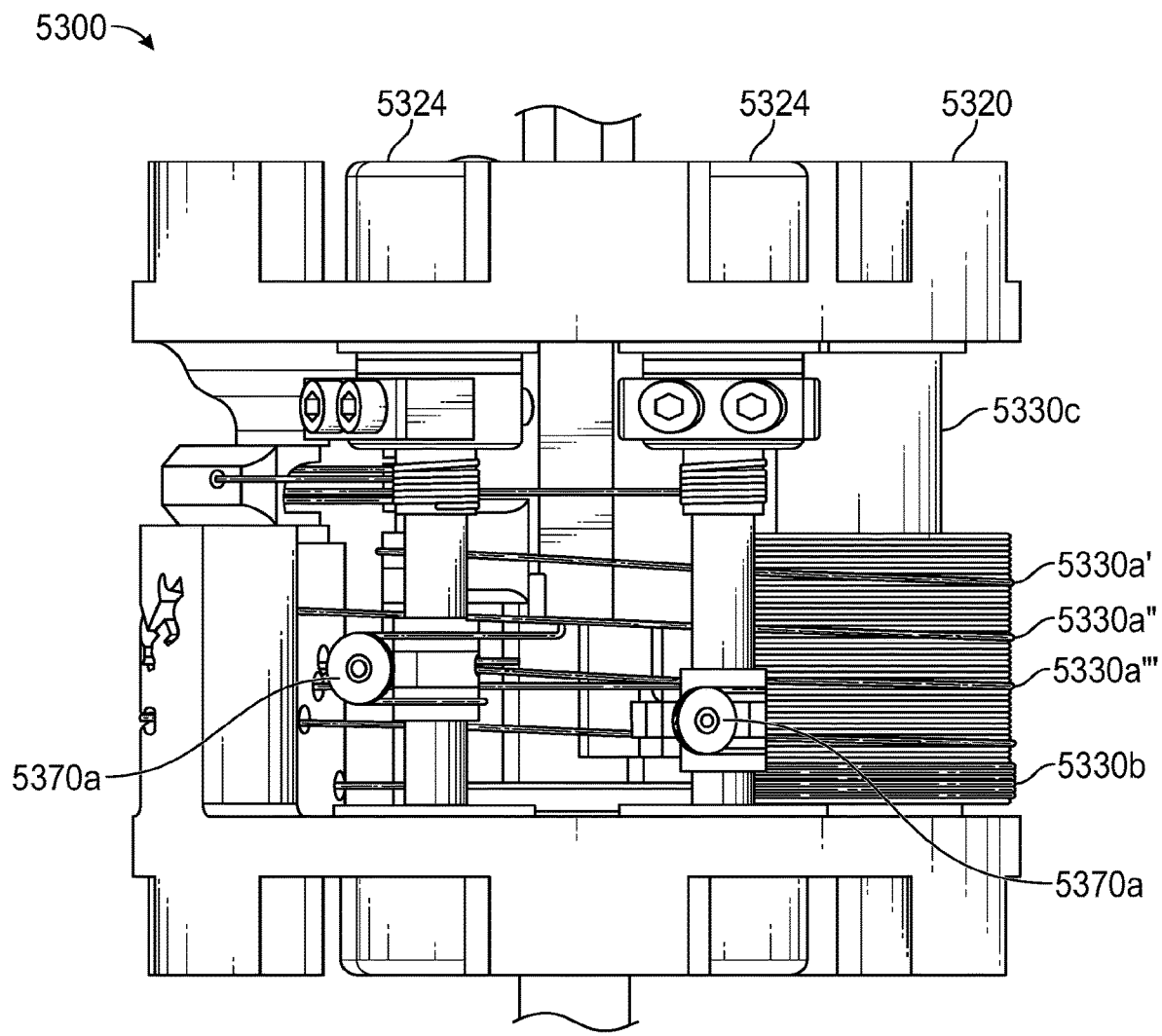
FIG. 50A illustrates a zoomed-in front view of an instrument incorporating the alternative architecture for actuating an end effector and shaft insertion of FIG. 49, according to one embodiment.
Figure 50B:
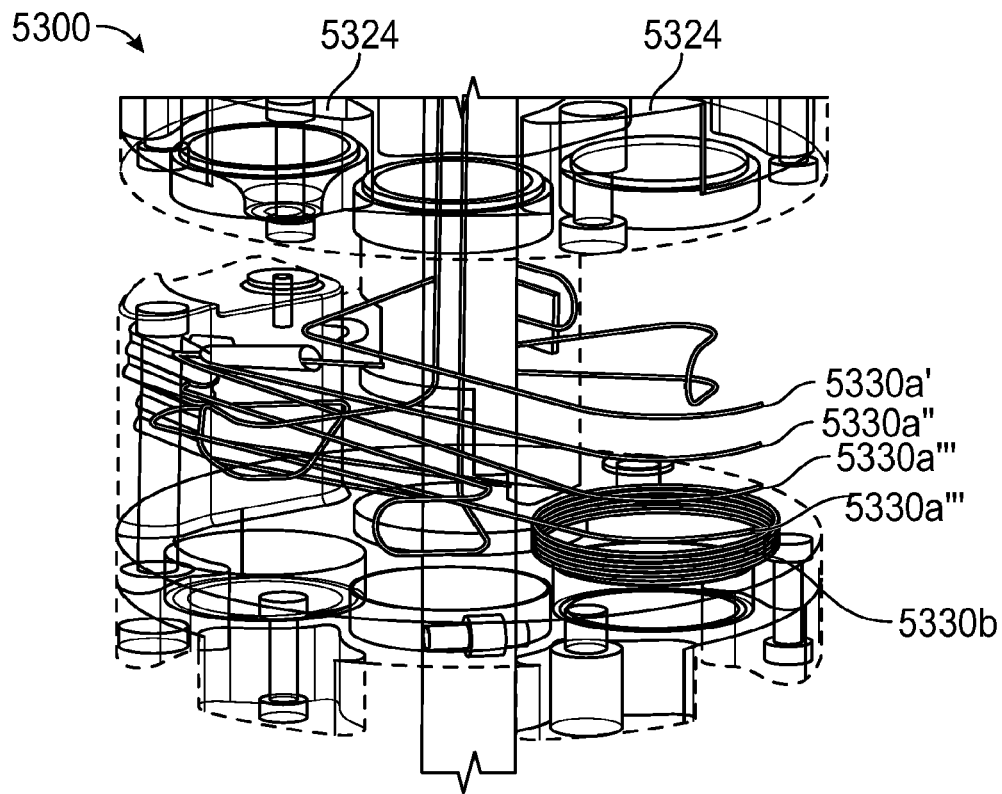
FIG. 50B illustrates a top perspective view of an instrument incorporating the alternative architecture for actuating an end effector and shaft insertion of FIG. 49, according to one embodiment.

FIG. 50A illustrates a zoomed-in front view of an instrument incorporating the alternative architecture for actuating an end effector and shaft insertion of FIG. 49, according to one embodiment. FIG. 50B illustrates a top perspective view of the instrument incorporating the alternative architecture for actuating an end effector and shaft insertion of FIG. 49. The instrument 5300 incorporates the first and second actuation mechanism shown in FIG. 49, and includes a handle 5320 comprising one or more mechanical inputs 5324, each corresponding to one or more spools 5370*a-e*, wherein at least one of the spools (5370*c*) comprises an insertion spool. One or more cables or cable segments 5330*a'*, 5330*a"*, 5330*a'''* and 5330*a''''*, each corresponding to a separate mechanical input 5324, terminate at the drive spool 5370*c*. Each of these cables 5330*a'*, 5330*a"*, 5330*a'''* and 5330*a''''* can engage with one or more spools akin to the one or more cables 5330*a* (shown in the schematic in FIG. 49). In a first actuation mechanism, these cables can serve as end effector cables, such that manipulation of their corresponding mechanical inputs 5324 causes a change of length of the cables within the handle. In some embodiments, the change of length of the one or more cables within the handle can include a change of the path length of one or more cables or cable segments within the handle. In some embodiments, a path length of the cables within the handle is changed. In some instances, the change of length in the one or more cables 5330*a'*, 5330*a"*, 5330*a'''*, 5330*a''''* within the handle 5320 that actuate the end effector is counterbalanced by a length of cable 5330*b*, which is akin to the similarly reference cable 5330*b* in FIG. 49. In other instances, under pure end effector actuation, the length of the cable 5330*b* in the handle is not changing. In a second actuation mechanism, the cable 5330*b* can serve as an insertion cable, such that manipulation of its corresponding mechanical input 5324 causes cable 5330*b* to be wound around the insertion spool 5370*c*. The amount of cable 5330*b* that is wound around the insertion spool 5370*c* that causes shaft insertion is counterbalanced by a length of the one or more cables 5330*a'*, 5330*a"*, 5330*a'''*, 5330*a''''* being unwound.

Figure 51:
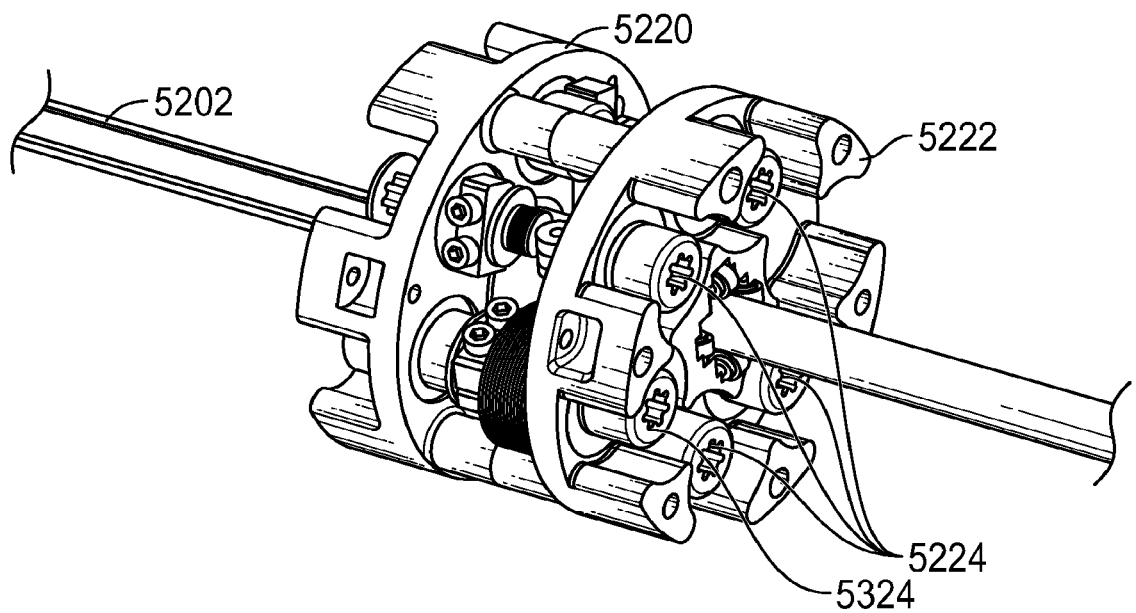
FIG. 51 illustrates a top perspective view of a handle and shaft of an instrument, according to one embodiment.

FIG. 51 illustrates a top perspective view of a handle and shaft of an instrument, according to one embodiment. The shaft 5202 is translatable relative to the handle 5220. From this view, one can see the one or more mechanical inputs 5224, which upon rotation, actuate the end effector. In addition, one can see the one or more mechanical inputs 5324, which upon rotate, allow for translation of the shaft 5202 relative to the handle 5220 along an axis of insertion. The attachment interface 5222 includes the one or more mechanical inputs 5224, 5324 e.g., receptacles, pulleys or spools, that are designed to reciprocally mate with one or more torque couplers 4314 on an attachment interface 4310 of the IDM 4300 (shown in FIG. 31).

Figure 52A:
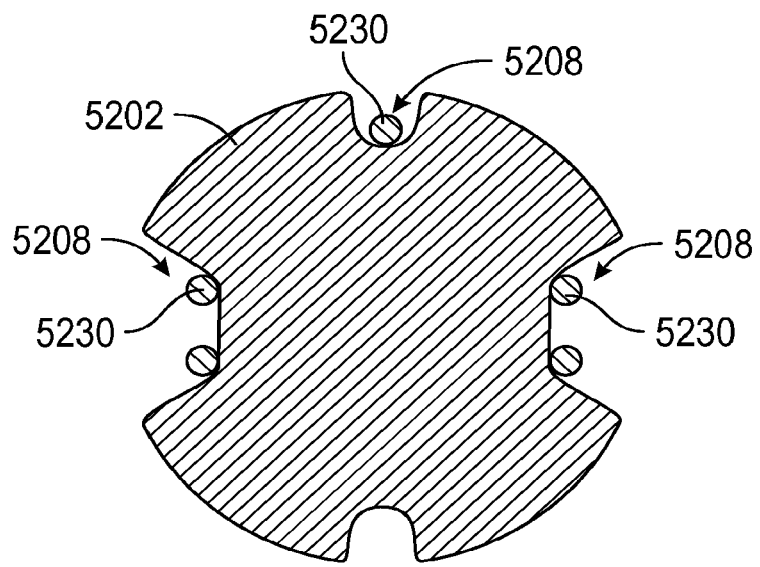
FIG. 52A illustrates a schematic view of a cross-section of an instrument shaft utilizing the insertion architecture shown in FIG. 40, according to one embodiment.
Figure 52B:
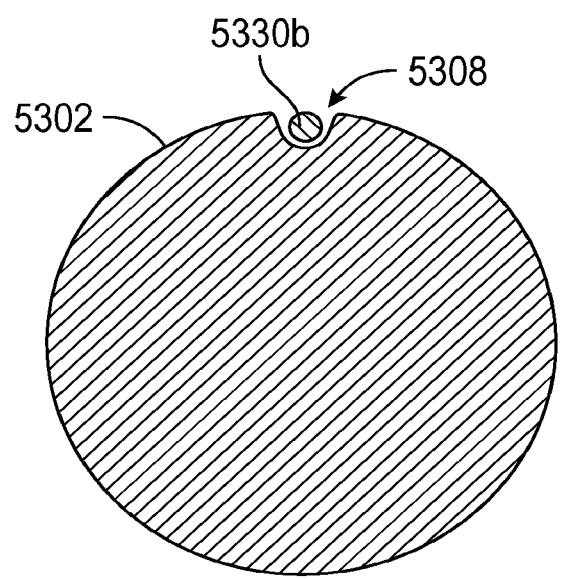
FIG. 52B illustrates a schematic view of a cross-section of an instrument shaft utilizing the insertion architecture shown in FIG. 49, according to one embodiment.

FIG. 52A illustrates a schematic view of a cross-section of an instrument shaft utilizing the insertion architecture shown in FIG. 40, while FIG. 52B illustrates a schematic view of a cross-section of an instrument shaft utilizing the alternative insertion architecture shown in FIG. 49. While not visible, each of the cross-sections in FIGS. 52A and 52B include openings or lumens that extend therethrough. As shown in FIG. 52A, the insertion architecture of FIG. 40 results in one or more cables 5230 that extend through grooves or channels 5208 that extend along an outer surface of the shaft 5202. In contrast, as shown in FIG. 52B, the insertion architecture of FIG. 49 results in one or more cables 5330*b* that extend through less grooves or channels 1308 (here a single channel) along an outer surface of the shaft 5202. This is because in the alternative architecture of FIG. 49, cables are more inclined to extend within the body of the shaft 5502. For example, there are no end effector cables on the outside of the shaft 5502. With less cables extending on the outside of the shaft 5502, the architecture in FIG. 49 can result in an overall smoother shaft surface with less grooves or channels extending on an outer surface.

The architectures described above (e.g., shown in FIGS. 40 and 49) can be used to actuate an end effector and accommodate instrument insertion. In addition, these architectures can be incorporated into specific types of instruments to assist in surgical procedures.

Figure 53:
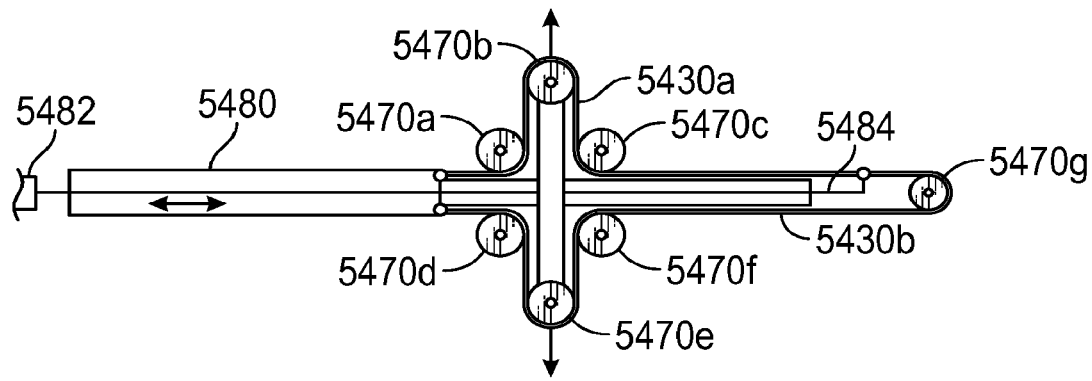
FIG. 53 illustrates a schematic diagram showing an architecture for driving a knife in a vessel sealer, according to one embodiment.
Figure 54:
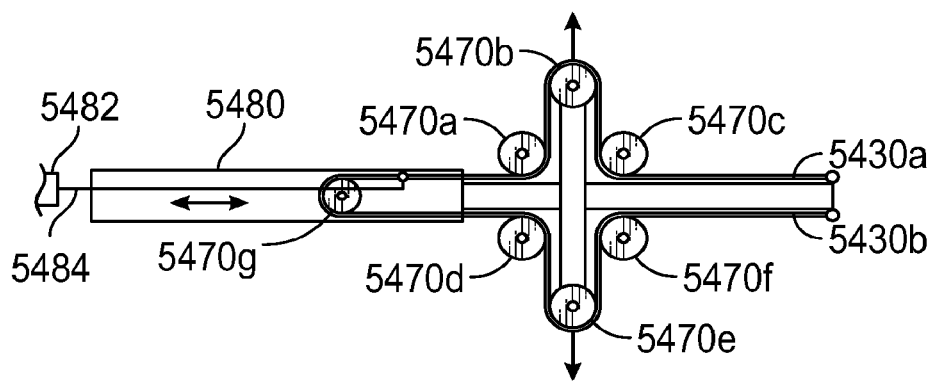
FIG. 54 illustrates a schematic diagram showing an alternative architecture for driving a knife in a vessel sealer, according to one embodiment.
Figure 55:
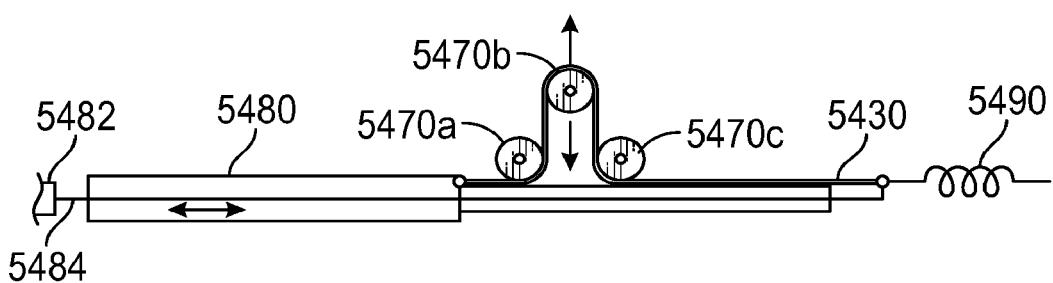
FIG. 55 illustrates a schematic diagram showing yet another alternative architecture for driving a knife in a vessel sealer, according to one embodiment.

One such instrument is a vessel sealer. With a vessel sealer, a knife or cutter can be driven through to cut tissue. In some embodiments, motion of the knife is rotational. In other embodiments, motion of the knife is translational. FIGS. 53-55 show different architectures that can be incorporated into a vessel sealer instrument to drive a knife through a vessel sealer. The architectures shown in these figures are like the architecture and related mechanisms shown in FIG. 40, but in other embodiments, the architectures can be like the architecture and related mechanisms shown in FIG. 49.

FIGS. 53-55 illustrate schematic diagrams showing different architectures for driving a knife in a vessel sealer. The architectures create a differential in path length amongst cables, and turns this differential path length change into linear motion of the knife. In the embodiments in FIGS. 53 and 54, two cables 5430a, 5430b are placed in counter tension, while in the embodiment in FIG. 55, a single cable 5430 and spring 5490 is used for counter tension. In the embodiments where two cables are placed in counter tension, linear motion of the knife is achieved by having both differentials on the same input axis, but in opposite directions (e.g., one is unwrapping cable while the other is wrapping cable). The dual, opposing cable approach also utilizes a redirect pulley to close the tension loop, and this can be mounted at or near a proximal end or at or near a distal end of a shaft (shown respectively in FIGS. 53 and 54). Once you have cable that is being pulled in and out, the knife can be coupled to a section of cable to create an in and out motion of the knife.

FIG. 53 illustrates a schematic diagram showing an architecture for driving a knife 5482 in a vessel sealer 5480. The architecture comprises a first cable 5430a and a second cable 5430b, wherein the first cable 5430a and second cable 5430b are in counter tension. The architecture further comprises one or more spools or pulley members 5470a, 5470b, 5470c that are engaged by the first cable 5430a, and one or more spools or pulley members 5470d, 5470e, 5470f that are engaged by the second cable 5430b, and a redirect spool or pulley 5470g that closes the tension loop. The redirect pulley 5470g is positioned at or near a proximal portion of the shaft. With the first cable 5430a and second cable 5430b in counter tension to one another, the knife 5482 can be coupled to a section of cable (e.g., first cable 5430a) via a connector such as elongate member 5484, thereby creating an in and out motion of the knife 5482 relative to the vessel sealer 5480. In some embodiments, elongate member 5484 comprises a push rod. In other embodiments, elongate member 5484 withstands the driving compression forces without buckling.

FIG. 54 illustrates a schematic diagram showing an alternative architecture for driving a knife in a vessel sealer. The architecture is similar to that shown in FIG. 53; however, in the present embodiment, the redirect pulley is positioned at or near a distal portion of the shaft.

FIG. 55 illustrates a schematic diagram showing yet another alternative architecture for driving a knife in a vessel sealer. Unlike the prior embodiments in FIGS. 53 and 54, the architecture in the present embodiment utilizes a single cable 5430 that is in counter tension with a spring 5490. The architecture further comprises one or more spools or pulley members 5470a, 5470b, 5470c that are engaged by the first cable 5430a. With the cable 5430 in counter tension with the spring 5490, the knife 5482 can be coupled to a section of the cable 5430, thereby creating an in and out motion of the knife 5482 relative to the vessel sealer 5480.

Another device that can serve as an insertion instrument is a camera. The camera can be used for endoscopic surgery. The architecture can vary depending on whether the camera is a rigid camera or an articulating camera, for which actuation for articulation will have to be provided.

Figure 56:
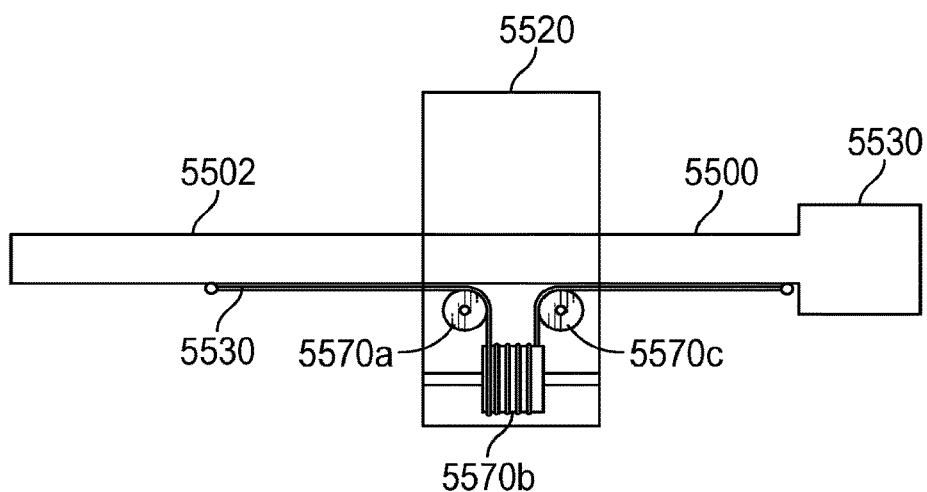
FIG. 56 illustrates a schematic diagram showing an architecture for making a rigid camera an insertion instrument, according to one embodiment.

FIG. 56 illustrates a schematic diagram showing an architecture for making a rigid camera an insertion instrument. The camera 5500 comprises a distal image payload connected by a shaft 5502 to a camera handle 5530 which has interface buttons and a cable coming out of it. The cable 5530 is received in a channel or groove formed on the outside of the shaft 5502, while the insertion handle 5520 is positioned around the shaft 5502. This in effect adds a second handle to the endoscope which enables insertion capability. The cable 5530 extends through one or more spools 5570a, 5570b, 5570c. In the present embodiment, spool 5570b can be a capstan. In some embodiments, the capstan can comprise a zero-walk capstan (as shown in FIG. 45), while in other embodiments, the capstan can allow cable walk (as shown in FIGS. 46 and 47). Via the capstan mechanism, the camera is capable of translation along an axis of insertion. In some embodiments, the core payload maintains the same sealing architecture as a rigid scope, so it can be expected to be sterilized with the same methods. For a rigid scope, this means it can be autoclaved. The additional insertion handle 5520 may also look like an instrument from a sterilization perspective and can be autoclaved as well.

While FIG. 56 shows an architecture for making a rigid camera an insertion instrument, articulating cameras present additional complexity, as mechanisms would be added to the camera to provide for articulation. For the articulating camera, one or more cables (e.g., actuation or wrist cables) can be provided to accommodate articulating movement. The camera can also be housed in a sealed area, such that if one is to run the one or more cables on the outside, one can also create a sealed compartment for the camera that excludes the one or more cables. With this architecture, it may be possible that some particles and debris get into small spaces within the sealed area. In some embodiments, to prevent the contamination, one solution may be to add two articulation motors within the sealed camera area rather than relying on the IDM for articulation motion. This greatly simplifies the cleaning and sealing of the camera components by taking the cables from the outside of the tube and putting them in the sealed inside. Another benefit of adding the two articulation motors within the sealed camera is that articulation of the camera can be controlled as soon as the camera is plugged into a vision box. This enables features like keeping the camera straight during installation or removal and being able to articulate the camera from the camera handle to look around during off-robot use. This then makes the articulation camera look a lot like the rigid camera from a sterilization perspective such that it is possible to be autoclaved.

Figure 57:
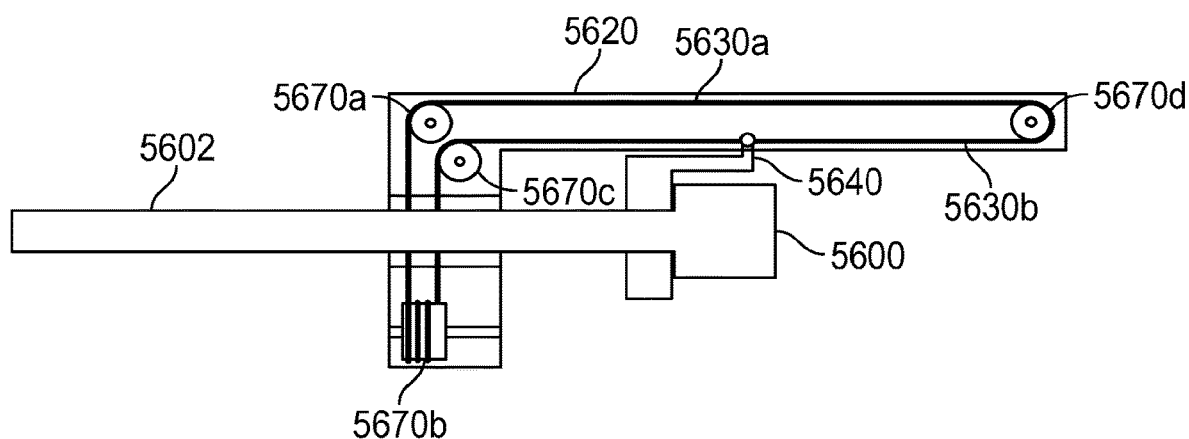
FIG. 57 shows a first insertion architecture that allows a camera to be separated from an insertion handle, according to one embodiment.

If a camera is not able to be autoclaved, then the sealed camera core and the insertion section may need to be separated for cleaning and insertion. This is because it is desirable to autoclave an insertion handle to achieve reliable sterilization. FIG. 57 shows a first insertion architecture that allows a camera to be separated from an insertion handle, while FIGS. 58 and 59 show a second insertion architecture that allows a camera to be separated from an insertion handle, thereby allowing for better sterilization.

FIG. 57 shows a first insertion architecture that allows a camera to be separated from an insertion handle. The architecture has an autoclavable insertion handle 5620 that latches onto an IDM and is separable from the camera core 1600. The camera core 1600 comprises a shaft 5602 that extends through the handle 5620. The handle 5620 comprises one or more wires 5630a, 5630b that extend through spools 5670a, 5670b, 5670c, 5670d. In the present embodiment, spool 5670b comprises a capstan. In some embodiments, the spool 5670b comprises a leadscrew. In some embodiments, the capstan is a zero-walk capstan (as shown in FIG. 45), while in other embodiments, the capstan allows cable walk. The insertion handle 5620 can be removably attached to the camera core 5600 via a connector 5640. In some embodiments, the connector 5640 comprises a bracket. In other embodiments, the connector 5640 comprises a vertical plate that the camera latches to. As the insertion handle 5620 is removably attached to the camera core 1600, each is capable of separation for cleaning.

Figure 58:
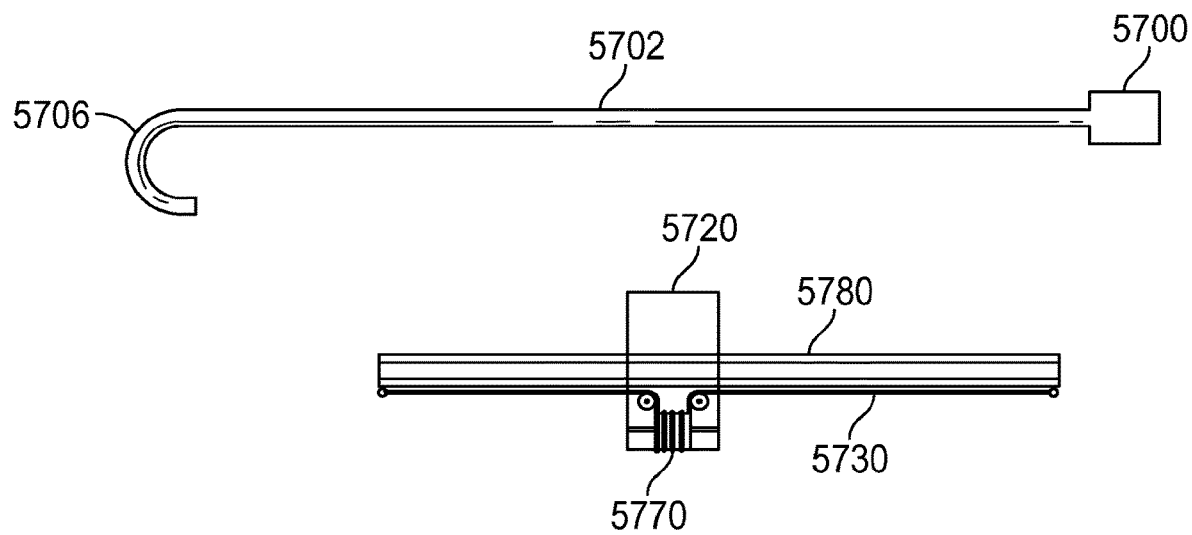
FIGS. 58 and 59 show a second insertion architecture that allows a camera to be separated from an insertion handle, according to one embodiment.
Figure 59:
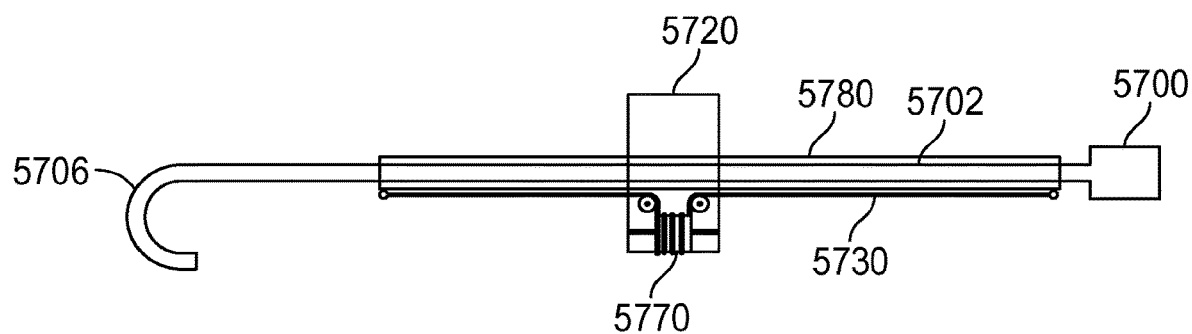
Figure 60:
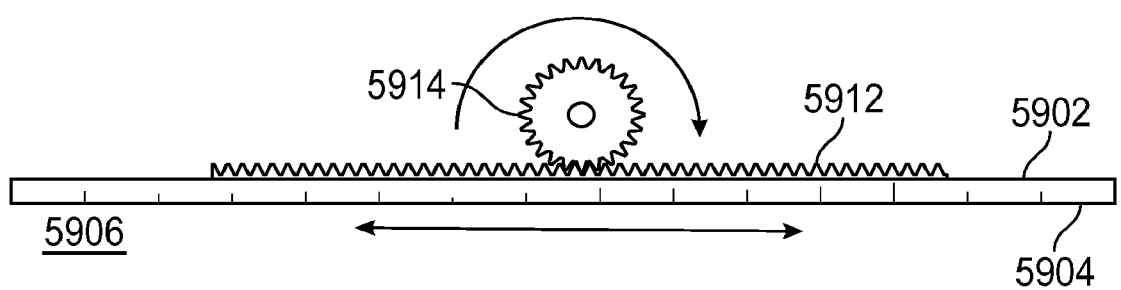
FIG. 60 illustrates a diagram showing an alternative architecture for shaft translation, according to another embodiment.
Figure 61:
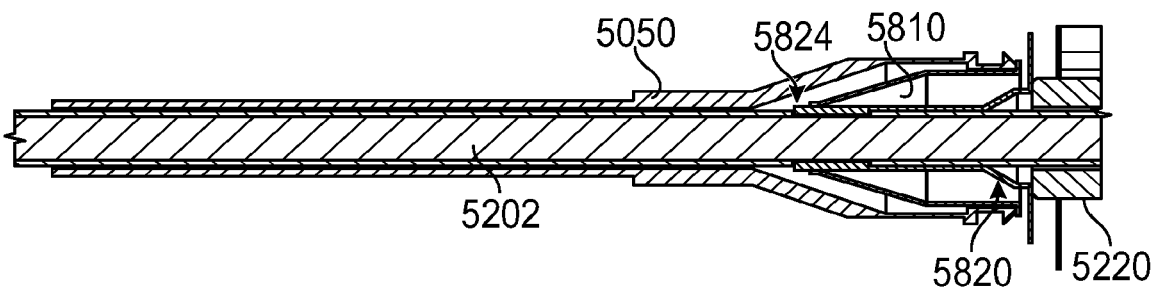
FIG. 61 shows a side cross-sectional view of an instrument having multiple seals to prevent air leakage from a patient.

FIGS. 58 and 59 show a second architecture that allows a camera to be separated from an insertion handle. In the present embodiment, an overtube 5780 is provided that has an insertion cable 5730 attached to it and through which a camera 5700 can be loaded for a procedure. FIG. 60 shows the camera 5700 detached and separated from the overtube 5780, while FIG. 61 shows the camera 5700 loaded into the overtube 5780. To load the camera 5700 into the overtube, a distal tip 5706 and shaft 5702 of the camera 5700 passes through the overtube 5780. The overtube 5780 is connected to a handle 5720 which houses a spool 5770 in the form of a capstan. This architecture has the benefit of keeping the camera 5700 separate from an insertion handle 5720 if desired, so that both components can be easily cleaned. Furthermore, the camera 5700 is kept low profile in use, as it is to be fit into the overtube 5780. As the insertion handle 5720 is removably attached to the camera core 5700, each is capable of separation for cleaning.

FIG. 60 illustrates a diagram showing an alternative architecture for shaft translation, according to another embodiment. In the present embodiment, the instrument comprises a shaft 5902 having a proximal portion 5904 and a distal portion 5906. Insertion of the shaft 5902 can be driven by a rack gear 5912 and pinion 5914, wherein rotation of the pinion 5914 results in translation of the rack gear 5912 and the shaft 5902 that is coupled to the rack gear 5912. In some embodiments, the rack gear 5912 is positioned on the instrument shaft 5902, while the pinion 5914 is positioned within the housing of the instrument handle. A motor driver can be used to translate the shaft 5902 relative to the handle. In some embodiments, a spur gear can be used, in addition to a cycloid pin rack profile. In some embodiments, the rack gear 5912 and pinion 5914 can be used on its own to cause insertion or translation of the shaft 5902. In other embodiments, the rack gear 5912 and pinion 5914 can accompany and complement any of the insertion mechanisms described above. The rack gear 5912 and pinion 5914 can be used with any of the types of instruments described above to provide linear insertion of the instrument shaft relative to the handle.

When performing surgical procedures, such as laparoscopic procedures, surgeons use insufflation. This means that cannulas inserted into a patient are sealed against the surgical tool shafts to maintain positive pressure inside a patient's body. Seals can be coupled to the surgical tool shafts to prevent air from leaking from a patient's body. These seals are often designed to accommodate tools having round cross-sections. It can be difficult to apply the same seals to tools having non-circular shapes and concave features on the outer surfaces of the shaft, as passages formed by these surfaces can allow the release of air pressure at the tool seal. For example, instruments having instrument based insertion architectures can have cross-sections (as shown in FIG. 52A) with grooves 5208 where air can leak from a patient.

To address this challenge, a system including multiple seals can be provided to prevent air leakage in a patient. In particular, a novel seal can be provided that works with a cannula seal having a circular outer shape, which is customary with instruments having circular cross-sections. The novel seal can pass through the circular cannula seal, thereby providing a consistent rotary seal. The novel seal would advantageously discretize any rotary and linear motion to create two boundaries at which a seal is created. The discretization is achieved by having an intermediate tool seal piece.

Figure 62:
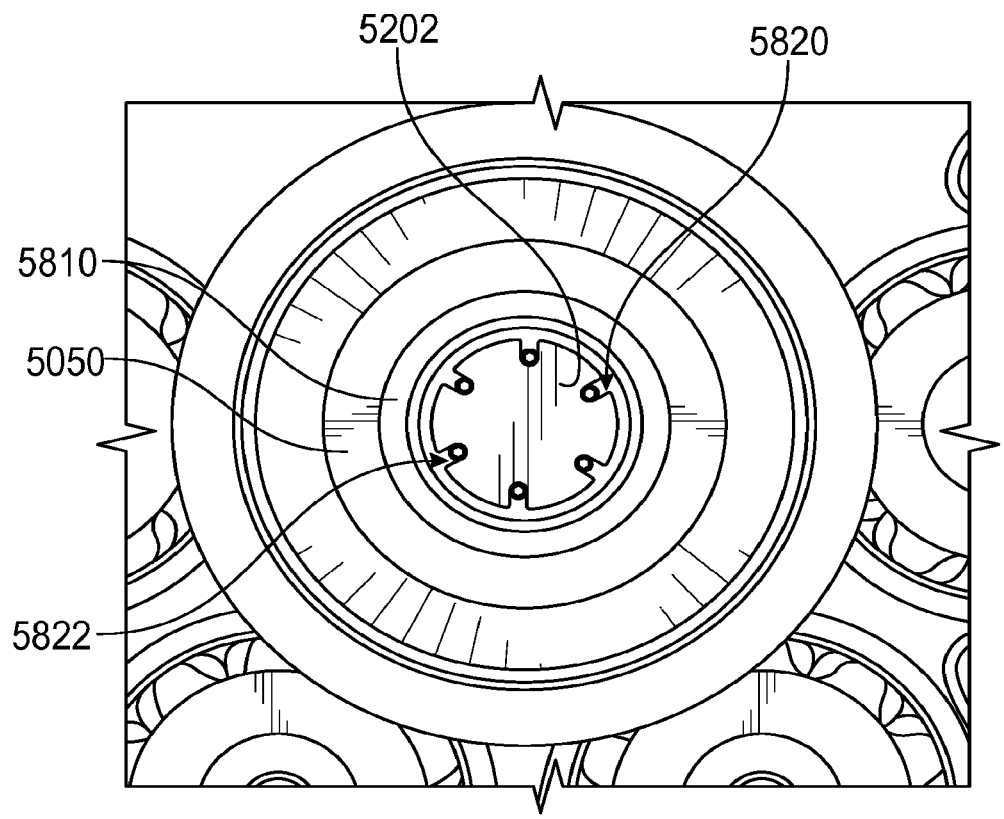
FIG. 62 shows a front cross-sectional view of the instrument having the multiple seals.

FIG. 61 shows a side cross-sectional view of an instrument having multiple seals to prevent air leakage from a patient. FIG. 62 shows a front cross-sectional view of the instrument having the multiple seals. The instrument 5200 is inserted into a cannula 5050, and is akin to the instrument shown in FIG. 39 having an instrument based insertion architecture. The instrument can include a shaft 5202 translatable relative to a handle 5220. The shaft 5202 can have one or more channels or grooves 5208 extending along an outer surface thereof, thereby creating passages that could allow air to leak from a patient.

To prevent air leakage, a multi-seal system advantageously couples to the instrument. In some embodiments, the multi-seal system comprises a first seal 5810 and a second seal 5820 that can work in conjunction to reduce the risk of air leakage. In some embodiments, the first seal 5810 and second seal 5820 are coaxial. As shown in FIG. 60, the second seal 5820 can be received in an interior of the first seal 5810. The first seal 5810 can have a cross-section having a round outer perimeter and round inner perimeter, while the second seal 5820 can have a cross-section having a round outer perimeter and an inner perimeter with inner protrusions, tabs or nubs 5822, as shown in FIG. 62. The advantage of having a second seal 5820 with the inner protrusions is that the inner protrusions can fill in voids, such as grooves 5208, that may extend along an outside of the instrument shaft 5202, thereby reducing the risk of air leakage from a patient during surgery.

The multi-seal advantageously discretizes rotary and linear motion to create two boundaries at which a seal is created. The second seal 5820, with its inner protrusions 5822, can slide down the outer grooves of the instrument shaft 5202, thereby creating a sliding linear seal for instrument shaft motion. One skilled in the art will appreciate that while the second seal 5820 is shown with a plurality of inner protrusions that are rounded and spaced substantially symmetrically around an inner perimeter, the inner portion of the second seal 5820 can assume other shapes as well, so long as the molding process substantially matches the interior of the second seal 5820 to the outer surface of the instrument shaft 5202. When received in the grooves 5208 of the instrument 5200, each of the inner nubs 5822 of the second seal 5820 creates a rotary seal point 5824. These rotary seal points allow the instrument 5200 and second seal 5820 to rotationally lock and rotate together upon rotation of the instrument shaft 5202. While the present embodiment shows a multi-seal having dual seals, in other embodiments, three, four, or more seals can work together to reduce the risk of air leakage from a patient during surgery.

XV. Software

In some embodiments, one or more aspects of a system including adjustable arm supports and corresponding robotic arms can be controlled via software. For example, the system can be designed so that all actuations are robotically controlled by the system, and the system knows the position of all end effectors relative to the tabletop. This may provide a unique advantage that existing robotic surgery systems do not have. Further, this may allow for advantageous workflows including: adjusting the table top intraoperatively (e.g., tilt, Trendelenburg, height, flexure, etc.) while arms and arm positioning platforms move in sync; moving the robotic arms can move away from the operative field for draping or patient loading; after a clinician tells the system the type of procedure, the robotic arms can move to approximate positions near where ports are typically placed (Surgeons could modify and set port selection "presets" for how they like to do surgery); and performing "last mile" docking with cameras on the end effectors and vision targets on cannulas (other non-optical sensors around the end effector could provide similar functionality).

Further, some incarnations of robotic arm joints may require applying high forces to the arm to back-drive the motors and transmissions. This can be reduced with torque sensors in arm joints or a force sensor or joystick at the end effector to allow the robot to know where the clinician is trying to push it and move accordingly (admittance control) to lower back-drive forces felt at the output. Such back-drive regulation can be accomplished in software in some embodiments.

XVI. Additional Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A system, comprising:
a table;
a table support below the table;
an arm support coupled to at least one of the table or table support;
a first robotic arm translatably and rotatably coupled to the arm support to permit the first robotic arm to linearly move along the arm support and rotate relative to the arm support, the first robotic arm comprising a proximal portion and a distal portion and multiple joints between the proximal portion and the distal portion;
an insertion axis body coupled to a distal link of the first robotic arm, the insertion axis body extending along an axis, the insertion axis body coupled to the distal link via a first joint that permits adjustment of an angle between the axis of the insertion axis body and a longitudinal axis of the distal link; and
first and second instrument drivers translatably coupled to the insertion axis body, the first instrument driver configured to receive a first surgical instrument and the second instrument driver configured to receive a second surgical instrument, the first instrument driver configured to translate along the insertion axis body to insert and retract the first surgical instrument along a first insertion axis parallel to the axis of the insertion axis body, the second instrument driver configured to translate along the insertion axis body to insert and retract the second surgical instrument along a second insertion axis parallel to the axis of the insertion axis body.

2. The system of claim 1, wherein the first and second surgical instruments are telescoping instruments, with the first surgical instrument positioned within a channel of the second surgical instrument.

3. The system of claim 1, wherein the first and second instrument drivers are configured to drive the first and second surgical instruments, respectively, independently of each other.

4. The system of claim 1, wherein the first and second insertion axes are coaxial.

5. The system of claim 1, wherein the first and second instrument drivers are removable from the distal portion.

6. The system of claim 1, wherein the first instrument driver is rotatably coupled to the insertion axis body, the first instrument driver configured to rotate about the first insertion axis to roll the first surgical instrument about the first insertion axis.

7. The system of claim 1, further comprising the first and second surgical instruments, the first surgical instrument having a first housing and a first shaft extending from the first housing, the first instrument driver being configured to translate the first housing along the insertion axis body to insert and retract the first shaft along the first insertion axis, the second surgical instrument having a second housing and a second shaft extending from the second housing, the second instrument driver being configured to translate the second housing along the insertion axis body to insert and retract the second shaft along the second insertion axis.

8. The system of claim 1, wherein the insertion axis body is movable between a deployed configuration and a stowed configuration, wherein, in the deployed configuration, the insertion axis body and the first and second instrument drivers are elevated above the table, and, in the stowed configuration, the insertion axis body and the first and second instrument drivers are below the table with the angle between the axis of the insertion axis body and the longitudinal axis of the distal link reduced relative to the deployed configuration so that the stowed configuration is more compact than the deployed configuration.

9. The system of claim 1, wherein the first joint is a wrist joint that permits adjustment of pitch and adjustment of yaw between the insertion axis body and the distal link.

10. The system of claim 1, further comprising the first and second surgical instruments, wherein the first surgical instrument is an endoscope and the second surgical instrument is a sheath that surrounds the endoscope.

11. A system, comprising:
 a table;
 a table support below the table;
 an arm support coupled to at least one of the table or table support;
 a first robotic arm translatably and rotatably coupled to the arm support to permit the first robotic arm to linearly move along the arm support and rotate relative to the arm support, the first robotic arm comprising a proximal portion and a distal portion and multiple joints between the proximal portion and the distal portion;
 an insertion axis body at the distal portion, the insertion axis body extending along an axis, the insertion axis body coupled to a distal link of the first robotic arm via a wrist joint that permits adjustment of an angle between the axis of the insertion axis body and a longitudinal axis of the distal link;
 a first instrument driver translatably coupled to the insertion axis body, the first instrument driver configured to receive a first housing of a first surgical instrument, the first instrument driver configured to translate along the axis of the insertion axis body to insert and retract a first shaft of the first surgical instrument along a first insertion axis parallel to the axis of the insertion axis body, the first instrument driver comprising a first plurality of torque couplers configured to engage a first plurality of mechanical inputs of the first housing; and
 a second instrument driver translatably coupled to the insertion axis body, the second instrument driver configured to receive a second housing of a second surgical instrument, the second instrument driver configured to translate along the longitudinal axis of the insertion axis body to insert and retract a second shaft of the second surgical instrument along a second insertion axis parallel to the axis of the insertion axis body, the second instrument driver comprising a second plurality of torque couplers configured to engage a second plurality of mechanical inputs of the second housing.

12. The system of claim 11, wherein the first and second surgical instruments are telescoping instruments, with the first surgical instrument positioned within a channel of the second surgical instrument.

13. The system of claim 11, wherein the first and second instrument drivers are configured to drive the first and second surgical instruments, respectively, independently of each other, wherein the first instrument driver is configured to apply torque to the first plurality of torque couplers to thereby actuate the first surgical instrument via the first plurality of mechanical inputs, wherein the second instrument driver is configured to apply torque to the second plurality of torque couplers to thereby actuate the second surgical instrument via the second plurality of mechanical inputs.

14. The system of claim 11, wherein the first and second insertion axes are coaxial.

15. The system of claim 11, wherein the first and second instrument drivers are removable from the distal portion.

16. A system, comprising:
 a table;
 a table support below the table;
 an arm support coupled to at least one of the table or table support;
 a first robotic arm translatably and rotatably coupled to the arm support to permit the first robotic arm to linearly move along the arm support and rotate relative to the arm support, the first robotic arm comprising a proximal portion and a distal portion and multiple joints between the proximal portion and the distal portion;
 an insertion axis body at the distal portion, the insertion axis body extending along an axis, the insertion axis body coupled to a distal link of the first robotic arm via a wrist joint that permits adjustment of an angle between the axis of the insertion axis body and a longitudinal axis of the distal link; and
 first and second instrument drivers translatably coupled to the insertion axis body, the first and second instrument drivers axially aligned and configured to receive first and second instruments coupled to each other in a telescoping configuration, the first instrument driver configured to translate along the axis of the insertion axis body to insert and retract a shaft of the first instrument along a first insertion axis parallel to the axis of the insertion axis body, the second instrument driver configured to translate along the insertion axis body to insert and retract the second instrument along a second insertion axis coaxial with the first insertion axis,
 the insertion axis body movable between a deployed configuration and a stowed configuration, wherein, in the deployed configuration, the insertion axis body and the first and second instrument drivers are elevated above the table, and, in the stowed configuration, the insertion axis body and the first and second instrument drivers are below the table with the angle between the axis of the insertion axis body and the longitudinal axis of the distal link reduced relative to the deployed configuration so that the stowed configuration is more compact than the deployed configuration.

17. The system of claim 16, wherein the first and second instrument drivers are configured to translate along the insertion axis body.

18. The system of claim 16, wherein the first and second instrument drivers are configured to drive the first and second instruments, respectively, independently of each other.

19. The system of claim 16, further comprising the first and second instruments, wherein the first instrument is an endoscope and the second instrument is a sheath that surrounds the endoscope.

20. The system of claim 16, wherein the first instrument is removable from the insertion axis body.

* * * * *